US009790212B2

United States Patent
Blackledge, Jr. et al.

(10) Patent No.: US 9,790,212 B2
(45) Date of Patent: *Oct. 17, 2017

(54) ENHANCER OF ZESTE HOMOLOG 2 INHIBITORS

(71) Applicant: GlaxoSmithKline Intellectual Property (No.2) Limited, Brentford, Middlesex (GB)

(72) Inventors: Charles William Blackledge, Jr., Collegeville, PA (US); Joelle Lorraine Burgess, Collegeville, PA (US); Neil W. Johnson, Collegeville, PA (US); Jiri Kasparec, Collegeville, PA (US); Steven David Knight, Collegeville, PA (US); Louis V. LaFrance, III, Collegeville, PA (US); Juan I. Luengo, Collegeville, PA (US); William Henry Miller, Collegeville, PA (US); Kenneth Allen Newlander, Collegeville, PA (US); Stuart Paul Romeril, Collegeville, PA (US); Mark Schulz, Collegeville, PA (US); Dai-Shi Su, Collegeville, PA (US); Xinrong Tian, Collegeville, PA (US)

(73) Assignee: GLAXOSMITHKLINE INTELLECTUAL PROPERTY (NO. 2) LIMITED, Brentford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/292,200

(22) Filed: Oct. 13, 2016

(65) Prior Publication Data
US 2017/0029412 A1   Feb. 2, 2017

Related U.S. Application Data

(63) Continuation of application No. 14/787,866, filed as application No. PCT/IB2014/061012 on Apr. 25, 2014, now Pat. No. 9,505,745.

(60) Provisional application No. 61/936,460, filed on Feb. 6, 2014, provisional application No. 61/907,024, filed on Nov. 21, 2013, provisional application No. 61/842,038, filed on Jul. 2, 2013, provisional application No. 61/817,436, filed on Apr. 30, 2013.

(51) Int. Cl.
| | |
|---|---|
| *C07D 401/12* | (2006.01) |
| *A61K 31/4412* | (2006.01) |
| *C07D 409/14* | (2006.01) |
| *C07D 405/14* | (2006.01) |
| *C07D 413/14* | (2006.01) |
| *C07D 409/12* | (2006.01) |
| *C07D 403/12* | (2006.01) |
| *C07D 409/06* | (2006.01) |

(52) U.S. Cl.
CPC ......... *C07D 409/14* (2013.01); *C07D 401/12* (2013.01); *C07D 403/12* (2013.01); *C07D 405/14* (2013.01); *C07D 409/06* (2013.01); *C07D 409/12* (2013.01); *C07D 413/14* (2013.01)

(58) Field of Classification Search
None
See application file for complete search history.

(56) References Cited

U.S. PATENT DOCUMENTS

| | | |
|---|---|---|
| 8,410,088 B2 | 4/2013 | Kuntz et al. |
| 8,536,179 B2 | 9/2013 | Miller et al. |
| 8,598,167 B1 | 12/2013 | Kuntz et al. |
| 8,637,509 B2 | 1/2014 | Burgess et al. |
| 8,765,732 B2 | 7/2014 | Kuntz et al. |

(Continued)

FOREIGN PATENT DOCUMENTS

| | | |
|---|---|---|
| WO | WO 2008/086188 A2 | 7/2008 |
| WO | WO 2011/140324 A1 | 11/2011 |

(Continued)

OTHER PUBLICATIONS

Database Registry [Online]. Chemical Abstracts Service, Colombus, OH. Database Accession No. 1370941-72-2, XP002726952, Apr. 29, 2012.

(Continued)

*Primary Examiner* — Zinna Northington Davis
(74) *Attorney, Agent, or Firm* — Duke M. Fitch; Kathryn A. Lutomski; Edward R. Gimmi

(57) ABSTRACT

This invention relates to novel compounds according to Formula (III)(a) which are inhibitors of Enhancer of Zeste Homolog 2 (EZH2), and to pharmaceutical compositions containing them.

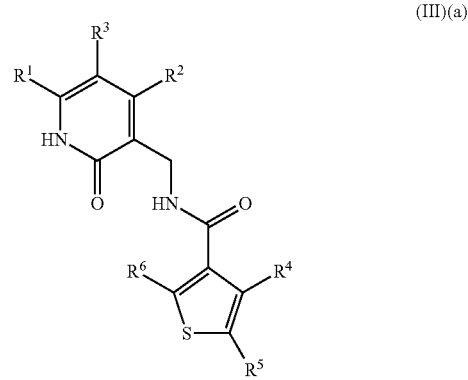

(III)(a)

20 Claims, No Drawings

(56) References Cited

U.S. PATENT DOCUMENTS

| | | | |
|---|---|---|---|
| 8,765,792 | B2 | 7/2014 | Knight et al. |
| 8,846,935 | B2 | 9/2014 | Duquenne et al. |
| 9,505,745 | B2 * | 11/2016 | Blackledge, Jr. .... C07D 405/14 |
| 2009/0181983 | A1 | 7/2009 | Corte, Jr. |
| 2012/0264734 | A1 | 10/2012 | Kuntz et al. |
| 2013/0053383 | A1 | 2/2013 | Duquenne et al. |
| 2013/0245016 | A1 | 9/2013 | Knight et al. |
| 2013/0345200 | A1 | 12/2013 | Brackley et al. |
| 2014/0142083 | A1 | 5/2014 | Kuntz et al. |
| 2015/0126522 | A1 | 5/2015 | Burgess et al. |

FOREIGN PATENT DOCUMENTS

| | | |
|---|---|---|
| WO | WO 2012/005805 A1 | 1/2012 |
| WO | WO 2012/118812 A2 | 9/2012 |
| WO | WO 2013/049770 A2 | 4/2013 |
| WO | WO 2013/120104 A2 | 8/2013 |
| WO | WO 2013/155317 A1 | 10/2013 |

OTHER PUBLICATIONS

Database Reg [Online]. Chem. Abst. Serv., Colombus, OH. Database Accession No. 1375256-70-4, XP002726953, Jun. 5, 2012. CAS Reg. Nos. 1375256-70-4, 1375251-00-5, 1375241-78-3.

Database Registry [Online]. Chemical Abstracts Service, Colombus, OH. Database Accession No. 1295835-68-5, XP002726954, May 17, 2011.

Database Registry [Online]. Chemical Abstracts Service, Colombus, OH. Database Accession No. 1281164-83-7, XP002726955, Apr. 17, 2011.

Database Registry [Online]. Chemical Abstracts Service, Colombus, OH. Database Accession No. 1061629-12-6, XP002726956, Oct. 15, 2008.

Database Registry [Online]. Chemical Abstracts Service, Colombus, OH. Database Accession No. 1388488-52-5, XP002726957, Aug. 9, 2012.

Renault, et al. Chemical Biology & Drug Design, 81(4): 442-454 (2013).

* cited by examiner

ENHANCER OF ZESTE HOMOLOG 2 INHIBITORS

FIELD OF THE INVENTION

This invention relates to compounds which inhibit Enhancer of Zeste Homolog 2 (EZH2) and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptide repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism. In addition, EZH2 overexpression in immortalized or primary epithelial cells promotes anchorage independent growth and invasion and requires EZH2 catalytic activity (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer.

SUMMARY OF THE INVENTION

The present invention relates to compounds according to Formula (I):

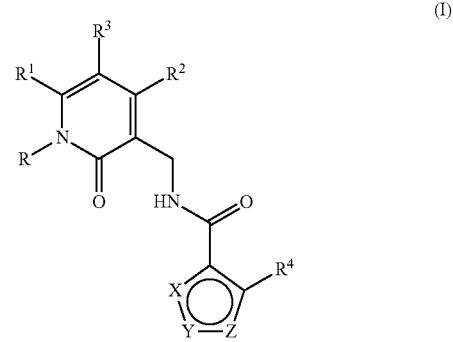

wherein:
X is O, N, S, $CR^6$, or $NR^7$;
Y is O, N, S, $CR^6$, or $NR^7$;
Z is $CR^5$ or $NR^8$; wherein when X is O, S, or $NR^7$, Y is N or $CR^6$ and Z is $CR^5$;
when Y is O, S, or $NR^7$, X is N or $CR^6$ and Z is $CR^5$; and
when Z is $NR^8$, Y is N or $CR^6$ and X is N or $CR^6$;
R is hydrogen or $(C_1-C_4)$alkyl;
$R^1$, $R^2$, and $R^3$ are each independently selected from the group consisting of hydrogen, $(C_1-C_4)$alkoxy, $(C_1-C_8)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $R^aO(O)CNH(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, halogen, cyano, —C(O)$R^a$, —CO$_2R^a$, —C(O)NR$^a$R$^b$, —C(O)NR$^a$NR$^a$R$^b$, —SR$^a$, —S(O)R$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —NR$^b$NR$^a$R$^b$, —NR$^b$NR$^c$C(O)R$^b$, —NR$^b$NR$^c$C(O)NR$^a$R$^b$, —NR$^b$NR$^c$C(O)OR$^a$, —OR$^a$, —OC(O)R$^a$, and —OC(O)NR$^a$R$^b$, wherein each $(C_3-C_8)$cycloalkyl, $(C_6-C_{10})$bicycloalkyl, heterocycloalkyl, aryl, or heteroaryl is optionally substituted 1, 2, or 3 times, independently, by hydroxyl, halogen, nitro, $(C_1-C_4)$alkyl, cyano, $(C_1-C_4)$alkoxy, —NR$^a$R$^b$ or —CO$_2$R$^a$;

$R^4$ is selected from the group consisting of hydrogen, $(C_1-C_3)$alkoxy, $(C_1-C_3)$alkyl, hydroxyl, halogen, cyano, $(C_3-C_6)$cycloalkyl, heterocycloalkyl, —$NR^aR^b$, halo$(C_1-C_3)$alkyl, and hydroxy$(C_1-C_3)$alkyl;

$R^5$ is selected from the group consisting of $(C_4-C_8)$alkyl, $(C_2-C_8)$alkenyl, $(C_3-C_8)$alkoxy, $(C_4-C_8)$cycloalkyl, $(C_3-C_8)$cycloalkyl$(C_1-C_2)$alkyl-, $(C_3-C_8)$cycloalkyloxy-, heterocycloalkyl, heterocycloalkyl$(C_1-C_2)$alkyl-, heterocycloalkyloxy-, aryl, heteroaryl, and —$NR^aR^b$, wherein said $(C_4-C_8)$alkyl, $(C_2-C_8)$alkenyl, $(C_3-C_8)$alkoxy, $(C_4-C_8)$cycloalkyl, $(C_3-C_8)$cycloalkyl$(C_1-C_2)$alkyl-, $(C_3-C_8)$cycloalkyloxy-, heterocycloalkyl, heterocycloalkyl$(C_1-C_2)$alkyl-, heterocycloalkyloxy-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, heterocycloalkyl, aryl, or heteroaryl, wherein said $(C_3-C_8)$cycloalkyl, heterocycloalkyl, aryl, or heteroaryl is optionally substituted 1 or 2 times, independently, by halogen, $(C_1-C_4)$alkyl, halo$(C_1-C_4)$alkyl, —$CO(C_1-C_4)$alkyl, —$CO_2(C_1-C_4)$alkyl, —$NR^aR^b$, —$NHCO_2R^a$, hydroxyl, oxo, $(C_1-C_4)$alkoxy, or $(C_1-C_4)$alkoxy$(C_1-C_4)$alkyl-; or any 2 optional substituents on said $(C_2-C_8)$alkenyl taken together with the carbon atom(s) to which they are attached represent a 5-8 membered ring, optionally containing a heteroatom selected from oxygen, nitrogen, and sulfur, wherein said ring is optionally substituted 1 or 2 times, independently, by $(C_1-C_4)$alkyl, halo$(C_1-C_4)$alkyl, —$CO(C_1-C_4)$alkyl, —$CO_2(C_1-C_4)$alkyl, —$NR^aR^b$, —$NHCO_2R^a$, hydroxyl, oxo, $(C_1-C_4)$alkoxy, or $(C_1-C_4)$alkoxy$(C_1-C_4)$alkyl-;

$R^6$ is selected from the group consisting of hydrogen, halogen, $(C_1-C_8)$alkyl, $(C_1-C_4)$alkoxy, —$B(OH)_2$, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, cyano, —$C(O)R^a$, —$CO_2R^a$, —$C(O)NR^aR^b$, —$C(O)NR^b$-$NR^aR^b$, —$SR^a$, —$S(O)R^a$, —$SO_2R^a$, —$SO_2NR^aR^b$, nitro, —$NR^aR^b$, $R^aR^bN(C_1-C_4)$alkyl-, —$NR^bC(O)R^b$, —$NR^bC(O)NR^aR^b$, —$NR^bC(O)OR^a$, —$NR^aSO_2R^b$, —$NR^aSO_2NR^aR^b$, —$NR^bNR^aR^b$, —$NR^bNR^bC(O)R^b$, —$NR^bNR^bC(O)NR^aR^b$, —$NR^bNR^bC(O)OR^a$, —$OR^a$, —$OC(O)R^a$, and —$OC(O)NR^aR^b$, wherein each cycloalkyl, bicycloalkyl, heterocycloalkyl, aryl, or heteroaryl group is optionally substituted 1, 2, or 3 times, independently, by $R^c$—$(C_1-C_6)$alkyl-O—, $R^c$—$(C_1-C_6)$alkyl-S—, $R^c$—$(C_1-C_6)$alkyl-, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^bC(O)R^b$, —$NR^bC(O)NR^aR^b$, —$NR^bC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^7$ is selected from the group consisting of hydrogen, $(C_1-C_8)$alkyl, $(C_3-C_8)$cycloalkyl, $(C_3-C_8)$cycloalkyl$(C_1-C_4)$alkyl-, $(C_6-C_{10})$bicycloalkyl, heterocycloalkyl, heterocycloalkyl$(C_1-C_4)$alkyl-, aryl, aryl$(C_1-C_4)$alkyl, heteroaryl, heteroaryl$(C_1-C_4)$alkyl, —$C(O)R^a$, —$CO_2R^a$, —$C(O)NR^aR^b$, —$C(O)NR^bNR^aR^b$, —$SO_2R^a$, —$SO_2NR^aR^b$, and $R^aR^bN(C_1-C_4)$alkyl-, wherein each cycloalkyl, bicycloalkyl, heterocycloalkyl, aryl, or heteroaryl group is optionally substituted 1, 2, or 3 times, independently, by $R^c$—$(C_1-C_6)$alkyl-O—, $R^c$—$(C_1-C_6)$alkyl-S—, $R^c$—$(C_1-C_6)$alkyl-, $(C_1-C_4)$alkyl-heterocycloalkyl-, halogen, $(C_1-C_6)$alkyl, $(C_3-C_8)$cycloalkyl, halo$(C_1-C_6)$alkyl, cyano, —$C(O)R^a$, —$CO_2R^a$, —$C(O)NR^aR^b$, —$SR^a$, —$S(O)R^a$, —$SO_2R^a$, —$SO_2NR^aR^b$, nitro, —$NR^aR^b$, —$NR^bC(O)R^b$, —$NR^bC(O)NR^aR^b$, —$NR^bC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, or heteroaryl$(C_1-C_4)$alkyl;

$R^8$ is selected from the group consisting of $(C_4-C_8)$alkyl, $(C_4-C_8)$cycloalkyl, heterocycloalkyl, heterocycloalkyl$(C_1-C_2)$alkyl-, aryl, and heteroaryl, wherein said $(C_4-C_8)$alkyl, $(C_4-C_8)$cycloalkyl, heterocycloalkyl, heterocycloalkyl$(C_1-C_2)$alkyl-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl;

each $R^c$ is independently —$S(O)R^a$, —$SO_2R^a$, —$NR^aR^b$, —$NR^bC(O)OR^a$, —$NR^aSO_2R^b$, or —$CO_2R^a$; and $R^a$ and $R^b$ are each independently hydrogen, $(C_1-C_4)$alkyl, $(C_1-C_4)$alkoxy$(C_1-C_4)$alkyl-, $(C_3-C_{10})$cycloalkyl, heterocycloalkyl, aryl, aryl$(C_1-C_4)$alkyl-, heteroaryl$(C_1-C_4)$alkyl-, or heteroaryl, wherein any said cycloalkyl, heterocycloalkyl, aryl, or heteroaryl group is optionally substituted 1, 2, or 3 times, independently, by halogen, hydroxyl, $(C_1-C_4)$alkoxy, amino, —$NH(C_1-C_4)$alkyl, —$N((C_1-C_4)$alkyl$)_2$, $(C_1-C_4)$alkyl, halo$(C_1-C_4)$alkyl, —$CO_2H$, —$CO_2(C_1-C_4)$alkyl, —$CONH_2$, —$CONH(C_1-C_4)$alkyl, —$CON((C_1-C_4)$alkyl$)_2$, —$SO_2(C_1-C_4)$alkyl, —$SO_2NH_2$, —$SO_2NH(C_1-C_4)$alkyl, or —$SO_2N((C_1-C_4)$alkyl$)_2$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by $(C_1-C_4)$alkyl, halo$(C_1-C_4)$alkyl, amino, —$NH(C_1-C_4)$alkyl, —$N((C_1-C_4)$alkyl$)_2$, hydroxyl, oxo, $(C_1-C_4)$alkoxy, or $(C_1-C_4)$alkoxy$(C_1-C_4)$alkyl-, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or pharmaceutically acceptable salts thereof.

Another aspect of this invention relates to a method of inducing apoptosis in cancer cells of solid tumors; treating solid tumor cancers.

Another aspect of the invention relates to pharmaceutical preparations comprising compounds of Formula (I) and pharmaceutically acceptable excipients.

In another aspect, there is provided the use of a compound of Formula (I) and/or a pharmaceutically acceptable salt or solvate thereof, in the preparation of a medicament for use in the treatment of a disorder mediated by EZH2, such as by inducing apoptosis in cancer cells.

In another aspect, this invention provides for the use of a compound of Formula (I) or a pharmaceutically acceptable salt thereof for the treatment of diseases mediated by EZH2. The invention further provides for the use of a compound of Formula (I) or a pharmaceutically acceptable salt thereof as an active therapeutic substance in the treatment of a disease mediated by EZH2.

In another aspect, the invention provides a compound of Formula (I) or a pharmaceutically acceptable salt thereof for use in therapy.

In another aspect there is provided methods of co-administering the presently invented compounds of Formula (I) with other active ingredients.

DETAILED DESCRIPTION OF THE INVENTION

This invention relates to compounds of the Formula (I) as defined above.

In one embodiment, this invention relates to compounds of Formula (I), wherein X is O, N, S, $CR^6$, or $NR^7$; Y is O, N, S, $CR^6$, or $NR^7$; wherein when X is O, S, or $NR^7$, Y is N or $CR^6$; and when Y is O, S, or $NR^7$, X is N or $CR^6$; and Z is $CR^5$. In one embodiment, this invention relates to compounds of Formula (I), wherein X is O, S, or $NR^7$; Y is N or $CR^6$; and Z is $CR^5$. In another embodiment, this invention relates to compounds of Formula (I), wherein X is O or S; Y is N or $CR^6$; and Z is $CR^5$. In another embodiment, this invention relates to compounds of Formula (I), wherein X is O or S; Y is $CR^6$; and Z is $CR^5$. In another embodiment, this invention relates to compounds of Formula (I), wherein X is O or S; Y is N; and Z is $CR^5$. In another embodiment, this invention relates to compounds of Formula (I), wherein X is S; Y is $CR^6$; and Z is $CR^5$. In another embodiment, this invention relates to compounds of Formula (I), wherein Y is O, S, or $NR^7$; X is N or $CR^6$; and Z is $CR^5$. In another embodiment, this invention relates to compounds of Formula (I), wherein Y is O or S; X is N or $CR^6$; and Z is $CR^5$. In another embodiment, this invention relates to compounds of Formula (I), wherein Y is O or S; X is $CR^6$; and Z is $CR^5$. In another embodiment, this invention relates to compounds of Formula (I), wherein Y is O or S; X is N; and Z is $CR^5$. In another embodiment, this invention relates to compounds of Formula (I), wherein Y is S; X is $CR^6$; and Z is $CR^5$. In another embodiment, this invention relates to compounds of Formula (I), wherein Z is $NR^8$; Y is N or $CR^6$; and X is N or $CR^6$.

In another embodiment, this invention relates to compounds of Formula (I), wherein R is hydrogen or methyl. In a specific embodiment, this invention relates to compounds of Formula (I), wherein R is methyl. In another specific embodiment, this invention relates to compounds of Formula (I), wherein R is hydrogen.

In another embodiment, this invention relates to compounds of Formula (I), wherein $R^1$, $R^2$, and $R^3$ are each independently selected from the group consisting of hydrogen, $(C_1-C_4)$alkoxy, $(C_1-C_4)$alkyl, $(C_1-C_4)$alkoxy$(C_1-C_4)$alkyl-, halo$(C_1-C_4)$alkyl, $(C_3-C_8)$cycloalkyl, hydroxy$(C_1-C_4)$alkyl, $(C_3-C_8)$cycloalkyl$(C_1-C_4)$alkyl-, $(C_1-C_4)$alkylO(O)CNH$(C_1-C_4)$alkyl-, heterocycloalkyl, heterocycloalkyl$(C_1-C_4)$alkyl-, aryl, aryl$(C_1-C_4)$alkyl-, heteroaryl, and heteroaryl$(C_1-C_4)$alkyl-, wherein each $(C_3-C_8)$cycloalkyl, heterocycloalkyl, aryl, or heteroaryl is optionally substituted 1 or 2 times, independently, by hydroxyl, halogen, nitro, $(C_1-C_4)$alkyl, cyano, $(C_1-C_4)$alkoxy, —NH$(C_1-C_4)$alkyl, —N$((C_1-C_4)$alkyl$)_2$, or —$CO_2(C_1-C_4)$alkyl. In another embodiment, this invention relates to compounds of Formula (I), wherein $R^1$, $R^2$, and $R^3$ are each independently selected from the group consisting of hydrogen, $(C_1-C_4)$alkoxy, $(C_1-C_4)$alkyl, $(C_1-C_4)$alkoxy$(C_1-C_4)$alkyl-, halo$(C_1-C_4)$alkyl, and hydroxy$(C_1-C_4)$alkyl.

In another embodiment, this invention relates to compounds of Formula (I), wherein $R^1$ and $R^2$ are each independently $(C_1-C_4)$alkoxy, $(C_1-C_4)$alkyl, or halo$(C_1-C_4)$alkyl.

In another embodiment, this invention relates to compounds of Formula (I), wherein $R^1$ and $R^2$ are each independently methyl, n-propyl, trifluoromethyl, or methoxy.

In another embodiment, this invention relates to compounds of Formula (I), wherein $R^1$ and $R^2$ are each independently $(C_1-C_4)$alkyl.

In a specific embodiment, this invention relates to compounds of Formula (I), wherein $R^1$ is methyl.

In another specific embodiment, this invention relates to compounds of Formula (I), wherein $R^2$ is methyl.

In another specific embodiment, this invention relates to compounds of Formula (I), wherein $R^1$ and $R^2$ are each methyl.

In another specific embodiment, this invention relates to compounds of Formula (I), wherein $R^3$ is hydrogen.

In another embodiment, this invention relates to compounds of Formula (I), wherein $R^4$ is selected from the group consisting of hydrogen, $(C_1-C_3)$alkyl, hydroxyl, halogen, halo$(C_1-C_3)$alkyl, and hydroxy$(C_1-C_3)$alkyl. In another embodiment, this invention relates to compounds of Formula (I), wherein $R^4$ is $(C_1-C_3)$alkyl or halogen. In a specific embodiment, this invention relates to compounds of Formula (I), wherein $R^4$ is methyl or chlorine. In another specific embodiment, this invention relates to compounds of Formula (I), wherein $R^4$ is methyl.

In another embodiment, this invention relates to compounds of Formula (I), wherein $R^5$ is selected from the group consisting of $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, heteroaryl, and —$NR^aR^b$, wherein said $(C_4-C_8)$alkyl, $(C_3-C_8)$alkoxy, $(C_4-C_8)$cycloalkyl, $(C_3-C_8)$cycloalkyloxy-, heterocycloalkyl, heterocycloalkyloxy-, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl.

In another embodiment, this invention relates to compounds of Formula (I), wherein $R^5$ is selected from the group consisting of $(C_3-C_6)$alkoxy, $(C_3-C_6)$cycloalkyloxy-, heterocycloalkyloxy-, heterocycloalkyl, —NH$((C_3-C_6)$cycloalkyl), —N$((C_1-C_3)$alkyl$)((C_3-C_6)$cycloalkyl), —NH(heterocycloalkyl), and —N$((C_1-C_3)$alkyl)(heterocycloalkyl), wherein any said $(C_3-C_6)$alkoxy, $(C_3-C_6)$cycloalkyloxy-, heterocycloalkyloxy-, heterocycloalkyl, or $(C_3-C_6)$cycloalkyl is optionally substituted 1 or 2 times, independently, by halogen, hydroxyl, $(C_1-C_3)$alkoxy, amino, —NH$(C_1-C_3)$alkyl, —N$((C_1-C_3)$alkyl$)_2$, $(C_1-C_3)$alkyl, $(C_1-C_3)$alkoxy$(C_1-C_3)$alkyl-, amino$(C_1-C_3)$alkyl-, $((C_1-C_3)$alkyl)NH$(C_1-C_3)$alkyl-, $((C_1-C_3)$alkyl$)_2$N$(C_1-C_3)$alkyl-, $(C_3-C_8)$cycloalkyl, cyano, —$CO_2R^a$, —$C(O)NR^aR^b$, —$SO_2NR^aR^b$, phenyl, or heteroaryl.

In another embodiment, this invention relates to compounds of Formula (I), wherein $R^5$ is selected from the group consisting of $(C_3-C_6)$alkoxy, $(C_3-C_8)$cycloalkyloxy-, and heterocycloalkyloxy-, each of which is optionally substituted by hydroxyl, $(C_1-C_3)$alkoxy, amino, —NH$(C_1-C_3)$alkyl, —N$((C_1-C_3)$alkyl$)_2$, $(C_1-C_3)$alkyl, —$CO_2R^a$, —$C(O)NR^aR^b$, —$SO_2NR^aR^b$, phenyl, or heteroaryl.

In another embodiment, this invention relates to compounds of Formula (I), wherein $R^5$ is $(C_3-C_6)$cycloalkyloxy- which is optionally substituted 1, 2, or 3 times, independently, by halogen, —$OR^a$, —$NR^aR^b$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl. In another embodiment, this invention relates to compounds of Formula (I), wherein $R^5$ is $(C_3-C_6)$cycloalkyloxy- which is optionally substituted 1 or 2 times, independently, by halogen, hydroxyl, $(C_1-C_3)$alkoxy, amino, —NH$(C_1-C_3)$alkyl, —N$((C_1-C_3)$alkyl$)_2$, $(C_1-C_3)$alkyl, $(C_1-C_3)$alkoxy$(C_1-C_3)$alkyl-, amino$(C_1-C_3)$alkyl-, $((C_1-C_3)$alkyl)

NH($C_1$-$C_3$)alkyl-, (($C_1$-$C_3$)alkyl)$_2$N($C_1$-$C_3$)alkyl-, ($C_3$-$C_8$)cycloalkyl, cyano, —CO$_2$R$^a$, —C(O)NR$^a$R$^b$, —SO$_2$NR$^a$R$^b$, phenyl, or heteroaryl.

In another embodiment, this invention relates to compounds of Formula (I), wherein R$^5$ is heterocycloalkyloxy- which is optionally substituted 1, 2, or 3 times, independently, by halogen, —OR$^a$, —NR$^a$R$^b$, nitro, ($C_1$-$C_3$)alkyl, R$^a$R$^b$N($C_1$-$C_3$)alkyl-, R$^a$O($C_1$-$C_3$)alkyl-, ($C_3$-$C_8$)cycloalkyl, cyano, —CO$_2$R$^a$, —C(O)NR$^a$R$^b$, —SO$_2$NR$^a$R$^b$, aryl, or heteroaryl. In another embodiment, this invention relates to compounds of Formula (I), wherein R$^5$ is heterocycloalkyloxy- which is optionally substituted 1 or 2 times, independently, by halogen, hydroxyl, ($C_1$-$C_3$)alkoxy, amino, —NH($C_1$-$C_3$)alkyl, —N(($C_1$-$C_3$)alkyl)$_2$, ($C_1$-$C_3$)alkyl, ($C_1$-$C_3$)alkoxy($C_1$-$C_3$)alkyl-, amino($C_1$-$C_3$)alkyl-, (($C_1$-$C_3$)alkyl)NH($C_1$-$C_3$)alkyl-, (($C_1$-$C_3$)alkyl)$_2$N($C_1$-$C_3$)alkyl-, ($C_3$-$C_8$)cycloalkyl, cyano, —CO$_2$R$^a$, —C(O)NR$^a$R$^b$, —SO$_2$NR$^a$R$^b$, phenyl, or heteroaryl.

In another embodiment, this invention relates to compounds of Formula (I), wherein R$^5$ is selected from the group consisting of cyclopentyloxy, cyclohexyloxy, pyrrolidinyloxy, piperidinyloxy, and tetrahydropyranyloxy, each of which is optionally substituted by hydroxyl, ($C_1$-$C_3$)alkoxy, amino, —NH($C_1$-$C_3$)alkyl, —N(($C_1$-$C_3$)alkyl)$_2$, ($C_1$-$C_3$)alkyl, —CO$_2$R$^a$, —C(O)NR$^a$R$^b$, —SO$_2$NR$^a$R$^b$, phenyl, furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, or pyrimidinyl, wherein R$^a$ is ($C_1$-$C_4$)alkyl or phenyl($C_1$-$C_2$)alkyl and R$^b$ is hydrogen or ($C_1$-$C_4$)alkyl.

In another embodiment, this invention relates to compounds of Formula (I), wherein R$^5$ is —NR$^a$R$^b$. In another embodiment, this invention relates to compounds of Formula (I), wherein R$^5$ is —NR$^a$R$^b$; R$^a$ is azetidinyl, oxetanyl, pyrrolidinyl, piperidinyl, piperazinyl, morpholinyl, thiomorpholinyl, or tetrahydropyranyl, each of which is optionally substituted 1 or 2 times, independently, by ($C_1$-$C_4$)alkyl; and R$^b$ is hydrogen or ($C_1$-$C_4$)alkyl. In another embodiment, this invention relates to compounds of Formula (I), wherein R$^5$ is —NR$^a$R$^b$; R$^a$ is azetidinyl, oxetanyl, pyrrolidinyl, piperidinyl, piperazinyl, morpholinyl, thiomorpholinyl, or tetrahydropyranyl; and R$^b$ is methyl or ethyl.

In another embodiment, this invention relates to compounds of Formula (I), wherein R$^5$ is —NR$^a$R$^b$; R$^a$ is cyclopentyl or cyclohexyl, each of which is optionally substituted by amino, —NH($C_1$-$C_4$)alkyl, or —N(($C_1$-$C_4$)alkyl)$_2$; and R$^b$ is hydrogen or ($C_1$-$C_4$)alkyl. In another embodiment, this invention relates to compounds of Formula (I), wherein R$^5$ is —NR$^a$R$^b$; R$^a$ is cyclopentyl or cyclohexyl, each of which is optionally substituted by —N(($C_1$-$C_2$)alkyl)$_2$; and R$^b$ is methyl or ethyl. In another embodiment, this invention relates to compounds of Formula (I), wherein R$^5$ is —NR$^a$R$^b$; R$^a$ is cyclohexyl which is optionally substituted by amino, —NH($C_1$-$C_4$)alkyl, or —N(($C_1$-$C_4$)alkyl)$_2$; and R$^b$ is hydrogen or ($C_1$-$C_4$)alkyl. In another embodiment, this invention relates to compounds of Formula (I), wherein R$^5$ is —NR$^a$R$^b$; R$^a$ is cyclohexyl which is optionally substituted by —N(($C_1$-$C_2$)alkyl)$_2$; and R$^b$ is methyl or ethyl.

In another embodiment, this invention relates to compounds of Formula (I), wherein R$^5$ is ($C_2$-$C_8$)alkenyl which is optionally substituted 1, 2, or 3 times, independently, by halogen, —OR$^a$, —NR$^a$R$^b$, —NHCO$_2$R$^a$, nitro, ($C_1$-$C_3$)alkyl, R$^a$R$^b$N($C_1$-$C_3$)alkyl-, R$^a$O($C_1$-$C_3$)alkyl-, ($C_3$-$C_8$)cycloalkyl, cyano, —CO$_2$R$^a$, —C(O)NR$^a$R$^b$, —SO$_2$NR$^a$R$^b$, heterocycloalkyl, aryl, or heteroaryl, wherein said ($C_3$-$C_8$)cycloalkyl, heterocycloalkyl, aryl, or heteroaryl is optionally substituted 1 or 2 times, independently, by halogen, ($C_1$-$C_4$)alkyl, halo($C_1$-$C_4$)alkyl, —CO($C_1$-$C_4$)alkyl, —CO$_2$($C_1$-$C_4$)alkyl, —NR$^a$R$^b$, —NHCO$_2$R$^a$, hydroxyl, oxo, ($C_1$-$C_4$)alkoxy, or ($C_1$-$C_4$)alkoxy($C_1$-$C_4$)alkyl-; or any 2 optional substituents on said ($C_2$-$C_8$)alkenyl taken together with the carbon atom(s) to which they are attached represent a 5-8 membered ring, optionally containing a heteroatom selected from oxygen, nitrogen, and sulfur, wherein said ring is optionally substituted 1 or 2 times, independently, by ($C_1$-$C_4$)alkyl, halo($C_1$-$C_4$)alkyl, —CO($C_1$-$C_4$)alkyl, —CO$_2$($C_1$-$C_4$)alkyl, —NR$^a$R$^b$, —NHCO$_2$R$^a$, hydroxyl, oxo, ($C_1$-$C_4$)alkoxy, or ($C_1$-$C_4$)alkoxy($C_1$-$C_4$)alkyl-.

In another embodiment, this invention relates to compounds of Formula (I), wherein R$^5$ is ($C_2$-$C_4$)alkenyl which is optionally substituted 1 or 2 times, independently, by ($C_3$-$C_6$)cycloalkyl, 5- or 6-membered heterocycloalkyl, phenyl, or 5- or 6-membered heteroaryl, each of which is optionally substituted 1 or 2 times, independently, by halogen, ($C_1$-$C_4$)alkyl, halo($C_1$-$C_4$)alkyl, —CO($C_1$-$C_4$)alkyl, —CO$_2$($C_1$-$C_4$)alkyl, —NR$^a$R$^b$, —NHCO$_2$R$^a$, hydroxyl, oxo, ($C_1$-$C_4$)alkoxy, or ($C_1$-$C_4$)alkoxy($C_1$-$C_4$)alkyl-; or any 2 optional substituents on said ($C_2$-$C_4$)alkenyl taken together with the carbon atom(s) to which they are attached represent a 5-6 membered ring, optionally containing a heteroatom selected from oxygen, nitrogen, and sulfur, wherein said ring is optionally substituted by ($C_1$-$C_4$)alkyl, halo($C_1$-$C_4$)alkyl, —CO($C_1$-$C_4$)alkyl, —CO$_2$($C_1$-$C_4$)alkyl, —NR$^a$R$^b$, —NHCO$_2$R$^a$, hydroxyl, oxo, ($C_1$-$C_4$)alkoxy, or ($C_1$-$C_4$)alkoxy($C_1$-$C_4$)alkyl-.

In another embodiment, this invention relates to compounds of Formula (I), wherein R$^5$ is ($C_2$-$C_4$)alkenyl which is optionally substituted by ($C_3$-$C_6$)cycloalkyl, 5- or 6-membered heterocycloalkyl, phenyl, or 5- or 6-membered heteroaryl, each of which is optionally substituted by halogen, ($C_1$-$C_4$)alkyl, halo($C_1$-$C_4$)alkyl, amino, —NH($C_1$-$C_4$)alkyl, —N(($C_1$-$C_4$)alkyl)$_2$, hydroxyl, oxo, ($C_1$-$C_4$)alkoxy, or ($C_1$-$C_4$)alkoxy($C_1$-$C_4$)alkyl-. In another embodiment, this invention relates to compounds of Formula (I), wherein R$^5$ is ($C_2$-$C_4$)alkenyl which is optionally substituted by cyclopentyl, cyclohexyl, pyrrolidinyl, tetrahydrofuranyl, dihydrofuranyl, piperidinyl, tetrahydropyranyl, or dihydropyranyl, each of which is optionally substituted by ($C_1$-$C_4$)alkyl, halo($C_1$-$C_4$)alkyl, amino, —NH($C_1$-$C_4$)alkyl, —N(($C_1$-$C_4$)alkyl)$_2$, hydroxyl, oxo, ($C_1$-$C_4$)alkoxy, or ($C_1$-$C_4$)alkoxy($C_1$-$C_4$)alkyl-. In another embodiment, this invention relates to compounds of Formula (I), wherein R$^5$ is ($C_2$-$C_4$)alkenyl which is optionally substituted by cyclohexyl, piperidinyl, or tetrahydropyranyl, each of which is optionally substituted by ($C_1$-$C_4$)alkyl, halo($C_1$-$C_4$)alkyl, amino, —NH($C_1$-$C_4$)alkyl, or —N(($C_1$-$C_4$)alkyl)$_2$. In another embodiment, this invention relates to compounds of Formula (I), wherein R$^5$ is ($C_2$-$C_4$)alkenyl which is optionally substituted by cyclopentyl or cyclohexyl, each of which is optionally substituted by amino, —NH($C_1$-$C_4$)alkyl, or —N(($C_1$-$C_4$)alkyl)$_2$. In another embodiment, this invention relates to compounds of Formula (I), wherein R$^5$ is ($C_2$-$C_4$)alkenyl which is optionally substituted by piperidinyl or tetrahydropyranyl.

In another embodiment, this invention relates to compounds of Formula (I), wherein R$^5$ is ($C_2$-$C_4$)alkenyl containing 2 substituents which taken together with the carbon atom(s) to which they are attached represent a 5-6 membered ring, optionally containing a heteroatom selected from oxygen, nitrogen, and sulfur, wherein said ring is optionally substituted by ($C_1$-$C_4$)alkyl, halo($C_1$-$C_4$)alkyl, —CO($C_1$-$C_4$)alkyl, —CO$_2$($C_1$-$C_4$)alkyl, —NR$^a$R$^b$, —NHCO$_2$R$^a$, hydroxyl, oxo, ($C_1$-$C_4$)alkoxy, or ($C_1$-$C_4$)alkoxy($C_1$-$C_4$)alkyl-. In another embodiment, this invention relates to compounds of Formula (I), wherein $R^5$ is $(C_2-C_4)$alkenyl containing 2 substituents which taken together with the carbon atom(s) to which they are attached represent a 5-6 membered ring, optionally containing a heteroatom selected from oxygen, nitrogen, and sulfur, wherein said ring is optionally substituted by $(C_1-C_4)$alkyl, halo$(C_1-C_4)$alkyl, amino, —NH$(C_1-C_4)$alkyl, or —N$((C_1-C_4)$alkyl$)_2$. In another embodiment, this invention relates to compounds of Formula (I), wherein $R^5$ is $(C_2-C_4)$alkenyl containing 2 substituents which taken together with the carbon atom(s) to which they are attached represent a piperidinyl ring which is optionally substituted by $(C_1-C_4)$alkyl.

In another embodiment, this invention relates to compounds of Formula (I), wherein $R^5$ is $(C_3-C_8)$cycloalkyl$(C_1-C_2)$alkyl- or heterocycloalkyl$(C_1-C_2)$alkyl-, each of which is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, heterocycloalkyl, aryl, or heteroaryl, wherein said $(C_3-C_8)$cycloalkyl, heterocycloalkyl, aryl, or heteroaryl is optionally substituted 1 or 2 times, independently, by halogen, $(C_1-C_4)$alkyl, halo$(C_1-C_4)$alkyl, —$CO(C_1-C_4)$alkyl, —$CO_2(C_1-C_4)$alkyl, —$NR^aR^b$, —$NHCO_2R^a$, hydroxyl, oxo, $(C_1-C_4)$alkoxy, or $(C_1-C_4)$alkoxy$(C_1-C_4)$alkyl-. In another embodiment, this invention relates to compounds of Formula (I), wherein $R^5$ is $(C_3-C_8)$cycloalkyl$(C_1-C_2)$alkyl- or heterocycloalkyl$(C_1-C_2)$alkyl-, each of which is optionally substituted 1 or 2 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, heterocycloalkyl, aryl, or heteroaryl. In another embodiment, this invention relates to compounds of Formula (I), wherein $R^5$ is $(C_3-C_8)$cycloalkyl$(C_1-C_2)$alkyl- or heterocycloalkyl$(C_1-C_2)$alkyl-, each of which is optionally substituted 1 or 2 times, independently, by —$NR^aR^b$, —$NHCO_2R^a$, $(C_1-C_3)$alkyl, or $R^aR^bN(C_1-C_3)$alkyl-. In another embodiment, this invention relates to compounds of Formula (I), wherein $R^5$ is $(C_3-C_6)$cycloalkyl$(C_1-C_2)$alkyl- or heterocycloalkyl$(C_1-C_2)$alkyl-, each of which is optionally substituted 1 or 2 times, independently, by $(C_1-C_3)$alkyl, amino, —NH$(C_1-C_4)$alkyl, or —N$((C_1-C_4)$alkyl$)_2$, wherein said heterocycloalkyl moiety is monocyclic. In another embodiment, this invention relates to compounds of Formula (I), wherein $R^5$ is $(C_5-C_6)$cycloalkyl$(C_1-C_2)$alkyl- or heterocycloalkyl$(C_1-C_2)$alkyl-, each of which is optionally substituted 1 or 2 times, independently, by $(C_1-C_3)$alkyl, amino, —NH$(C_1-C_4)$alkyl, or —N$((C_1-C_4)$alkyl$)_2$, wherein said heterocycloalkyl moiety is selected from the group consisting of piperidinyl, piperazinyl, morpholinyl, and tetrahydropyranyl. In another embodiment, this invention relates to compounds of Formula (I), wherein $R^5$ is cyclohexylmethyl which is optionally substituted 1 or 2 times, independently, by $(C_1-C_3)$alkyl, amino, —NH$(C_1-C_4)$alkyl, or —N$((C_1-C_4)$alkyl$)_2$. In another embodiment, this invention relates to compounds of Formula (I), wherein $R^5$ is piperidin-1-ylmethyl which is optionally substituted 1 or 2 times, independently, by $(C_1-C_3)$alkyl, amino, —NH$(C_1-C_4)$alkyl, or —N$((C_1-C_4)$alkyl$)_2$.

In another embodiment, this invention relates to compounds of Formula (I), wherein $R^6$ is selected from the group consisting of hydrogen, —$SO_2(C_1-C_4)$alkyl, halogen, $(C_1-C_6)$alkyl, $(C_1-C_4)$alkoxy, phenyl, heteroaryl, and cyano, wherein said phenyl or heteroaryl group is optionally substituted 1 or 2 times, independently, by $(C_1-C_4)$alkoxy, —$NR^aR^b$, $R^aR^bN(C_1-C_4)$alkyl-, $(C_1-C_4)$alkylheterocycloalkyl-, halogen, $(C_1-C_4)$alkyl, $(C_3-C_8)$cycloalkyl, or heterocycloalkyl.

In another embodiment, this invention relates to compounds of Formula (I), wherein $R^6$ is selected from the group consisting of hydrogen, cyano, halogen, $(C_1-C_4)$alkoxy, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, and triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, or triazinyl is optionally substituted by $(C_1-C_4)$alkoxy, —$NR^aR^b$, $R^aR^bN(C_1-C_4)$alkyl-, $(C_1-C_4)$alkylheterocycloalkyl-, halogen, $(C_1-C_4)$alkyl, $(C_3-C_8)$cycloalkyl, or heterocycloalkyl.

In another embodiment, this invention relates to compounds of Formula (I), wherein $R^6$ is phenyl which is optionally substituted by —$NR^aR^b$ or $R^aR^bN(C_1-C_4)$alkyl-.

In another embodiment, this invention relates to compounds of Formula (I), wherein $R^6$ is pyridinyl which is optionally substituted by —$NR^aR^b$ or $R^aR^bN(C_1-C_4)$alkyl-.

In another embodiment, this invention relates to compounds of Formula (I), wherein $R^6$ is hydrogen, halogen, $(C_1-C_4)$alkyl, or $(C_1-C_4)$alkoxy. In another embodiment, this invention relates to compounds of Formula (I), wherein $R^6$ is hydrogen or halogen. In a specific embodiment, this invention relates to compounds of Formula (I), wherein $R^6$ is hydrogen, fluorine, chlorine, or bromine. In a specific embodiment, this invention relates to compounds of Formula (I), wherein $R^6$ is hydrogen or chlorine. In a more specific embodiment, this invention relates to compounds of Formula (I), wherein $R^6$ is chlorine. In another specific embodiment, this invention relates to compounds of Formula (I), wherein $R^6$ is hydrogen.

In another embodiment, this invention relates to compounds of Formula (I), wherein $R^7$ is selected from the group consisting of hydrogen, $(C_1-C_6)$alkyl, $(C_3-C_6)$cycloalkyl, phenyl, and heteroaryl, wherein said phenyl or heteroaryl group is optionally substituted 1 or 2 times, independently, by $(C_1-C_4)$alkoxy, —$NR^aR^b$, $R^aR^bN(C_1-C_4)$alkyl-, $(C_1-C_4)$alkylheterocycloalkyl-, halogen, $(C_1-C_4)$alkyl, $(C_3-C_8)$cycloalkyl, or heterocycloalkyl.

In another embodiment, this invention relates to compounds of Formula (I), wherein $R^7$ is hydrogen or $(C_1-C_4)$alkyl.

In another embodiment, this invention relates to compounds of Formula (I), wherein $R^7$ is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, and triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, phenyl, pyridinyl, pyridazinyl, pyrazinyl, pyrimidinyl, or triazinyl is optionally substituted by $(C_1-C_4)$alkoxy, —$NR^aR^b$, $R^aR^bN(C_1-C_4)$alkyl-, $(C_1-C_4)$alkylheterocycloalkyl-, halogen, $(C_1-C_4)$alkyl, $(C_3-C_8)$cycloalkyl, or heterocycloalkyl.

In another embodiment, this invention relates to compounds of Formula (I), wherein $R^7$ is phenyl which is optionally substituted by —$NR^aR^b$ or $R^aR^bN(C_1-C_4)$alkyl-. In another embodiment, this invention relates to compounds of Formula (I), wherein $R^7$ is pyridinyl which is optionally substituted by —$NR^aR^b$ or $R^aR^bN(C_1-C_4)$alkyl-.

In another embodiment, this invention relates to compounds of Formula (I), wherein $R^8$ is selected from the group consisting of $(C_4-C_8)$alkyl, $(C_4-C_8)$cycloalkyl, heterocycloalkyl, aryl, and heteroaryl, wherein said $(C_4-C_8)$alkyl, $(C_4-C_8)$cycloalkyl, heterocycloalkyl, aryl, or heteroaryl is optionally substituted 1, 2, or 3 times, independently, by halogen, —$OR^a$, —$NR^aR^b$, —$NHCO_2R^a$, nitro, $(C_1-C_3)$alkyl, $R^aR^bN(C_1-C_3)$alkyl-, $R^aO(C_1-C_3)$alkyl-, $(C_3-C_8)$cycloalkyl, cyano, —$CO_2R^a$, —$C(O)NR^aR^b$, —$SO_2NR^aR^b$, aryl, or heteroaryl.

In another embodiment, this invention relates to compounds of Formula (I), wherein $R^8$ is selected from the group consisting of $(C_4-C_6)$alkyl, $(C_4-C_6)$cycloalkyl, heterocycloalkyl, and phenyl, wherein said $(C_4-C_6)$alkyl, $(C_4-C_6)$cycloalkyl, heterocycloalkyl, or phenyl is optionally substituted 1 or 2 times, independently, by —$OR^a$, —$NR^aR^b$, —$NHCO_2R^a$, $(C_1-C_3)$alkyl, $R^aR^bN(C_1-C_3)$alkyl-, $R^aO(C_1-C_3)$alkyl-, —$CO_2R^a$, —$C(O)NR^aR^b$, or —$SO_2NR^aR^b$.

In a particular embodiment, this invention relates to compounds of Formula (I), wherein:
R is hydrogen or methyl;
X is O, S, or $NR^7$;
Y is N or $CR^6$;
Z is $CR^5$;
$R^1$ and $R^2$ are each independently $(C_1-C_4)$alkyl;
$R^3$ is hydrogen;
$R^4$ is methyl or chlorine;
$R^5$ is selected from the group consisting of $(C_3-C_6)$alkoxy, $(C_3-C_8)$cycloalkyloxy-, and heterocycloalkyloxy-, each of which is optionally substituted by hydroxyl, $(C_1-C_3)$alkoxy, amino, —$NH(C_1-C_3)$alkyl, —$N((C_1-C_3)$alkyl$)_2$, $(C_1-C_3)$alkyl, —$CO_2R^a$, —$C(O)NR^aR^b$, —$SO_2NR^aR^b$, phenyl, or heteroaryl;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is O, S, or $NR^7$;
Y is N or $CR^6$;
Z is $CR^5$;
$R^1$ and $R^2$ are each independently $(C_1-C_4)$alkyl;
$R^3$ is hydrogen;
$R^4$ is methyl or chlorine;
$R^5$ is —$NR^aR^b$;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is O, S, or $NR^7$;
Y is N or $CR^6$;
Z is $CR^5$;
$R^1$ and $R^2$ are each independently $(C_1-C_4)$alkyl;
$R^3$ is hydrogen;
$R^4$ is methyl or chlorine;
$R^5$ is $(C_2-C_4)$alkenyl which is optionally substituted by cyclohexyl, piperidinyl, or tetrahydropyranyl, each of which is optionally substituted by $(C_1-C_4)$alkyl, halo$(C_1-C_4)$alkyl, amino, —$NH(C_1-C_4)$alkyl, or —$N((C_1-C_4)$alkyl$)_2$;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is O, S, or $NR^7$;
Y is N or $CR^6$;
Z is $CR^5$;
$R^1$ and $R^2$ are each independently $(C_1-C_4)$alkyl;
$R^3$ is hydrogen;
$R^4$ is methyl or chlorine;
$R^5$ is $(C_5-C_6)$cycloalkyl$(C_1-C_2)$alkyl- or heterocycloalkyl$(C_1-C_2)$alkyl-, each of which is optionally substituted 1 or 2 times, independently, by $(C_1-C_3)$alkyl, amino, —$NH(C_1-C_4)$alkyl, or —$N((C_1-C_4)$alkyl$)_2$, wherein said heterocycloalkyl moiety is selected from the group consisting of piperidinyl, piperazinyl, morpholinyl, and tetrahydropyranyl;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is N or $CR^6$;
Y is O, S, or NR;
Z is $CR^5$;
$R^1$ and $R^2$ are each independently $(C_1-C_4)$alkyl;
$R^3$ is hydrogen;
$R^4$ is methyl or chlorine;
$R^5$ is selected from the group consisting of $(C_3-C_6)$alkoxy, $(C_3-C_8)$cycloalkyloxy-, and heterocycloalkyloxy-, each of which is optionally substituted by hydroxyl, $(C_1-C_3)$alkoxy, amino, —$NH(C_1-C_3)$alkyl, —$N((C_1-C_3)$alkyl$)_2$, $(C_1-C_3)$alkyl, —$CO_2R^a$, —$C(O)NR^aR^b$, —$SO_2NR^aR^b$, phenyl, or heteroaryl;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is N or $CR^6$;
Y is O, S, or NR;
Z is $CR^5$;
$R^1$ and $R^2$ are each independently $(C_1-C_4)$alkyl;
$R^3$ is hydrogen;
$R^4$ is methyl or chlorine;
$R^5$ is —$NR^aR^b$;
$R^6$ is hydrogen, halogen, $(C_1-C_4)$alkyl, or $(C_1-C_4)$alkoxy; and
$R^7$ is hydrogen or $(C_1-C_4)$alkyl;
or pharmaceutically acceptable salts thereof.

In another particular embodiment, this invention relates to compounds of Formula (I), wherein:
R is hydrogen or methyl;
X is N or $CR^6$;
Y is O, S, or NR;
Z is $CR^5$;
$R^1$ and $R^2$ are each independently $(C_1-C_4)$alkyl;
$R^3$ is hydrogen;
$R^4$ is methyl or chlorine;
$R^5$ is $(C_2-C_4)$alkenyl which is optionally substituted by cyclohexyl, piperidinyl, or tetrahydropyranyl, each of which is optionally substituted by $(C_1-C_4)$alkyl, halo$(C_1-C_4)$alkyl, amino, —$NH(C_1-C_4)$alkyl, or —$N((C_1-C_4)$alkyl$)_2$;

$R^6$ is hydrogen, halogen, $(C_1-C_4)$alkyl, or $(C_1-C_4)$alkoxy; and $R^7$ is hydrogen or $(C_1-C_4)$alkyl;

or pharmaceutically acceptable salts thereof.

In another particular embodiment, this invention relates to compounds of Formula (I), wherein:

R is hydrogen or methyl;

X is N or $CR^6$;

Y is O, S, or $NR^7$;

Z is $CR^5$;

$R^1$ and $R^2$ are each independently $(C_1-C_4)$alkyl;

$R^3$ is hydrogen;

$R^4$ is methyl or chlorine;

$R^5$ is $(C_5-C_6)$cycloalkyl$(C_1-C_2)$alkyl- or heterocycloalkyl$(C_1-C_2)$alkyl-, each of which is optionally substituted 1 or 2 times, independently, by $(C_1-C_3)$alkyl, amino, —NH$(C_1-C_4)$alkyl, or —N$((C_1-C_4)$alkyl$)_2$, wherein said heterocycloalkyl moiety is selected from the group consisting of piperidinyl, piperazinyl, morpholinyl, and tetrahydropyranyl;

$R^6$ is hydrogen, halogen, $(C_1-C_4)$alkyl, or $(C_1-C_4)$alkoxy; and $R^7$ is hydrogen or $(C_1-C_4)$alkyl;

or pharmaceutically acceptable salts thereof.

In another embodiment, this invention also relates to compounds of Formula (II):

(II)

[chemical structure]

or pharmaceutically acceptable salts thereof, wherein X is O, S, or $NR^7$; Y is N or $CR^6$; and $R^1$, $R^2$, $R^3$, $R^4$, $R^5$, $R^6$, and $R^7$ are defined according to Formula (I). In another embodiment, this invention relates to compounds of Formula (II), wherein X is O or S and Y is N or $CR^6$. In another embodiment, this invention relates to compounds of Formula (II), wherein X is O or S and Y is $CR^6$. In another embodiment, this invention relates to compounds of Formula (II), wherein X is O or S and Y is N. In another embodiment, this invention relates to compounds of Formula (II), wherein X is S and Y is $CR^6$.

In another embodiment, this invention also relates to compounds of Formula (II)(a):

(II)(a)

[chemical structure]

or pharmaceutically acceptable salts thereof, wherein $R^1$, $R^2$, $R^3$, $R^4$, $R^5$, and $R^6$ are defined according to Formula (I).

In another embodiment, this invention also relates to compounds of Formula (III):

(III)

[chemical structure]

or pharmaceutically acceptable salts thereof, wherein Y is O, S, or $NR^7$; X is N or $CR^6$; and $R^1$, $R^2$, $R^3$, $R^4$, $R^5$, $R^6$, and $R^7$ are defined according to Formula (I). In another embodiment, this invention relates to compounds of Formula (III), wherein Y is O or S and X is N or $CR^6$. In another embodiment, this invention relates to compounds of Formula (III), wherein Y is O or S and X is $CR^6$. In another embodiment, this invention relates to compounds of Formula (III), wherein Y is O or S and X is N. In another embodiment, this invention relates to compounds of Formula (III), wherein Y is S and X is $CR^6$.

In another embodiment, this invention also relates to compounds of Formula (III)(a):

(III)(a)

[chemical structure]

or pharmaceutically acceptable salts thereof, wherein $R^1$, $R^2$, $R^3$, $R^4$, $R^5$, and $R^6$ are defined according to Formula (I).

In another embodiment, this invention also relates to compounds of Formula (IV):

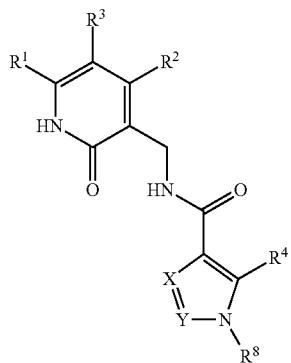

(IV)

or pharmaceutically acceptable salts thereof, wherein X is N or $CR^6$; Y is N or $CR^6$; and $R^1$, $R^2$, $R^3$, $R^4$, $R^6$, and $R^8$ are defined according to Formula (I). In another embodiment, this invention relates to compounds of Formula (IV), wherein X is N and Y is $CR^6$. In another embodiment, this invention relates to compounds of Formula (IV), wherein X is $CR^6$ and Y is N. In another embodiment, this invention relates to compounds of Formula (IV), wherein X and Y are each independently $CR^6$. In another embodiment, this invention relates to compounds of Formula (IV), wherein X and Y are each N.

Specific compounds of this invention include:

N-((4,6-dimethyl-2-oxo-1,2-dihydropyridin-3-yl)methyl)-4-isopropoxy-3-methylthiophene-2-carboxamide;

N-((4,6-dimethyl-2-oxo-1,2-dihydropyridin-3-yl)methyl)-4-(ethyl(tetrahydro-2H-pyran-4-yl)amino)-3-methylthiophene-2-carboxamide;

5-chloro-N-((4,6-dimethyl-2-oxo-1,2-dihydropyridin-3-yl)methyl)-4-(ethyl(tetrahydro-2H-pyran-4-yl)amino)-3-methylthiophene-2-carboxamide;

N-((4,6-dimethyl-2-oxo-1,2-dihydropyridin-3-yl)methyl)-4-(((trans)-4-(dimethylamino)cyclohexyl)(ethyl)amino)-3-methylthiophene-2-carboxamide;

N-((4,6-dimethyl-2-oxo-1,2-dihydropyridin-3-yl)methyl)-4-(((cis)-4-(dimethylamino)cyclohexyl)(ethyl)amino)-3-methylthiophene-2-carboxamide;

N-((4,6-dimethyl-2-oxo-1,2-dihydropyridin-3-yl)methyl)-5-(ethyl(tetrahydro-2H-pyran-4-yl)amino)-4-methylthiophene-3-carboxamide;

N-((4,6-dimethyl-2-oxo-1,2-dihydropyridin-3-yl)methyl)-5-(((cis)-4-(dimethylamino)cyclohexyl)(ethyl)amino)-4-methylthiophene-3-carboxamide;

N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide;

tert-butyl 4-((4-(((4,6-dimethyl-2-oxo-1,2-dihydropyridin-3-yl)methyl)carbamoyl)-3-methylthiophen-2-yl)(ethyl)amino)piperidine-1-carboxylate;

N-((4,6-dimethyl-2-oxo-1,2-dihydropyridin-3-yl)methyl)-5-(ethyl(piperidin-4-yl)amino)-4-methylthiophene-3-carboxamide;

N-((4,6-dimethyl-2-oxo-1,2-dihydropyridin-3-yl)methyl)-5-(1-(4-(dimethylamino)piperidin-1-yl)ethyl)thiophene-3-carboxamide;

N-[(4,6-dimethyl-2-oxo-1,2-dihydro-3-pyridinyl)methyl]-5-[ethyl(tetrahydro-2H-pyran-4-yl)amino]-1,4-dimethyl-1H-pyrazole-3-carboxamide;

5-(ethyl(tetrahydro-2H-pyran-4-yl)amino)-4-methyl-N-((6-methyl-2-oxo-4-(trifluoromethyl)-1,2-dihydropyridin-3-yl)methyl)thiophene-3-carboxamide;

5-(((trans)-4-(dimethylamino)cyclohexyl)(ethyl)amino)-4-methyl-N-((6-methyl-2-oxo-4-propyl-1,2-dihydropyridin-3-yl)methyl)thiophene-3-carboxamide;

5-(((trans)-4-(dimethylamino)cyclohexyl)(ethyl)amino)-4-methyl-N-((4-methyl-2-oxo-6-(trifluoromethyl)-1,2-dihydropyridin-3-yl)methyl)thiophene-3-carboxamide;

5-(((trans)-4-(dimethylamino)cyclohexyl)(ethyl)amino)-N-((4-methoxy-6-methyl-2-oxo-1,2-dihydropyridin-3-yl)methyl)-4-methylthiophene-3-carboxamide;

2-bromo-N-((4,6-dimethyl-2-oxo-1,2-dihydropyridin-3-yl)methyl)-5-(ethyl(tetrahydro-2H-pyran-4-yl)amino)-4-methylthiophene-3-carboxamide;

tert-butyl 4-((4-(((4,6-dimethyl-2-oxo-1,2-dihydropyridin-3-yl)methyl)carbamoyl)-3-methylthiophen-2-yl)(hydroxy)methyl)piperidine-1-carboxylate;

N-((4,6-dimethyl-2-oxo-1,2-dihydropyridin-3-yl)methyl)-5-(hydroxy(piperidin-4-yl)methyl)-4-methylthiophene-3-carboxamide;

N-((4,6-dimethyl-2-oxo-1,2-dihydropyridin-3-yl)methyl)-4-methyl-5-(1-(tetrahydro-2H-pyran-4-yl)pyrrolidin-2-yl)thiophene-3-carboxamide;

N-((4,6-dimethyl-2-oxo-1,2-dihydropyridin-3-yl)methyl)-4-methyl-5-(1-(piperidin-4-yl)-1H-pyrazol-4-yl)thiophene-3-carboxamide;

tert-butyl 3-(4-(((4,6-dimethyl-2-oxo-1,2-dihydropyridin-3-yl)methyl)carbamoyl)-3-methylthiophen-2-yl)pyrrolidine-1-carboxylate;

N-((4,6-dimethyl-2-oxo-1,2-dihydropyridin-3-yl)methyl)-4-methyl-5-(2-methylpyrrolidin-1-yl)thiophene-3-carboxamide;

N-((4,6-dimethyl-2-oxo-1,2-dihydropyridin-3-yl)methyl)-4-methyl-5-(1-morpholinoethyl)thiophene-3-carboxamide;

N-((4,6-dimethyl-2-oxo-1,2-dihydropyridin-3-yl)methyl)-5-(1-(4-(dimethylamino)piperidin-1-yl)ethyl)-4-methylthiophene-3-carboxamide;

N-((4,6-dimethyl-2-oxo-1,2-dihydropyridin-3-yl)methyl)-5-(1-(4-(dimethylamino)piperidin-1-yl)propyl)-4-methylthiophene-3-carboxamide;

N-((4,6-dimethyl-2-oxo-1,2-dihydropyridin-3-yl)methyl)-4-methyl-5-(1-morpholinopropyl)thiophene-3-carboxamide;

N-((4,6-dimethyl-2-oxo-1,2-dihydropyridin-3-yl)methyl)-5-(ethyl(tetrahydro-2H-pyran-4-yl)amino)thiophene-2-carboxamide;

5-(ethyl(tetrahydro-2H-pyran-4-yl)amino)-4-methyl-N-((1,4,6-trimethyl-2-oxo-1,2-dihydropyridin-3-yl)methyl)thiophene-3-carboxamide;

5-(((trans)-4-(dimethylamino)cyclohexyl)(ethyl)amino)-4-methyl-N-((1,4,6-trimethyl-2-oxo-1,2-dihydropyridin-3-yl)methyl)thiophene-3-carboxamide;

(E)-N-((4,6-dimethyl-2-oxo-1,2-dihydropyridin-3-yl)methyl)-4-methyl-5-(1-(piperidin-4-yl)prop-1-en-1-yl)thiophene-3-carboxamide;

tert-butyl((trans)-4-((E)-1-(4-(((4,6-dimethyl-2-oxo-1,2-dihydropyridin-3-yl)methyl)carbamoyl)-3-methylthiophen-2-yl)prop-1-en-1-yl)cyclohexyl)carbamate;

5-((E)-1-(((trans)-4-aminocyclohexyl)prop-1-en-1-yl)-N-((4,6-dimethyl-2-oxo-1,2-dihydropyridin-3-yl)methyl)-4-methylthiophene-3-carboxamide;

N-((4,6-dimethyl-2-oxo-1,2-dihydropyridin-3-yl)methyl)-5-((E)-1-((trans)-4-(dimethylamino)cyclohexyl)prop-1-en-1-yl)-4-methylthiophene-3-carboxamide;

5-(((trans)-4-aminocyclohexyl)(hydroxy)methyl)-N-((4,6-dimethyl-2-oxo-1,2-dihydropyridin-3-yl)methyl)-4-methylthiophene-3-carboxamide;

N-((4,6-dimethyl-2-oxo-1,2-dihydropyridin-3-yl)methyl)-5-(((trans)-4-(dimethylamino)cyclohexyl)(hydroxy)methyl)-4-methylthiophene-3-carboxamide;

tert-butyl 4-(1-(4-(((4,6-dimethyl-2-oxo-1,2-dihydropyridin-3-yl)methyl)carbamoyl)-3-methylthiophen-2-yl)propyl)piperidine-1-carboxylate;

N-((4,6-dimethyl-2-oxo-1,2-dihydropyridin-3-yl)methyl)-4-methyl-5-(1-(piperidin-4-yl)propyl)thiophene-3-carboxamide;

(S)-(−)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide;

(R)-(+)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide;

5-(1-((trans)-4-aminocyclohexyl)propyl)-N-((4,6-dimethyl-2-oxo-1,2-dihydropyridin-3-yl)methyl)-4-methylthiophene-3-carboxamide;

(−)-N-((4,6-dimethyl-2-oxo-1,2-dihydropyridin-3-yl)methyl)-5-(1-((trans)-4-(dimethylamino)cyclohexyl)propyl)-4-methylthiophene-3-carboxamide;

(+)-N-((4,6-dimethyl-2-oxo-1,2-dihydropyridin-3-yl)methyl)-5-(1-((trans)-4-(dimethylamino)cyclohexyl)propyl)-4-methylthiophene-3-carboxamide;

(+)-N-((4,6-dimethyl-2-oxo-1,2-dihydropyridin-3-yl)methyl)-5-(1-((cis)-4-(dimethylamino)cyclohexyl)propyl)-4-methylthiophene-3-carboxamide;

(−)-N-((4,6-dimethyl-2-oxo-1,2-dihydropyridin-3-yl)methyl)-5-(1-((cis)-4-(dimethylamino)cyclohexyl)propyl)-4-methylthiophene-3-carboxamide;

N-((4,6-dimethyl-2-oxo-1,2-dihydropyridin-3-yl)methyl)-4-methyl-5-(1-(piperidin-4-ylidene)propyl)thiophene-3-carboxamide;

N-((4,6-dimethyl-2-oxo-1,2-dihydropyridin-3-yl)methyl)-4-methyl-5-(1-(piperidin-4-yl)vinyl)thiophene-3-carboxamide;

2-bromo-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide;

2-cyano-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide;

2-bromo-5-(diethylamino)-N-((4,6-dimethyl-2-oxo-1,2-dihydropyridin-3-yl)methyl)-4-methylthiophene-3-carboxamide;

2-chloro-N-((4,6-dimethyl-2-oxo-1,2-dihydropyridin-3-yl)methyl)-5-(ethyl(tetrahydro-2H-pyran-4-yl)amino)-4-methylthiophene-3-carboxamide;

N-((4,6-dimethyl-2-oxo-1,2-dihydropyridin-3-yl)methyl)-5-(ethyl(tetrahydro-2H-pyran-4-yl)amino)-2,4-dimethylthiophene-3-carboxamide;

2-cyano-N-((4,6-dimethyl-2-oxo-1,2-dihydropyridin-3-yl)methyl)-5-(ethyl(tetrahydro-2H-pyran-4-yl)amino)-4-methylthiophene-3-carboxamide;

N-((4,6-dimethyl-2-oxo-1,2-dihydropyridin-3-yl)methyl)-5-(ethyl(tetrahydro-2H-pyran-4-yl)amino)-4-methyl-2-(4-methylpiperazin-1-yl)thiophene-3-carboxamide;

tert-butyl 3-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)pyrrolidine-1-carboxylate;

N-((4,6-dimethyl-2-oxo-1,2-dihydropyridin-3-yl)methyl)-5-(ethyl(tetrahydro-2H-pyran-4-yl)amino)-4-methyl-2-(pyrrolidin-3-yl)thiophene-3-carboxamide;

tert-butyl 4-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)piperidine-1-carboxylate;

N-((4,6-dimethyl-2-oxo-1,2-dihydropyridin-3-yl)methyl)-5-(ethyl(tetrahydro-2H-pyran-4-yl)amino)-4-methyl-2-(piperidin-4-yl)thiophene-3-carboxamide;

N-((4,6-dimethyl-2-oxo-1,2-dihydropyridin-3-yl)methyl)-5-(ethyl(tetrahydro-2H-pyran-4-yl)amino)-4-methyl-2-(1-methyl-1,2,3,6-tetrahydropyridin-4-yl)thiophene-3-carboxamide;

N-((4,6-dimethyl-2-oxo-1,2-dihydropyridin-3-yl)methyl)-5-(ethyl(tetrahydro-2H-pyran-4-yl)amino)-4-methyl-2-(1-(methylsulfonyl)pyrrolidin-3-yl)thiophene-3-carboxamide;

N-((4,6-dimethyl-2-oxo-1,2-dihydropyridin-3-yl)methyl)-5-(ethyl(tetrahydro-2H-pyran-4-yl)amino)-4-methyl-2-(1-(methylsulfonyl)piperidin-4-yl)thiophene-3-carboxamide;

N-((4,6-dimethyl-2-oxo-1,2-dihydropyridin-3-yl)methyl)-5-(ethyl((trans)-4-(ethyl(methyl)amino)cyclohexyl)amino)-4-methylthiophene-3-carboxamide;

ethyl(4-(((4,6-dimethyl-2-oxo-1,2-dihydropyridin-3-yl)methyl)carbamoyl)-3-methylthiophen-2-yl)(ethyl)carbamate;

N-((4,6-dimethyl-2-oxo-1,2-dihydropyridin-3-yl)methyl)-5-(ethyl(1-isopropylpiperidin-4-yl)amino)-4-methylthiophene-3-carboxamide;

N-((4,6-dimethyl-2-oxo-1,2-dihydropyridin-3-yl)methyl)-5-(ethyl(3-fluoropiperidin-4-yl)amino)-4-methylthiophene-3-carboxamide;

N-((4,6-dimethyl-2-oxo-1,2-dihydropyridin-3-yl)methyl)-4-methyl-5-(2-(piperidin-4-yl)pyrrolidin-1-yl)thiophene-3-carboxamide;

5-([2,4'-bipiperidin]-1-yl)-N-((4,6-dimethyl-2-oxo-1,2-dihydropyridin-3-yl)methyl)-4-methylthiophene-3-carboxamide;

N-((4,6-dimethyl-2-oxo-1,2-dihydropyridin-3-yl)methyl)-4-methyl-5-(1,2,3,4-tetrahydroisoquinolin-5-yl)thiophene-3-carboxamide;

(Z)-N-((4,6-dimethyl-2-oxo-1,2-dihydropyridin-3-yl)methyl)-4-methyl-5-(5-morpholinopent-2-en-3-yl)thiophene-3-carboxamide;

(Z)-N-((4,6-dimethyl-2-oxo-1,2-dihydropyridin-3-yl)methyl)-4-methyl-5-(6-(4-methylpiperazin-1-yl)hex-2-en-3-yl)thiophene-3-carboxamide;

N-((4,6-dimethyl-2-oxo-1,2-dihydropyridin-3-yl)methyl)-4-methyl-5-(6-(4-methylpiperazin-1-yl)hexan-3-yl)thiophene-3-carboxamide;

(Z)-N-((4,6-dimethyl-2-oxo-1,2-dihydropyridin-3-yl)methyl)-5-(6-(4-(dimethylamino)piperidin-1-yl)hex-2-en-3-yl)-4-methylthiophene-3-carboxamide;

N-((4,6-dimethyl-2-oxo-1,2-dihydropyridin-3-yl)methyl)-5-(ethyl(tetrahydro-2H-pyran-4-yl)amino)-2-(furan-3-yl)-4-methylthiophene-3-carboxamide;

N-((4,6-dimethyl-2-oxo-1,2-dihydropyridin-3-yl)methyl)-5-(ethyl(tetrahydro-2H-pyran-4-yl)amino)-2-(furan-2-yl)-4-methylthiophene-3-carboxamide;

N-((4,6-dimethyl-2-oxo-1,2-dihydropyridin-3-yl)methyl)-5-(((trans)-4-(dimethylamino)cyclohexyl)(ethyl)amino)-2-(furan-3-yl)-4-methylthiophene-3-carboxamide; and N-((4,6-dimethyl-2-oxo-1,2-dihydropyridin-3-yl)methyl)-5-(ethyl(tetrahydro-2H-pyran-4-yl)amino)-4-methyl-2-(1-methyl-1H-pyrazol-4-yl)thiophene-3-carboxamide;

or pharmaceutically acceptable salts thereof.

Typically, but not absolutely, the salts of the present invention are pharmaceutically acceptable salts. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labeled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as pharmaceutical formulation) comprising a compound of Formula (I) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In accordance with another aspect of the invention there is provided a process for the preparation of a pharmaceutical composition comprising mixing (or admixing) a compound of Formula (I) or salt thereof with at least one excipient.

The present invention also provides a method of treatment in a mammal, especially a human. The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histicytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein refers to either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and *vinca* alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, anti-tumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deacetylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C$_{225}$). Bevacizumab (Avastin®) is an example of a monoclonal antibody directed against VEGFR. Examples of small molecule inhibitors of epidermal growth factor receptors include but are not limited to lapatinib (Tykerb®) and erlotinib (TARCEVA®). Imatinib mesylate (GLEEVEC®) is one example of a PDGFR inhibitor. Examples of VEGFR inhibitors include pazopanib (Votrient®), ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the G2/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325 (1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Int. Med., 111:273, 1989) and for the treatment of breast cancer (Holmes et al., J. Nat. Cancer Inst., 83:1797, 1991.). It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Keams, C. M. et. al., Seminars in Oncology, 3(6) p. 16-23, 1995).

Docetaxel, (2R,3S)—N-carboxy-3-phenylisoserine N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of *vinca* alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic *vinca* alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetra-hydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-O—(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenialeukopenia tends to be more severe than thrombocytopenia.

Teniposide, 4'-demethyl-epipodophyllotoxin 9[4,6-O—(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenialeukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenialeukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenialeukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenialeukopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H, 12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of Formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavoring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of Formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of Formula (I) per se. It is envisaged that similar dosages would be appropriate for treatment of the other conditions referred to above.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_6)$alkyl" refers to an alkyl moiety containing from 1 to 6 carbon atoms. Exemplary alkyls include, but are not limited to, methyl, ethyl, n-propyl, isopropyl, n-butyl, isobutyl, s-butyl, t-butyl, pentyl, and hexyl.

When the term "alkyl" is used in combination with other substituent groups, such as "halo$(C_1-C_4)$alkyl", "hydroxy$(C_1-C_4)$alkyl" or "aryl$(C_1-C_4)$alkyl-", the term "alkyl" is intended to encompass a divalent straight or branched-chain hydrocarbon radical, wherein the point of attachment is through the alkyl moiety. The term "halo$(C_1-C_4)$alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo$(C_1-C_4)$alkyl" groups useful in the present invention include, but are not limited to, $-CF_3$ (trifluoromethyl), $-CCl_3$ (trichloromethyl), 1,1-difluoroethyl, 2,2,2-trifluoroethyl, and hexafluoroisopropyl. Examples of "aryl$(C_1-C_4)$alkyl-" groups useful in the present invention include, but are not limited to, benzyl(phenylmethyl), 1-methylbenzyl (1-phenylethyl), 1,1-dimethylbenzyl (1-phenylisopropyl), and phenethyl (2-phenylethyl). Examples of "hydroxy$(C_1-C_4)$alkyl" groups useful in the present invention include, but are not limited to, hydroxymethyl, hydroxyethyl, and hydroxyisopropyl.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include, but are not limited to, methoxy, ethoxy, n-propoxy, isopropoxy, n-butoxy, s-butoxy, isobutoxy, and t-butoxy.

When "cycloalkyl" is used it refers to a non-aromatic, saturated, cyclic hydrocarbon ring containing the specified number of carbon atoms. So, for example, the term "$(C_3-C_8)$cycloalkyl" refers to a non-aromatic cyclic hydrocarbon ring having from three to eight carbon atoms. Exemplary "$(C_3-C_8)$cycloalkyl" groups useful in the present invention include, but are not limited to, cyclopropyl, cyclobutyl, cyclopentyl, cyclohexyl, cycloheptyl, and cyclooctyl.

As used herein, the term "cycloalkyloxy-" refers to a group containing a cycloalkyl radical, defined hereinabove, attached through an oxygen linking atom. Exemplary "$(C_3-C_8)$cycloalkyloxy-" groups useful in the present invention include cyclopropyloxy, cyclobutyloxy, cyclopentyloxy, cyclohexyloxy, cycloheptyloxy, and cyclooctyloxy.

As used herein, the term "bicycloalkyl" refers to a saturated, bridged, fused, or spiro, bicyclic hydrocarbon ring system containing the specified number of carbon atoms. Exemplary "$(C_6-C_{10})$bicycloalkyl" groups include, but are not limited to bicyclo[2.1.1]hexyl, bicyclo[2.1.1]heptyl, bicyclo[3.2.1]octyl, bicyclo[2.2.2]octyl, bicyclo[3.2.2]nonyl, bicyclo[3.3.1]nonyl, bicyclo[3.3.2]decyl, bicyclo[4.3.1]decyl, bicyclo[2.2.0]hexyl, bicyclo[3.1.0]hexyl, bicyclo[3.2.0]heptyl, bicyclo[4.1.0]heptyl, octahydropentalenyl, bicyclo[4.2.0]octyl, decahydronaphthalenyl, spiro[3.3]heptyl, spiro[2.4]heptyl, spiro[3.4]octyl, spiro[2.5]octyl, spiro[4.4]nonyl, spiro[3.5]nonyl, and spiro[4.5]decyl.

The terms "halogen" and "halo" represent chloro, fluoro, bromo, or iodo substituents. "Hydroxy" or "hydroxyl" is intended to mean the radical $-OH$.

"Heterocycloalkyl" represents a group or moiety comprising a non-aromatic, monovalent monocyclic or bicyclic radical, which is saturated or partially unsaturated, containing 3 to 12 ring atoms, which includes 1 to 3 heteroatoms independently selected from nitrogen, oxygen and sulfur, including N-oxides, sulfur oxides, and dioxides. Illustrative examples of heterocycloalkyls useful in the present invention include, but are not limited to, aziridinyl, azetidinyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-dithianyl, hexahydro-1H-1,4-diazepinyl, octahydro-1H-indolyl, hexahydro-1H-indolyl, octahydro-1H-isoindolyl, hexahydro-1H-isoindolyl, decahydroquinolinyl, decahydroisoquinolinyl, octahydroquinolinyl, octahydroisoquinolinyl, azaspiro[4.5]decanyl, azaspiro[4.5]decenyl, azaspiro[5.5]undecanyl, azaspiro[5.5]undecenyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl, and 1,5,9-triazacyclododecyl.

As used herein, "5- or 6-membered heterocycloalkyl" represents a group or moiety comprising a non aromatic, monovalent monocyclic radical, which is saturated or partially unsaturated, containing 5 or 6 ring atoms, which includes one or two heteroatoms selected independently from oxygen, sulfur, and nitrogen. Illustrative examples of 5- or 6-membered heterocycloalkyl groups useful in the present invention include, but are not limited to pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, 1,4-dithianyl, 1,4-oxathiolanyl, 1,4-oxathianyl, and 1,4-dithianyl.

As used herein, the term "heterocycloalkyloxy-" refers to a group containing a heterocycloalkyl radical, defined hereinabove, attached through an oxygen linking atom. Illustrative examples of heterocycloalkyloxy groups useful in the present invention include, but are not limited to, aziridinyloxy, azetidinyloxy, pyrrolidinyloxy, pyrazolidinyloxy, pyrazolinyloxy, imidazolidinyloxy, imidazolinyloxy, oxazolinyloxy, thiazolinyloxy, tetrahydrofuranyloxy, dihydrofuranyloxy, 1,3-dioxolanyloxy, piperidinyloxy, piperazinyloxy, morpholinyloxy, thiomorpholinyloxy, tetrahydropyranyloxy, dihydropyranyloxy, 1,3-dioxanyloxy, 1,4-dioxanyloxy, 1,3-oxathiolanyloxy, 1,3-oxathianyloxy, 1,3-dithianyloxy, hexahydro-1H-1,4-diazepinyloxy, azabicylo[3.2.1]octyloxy, azabicylo[3.3.1]nonyloxy, azabicylo[4.3.0]nonyloxy, oxabicylo[2.2.1]heptyloxy, 1,1-dioxidotetrahydro-2H-thiopyranyloxy, and 1,5,9-triazacyclododecyloxy.

The term "aryl" refers to a monocyclic or fused bicyclic groups having 6 to 14 carbon atoms and having at least one aromatic ring that complies with Hickel's Rule. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl.

As used herein, the term "heteroaryl" refers to an aromatic ring system containing carbon(s) and at least one heteroatom selected from nitrogen, oxygen and sulfur, including N-oxides. Heteroaryl may be monocyclic or polycyclic, substituted or unsubstituted. A monocyclic heteroaryl group may have 1 to 4 heteroatoms in the ring, while a polycyclic heteroaryl may contain 1 to 8 heteroatoms. Bicyclic heteroaryl rings may contain from 8 to 10 member atoms. Monocyclic heteroaryl rings may contain from 5 to 6 member atoms (carbons and heteroatoms). Exemplary 5- or 6-membered heteroaryls include, but are not limited to, furanyl, thiophenyl, thienyl, pyrrolyl, imidazolyl, pyrazolyl, triazolyl, tetrazolyl, thiazolyl, isothiazolyl, 1,2,3-triazolyl, 1,2,4-triazolyl, oxazolyl, isoxazolyl, 1,2,3-oxadiazolyl, 1,2,5-oxadiazolyl, thiadiazolyl, isothiazolyl, tetrazolyl, pyridinyl, pyridazinyl, pyrazinyl, pyrimidinyl, and triazinyl. Other exemplary heteroaryl groups include, but are not limited to benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, the term "cyano" refers to the group —CN.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substituent group. The phrase should not be interpreted as duplicative of the substitutions herein described and depicted.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

Compound Preparation

Abbreviations $Ac_2O$ acetic anhydride
AcOH acetic acid

Boc$_2$O di-tert-butyl dicarbonate
CHCl$_3$ chloroform
CH$_3$CN acetonitrile
Cs$_2$CO$_3$ cesium carbonate
CuBr copper (I) bromide
DCE 1,2-dichloroethane
DCM dichloromethane
DIPEA diisopropylethylamine
DMF N,N-dimethylformamide
DMSO dimethyl sulfoxide
EtOAc ethyl acetate
EDC N-(3-dimethylaminopropyl)-N'-ethylcarbodiimide hydrochloride
ES electrospray
Et$_2$O diethyl ether
EtOH ethanol
h hour(s)
H$_2$ hydrogen gas
HBr hydrobromic acid
HCl hydrochloric acid
H$_2$O water
H$_2$SO$_4$ sulfuric acid
HOAt 1-hydroxy-7-azabenzotriazole
HOBt 1-hydroxybenzotriazole
HPLC high-performance liquid chromatography
I$_2$ iodine
In(OTf)$_3$ indium (III) trifluoromethanesulfonate
KOEt potassium ethoxide
LCMS liquid chromatography mass spectrometry
LiClO$_4$ lithium perchlorate
LiOH lithium hydroxide
Me$_3$OBF$_4$ trimethyloxonium tetrafluoroborate
MeOH methanol
MgCl$_2$ magnesium chloride
MgSO$_4$ magnesium sulfate
min minute(s)
MS mass spectrometry
NaBH$_4$ sodium borohydride
NaBH$_3$CN sodium cyanoborohydride
NaBH(OAc)$_3$ sodium triacetoxyborohydride
NaCl sodium chloride
Na$_2$CO$_3$ sodium carbonate
NaH sodium hydride
NaHCO$_3$ sodium bicarbonate
NaOAc sodium acetate
NaOH sodium hydroxide
NaOMe sodium methoxide
Na$_2$SO$_4$ sodium sulphate
Na$_2$S$_2$O$_3$ sodium thiosulfate
NBS N-bromosuccinimide
NCS N-chlorosuccinimide
NH$_3$ ammonia
NH$_4$Cl ammonium chloride
NH$_4$OAc ammonium acetate
NH$_4$OH ammonium hydroxide
NIS N-iodosuccinimide
NMM N-methylmorpholine
PCl$_5$ phosphorous pentachloride
Pd/C palladium on carbon
PdCl$_2$(dppf) [1,1'-bis(diphenylphosphino)ferrocene]dichloropalladium(II)
Pd$_2$(dba)$_3$ tris(dibenzylideneacetone)dipalladium(0)
Pd(PPh$_3$)$_4$ tetrakis(triphenylphosphine)palladium(0)
POCl$_3$ phosphoryl chloride
PtO$_2$ platinum oxide
RT room temperature
SOCl$_2$ thionyl chloride
TBME tert-butyl methyl ether
t-BuOH tert-butanol
t-BuOK potassium tert-butoxide
TEA triethylamine
THF tetrahydrofuran
Ti(OCH(CH$_3$)$_2$)$_4$ titanium(IV) isopropoxide
TFA trifluoroacetic acid
Xantphos (9,9-dimethyl-9H-xanthene-4,5-diyl)bis(diphenylphosphine)
Zn(OTf)$_2$ zinc trifluoromethanesulfonate Generic Synthesis Schemes The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

The compounds of Formula (I) can be prepared according to Scheme 1 or analogous methods. An appropriately substituted alcohol is coupled to an appropriately substituted 4-bromo-thiophene-2-carboxylic acid (or its regiosomer) via a copper mediated reaction to produce an alkoxy-substituted thiophene. Coupling of the carboxylic acid with an appropriately substituted amine affords compounds of Formula (I).

Scheme 1: Synthesis of Compounds of Formula (I).

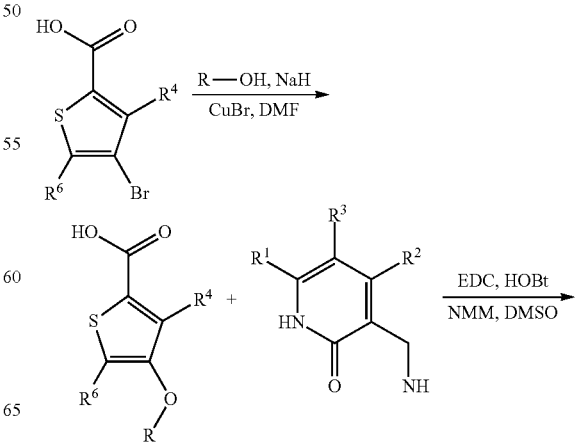

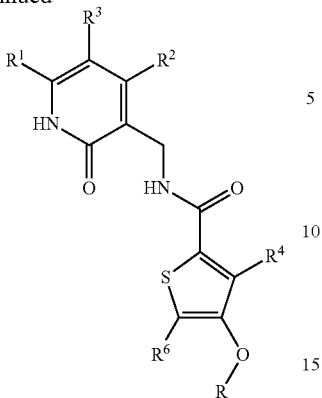

The compounds of Formula (I) can also be prepared according to Scheme 2 or analogous methods. Esterification of an appropriately substituted 4-bromo-thiophene-2-carboxylic acid (or its regiosomer) provides the corresponding ester. A palladium-mediated coupling reaction with benzophenone imine affords the aminothiophene. Successive reductive alkylations of the amino group with appropriately substituted aldehydes or ketones furnishes the substituted amines. Saponification of the ester, followed by coupling of the resultant carboxylic acid with an appropriately substituted amine affords compounds of Formula (I).

Scheme 2: Synthesis of Compounds of Formula (I).

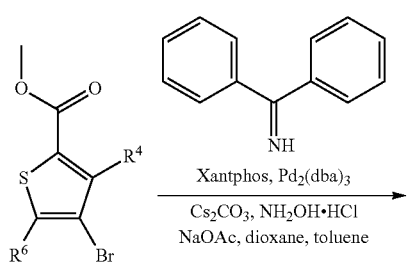

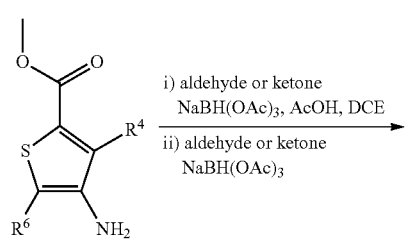

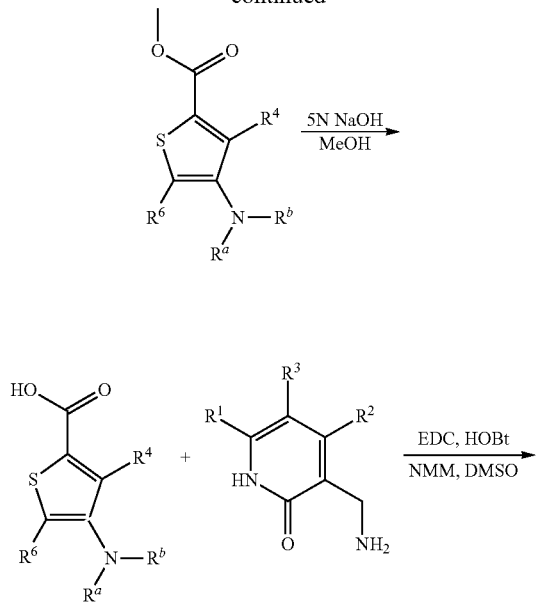

The compounds of Formula (I) can also be prepared according to Scheme 3 or analogous methods. Esterification of an appropriately substituted thiophene-3-carboxylic acid (or its regiosomer) provides the corresponding ester. An indium-mediated acylation reaction with an appropriately substituted anyhydride (or acylchloride) affords the 5-acyl-thiophene. Reduction of the ketone, followed by conversion of the alcohol to the corresponding chloride with thionylchloride and subsequent displacement with appropriately substituted amines (or alcohols) furnishes the substituted derivatives. Saponification of the ester, followed by coupling of the resultant carboxylic acid with an appropriately substituted amine affords compounds of Formula (I).

Scheme 3: Synthesis of Compounds of Formula (I).

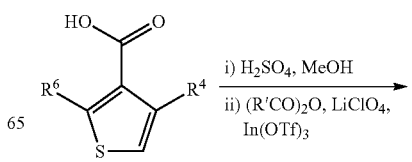

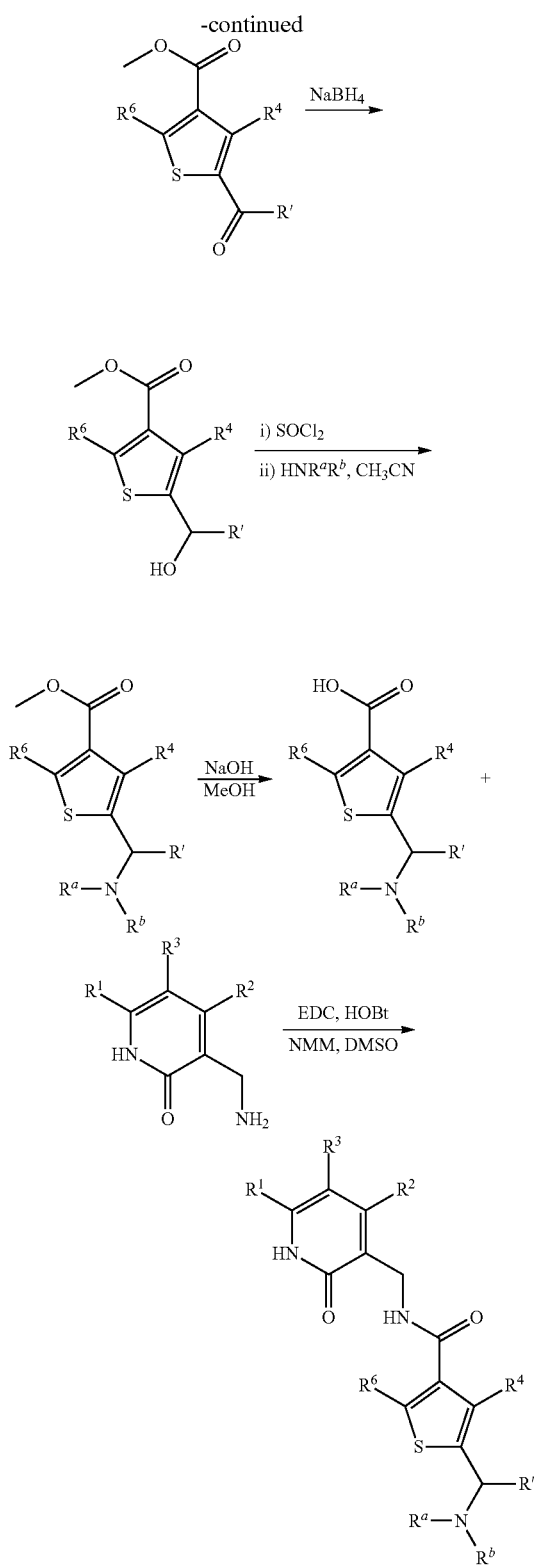

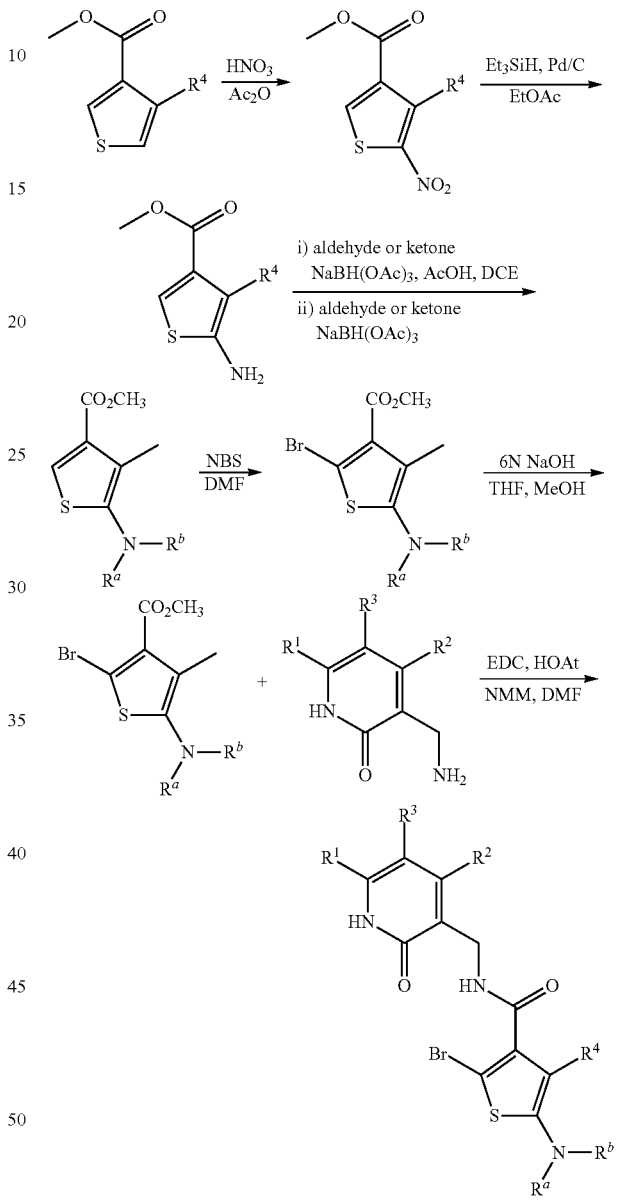

mination on the thiophene ring affords the corresponding bromothiophenes. Saponification of the ester, followed by coupling of the resultant carboxylic acid with an appropriately substituted amine affords compounds of Formula (I).

Scheme 4: Synthesis of Compounds of Formula (I).

The compounds of Formula (I) can also be prepared according to Scheme 4 or analogous methods. Nitration of an appropriately substituted 4-thiophene-3-carboxylate, followed by reduction of the nitro group provides the corresponding aminothiophenes. Successive reductive alkylations of the amino group with appropriately substituted aldehydes or ketones furnish the substituted amines. Bro- The compounds of Formula (I) can also be prepared according to Scheme 5 or analogous methods. Iodination of an appropriately substituted 4-thiophene-3-carboxylate provides the corresponding iodothiophene. A copper-mediated coupling of an appropriately substituted aldehyde, followed by oxidation of the resultant alcohol furnishes the corresponding thiophene-ketone. A Wittig olefination, followed by reduction of the double bond provides the corresponding substituted thiophene. Saponification of the ester, followed by coupling of the resultant carboxylic acid with an appropriately substituted amine affords compounds of Formula (I).

Scheme 5: Synthesis of Compounds of Formula (I).

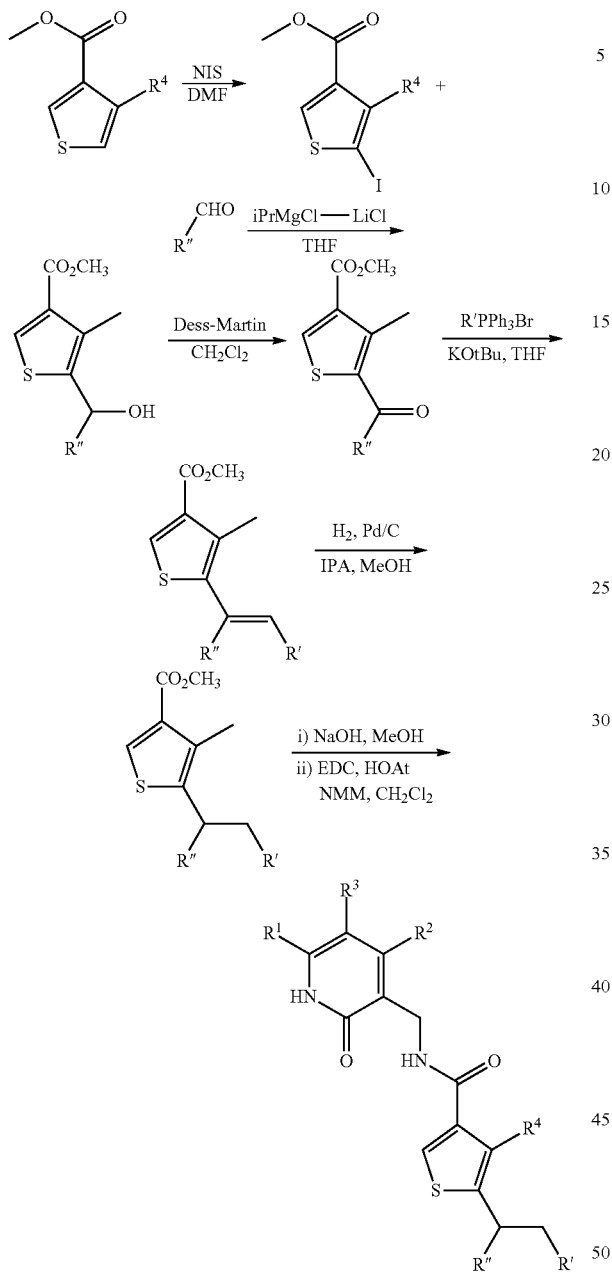

Scheme 6: Synthesis of Compounds of Formula (I).

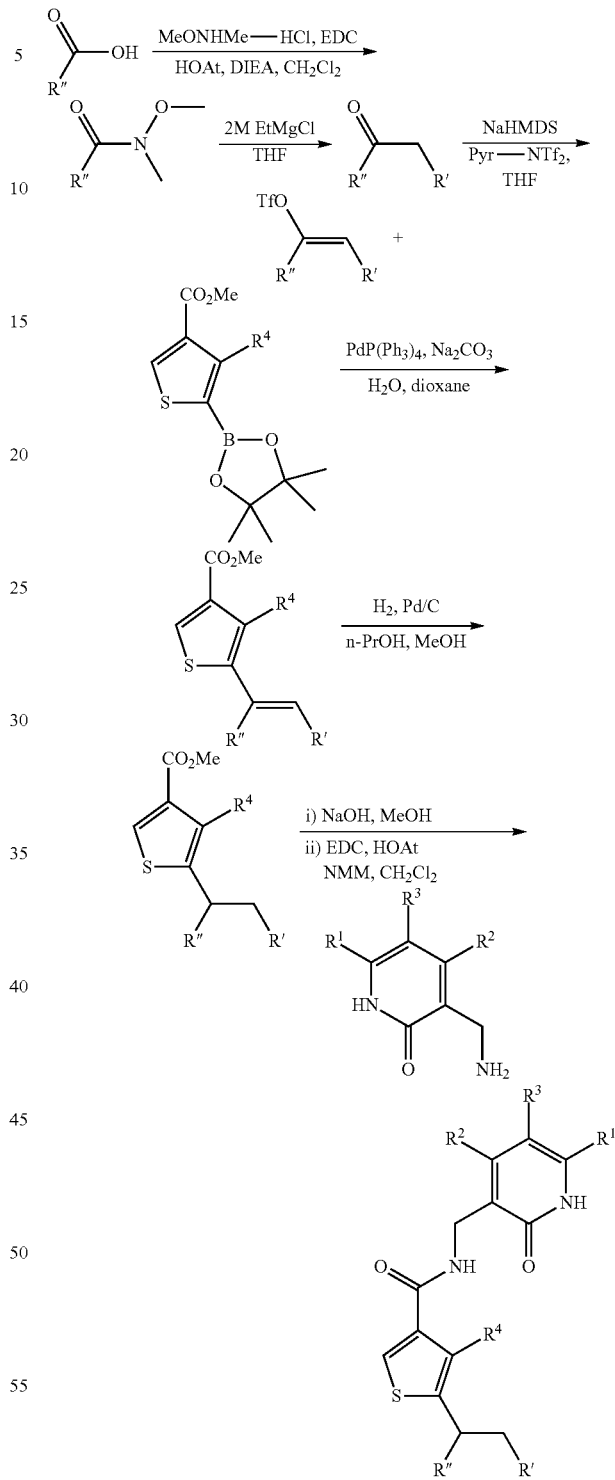

Alternatively, compounds of Formula (I) from Scheme 5 can also be prepared according to Scheme 6 or analogous methods. Conversion of an appropriately substituted carboxylic acid to its corresponding Weinreb amide, followed by treatment with an alkyl Grignard reagent provides the corresponding substituted ketone. Formation of the vinyltriflate, followed by a palladium-mediated cross-coupling with an appropriately substituted thiopheneboronate furnishes the corresponding substituted thiophene. Reduction of the double bond, followed by saponification of the ester and coupling of the resultant carboxylic acid with an appropriately substituted amine affords compounds of Formula (I).

EXPERIMENTALS

The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (CH$_3$CN-0.1% TFA): B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a Hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% (H$_2$O 0.02% TFA) in vessel A and 100% (CH$_3$CN 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% (H$_2$O 0.02% TFA) in vessel A and 100% (CH$_3$CN 0.018% TFA) in vessel B. The stationary phase was Zobax (C8) with a 3.5 um particle size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50× 4.6 mm, 1.8 μm) eluting with CH$_3$CN:NH$_4$OAc buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal. All NMRs in DMSO-d$_6$ unless otherwise noted.

Analytical HPLC: Products were analyzed by Agilent 1100 Analytical Chromatography system, with 4.5×75 mm Zorbax XDB-C18 column (3.5 um) at 2 mL/min with a 4 min gradient from 5% CH$_3$CN (0.1% formic acid) to 95% CH$_3$CN (0.1% formic acid) in H$_2$O (0.1% formic acid) and a 1 min hold.

Intermediates

Intermediate 1

3-(Aminomethyl)-4,6-dimethyl-2(1H)-pyridinone hydrochloride

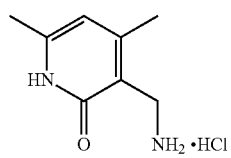

Pd/C (10%) (3.24 g) was charged into a 2 L dry Parr bottle and a small amount of AcOH was added. Next was added 4,6-dimethyl-2-oxo-1,2-dihydro-pyridine-3-carbonitrile (30 g, 202.7 mmol), NaOAc (30.75 g, 375.0 mmol), PtO$_2$ (0.218 g), and AcOH (1 L). The bottle was capped, placed on a Parr apparatus, and shaken under an atmosphere of H2 (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, Et$_2$O, and dried. The product was collected as 36 g. This batch was combined with other batches prepared on smaller scales and triturated with Et$_2$O to give 51 g of pure title compound. $^1$H NMR (400 MHz, DMSO-d$_6$) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(Aminomethyl)-6-methyl-4-(trifluoromethyl)-2(1H)-pyridinone hydrochloride

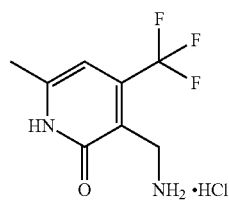

To a dried 500 mL Parr bottle equipped with nitrogen inlet were added NaOAc (1.502 g, 18.30 mmol), 10% Pd/C (1.579 g, 0.742 mmol), PtO$_2$ (0.011 g, 0.049 mmol) and a small amount of AcOH to wet the catalysts, under nitrogen stream. Next was added 2-hydroxy-6-methyl-4-(trifluoromethyl)-3-pyridinecarbonitrile (2.0 g, 9.89 mmol) followed by AcOH (175 mL) while under nitrogen atmosphere. The contents were sealed, placed on a Parr shaker, and reacted at 40 psi of H2 for ca. 6 hr, keeping the H2 pressure between 20 and 40 psi (vessel was refilled twice). The vessel was purged with nitrogen and the reaction mixture filtered through Celite®, and the filter pad was further washed with a small amount of AcOH. The volatiles were removed in vacuo to afford a residue, which was dried under high vacuum for 45 min. The solid was suspended in conc. HCl (12 mL), stirred, and filtered. The clear filtrate was concentrated in vacuo and the residue dried under high vacuum. The collected solid was suspended in conc. HCl (2 mL) and diluted with EtOH (13 mL). The contents were agitated and stored at ca. 0° C. (freezer) for 30 min to give a white solid. The solid was filtered and washed with cold EtOH (5 mL). The solid was filtered and dried in a vacuum oven for 1 h to give 3-(aminomethyl)-6-methyl-4-(trifluoromethyl)-2(1H)-pyridinone hydrochloride (0.95 g, 40%). LCMS ES (M+H)=206.9. $^1$H NMR (400 MHz, DMSO-d$_6$) δ ppm 2.31 (s, 3H), 3.40-3.62 (m, 2H), 3.87 (d, J=5.05 Hz, 2H), 8.12-8.37 (m, 3H).

Intermediate 3

3-(Aminomethyl)-6-methyl-4-propyl-2(1H)-pyridinone

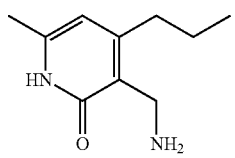

a) 6-Methyl-2-oxo-4-propyl-1,2-dihydro-3-pyridinecarbonitrile

To a solution of DMSO (300 mL) containing t-BuOK (20 g, 178 mmol) and cyanoacetamide (16.5 g, 196 mmol) was added (3E)-3-hepten-2-one (20 g, 178 mmol), and the contents were stirred at RT for 30 min. Additional t-BuOK (60 g, 534 mmol) was added and the reaction mixture was placed under an atmosphere of oxygen for an additional 1 h. The reaction mixture was purged with argon, diluted with 4 volumes of H$_2$O, and then 5 volumes of 4 N HCl, which were added slowly. The reaction mixture was filtered, washed with water, and dried to give 6-methyl-2-oxo-4-propyl-1,2-dihydro-3-pyridinecarbonitrile (10 g, 32%). $^1$H NMR (400 MHz, DMSO-d$_6$) δ ppm 12.25-12.40 (br s, 1H), 6.18 (s, 1H), 2.53 (t, 2H), 2.22 (s, 3H), 1.57-1.64 (m, 2H), 0.84 (t, 3H).

b) 3-(Aminomethyl)-6-methyl-4-propyl-2(1H)-pyridinone hydrochloride

To an ice-bath cooled THF (100 mL) solution of 6-methyl-2-oxo-4-propyl-1,2-dihydro-3-pyridinecarbonitrile (3 g, 17 mmol) was added NaBH$_4$ (1.5 g, 39.2 mmol) and 12 (4.3 g, 17 mmol), and the mixture was stirred for 30 min. The reaction mixture was then heated at reflux for 3 h, and then allowed to cool to RT. After cooling to 0° C., the reaction mixture was acidified by slow addition of 6 N HCl (1 mL). The reaction mixture was concentrated in vacuo and the crude product purified by reverse phase HPLC to give 3-(aminomethyl)-4-cyclohexyl-6-methyl-2(1H)-pyridinone as a solid (1.2 g, 60%). LCMS ES (M+H)=181.1. $^1$H NMR (400 MHz, DMSO-d$_6$) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 4

3-(Aminomethyl)-4-methoxy-6-methylpyridin-2(1H)-one hydrochloride

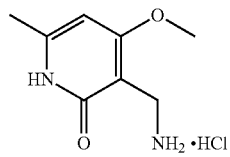

a) 4-Chloro-6-methyl-2-oxo-1,2-dihydropyridine-3-carbonitrile

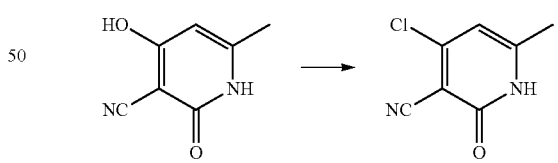

To a stirred solution of PCl$_5$ (18.03 g, 87 mmol) in CHCl$_3$ (100 mL) was added POCl$_3$ (8.07 mL, 87 mmol), followed by 4-hydroxy-6-methyl-2-oxo-1,2-dihydropyridine-3-carbonitrile (10 g, 66.6 mmol). The resultant suspension was heated at 72° C. until the disappearance of starting material (by LCMS). The reaction volume was reduced by about 1/2 in vacuo, at which time the mixture was poured into ice/water with vigourous stirring. Nitrogen was streamed over the mixture for 1 h to remove volatiles and produce a suspension. The solids were filtered, washed with a small amount of water, and dried under vacuum overnight. The isolated solid (9.7 g) was diluted with EtOH (97 mL) and the mixture was warmed for 30 min, then allowed to cool to RT for 1 h. The solid was filtered, washed with EtOH, and dried under vacuum to give 4-chloro-6-methyl-2-oxo-1,2-dihydropyridine-3-carbonitrile (4.37 g, 18.15 mmol, 27.2% yield, est. 70% purity). $^1$H NMR (400 MHz, DMSO-d$_6$) δ 12.85 (br. s., 1H), 6.54 (s, 1H), 2.28 (s, 3H). MS(ES) [M+H]$^+$ 168.9.

b) 4-Chloro-2-methoxy-6-methylnicotinonitrile

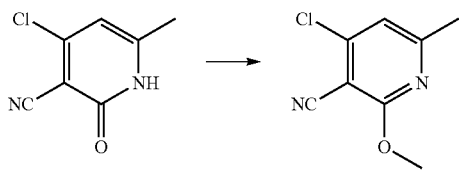

To a stirred suspension of 4-chloro-6-methyl-2-oxo-1,2-dihydropyridine-3-carbonitrile (2.96 g, 17.56 mmol) in DCM (100 mL) was added Me$_3$OBF$_4$ (3.25 g, 21.95 mmol). The reaction mixture was heated at 45° C. for 18 h, at which time was added 1 N NaOH/ice water (150 mL). The mixture was stirred for ~20 min. The organic layer was removed, washed with brine, dried over MgSO$_4$, filtered, and concentrated in vacuo. The residue was dissolved in DCM and toluene and purified twice by flash chromatography (Isco 40 g and 80 g silica columns; Gradient B: 5-40%; A: heptane, B: EtOAc) to afford 4-chloro-2-methoxy-6-methylnicotinonitrile (1.10 g, 5.90 mmol, 33.6% yield) as a white solid. $^1$H NMR (400 MHz, DMSO-d$_6$) δ 7.35 (s, 1H), 3.96-4.04 (m, 3H), 2.45-2.49 (m, 3H). MS(ES) [M+H]$^+$ 183.

c) 2,4-Dimethoxy-6-methylnicotinonitrile

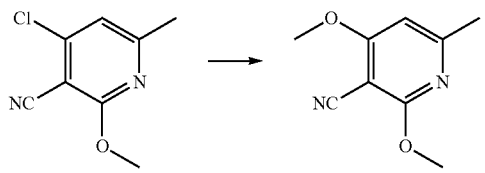

To a suspension of 4-chloro-2-methoxy-6-methylnicotinonitrile (1.10 g, 6.02 mmol) in MeOH (10 mL) was added NaOMe (0.5 M in MeOH, 48.2 mL, 24.10 mmol). The reaction mixture was heated at reflux under nitrogen for 1 h (suspension slowly dissolved). The reaction cooled in a ice bath for 5 min, then AcOH (1.379 mL, 24.10 mmol) was added. The mixture was stirred for 15 min, at which time the volatiles were removed in vacuo. The white solid was diluted with water to form a slurry and saturated NaHCO$_3$ (1-2 mL) was added. The solids were filtered and washed with a small amount of water to give 2,4-dimethoxy-6-methylnicotinonitrile (1.03 g, 5.66 mmol, 94% yield). $^1$H NMR (400 MHz, DMSO-d$_6$) δ 6.88 (s, 1H), 3.93 (s, 3H), 3.96 (s, 3H), 2.39-2.47 (m, 3H). MS(ES) [M+H]$^+$ 179.

d) tert-Butyl ((2,4-dimethoxy-6-methylpyridin-3-yl)methyl)carbamate

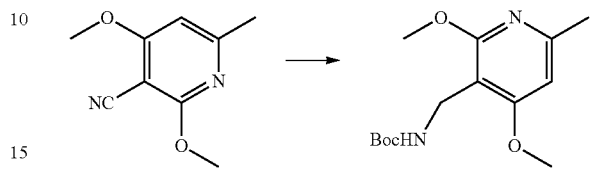

To a solution of 2,4-dimethoxy-6-methylnicotinonitrile (1.03 g, 5.78 mmol) in MeOH (25 mL) and THF (25 mL) was added TEA (4.03 mL, 28.9 mmol) and Boc$_2$O (4.03 mL, 17.34 mmol). The mixture was placed into an H-Cube reactor (Raney nickel cartridge, 1 mL/min, 40 psi) and heated at 40° C. for 24 h, at which time it was concentrated in vacuo. The residue was dissolved in a small amount of DCM and purified via flash column chromatography (40 g silica column; Gradient of B: 8-75%; A:heptane. B: EtOAc to give tert-butyl ((2,4-dimethoxy-6-methylpyridin-3-yl)methyl)carbamate (950 mg, 3.23 mmol, 55.9% yield) as a white solid (following trituration with Et$_2$O). $^1$H NMR (400 MHz, DMSO-d$_6$) δ 6.61 (s, 1H), 6.44 (br. s., 1H), 4.04 (d, J=5.1 Hz, 2H), 3.80 (s, 3H), 3.81 (s, 3H), 2.34 (s, 3H), 1.37 (s, 9H). MS(ES) [M+H]$^+$ 283.

e) 3-(Aminomethyl)-4-methoxy-6-methylpyridin-2(1H)-one hydrochloride

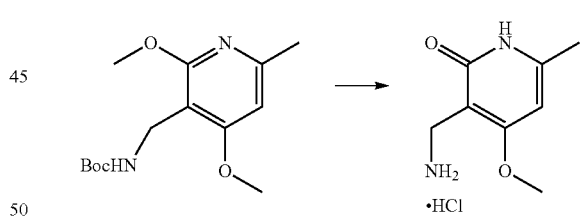

A solution of tert-butyl ((2,4-dimethoxy-6-methylpyridin-3-yl)methyl)carbamate (0.95 g, 3.36 mmol) in 4 M HCl in 1,4-dioxane (10.09 ml, 40.4 mmol) was heated at 90° C. until the starting material was consumed (by LCMS). The volatiles were removed in vacuo and the resulant residue was treated with EtOH (15 mL). A white solid precipitated. The volatiles were removed in vacuo and the residue was treated with TBME and concentrated (2×) to provide 3-(aminomethyl)-4-methoxy-6-methylpyridin-2(1H)-one hydrochloride (638 mg, 2.96 mmol, 88% yield) as a white solid. $^1$H NMR (400 MHz, DMSO-d$_6$) δ 11.77 (br. s., 1H), 7.98 (br. s., 3H), 6.20 (s, 1H), 3.80-3.90 (m, 3H), 3.72 (q, J=5.7 Hz, 2H), 2.16-2.30 (m, 3H). MS(ES) [M+H]$^+$ 169.

Intermediate 5

3-(Aminomethyl)-1,4,6-trimethylpyridin-2(1H)-one hydrochloride

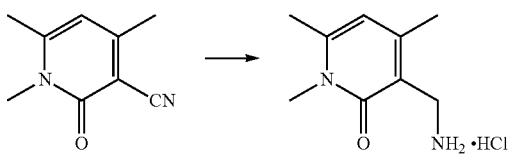

A dried 500 mL Parr bottle was charged with NaOAc (1.871 g, 22.81 mmol), Pd/C (1.968 g, 0.925 mmol) and PtO$_2$ (0.014 g, 0.062 mmol). A small amount of AcOH was added to wet the catalysts. 1,4,6-Trimethyl-2-oxo-1,2-dihydro-3-pyridinecarbonitrile (2.0 g, 12.33 mmol) was dissolved in AcOH (175 mL) [note: heating was necessary to achieve complete dissolution]. The warm solution was added to the Parr bottle. The Parr bottle was kept under nitrogen during reagent transfers. The reaction mixture was shaken at 40 psi of H2 for about 1 h. The agitation was stopped and the mixture was allowed to stand under H2 (40 psi) overnight. The next day the shaking was commenced until H2 consumption ceased. The agitation was stopped and the mixture was allowed to stand under H2 (40 psi) for 1 h, at which time the reaction mixture was filtered through Celite® and washed with a small amount of AcOH. The mixture was concentrated and the resultant residue was dissolved in concentrated HCl (12 mL). The solid NaCl was filtered off and the filtrate was concentrated. The residue was dissovled in concentrated HCl (1 mL) and further diluted with EtOH (13 mL). The flask was scratched and cooled to give a white solid. The mixture was cooled in a freezer for 30 min, at which time it was filtered and the solids washed with cold EtOH (5 mL). The collected solids were dried under vacuum (45° C.) to provide 3-(aminomethyl)-1,4,6-trimethyl-2(1H)-pyridinone hydrochloride (1.10 g, 5.43 mmol, 44.0% yield) as a white solid. $^1$H NMR (400 MHz, DMSO-d$_6$) δ 2.23 (s, 3H) 2.35 (s, 3H) 3.46 (s, 3H) 3.78 (q, J=5.73 Hz, 2H) 6.14 (s, 1H) 8.15 (br. s., 3H). MS(ES) [M+H]$^+$ 150.1.

Intermediate 6

Methyl 4-methylthiophene-3-carboxylate

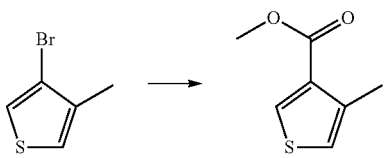

To a solution of 3-bromo-4-methylthiophene (25 g, 141 mmol) in THF (50 mL) under nitrogen at RT was added dropwise isopropylmagnesium chloride lithium chloride complex (1.3 N in THF, 120 mL, 156 mmol). The reaction was maintained for 24 h, at which time it was cooled to −78° C. and treated with methyl chloroformate (12 mL, 155 mmol) in one portion. The reaction was allowed to warm slowly to RT and stirred overnight. The reaction was concentrated under vacuum to remove most of the THF and diluted with EtOAc (200 mL). The solution was added to saturated NaHCO$_3$ (300 mL) and stirred for 60 min (the aqueous phase contained a white suspension). The mixture was transferred to a separatory funnel and the aqueous phase containing the white suspension was removed. The EtOAc phase washed with brine, dried over Na$_2$SO$_4$, filtered and concentrated under vacuum. The product was short path distilled under vacuum (3 to 2 mmHg). The main fraction distilled at 55 to 65° C. (oil bath 75 to 90° C.) and contained methyl 4-methylthiophene-3-carboxylate (15.3 g, 98 mmol, 69.4% yield) as a clear liquid (94% pure by LCMS). The forerun (3.2 g, 20.48 mmol, 14.5%) was 88% pure by LCMS. $^1$H NMR (400 MHz, CDCl$_3$) δ 8.10 (d, J=3.5 Hz, 1H), 6.95 (dd, J=1.1, 3.4 Hz, 1H), 3.87 (s, 3H), 2.49 (d, J=1.0 Hz, 3H). MS(ES) [M+H]$^+$ 156.8.

Intermediate 7

Methyl 5-amino-4-methylthiophene-3-carboxylate

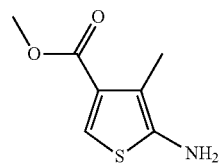

a) Methyl 4-methyl-5-nitrothiophene-3-carboxylate

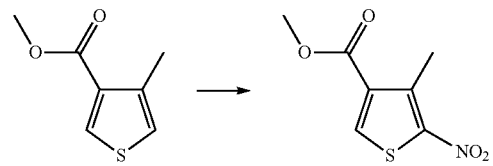

To a cold (0° C.) solution of Ac$_2$O (82 mL, 864 mmol) was added dropwise nitric acid (38.6 mL, 864 mmol), keeping the temperature below 5° C. The solution was maintained for 30 min, at which time a solution of methyl 4-methylthiophene-3-carboxylate (15 g, 96 mmol) in Ac$_2$O (82 mL, 864 mmol) was added dropwise, again keeping the temperature below 5° C. The reaction mixture was stirred at 5° C. for 30 min and poured into ice water (800 mL). The solids were filtered, suspended in water (300 mL), stirred for 30 min and filtered again. Methyl 4-methyl-5-nitrothiophene-3-carboxylate (20 g, 94 mmol, 98% yield) was isolated as white solid. $^1$H NMR (400 MHz, DMSO-d$_6$) δ 8.61 (s, 1H), 3.83 (s, 3H), 2.78 (s, 3H). MS(ES) [M+H]$^+$ 201.9.

b) Methyl 5-amino-4-methylthiophene-3-carboxylate

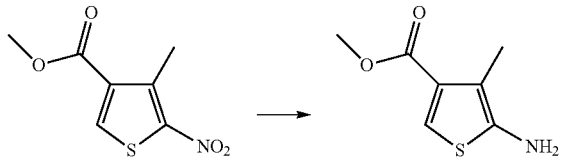

A solution of methyl 4-methyl-5-nitrothiophene-3-carboxylate (10 g, 49.7 mmol) in EtOAc (350 mL) was degassed under $N_2$. To the solution was added 10% Pd/C (wet Degussa, 13.22 g, 12.43 mmol), followed by triethylsilane (35.7 mL, 224 mmol) dropwise over 30 min (H2 evolution). The reaction mixture was stirred for 30 min at RT, at which time it was filtered through Celite®. The mixture was diluted with saturated $NH_4C_1$ (50 mL) and the layers were separated. The organic layer was extracted with 1 M HCl (2×50 mL). The acidic solution was neutralized with 6 M NaOH (to pH-8.5) and extracted with $Et_2O$ (200 mL). The organic layer was washed with brine, dried over $MgSO_4$, filtered and evaporated. Methyl 5-amino-4-methylthiophene-3-carboxylate (5.2 g, 28.9 mmol, 58.1% yield) was isolated as yellow solid. $^1$H NMR (400 MHz, CDCl3) δ 7.43 (s, 1H), 3.84 (s, 3H), 2.27 (s, 3H). MS(ES) $[M+H]^+$ 171.9.

Intermediate 8

Methyl 5-(ethylamino)-4-methylthiophene-3-carboxylate

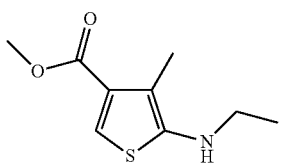

a) Methyl 5-((tert-butoxycarbonyl)amino)-4-methylthiophene-3-carboxylate

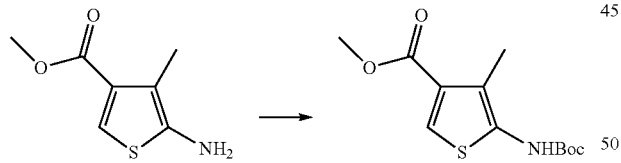

To a solution of methyl 5-amino-4-methylthiophene-3-carboxylate (1.28 g, 7.48 mmol) in MeOH (100 mL) was added $Boc_2O$ (6.08 ml, 26.2 mmol), followed by TEA (3.65 ml, 26.2 mmol). The reaction was stirred at 50° C. for 48 h. Additional $Boc_2O$ (2 eq) was added and the reaction mixture stirred for another 24 h. The solution was evaporated and the resulting oil was partitioned between water (100 mL) and EtOAc (100 mL). The organic layer was washed with brine, dried over $MgSO_4$, filtered and evaporated. Purification of the residue by column chromatography (10% EtAOc: hexane) gave methyl 5-((tert-butoxycarbonyl)amino)-4-methylthiophene-3-carboxylate (1.25 g, 4.38 mmol, 58.5% yield) as a colorless liquid. $^1$H NMR (400 MHz, CDCl3) δ 7.75 (s, 1H), 6.60 (br. s., 1H), 3.85 (s, 3H), 2.34 (s, 3H), 1.54 (s, 9H). MS(ES) $[M+H]^+$ 272.0.

b) Methyl 5-((tert-butoxycarbonyl)(ethyl)amino)-4-methylthiophene-3-carboxylate

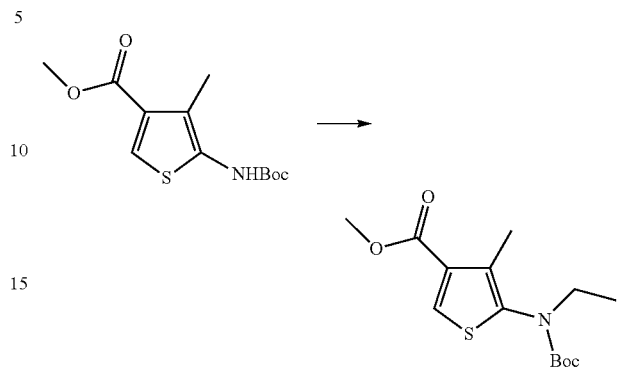

To a cooled (5° C.) solution of methyl 5-((tert-butoxycarbonyl)amino)-4-methylthiophene-3-carboxylate (1.25 g, 4.61 mmol) in anhydrous DMF (50 ml) was added 60% NaH (0.276 g, 6.91 mmol). The reaction was stirred for 30 min, at which time ethyl iodide (0.447 ml, 5.53 mmol) was added. The reaction (in an ice bath) was stirred for 3 h, at which time it was diluted with saturated $NH_4C_1$ and EtOAc (200 mL). The organic layer was washed with water and brine, dried over $MgSO_4$, filtered and evaporated to give methyl 5-((tert-butoxycarbonyl)(ethyl)amino)-4-methylthiophene-3-carboxylate (1.28 g, 4.06 mmol, 88% yield) as a colorless oil. $^1$H NMR (400 MHz, CDCl3) δ 7.96 (s, 1H), 3.87 (s, 3H), 3.61 (q, J=7.07 Hz, 2H), 2.26 (s, 3H), 1.41 (br. s., 9H), 1.16 (t, J=7.07 Hz, 3H). MS(ES) $[M+H]^+$ 322.0.

c) Methyl 5-(ethylamino)-4-methylthiophene-3-carboxylate

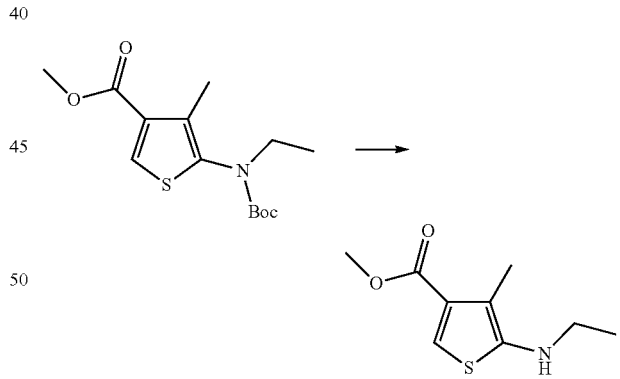

To a solution of methyl 5-((tert-butoxycarbonyl)(ethyl) amino)-4-methylthiophene-3-carboxylate (1.1 g, 3.67 mmol) in $CHCl_3$ (20 mL) was added TFA (10 mL). The reaction mixture was stirred for 1 h, at which time it was evaporated. The residue was partitioned between $Et_2O$ (100 mL) and 1 M $Na_2CO_3$ (50 mL). The organic layer was washed with brine, dried over $MgSO_4$, filtered and evaporated to give methyl 5-(ethylamino)-4-methylthiophene-3-carboxylate (920 mg, 4.39 mmol, 119% yield) as a yellow oil. $^1$H NMR (400 MHz, CDCl3) δ 7.44 (s, 1H), 3.78-3.86 (m, 3H), 3.19 (q, J=7.07 Hz, 3H), 2.26 (s, 3H), 1.29 (t, J=7.07 Hz, 4H). MS(ES) $[M+H]^+$ 199.0.

Intermediate 9

(E)-1-(trans)-4-((tert-butoxycarbonyl)amino)cyclohexyl)prop-1-en-1-yl trifluoromethanesulfonate

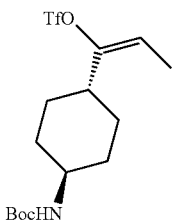

a) tert-Butyl ((trans)-4-(methoxy(methyl)carbamoyl)cyclohexyl)carbamate

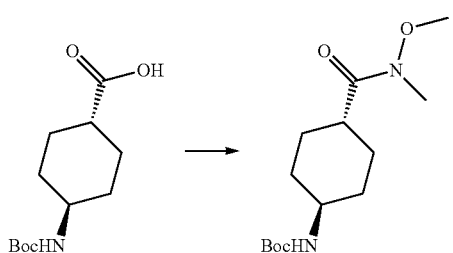 [SMILES: CC(C)(C)OC(=O)N[C@H]1CC[C@H](C(=O)O)CC1 ; CON(C)C(=O)[C@H]1CC[C@H](NC(=O)OC(C)(C)C)CC1]

To a stirred mixture of (trans)-4-((tert-butoxycarbonyl)amino)cyclohexanecarboxylic acid (2.0 g, 8.22 mmol), N,O-dimethylhydroxylamine hydrochloride (0.9 g, 9.23 mmol), and HOAt (1.2 g, 8.82 mmol) in DCM (30 mL) was added DIPEA (1.6 mL, 9.16 mmol) and EDC free base (1.5 g, 9.66 mmol). The reaction was stirred overnight at RT, at which time it was diluted with DCM, washed with 1 N HCl and brine, dried over $Na_2SO_4$, filtered and concentrated under vacuum. The reaction was purified by silica gel chromatography (Isco RediSep Rf Gold 80 g, 30 to 70% EtOAc in hexanes) (UV negative) to give tert-butyl ((trans)-4-(methoxy(methyl)carbamoyl)cyclohexyl)carbamate (2.05 g, 7.16 mmol, 87% yield) as a white solid. $^1$H NMR (400 MHz, CDCl3) δ 4.39 (br. s., 1H), 3.71 (s, 3H), 3.45 (br. s., 1H), 3.19 (s, 3H), 2.63 (t, J=11.62 Hz, 1H), 2.11 (d, J=9.85 Hz, 2H), 1.84-1.96 (m, 1H), 1.56-1.75 (m, 3H), 1.46 (s, 9H), 1.16 (dq, J=3.41, 12.59 Hz, 2H). MS(ES) [M+H]$^+$-isobutylene 231.0, M+Na$^+$ 309.1.

b) tert-Butyl ((trans)-4-propionylcyclohexyl)carbamate

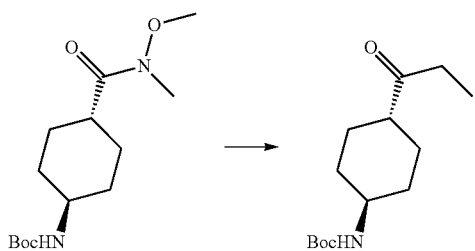 [SMILES: CON(C)C(=O)[C@H]1CC[C@H](NC(=O)OC(C)(C)C)CC1 ; CCC(=O)[C@H]1CC[C@H](NC(=O)OC(C)(C)C)CC1]

To a cooled (0° C.) solution of tert-butyl ((trans)-4-(methoxy(methyl)carbamoyl)cyclohexyl)carbamate (1.0 g, 3.49 mmol) in THF (15 mL) under nitrogen was added dropwise ethylmagnesium chloride (2 M in THF, 4.5 mL, 9.0 mmol) over 5 min. The reaction was maintained for 4 h at 0° C., at which time it was quenched with saturated $NH_4C_1$. The mixture was extracted with EtOAc, washed with brine, dried over $Na_2SO_4$, filtered and evaporated to dryness. The residue was purified by silica gel chromatography (Isco RediSep Rf Gold 80 g, 10 to 35% EtOAc in hexanes) (UV negative) to give tert-butyl ((trans)-4-propionylcyclohexyl)carbamate (0.77 g, 3.02 mmol, 86% yield) as a white solid. $^1$H NMR (400 MHz, CDCl3) δ 4.39 (br. s., 1H), 3.41 (br. s., 1H), 2.47 (q, J=7.24 Hz, 2H), 2.29 (tt, J=3.32, 12.09 Hz, 1H), 2.07-2.18 (m, 2H), 1.84-2.00 (m, 2H), 1.39-1.54 (m, 10H), 1.08-1.22 (m, 2H), 1.05 (t, J=7.33 Hz, 3H). MS(ES) [M+H]$^+$-Boc 156.0, [M+H]$^+$-isobutylene 199.9, M+Na$^+$ 278.1.

c) (E)-1-(trans)-4-((tert-butoxycarbonyl)amino)cyclohexyl)prop-1-en-1-yl trifluoromethanesulfonate

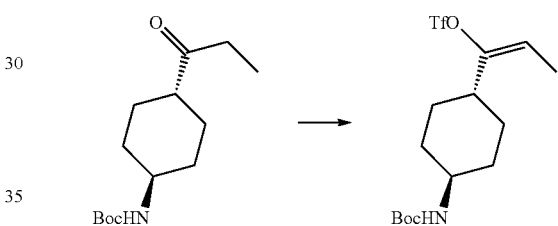

To a cooled (−78° C.) solution of tert-butyl ((trans)-4-propionylcyclohexyl)carbamate (0.7 g, 2.74 mmol) in THF (15 mL) under nitrogen was added dropwise sodium bis(trimethylsilyl)amide (1 M in THF, 5.5 mL, 5.50 mmol). The reaction became heterogeneous (white suspension). After 45 min, a solution of 1,1,1-trifluoro-N-(pyridine-2-yl)-N-((trifluoromethyl)sulfonyl)methanesulfonamide (1.1 g, 3.07 mmol) in THF (5 mL) was added. The reaction was stirred at −78° C. for 1 h (the reaction slowly became homogeneous), then was allowed to warm to 0° C. in an ice bath and stirred for another 30 min. The reaction was quenched with cold water, extracted with EtOAc, washed with brine, dried over $Na_2SO_4$, filtered and evaporated to dryness under vacuum. The residue was purified by silica gel chromatography (Isco RediSep Rf Gold 40 g, 5 to 20% EtOAc in hexanes) (UV negative) to give (E)-1-(trans)-4-((tert-butoxycarbonyl)amino)cyclohexyl)prop-1-en-1-yl trifluoromethanesulfonate (0.93 g, 2.401 mmol, 88% yield) as a colorless oil. The product solidified to a white solid under vacuum. $^1$H NMR shows a single olefinic proton, which is assumed to be the E-olefin based on chemical shifts. $^1$H NMR (400 MHz, CDCl3) δ 5.28-5.38 (m, 1H), 4.39 (br. s., 1H), 3.42 (br. s., 1H), 2.19 (t, J=11.49 Hz, 1H), 1.94-2.13 (m, 4H), 1.75 (dd, J=1.52, 6.82 Hz, 3H), 1.46 (s, 9H), 1.07-1.37 (m, 5H). MS(ES) [M+H]$^+$-isobutylene 332.0.

Intermediate 10

Methyl 4-methyl-5-(4,4,5,5-tetramethyl-1,3,2-dioxaborolan-2-yl)thiophene-3-carboxylate

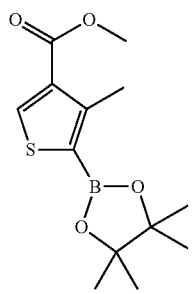 [SMILES: COC(=O)c1csc(B2OC(C)(C)C(C)(C)O2)c1C]

a) Methyl 5-iodo-4-methylthiophene-3-carboxylate

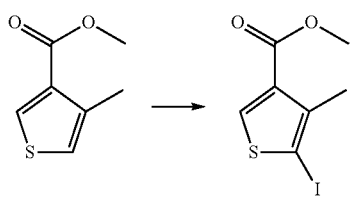

To a solution of methyl 4-methylthiophene-3-carboxylate (5.0 g, 32.0 mmol) in DMF (50 mL) was added NIS (12.5 g, 55.6 mmol). The reaction was heated at 100° C. for 24 h. The reaction was diluted with EtOAc, washed with aqueous $Na_2S_2O_3$ and brine, dried over $Na_2SO_4$, filtered and evaporated to dryness. The residue was purified by silica gel chromatography (Analogix, SF25-60 g, 0 to 10% EtOAc in hexanes) to give methyl 5-iodo-4-methylthiophene-3-carboxylate (7.89 g, 28.0 mmol, 87% yield) as a light tan solid. $^1$H NMR (400 MHz, CDCl3) δ 8.26 (s, 1H), 3.87 (s, 3H), 2.47 (s, 3H). MS(ES) [M+H]$^+$282.8.

b) Methyl 4-methyl-5-(4,4,5,5-tetramethyl-1,3,2-dioxaborolan-2-yl)thiophene-3-carboxylate

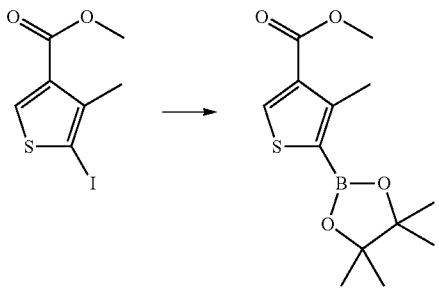 [SMILES: COC(=O)c1csc(I)c1C ; COC(=O)c1csc(B2OC(C)(C)C(C)(C)O2)c1C]

To a solution of methyl 5-iodo-4-methylthiophene-3-carboxylate (1.0 g, 3.54 mmol) and copper(I) iodide (70 mg, 0.368 mmol) in THF (15 mL) was added NaH (60% in mineral oil, 213 mg, 5.33 mmol) under a nitrogen atmosphere. To the reaction was added a solution of 1 N 4,4,5, 5-tetramethyl-1,3,2-dioxaborolane in THF (5.32 mL, 5.32 mmol) via syringe dropwise over 5 min. The reaction was stirred for 3 days at RT. LCMS show no starting bromide, 79% desired boronate plus boronic acid, and 20% des-bromo thiophene. The reaction was quenched with saturated $NH_4Cl$ and extracted with EtOAc. The organic phase was filtered, washed with brine, dried over $Na_2SO_4$, filtered, and evaporated to dryness. The residue was purified by silica gel chromatography (Isco RediSep Rf Gold 40 g, 10 to 100% DCM in hexanes) to give methyl 4-methyl-5-(4,4,5,5-tetramethyl-1,3,2-dioxaborolan-2-yl)thiophene-3-carboxylate (550 mg, 1.949 mmol, 55.0% yield) as a colorless oil. The product solidified to a waxy white solid under vacuum. The reaction was repeated on a 5.0 g, 17.72 mmol scale to give an additional (1.44 g, 5.10 mmol, 28.8%) product identical with the above. $^1$H NMR (400 MHz, CDCl3) δ 8.32 (s, 1H), 3.87 (s, 3H), 2.70 (s, 3H), 1.36 (s, 12H). MS(ES) [M+H]$^+$ 200.9 (boronic acid), [M+H]$^+$ 283.1 (boronate).

Intermediate 11

Methyl 5-(1-((trans)-4-(dimethylamino)cyclohexyl)propyl)-4-methylthiophene-3-carboxylate

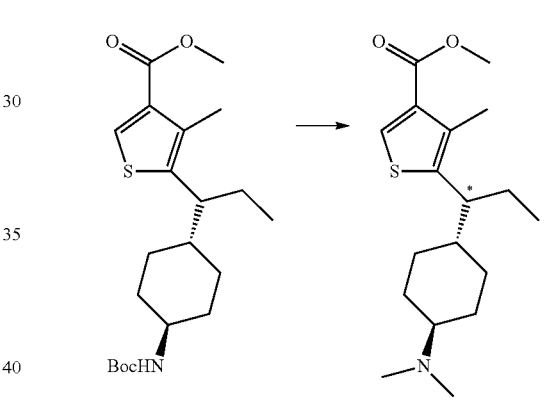

To a solution of methyl 5-(1-((trans)-4-((tert-butoxycarbonyl)amino)cyclohexyl)propyl)-4-methylthiophene-3-carboxylate (2.9 g, 7.33 mmol) in MeOH (4 mL) was added 4 N HCl in 1,4-dioxane (30 mL, 120 mmol). The reaction was stirred for 45 min, at which time it was evaporated to dryness, re-evaporated with MeOH (2×), and once with n-hexanes/DCM and dried under vacuum to give the amine hydrochloride as a white solid.

The solid from above was dissolved in EtOH (75 mL) and treated with formaldehyde (37 wt % in water, 6.0 mL, 81 mmol) and NaOAc (0.65 g, 7.92 mmol). The reaction was stirred for 15 min, at which time $NaBH(OAc)_3$ (6.3 g, 29.7 mmol) was added. The reaction was stirred at room temperature for 2 h. The reaction was evaporated to dryness under vacuum, taken up in DCM, washed with 1 N $Na_2CO_3$, dried over $Na_2SO_4$, filtered and concentrated under vacuum. The residue was purified by silica gel chromatography (Analogix®, Isco® RediSep Rf Gold 80 g, 4 to 16% $NH_4OH$/MeOH in DCM) to give methyl 5-(1-((trans)-4-(dimethylamino)cyclohexyl)propyl)-4-methylthiophene-3-carboxylate (2.17 g, 6.71 mmol, 91% yield) as a colorless oil. $^1$H NMR (400 MHz, CDCl3) δ 7.99 (s, 1H), 3.85 (s, 3H), 3.50 (s, 1H), 2.69 (ddd, J=3.92, 7.77, 11.05 Hz, 1H), 2.29 (s, 6H), 2.03-2.22 (m, 3H), 1.77-2.00 (m, 4H), 1.56-1.68 (m, 1H), 1.35-1.52 (m, 2H), 1.07-1.31 (m, 2H), 0.87-1.07 (m, 2H), 0.76 (t, J=7.33 Hz, 3H). MS(ES) [M+H]$^+$ 324.2.

The racemate was resolved by preparative chiral HPLC (Chiralpak® AD-H, 5 microns, 50 mm×250 mm, 250 nm UV absorption, 100 mL/min, 22° C., 0.1% isopropylamine in MeOH) to give the purified enantiomers of unknown absolute configuration at C*.

Data for (+)-methyl 5-(1-((trans)-4-(dimethylamino)cyclohexyl)propyl)-4-methylthiophene-3-carboxylate. [α]$_D$= +28.0° (methanol, c=0.5, 24° C.).

Data for (−)-methyl 5-(1-((trans)-4-(dimethylamino)cyclohexyl)propyl)-4-methylthiophene-3-carboxylate. [α]$_D$= −27.6° (methanol, c=0.5, 24° C.).

EXAMPLES

Example 1

N-((4,6-dimethyl-2-oxo-1,2-dihydropyridin-3-yl)methyl)-4-isopropoxy-3-methylthiophene-2-carboxamide

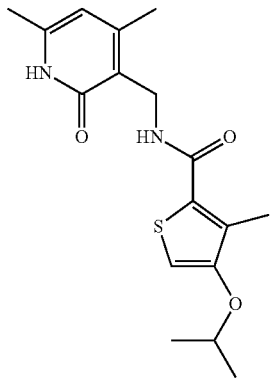

To a cooled (ice bath) solution of isopropyl alcohol (3.49 mL, 45.2 mmol) and DMF (20 mL) was added 60% NaH (1.809 g, 45.2 mmol) in portions. The mixture was stirred for 15 min, at which time the ice bath was removed. The reaction was stirred at RT overnight, at which time 4-bromo-3-methylthiophene-2-carboxylic acid (1.0 g, 4.52 mmol) and CuBr (0.162 g, 1.131 mmol) were added. The reaction was stirred well for 5 min, then heated at 120° C. overnight. The reaction was allowed to cool to RT and was poured into ice/saturated NH$_4$C$_1$. The mixture was extracted with EtOAc (3×) and the combined organics were dried over MgSO$_4$, filtered through Celite®, and concentrated to give crude 4-isopropoxy-3-methylthiophene-2-carboxylic acid as a solid.

To a mixture of the crude 4-isopropoxy-3-methylthiophene-2-carboxylic acid, 3-(aminomethyl)-4,6-dimethyl-2 (1H)-pyridinone hydrochloride (1.130 g, 5.99 mmol), HOAt (0.816 g, 5.99 mmol), and EDC (1.149 g, 5.99 mmol) in DMF (25 mL) was added NMM (2.196 mL, 19.97 mmol). The reaction was stirred at RT overnight, at which time it was poured into ice water (250 mL). The mixture was extracted with EtOAc (3×100 mL) and the combined organics were dried over MgSO$_4$, filtered and concentrated. The residue was dissolved in MeOH/DCM, adsorbed onto silica gel, and purified by column chromatography (40 g silica column; Gradient of B: 5-65%, A: DCM, B: 10% (2 M NH$_3$ in MeOH) in CHCl$_3$). The residue was further purified by preparative HPLC (Gilson; Gradient of B: 10-65%, A: water+0.1% TFA, B: CH$_3$CN+0.1% TFA). The resultant residue was dissolved in MeOH/DCM and a few drops of NH$_4$OH were added. The solution was filtered through a pad of silica and washed with 10% (2 M NH$_3$ in MeOH) in CHCl$_3$ (60 mL). The solution was concentrated and the residue solidified from evaporation with TBME to give N-((4,6-dimethyl-2-oxo-1,2-dihydropyridin-3-yl)methyl)-4-isopropoxy-3-methylthiophene-2-carboxamide (7 mg, 0.411%). $^1$H NMR (DMSO-d$_6$) δ 11.55 (br. s., 1H), 7.83-7.94 (m, 1H), 6.70 (s, 1H), 5.87 (s, 1H), 4.37-4.49 (m, 1H), 4.25 (d, J=5.3 Hz, 2H), 2.18 (s, 3H), 2.15 (s, 3H), 2.11 (s, 3H), 1.26 (d, J=6.1 Hz, 6H). MS(ES) [M+H]$^+$ 335.2.

Example 2

N-((4,6-Dimethyl-2-oxo-1,2-dihydropyridin-3-yl)methyl)-4-(ethyl(tetrahydro-2H-pyran-4-yl)amino)-3-methylthiophene-2-carboxamide

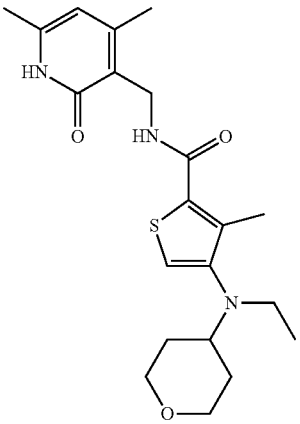 [SMILES: CCN(c1csc(C(=O)NCc2c(C)cc(C)[nH]c2=O)c1C)C1CCOCC1]

a) Methyl 4-bromo-3-methylthiophene-2-carboxylate

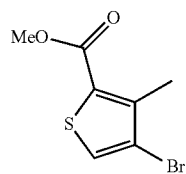

To a solution of 4-bromo-3-mehylthiophene-2-carboxylic acid (5.0 g, 22.62 mmol) in MeOH (75 mL) was added dropwise H$_2$SO$_4$ (6.03 mL, 113 mmol). The mixture was heated at 60° C. for 12 h. The reaction was allowed to cool to RT and was diluted with EtOAc and 1 N HCl. The organic layer was concentrated and the residue was precipitated from MeOH/water (9/1). The white solid was dried under vacuum to give methyl 4-bromo-3-methylthiophene-2-carboxylate (4.5 g, 76%). $^1$H NMR (400 MHz, DMSO-d$_6$) δ 8.06 (s, 1H) 3.83 (s, 3H) 2.47 (s, 3H). MS(ES) [M+H]$^+$ 236.8.

b) Methyl 4-amino-3-methylthiophene-2-carboxylate

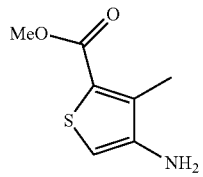

To a 20 mL microwave vial was added methyl 4-bromo-3-methylthiophene-2-carboxylate (2.0 g, 8.51 mmol), $Cs_2CO_3$ (5.54 g, 17.01 mmol), benzophenone imine (2.141 mL, 12.76 mmol), 1,4-dioxane (7 mL), and toluene (7 mL). The mixture was degassed with $N_2$ for 5 min, at which time it was treated with Xantphos (0.984 g, 1.701 mmol) and $Pd_2(dba)_3$ (0.779 g, 0.851 mmol). The vial was capped and heated in a microwave reactor at 80° C. for 12 h. The reaction was allowed to cool to RT and was diluted with saturated $NaHCO_3$. The mixture was extracted with EtOAc, washed with brine, filtered through $Na_2SO_4$ and evaporated. Purification of the residue by silica gel chromatography (Varian 971FP, 0-20% EtOAc/hexanes, SF25-40 g, 9 min) provided the crude imine intermediate as a yellow oil.

To the crude residue in MeOH (20 mL) was added NaOAc (3.49 g, 42.5 mmol) and hydroxylamine hydrochloride (2.365 g, 34.0 mmol). The mixture was stirred at RT for 1.5 h, at which time 0.1 N NaOH was added. The mixture was extracted with DCM and concentrated. The residue was purified by reverse phase preparative HPLC (Gilson; 5-55% $CH_3CN$/water+0.1% TFA, YMC ODS-A C18 column 75×30 mm ID S-5 um) and diluted with 0.1 N NaOH. The mixture was extracted with EtOAc and concentrated to give methyl 4-amino-3-methylthiophene-2-carboxylate (930 mg, 60.0%) as an oily semi-solid. $^1$H NMR (400 MHz, CDCl3) δ 6.40 (s, 1H) 3.87 (s, 3H) 2.43 (s, 3H). MS(ES) [M+H]$^+$ 171.9.

c) Methyl 4-(ethyl(tetrahydro-2H-pyran-4-yl)amino)-3-methylthiophene-2-carboxylate

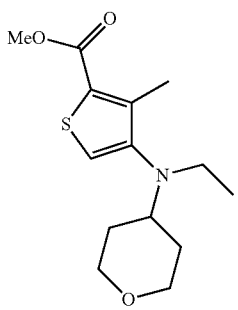 [SMILES: CCN(c1csc(C(=O)OC)c1C)C1CCOCC1]

To a solution of methyl 4-amino-3-methylthiophene-2-carboxylate (540 mg, 3.15 mmol) in DCE (10 mL) was added AcOH (0.361 mL, 6.31 mmol) and dihydro-2H-pyran-4(3H)-one (347 mg, 3.47 mmol). The reaction was maintained at RT for 20 min, at which time $NaBH(OAc)_3$ (2674 mg, 12.62 mmol) was added portion wise. The reaction was stirred for 90 min. LCMS showed the reaction was complete. To the reaction mixture was added acetaldehyde (0.214 mL, 3.78 mmol) and $NaBH(OAc)_3$ (~100 mg). The reaction was stirred for 1 h, at which time it was quenched with saturated $NaHCO_3$, extracted with DCM, and concentrated. The residue was purified by silica gel chromatography (Varian 971IF, 0-100% EtOAc/hexanes, SF25-40 g) to give methyl 4-(ethyl(tetrahydro-2H-pyran-4-yl)amino)-3-methylthiophene-2-carboxylate (700 mg, 74.4%) as an oil. $^1$H NMR (400 MHz, CDCl$_3$) δ 7.01 (s, 1H) 3.95-4.03 (m, 2H) 3.88 (s, 3H) 3.35 (td, J=11.68, 2.15 Hz, 2H) 3.02 (d, J=7.07 Hz, 3H) 2.43 (s, 3H) 1.73 (br. s., 2H) 1.63 (br. s., 2H) 0.93 (t, J=6.95 Hz, 3H). MS(ES) [M+H]$^+$ 284.0.

d) N-((4,6-Dimethyl-2-oxo-1,2-dihydropyridin-3-yl)methyl)-4-(ethyl(tetrahydro-2H-pyran-4-yl)amino)-3-methylthiophene-2-carboxamide

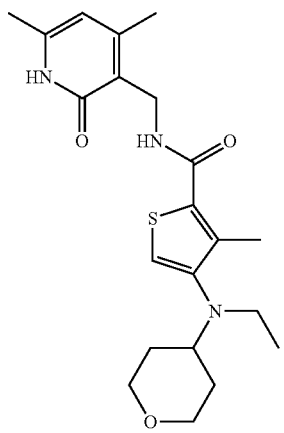 [SMILES: CCN(c1csc(C(=O)NCc2c(C)cc(C)[nH]c2=O)c1C)C1CCOCC1]

To a solution of methyl 4-(ethyl(tetrahydro-2H-pyran-4-yl)amino)-3-methylthiophene-2-carboxylate (150 mg, 0.529 mmol) in MeOH was added 5 N NaOH (0.635 mL, 3.18 mmol). The reaction was stirred at RT for 2 h, then at 40° C. for 4 h. The reaction was allowed to cool to RT and was diluted with 6 N HCl (0.529 mL, 3.18 mmol). The mixture was concentrated, diluted with DCM, and concentrated again.

To a solution of the crude residue in DMSO (5 mL) was added NMM (0.291 mL, 2.65 mmol), 3-(aminomethyl)-4,6-dimethylpyridin-2(1H)-one (97 mg, 0.635 mmol), EDC (203 mg, 1.059 mmol), HOBt (162 mg, 1.059 mmol), and more NMM (0.291 mL, 2.65 mmol). The reaction was maintained at RT for 18 h, at which time it was purified by reverse phase HPLC (Gilson; 5-50% $CH_3CN$/water+0.1% TFA, YMC ODS-A C18 column 75×30 mm ID S-5 um). The residue was partitioned between EtOAc/MeOH and 0.1 N NaOH. The organic layer was concentrated, diluted with DCM, and concentrated again to provide N-((4,6-dimethyl-2-oxo-1,2-dihydropyridin-3-yl)methyl)-4-(ethyl(tetrahydro-2H-pyran-4-yl)amino)-3-methylthiophene-2-carboxamide (100 mg, 44.5%) as a white foam. ¹H NMR (400 MHz, DMSO-d₆) δ 11.56 (br. s., 1H) 7.84 (t, J=5.18 Hz, 1H) 7.19 (s, 1H) 5.88 (s, 1H) 4.27 (d, J=5.05 Hz, 2H) 3.80-3.87 (m, 2H) 3.24 (t, J=10.99 Hz, 2H) 2.96 (q, J=6.82 Hz, 3H) 2.21 (d, J=8.84 Hz, 6H) 2.12 (s, 3H) 1.62 (br. s., 2H) 1.44 (dd, J=11.87, 3.79 Hz, 2H) 0.83 (t, J=6.95 Hz, 3H). MS(ES) [M+H]⁺ 404.1.

Example 3

5-Chloro-N-((4,6-dimethyl-2-oxo-1,2-dihydropyridin-3-yl)methyl)-4-(ethyl(tetrahydro-2H-pyran-4-yl)amino)-3-methylthiophene-2-carboxamide

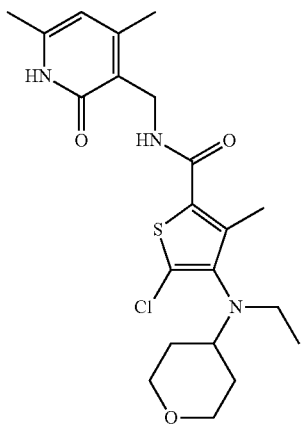 [SMILES: CCN(c1c(Cl)sc(C(=O)NCc2c(C)cc(C)[nH]c2=O)c1C)C1CCOCC1]

a) Methyl 5-chloro-4-(ethyl(tetrahydro-2H-pyran-4-yl)amino)-3-methylthiophene-2-carboxylate

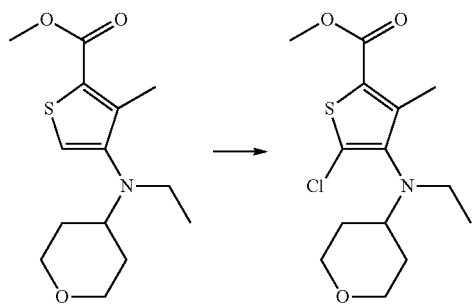 [SMILES: CCN(c1csc(C(=O)OC)c1C)C1CCOCC1 ; CCN(c1c(Cl)sc(C(=O)OC)c1C)C1CCOCC1]

To a solution of methyl 4-(ethyl(tetrahydro-2H-pyran-4-yl)amino)-3-methylthiophene-2-carboxylate (500 mg, 1.764 mmol) in CH₃CN (10 mL) was added NCS (353 mg, 2.65 mmol). The mixture was stirred at RT for 24 h, at which time it was quenched with 10% Na₂S₂O₃ and extracted with EtOAc. Purification by silica gel chromatography (Varian 971, 0-20% EtOAc/hexanes, SF25-40 g, 9 min) provided methyl 5-chloro-4-(ethyl(tetrahydro-2H-pyran-4-yl)amino)-3-methylthiophene-2-carboxylate (350 mg, 59.3%) as an oil. ¹H NMR (400 MHz, CDCl₃-d) δ 3.96 (br. s., 2H) 3.87 (s, 3H) 3.31-3.45 (m, 4H) 3.02-3.24 (m, 1H) 2.43 (s, 3H) 1.43-1.87 (m, 4H) 0.94 (t, 3H). MS(ES) [M+H]⁺ 318.0.

b) 5-Chloro-N-((4,6-dimethyl-2-oxo-1,2-dihydropyridin-3-yl)methyl)-4-(ethyl(tetrahydro-2H-pyran-4-yl)amino)-3-methylthiophene-2-carboxamide

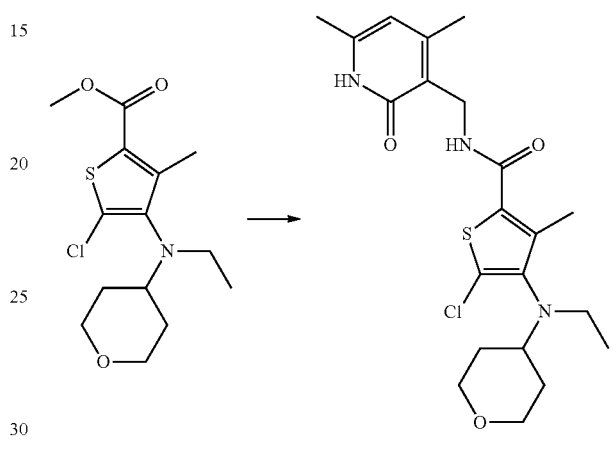

To a solution of methyl 5-chloro-4-(ethyl(tetrahydro-2H-pyran-4-yl)amino)-3-methylthiophene-2-carboxylate (150 mg, 0.472 mmol) in MeOH was added 5 N NaOH (0.566 mL, 2.83 mmol). The mixture was heated at 40° C. for 2 h, at which time 6 N HCl (0.472 mL, 2.83 mmol) was added. The mixture was concentrated, diluted with DCM, and concentrated again.

To a solution of the crude material in DMSO (5 mL) was added NMM (0.259 mL, 2.360 mmol) and 3-(aminomethyl)-4,6-dimethylpyridin-2(1H)-one (86 mg, 0.566 mmol), followed by EDC (181 mg, 0.944 mmol), HOBT (145 mg, 0.944 mmol), and more NMM (0.259 mL, 2.360 mmol). The reaction was stirred at RT for 48 h. The reaction mixture was purified directly by reverse phase Gilson HPLC (10-80% CH₃CN/water+0.1% TFA, YMC ODS-A C18 column, 75×30 mm, ID S-5 um, 12 nM column, 7 min). The residue was partitioned between EtOAc/MeOH and saturated NaHCO₃. The organics were concentrated, diluted with DCM, and concentrated again to provide 5-chloro-N-((4,6-dimethyl-2-oxo-1,2-dihydropyridin-3-yl)methyl)-4-(ethyl(tetrahydro-2H-pyran-4-yl)amino)-3-methylthiophene-2-carboxamide (130 mg, 59.7%) as an off white foam. ¹H NMR (400 MHz, DMSO-d₆) δ 11.55 (br. s., 1H) 8.01 (br. s., 1H) 5.88 (s, 1H) 4.25 (d, J=4.80 Hz, 2H) 3.82 (d, J=11.12 Hz, 2H) 3.23-3.31 (m, 3H) 3.12 (br. s., 2H) 2.23 (s, 3H) 2.19 (s, 3H) 2.12 (s, 3H) 1.67 (br. s., 2H) 1.36 (br. s., 2H) 0.85 (t, J=7.20 Hz, 3H). MS(ES) [M+H]⁺ 438.1.

Example 4

N-((4,6-dimethyl-2-oxo-1,2-dihydropyridin-3-yl)methyl)-4-(((trans)-4-(dimethylamino)cyclohexyl)(ethyl)amino)-3-methylthiophene-2-carboxamide

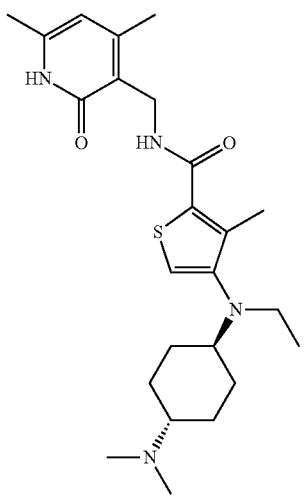 [SMILES: CCN(c1csc(C(=O)NCc2c(C)cc(C)[nH]c2=O)c1C)[C@H]1CC[C@H](N(C)C)CC1]

a) Methyl 4-(((trans)-4-(dimethylamino)cyclohexyl)(ethyl)amino)-3-methylthiophene-2-carboxylate and methyl 4-(((cis)-4-(dimethylamino)cyclohexyl)(ethyl)amino)-3-methylthiophene-2-carboxylate

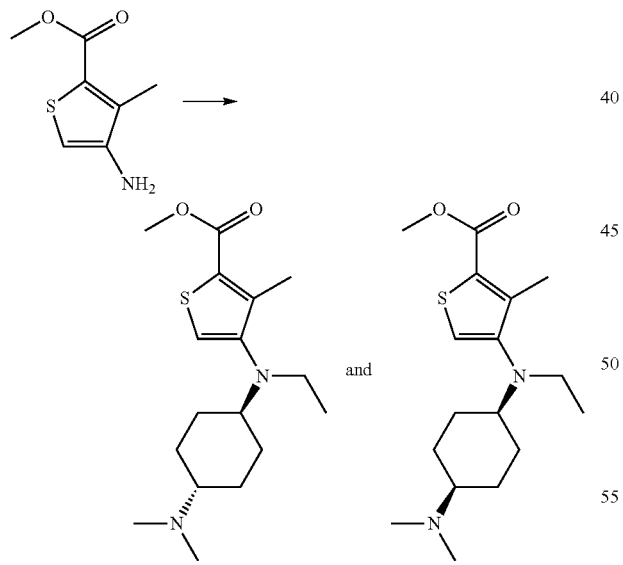

To a solution of methyl 4-amino-3-methylthiophene-2-carboxylate (215 mg, 1.256 mmol), in DCE (10 mL) was added AcOH (0.144 mL, 2.51 mmol) and 4-(dimethylamino)cyclohexanone (195 mg, 1.381 mmol). The reaction was maintained at RT for 40 min, at which time NaBH(OAc)$_3$ (1065 mg, 5.02 mmol) was added portionwise. The mixture was stirred at RT for 30 min, at which time acetaldehyde (0.085 mL, 1.507 mmol) and more NaBH(OAc)$_3$ (1065 mg, 5.02 mmol) were added. The reaction was stirred for 1 h, at which time it was quenched with NaHCO$_3$, extracted with DCM, and concentrated. Purification by reverse phase Gilson HPLC (10-90% CH$_3$CN/water+0.1% TFA, YMC ODS-A C18 column 75×30 mm ID S-5 um, 12 nM column) provided two products (cis and trans diastereomers).

The faster running fractions were concentrated. The residue was partitioned between EtOAc/MeOH and 0.1 N NaOH/brine and the organics were concentrated to give methyl 4-(((trans)-4-(dimethylamino)cyclohexyl)(ethyl)amino)-3-methylthiophene-2-carboxylate (140 mg, 34.4%). Analytical HPLC (Agilent 1100 Series, 5-95% MeCN/H$_2$O+0.1% TFA in each mobile phase, 254 nm, 5 min) shows 95% pure (retention time 1.87 min). $^1$H NMR (400 MHz, CDCl3-d) δ 6.96 (s, 1H) 3.88 (s, 3H) 3.00 (q, J=6.91 Hz, 2H) 2.71 (t, J=2.78 Hz, 1H) 2.42 (s, 3H) 2.30 (s, 6H) 2.17 (br. s., 1H) 1.94 (dd, J=10.11, 2.02 Hz, 4H) 1.19-1.38 (m, 5H) 0.91 (t, J=6.95 Hz, 3H). MS(ES) [M+H]$^+$ 325.1.

The slower running fractions were concentrated. The residue was partitioned between EtOAc/MeOH and 0.1 N NaOH/brine and the organics were concentrated to give methyl 4-(((cis)-4-(dimethylamino)cyclohexyl)(ethyl)amino)-3-methylthiophene-2-carboxylate (110 mg, 27.0%). Analytical HPLC (Agilent 1100 Series, 5-95% MeCN/H$_2$O+0.1% TFA in each mobile phase, 254 nm, 5 min) shows 95% pure (retention time 2.42 min). $^1$H NMR (400 MHz, CDCl3-d) δ 6.98 (s, 1H) 3.88 (s, 3H) 3.14-3.20 (m, 1H) 2.97-3.03 (m, 2H) 2.46 (s, 3H) 2.33 (s, 6H) 2.28 (d, J=9.35 Hz, 1H) 1.86-1.95 (m, 2H) 1.70-1.78 (m, 2H) 1.42-1.49 (m, 4H) 0.90 (t, J=6.95 Hz, 3H). MS(ES) [M+H]$^+$ 325.1.

b) N-((4,6-Dimethyl-2-oxo-1,2-dihydropyridin-3-yl)methyl)-4-(((trans)-4-(dimethylamino)cyclohexyl)(ethyl)amino)-3-methylthiophene-2-carboxamide

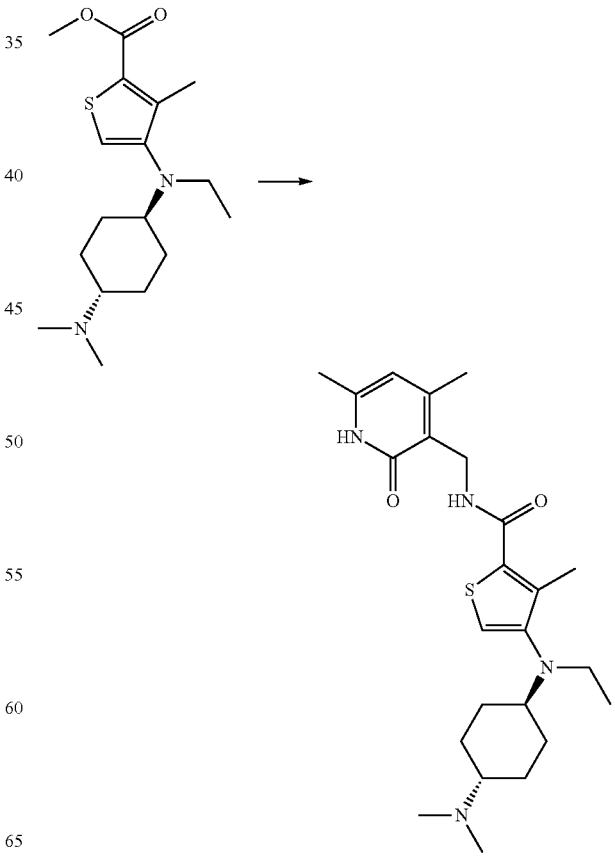

To a solution of methyl 4-(((trans)-4-(dimethylamino)cyclohexyl)(ethyl)amino)-3-methylthiophene-2-carboxylate (140 mg, 0.431 mmol) in MeOH was added 5 N NaOH (0.518 mL, 2.59 mmol). The mixture was stirred overnight at 40° C., at which time 6 N HCl (0.431 mL, 2.59 mmol) was added. The mixture was concentrated, diluted with DCM, and concentrated again.

To a solution of the crude residue in DMSO (5 mL) was added NMM (0.237 mL, 2.157 mmol) and 3-(aminomethyl)-4,6-dimethylpyridin-2(1H)-one (79 mg, 0.518 mmol), followed by EDC (165 mg, 0.863 mmol), HOBT (132 mg, 0.863 mmol), and more NMM (0.237 mL, 2.157 mmol). The reaction was stirred at RT for 48 h. The reaction was purified directly by reverse phase Gilson HPLC (10-60% CH$_3$CN/water+0.1% TFA, YMC ODS-A C18 column 75×30 mm ID S-5 um, 12 nM column). The residue was partitioned between EtOAc/MeOH and 0.1N NaOH. The organics were concentrated, diluted with DCM, concentrated, diluted with hexanes, and concentrated to provide N-((4,6-dimethyl-2-oxo-1,2-dihydropyridin-3-yl)methyl)-4-(((trans)-4-(dimethylamino)cyclohexyl)(ethyl)amino)-3-methylthiophene-2-carboxamide (80 mg, 0.169 mmol, 39.2%) as a white foam. $^1$H NMR (400 MHz, DMSO-d$_6$) δ 11.55 (s, 1H) 7.82 (t, J=5.31 Hz, 1H) 7.10 (s, 1H) 5.88 (s, 1H) 4.26 (d, J=5.31 Hz, 2H) 2.89-3.00 (m, 2H) 2.59-2.69 (m, 1H) 2.10-2.23 (m, 16H) 1.76-1.83 (m, Hz, 4H) 1.14-1.32 (m, 4H) 0.82 (t, J=6.95 Hz, 3H). MS(ES) [M+H]$^+$ 445.2.

Example 5

N-((4,6-dimethyl-2-oxo-1,2-dihydropyridin-3-yl)methyl)-4-(((cis)-4-(dimethylamino)cyclohexyl)(ethyl)amino)-3-methylthiophene-2-carboxamide

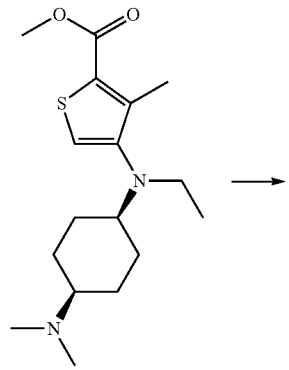

To a 50 solution of methyl 4-(((cis)-4-(dimethylamino)cyclohexyl)(ethyl)amino)-3-methylthiophene-2-carboxylate (110 mg, 0.339 mmol) in MeOH was added 5 N NaOH (0.407 mL, 2.034 mmol). The mixture was stirred overnight at 40° C., at which time 6 N HCl (0.339 mL, 2.034 mmol) was added. The mixture was concentrated, diluted with DCM, and concentrated again.

To a solution of the crude residue in DMSO (5 mL) was added NMM (0.186 mL, 1.695 mmol) and 3-(aminomethyl)-4,6-dimethylpyridin-2(1H)-one (61.9 mg, 0.407 mmol), followed by EDC (130 mg, 0.678 mmol), HOBT (104 mg, 0.678 mmol), and more NMM (0.186 mL, 1.695 mmol). The reaction was stirred at RT for 48 h. The reaction was purified directly by reverse phase Gilson HPLC (10-60% CH$_3$CN/water+0.1% TFA, YMC ODS-A C18 column 75×30 mm ID S-5 um, 12 nM column). The residue was partitioned between EtOAc/MeOH and 0.1N NaOH. The organics were concentrated, diluted with DCM, concentrated, diluted with hexanes, and concentrated to provide N-((4,6-dimethyl-2-oxo-1,2-dihydropyridin-3-yl)methyl)-4-(((cis)-4-(dimethylamino)cyclohexyl)(ethyl)amino)-3-methylthiophene-2-carboxamide (50 mg, 0.107 mmol, 31.5%) as a light yellow solid. $^1$H NMR (400 MHz, DMSO-d$_6$) δ 11.55 (br. s., 1H) 7.83 (t, J=5.18 Hz, 1H) 7.12 (s, 1H) 5.88 (s, 1H) 4.27 (d, J=5.31 Hz, 2H) 2.96-3.02 (m, 1H) 2.91 (q, J=6.82 Hz, 2H) 2.18-2.25 (m, 6H) 2.10-2.16 (m, 9H) 1.95-2.03 (m, 1H) 1.66-1.77 (m, 4H) 1.26-1.42 (m, 4H) 0.82 (t, J=6.82 Hz, 3H). MS(ES) [M+H]$^+$ 445.2.

Example 6

N-((4,6-dimethyl-2-oxo-1,2-dihydropyridin-3-yl)methyl)-5-(ethyl(tetrahydro-2H-pyran-4-yl)amino)-4-methylthiophene-3-carboxamide

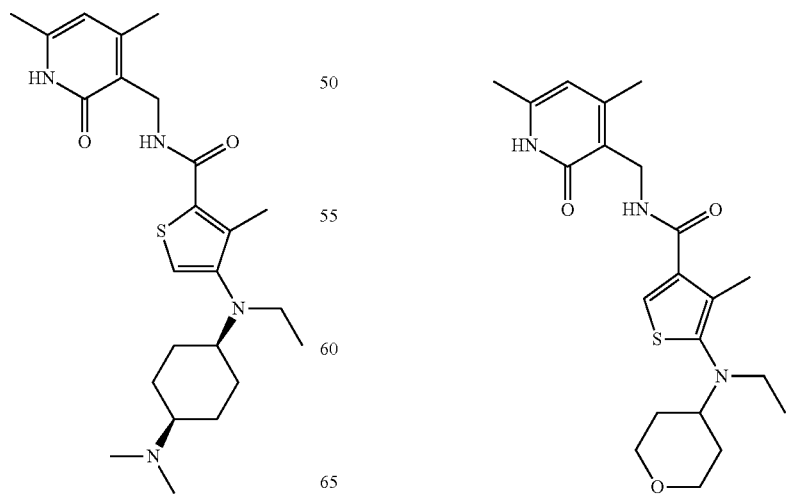

a) Methyl 5-(ethyl(tetrahydro-2H-pyran-4-yl)amino)-4-methylthiophene-3-carboxylate

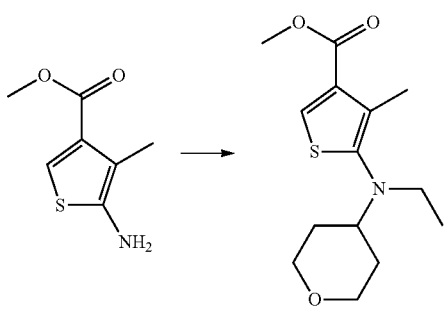

Following the general procedure of Example 2c, commercially available methyl 5-amino-4-methylthiophene-3-carboxylate was converted to methyl 5-(ethyl(tetrahydro-2H-pyran-4-yl)amino)-4-methylthiophene-3-carboxylate (750 mg, 89%). $^1$H NMR (400 MHz, CDCl3) δ 7.95 (s, 1H) 3.99 (dt, J=10.36, 2.02 Hz, 2H) 3.86 (s, 3H) 3.37 (td, J=11.87, 2.02 Hz, 2H) 2.94-3.04 (m, 3H) 2.35 (s, 3H) 1.75-1.82 (m, 2H) 1.58-1.62 (m, 2H) 0.96 (t, J=7.20 Hz, 3H). MS(ES) [M+H]$^+$ 284.0.

b) N-((4,6-Dimethyl-2-oxo-1,2-dihydropyridin-3-yl)methyl)-5-(ethyl(tetrahydro-2H-pyran-4-yl)amino)-4-methylthiophene-3-carboxamide

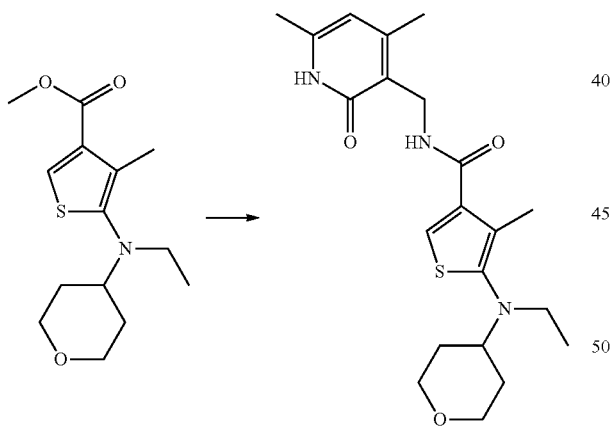

Following the general procedure of Example 2d, methyl 5-(ethyl(tetrahydro-2H-pyran-4-yl)amino)-4-methylthiophene-3-carboxylate was converted to N-((4,6-dimethyl-2-oxo-1,2-dihydropyridin-3-yl)methyl)-5-(ethyl(tetrahydro-2H-pyran-4-yl)amino)-4-methylthiophene-3-carboxamide (210 mg, 70%) as a white solid. $^1$H NMR (400 MHz, DMSO-d$_6$) δ 11.48 (br. s., 1H) 7.97 (t, J=5.05 Hz, 1H) 7.65 (s, 1H) 5.86 (s, 1H) 4.23 (d, J=4.80 Hz, 2H) 3.83 (dd, J=11.75, 2.40 Hz, 2H) 3.22-3.29 (m, 2H) 2.88-2.96 (m, 3H) 2.18 (s, 3H) 2.15 (s, 3H) 2.11 (s, 3H) 1.69 (dd, J=12.38, 1.52 Hz, 2H) 1.34-1.44 (m, 2H) 0.87 (t, J=7.07 Hz, 3H). MS(ES) [M+H]$^+$ 404.1.

Examples 7 and 8

N-((4,6-dimethyl-2-oxo-1,2-dihydropyridin-3-yl)methyl)-5-(((cis)-4-(dimethylamino)cyclohexyl)(ethyl)amino)-4-methylthiophene-3-carboxamide (Example 7) and N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide (Example 8)

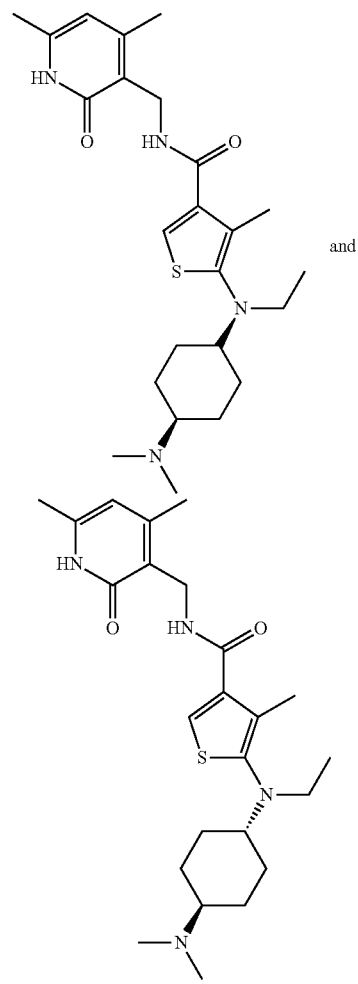

and a) Methyl 5-((-4-(dimethylamino)cyclohexyl)(ethyl)amino)-4-methylthiophene-3-carboxylate (mixture of cis and trans isomers)

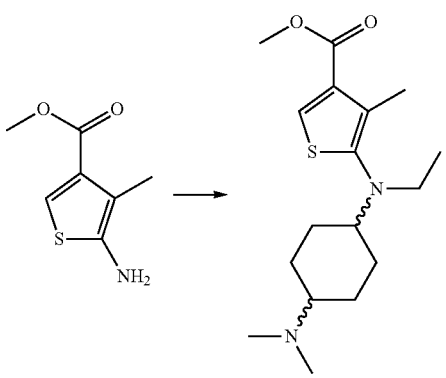

To a solution of methyl 5-amino-4-methylthiophene-3-carboxylate (290 mg, 1.694 mmol) in DCE (10 mL) were added AcOH (0.194 mL, 3.39 mmol) and 4-(dimethylamino)cyclohexanone (263 mg, 1.863 mmol). The reaction was maintained at RT for 40 min, at which time NaBH(OAc)₃ (1436 mg, 6.78 mmol) was added portionwise. The mixture was stirred at RT for 30 min, at which time acetaldehyde (0.115 mL, 2.03 mmol) and more NaBH(OAc)₃ (359 mg, 1.69 mmol) were added. The reaction was stirred for 1 h, at which time it was quenched with NaHCO₃, extracted with DCM, and concentrated to provide a mixture of N-((4,6-dimethyl-2-oxo-1,2-dihydropyridin-3-yl)methyl)-5-(((cis)-4-(dimethylamino)cyclohexyl)(ethyl)amino)-4-methylthiophene-3-carboxamide and N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide (590 mg, 1.81 mmol) as a brown oil. MS(ES) [M+H]⁺ 325.1.

b) N-((4,6-Dimethyl-2-oxo-1,2-dihydropyridin-3-yl)methyl)-5-((-4-(dimethylamino)cyclohexyl)(ethyl)amino)-4-methylthiophene-3-carboxamide (mixture of cis and trans isomers)

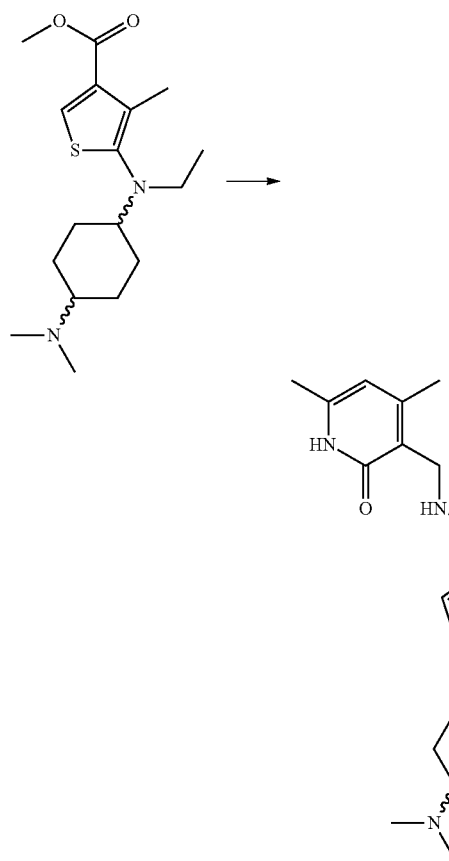

To a crude solution of methyl 5-((4-(dimethylamino)cyclohexyl)(ethyl)amino)-4-methylthiophene-3-carboxylate (590 mg, 1.81 mmol) in MeOH was added 5 N NaOH (2.18 mL, 10.91 mmol). The mixture was stirred overnight at 40° C., at which time 6 N HCl (1.81 mL, 10.91 mmol) was added. The mixture was concentrated, diluted with DCM, and concentrated again.

To a solution of the crude residue from above in DMSO (10 mL) were added NMM (1.00 mL, 9.09 mmol) and 3-(aminomethyl)-4,6-dimethylpyridin-2(1H)-one (332 mg, 2.18 mmol), followed by EDC (697 mg, 3.64 mmol), HOBT (555 mg, 3.64 mmol), and more NMM (1.00 mL, 9.09 mmol). The reaction was stirred at RT for 48 h. The reaction was purified directly by reverse phase Gilson HPLC (5-80% CH₃CN/water+0.1% TFA, YMC ODS-A C18 column 75×30 mm ID S-5 um, 12 nM column). The residue was partitioned between EtOAc/MeOH and 0.1N NaOH. The organics were concentrated, diluted with DCM, and concentrated to provide N-((4,6-dimethyl-2-oxo-1,2-dihydropyridin-3-yl)methyl)-5-((-4-(dimethylamino)cyclohexyl)(ethyl)amino)-4-methylthiophene-3-carboxamide (440 mg) as a mixture of cis and trans isomers.

The mixture was further purified by HPLC (Gilson; IC 20×250 mm column; 20 mL/min; 30:70 MeOH:CH₃CN with 0.1% isopropylamine) and the isomers were separated. Peak 1 (retention time=7.3 min) fractions were concentrated to give N-((4,6-dimethyl-2-oxo-1,2-dihydropyridin-3-yl)methyl)-5-(((cis)-4-(dimethylamino)cyclohexyl)(ethyl)amino)-4-methylthiophene-3-carboxamide (Example 7; 65 mg, 7.64%) as an off-white solid.

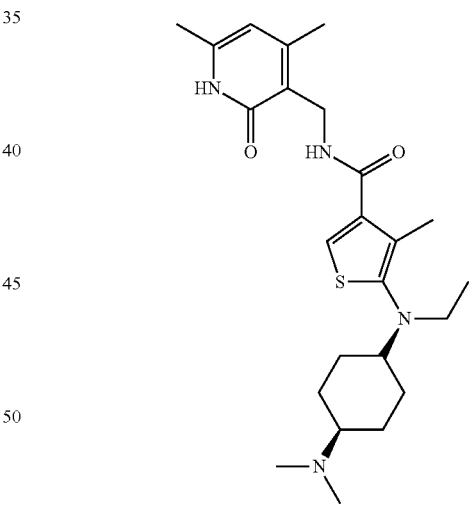

Isomeric purity>99.5%. MS(ES) [M+H]⁺ 445.2. ¹H NMR (400 MHz, CDCl₃) δ 11.67 (br. s., 1H) 7.43 (s, 1H) 7.36 (t, J=5.81 Hz, 1H) 5.96 (s, 1H) 4.52 (d, J=5.81 Hz, 2H) 2.95 (q, J=7.07 Hz, 3H) 2.40 (s, 3H) 2.32 (s, 3H) 2.28 (s, 9H) 2.16 (d, J=3.54 Hz, 1H) 1.83-1.91 (m, 2H) 1.70-1.78 (m, 2H) 1.42-1.49 (m, 4H) 0.91 (t, J=7.07 Hz, 3H). Additional NMR experiments (NOE) confirmed the cis-stereochemistry.

Peak 2 (retention time=9.5 min) fractions were concentrated to give N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide (Example 8; 210 mg, 24.68%) as an off-white solid.

73

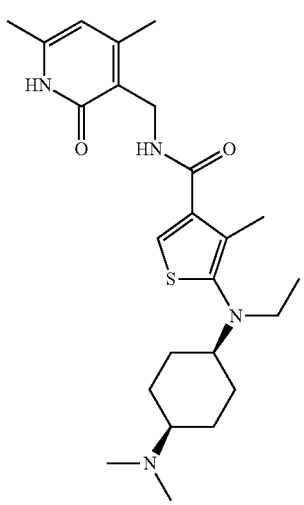 [SMILES: CCN(c1scc(C(=O)NCc2c(C)cc(C)[nH]c2=O)c1C)[C@H]1CC[C@@H](N(C)C)CC1]

Isomeric purity>99.5%. MS(ES) [M+H]+ 445.2 1H NMR (400 MHz, CDCl3) δ 11.85 (br. s., 1H) 7.42 (s, 1H) 7.36 (t, J=5.81 Hz, 1H) 5.96 (s, 1H) 4.52 (d, J=6.06 Hz, 2H) 2.93-2.98 (m, 2H) 2.69-2.76 (m, 1H) 2.40 (s, 3H) 2.28-2.30 (m, 9H) 2.26 (s, 3H) 2.10-2.13 (m, 1H) 1.90-1.99 (m, 5H) 1.21-1.31 (m, 4H) 0.92 (t, J=7.07 Hz, 3H). Additional NMR experiments (NOE) confirmed the trans-stereochemistry.

Example 9

N-((4,6-dimethyl-2-oxo-1,2-dihydropyridin-3-yl)methyl)-5-methyl-1-phenyl-1H-pyrazole-4-carboxamide

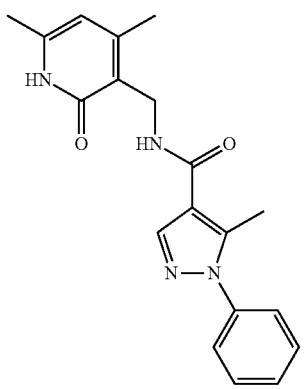 [SMILES: Cc1cc(C)c(CNC(=O)c2cnn(-c3ccccc3)c2C)c(=O)[nH]1]

To a 50 mL round bottom flask containing stir bar were introduced 5-methyl-1-phenyl-1H-pyrazole-4-carboxylic acid (202 mg, 1.000 mmol), 3-(aminomethyl)-4,6-dimethylpyridin-2(1H)-one hydrochloride (225 mg, 1.200 mmol), HOAT (272 mg, 2.000 mmol), EDC (383 mg, 2.000 mmol), followed by DMSO (5 mL). The contents were light brown and heterogenous. To the reaction mixture was added NMM (0.440 mL, 4.00 mmol) and the mixture was stirred under nitrogen at RT for 20 h, at which time water (30 mL) was added. The contents were stirred for 30 min, at which time the reaction was vacuum filtered to afford a light tan colored solid and yellowish filtrate. The solid was dried in a vacuum oven at 40° C. overnight to give N-((4,6-dimethyl-2-oxo-1,2-dihydropyridin-3-yl)methyl)-5-methyl-1-phenyl-1H-pyrazole-4-carboxamide (280 mg, 83% yield) as an off-white powder. 1H NMR (400 MHz, DMSO-d6) δ 2.12 (s, 3H) 2.18 (s, 3H) 4.27 (d, J=4.80 Hz, 2H) 5.87 (s, 1H) 7.44-7.58 (m, 5H) 7.98 (s, 1H) 8.13 (s, 1H) 11.50 (s, 1H). MS(ES) [M+H]+ 337.2.

Example 10

N-((4,6-dimethyl-2-oxo-1,2-dihydropyridin-3-yl)methyl)-5-methyl-1-((tetrahydro-2H-pyran-4-yl)methyl)-1H-pyrazole-4-carboxamide

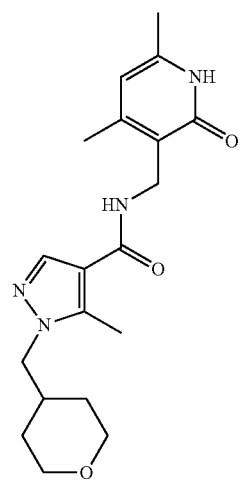 [SMILES: Cc1cc(C)c(CNC(=O)c2cnn(CC3CCOCC3)c2C)c(=O)[nH]1]

a) Ethyl 5-methyl-1-((tetrahydro-2H-pyran-4-yl)methyl)-1H-pyrazole-4-carboxylate

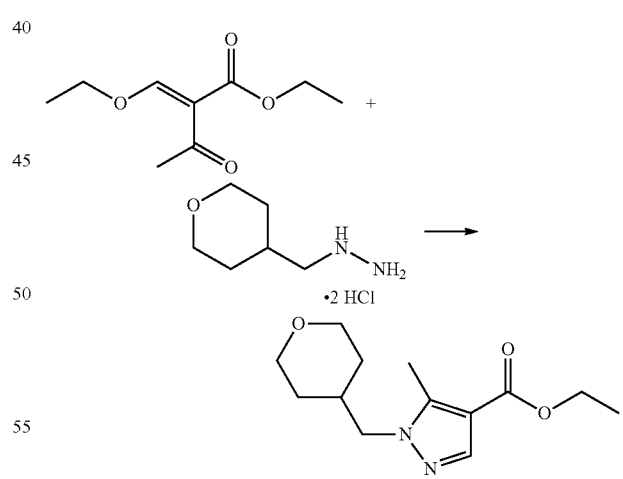

A mixture of ((tetrahydro-2H-pyran-4-yl)methyl)hydrazine dihydrochloride (1 g, 4.92 mmol) and (E)-ethyl 2-(ethoxymethylene)-3-oxobutanoate (1.834 g, 9.85 mmol) in EtOH (20 mL) was heated at reflux for 2 h, at which time the solvent was evaporated. The residue was purified by silica gel chromatography (Varian 971IF, 0-100% EtOAc/hexanes, SF25-40 g, 25 min) to give ethyl 5-methyl-1-((tetrahydro-2H-pyran-4-yl)methyl)-1H-pyrazole-4-carboxylate (220 mg, 0.785 mmol, 15.94% yield) as an oil.

Impure fractions were evaporated separately to give additional, less pure product (750 mg). ¹H NMR (400 MHz, CDCl₃) δ 7.93 (s, 1H) 4.28-4.33 (m, 2H) 3.95-4.02 (m, 4H) 3.37 (td, J=11.62, 2.02 Hz, 2H) 2.58 (s, 3H) 2.19-2.29 (m, 1H) 1.48-1.53 (m, 2H) 1.35-1.45 (m, 5H). MS(ES) [M+H]⁺ 253.1.

b) N-((4,6-dimethyl-2-oxo-1,2-dihydropyridin-3-yl)methyl)-5-methyl-1-((tetrahydro-2H-pyran-4-yl)methyl)-1H-pyrazole-4-carboxamide

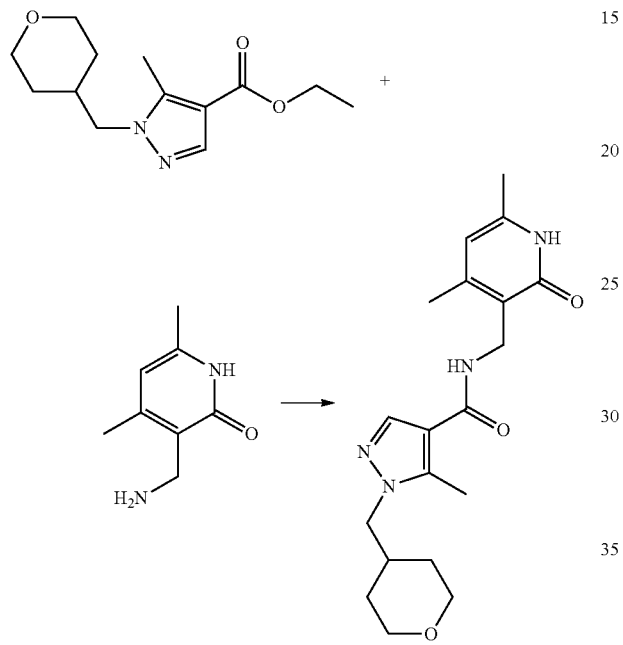

To a solution of ethyl 5-methyl-1-((tetrahydro-2H-pyran-4-yl)methyl)-1H-pyrazole-4-carboxylate (220 mg, 0.872 mmol) in MeOH was added 5 N NaOH (1.046 mL, 5.23 mmol). The reaction was heated at 50° C. for 8 h, at which time it was allowed to cool to RT and diluted with 6 N HCl (0.872 mL, 5.23 mmol). The mixture was concentrated, diluted with DCM, and concentrated again.

To a solution of the crude residue in DMSO (5 mL) was added NMM (0.479 mL, 4.36 mmol), 3-(aminomethyl)-4,6-dimethylpyridin-2(1H)-one (159 mg, 1.046 mmol), EDC (201 mg, 1.046 mmol), HOBT (160 mg, 1.046 mmol) and more NMM (0.479 mL, 4.36 mmol). The reaction was maintained at RT for 12 h, at which time it was purified by reverse phase HPLC (Gilson; 5-55% CH₃CN/water+0.1% TFA, YMC ODS-A C18 column 75×30 mm ID S-5 um). The residue was partitioned between EtOAc/MeOH and saturated aqueous NaHCO₃. The organic layer was concentrated and the residue was triturated with DCM to provide N-((4,6-dimethyl-2-oxo-1,2-dihydropyridin-3-yl)methyl)-5-methyl-1-((tetrahydro-2H-pyran-4-yl)methyl)-1H-pyrazole-4-carboxamide (55 mg, 0.146 mmol, 16.72% yield) as an off-white solid. ¹H NMR (400 MHz, DMSO-d₆) δ 11.31-11.54 (m, 1H) 7.88 (s, 1H) 7.79 (t, J=4.93 Hz, 1H) 5.85 (s, 1H) 4.21 (d, J=5.05 Hz, 2H) 3.91 (d, J=7.33 Hz, 2H) 3.81 (dd, J=11.37, 2.78 Hz, 2H) 3.22 (td, J=11.56, 1.89 Hz, 2H) 2.48 (s, 3H) 2.16 (s, 3H) 2.11 (s, 3H) 1.99-2.05 (m, 1H) 1.33-1.39 (m, 2H) 1.20-1.30 (m, 2H). MS(ES) [M+H]⁺ 359.2. Additional NMR studies (NOE) confirmed the assigned structure.

Example 11 tert-Butyl 4-((4-(((4,6-dimethyl-2-oxo-1,2-dihydropyridin-3-yl)methyl)carbamoyl)-3-methylthiophen-2-yl)(ethyl)amino)piperidine-1-carboxylate

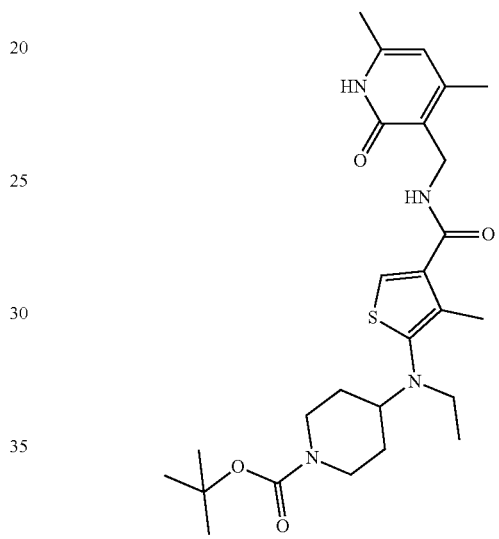

To a solution of 5-((1-(tert-butoxycarbonyl)piperidin-4-yl)(ethyl)amino)-4-methylthiophene-3-carboxylic acid (200 mg, 0.543 mmol), prepared by following the general procedures of Examples 2c and 2d (using tert-butyl 4-aminopiperidine-1-carboxylate as a starting material), in DMSO (2 mL) and DMF (4 mL) was added EDC (125 mg, 0.651 mmol), followed by HOBT (100 mg, 0.651 mmol). After 10 min, TEA (0.303 mL, 2.171 mmol) was added and the solution was maintained for 18 h at RT. Water (50 mL) and EtOAc (50 mL) were added. The layers were separated and the organic layer was washed with brine, dried over MgSO₄, filtered and evaporated. The resulting oil was purified by column chromatography (10% EtOH:EtOAc) to give tert-butyl 4-((4-(((4,6-dimethyl-2-oxo-1,2-dihydropyridin-3-yl)methyl)carbamoyl)-3-methylthiophen-2-yl)(ethyl)amino)piperidine-1-carboxylate (170 mg, 0.321 mmol, 59.2% yield) as a white foam. ¹H NMR (400 MHz, methanol-d₄) δ 7.55 (s, 1H), 6.13 (s, 1H), 4.39-4.54 (m, 2H), 4.04 (d, J=13.14 Hz, 2H), 2.95-3.07 (m, 5H), 2.37 (s, 3H), 2.26 (s, 3H), 2.22 (s, 3H), 1.85 (d, J=11.37 Hz, 2H), 1.45 (s, 9H), 1.37 (dq, J=4.29, 12.04 Hz, 2H), 0.95 (t, J=7.07 Hz, 3H). MS(ES) [M+H]⁺ 503.4.

Example 12

N-((4,6-dimethyl-2-oxo-1,2-dihydropyridin-3-yl)methyl)-5-(ethyl(piperidin-4-yl)amino)-4-methylthiophene-3-carboxamide hydrochloride

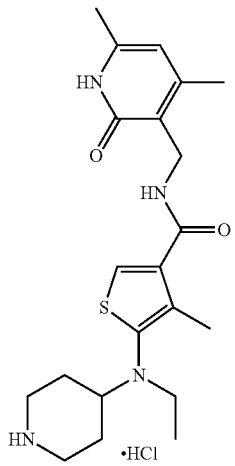 [SMILES: CCN(c1scc(C(=O)NCc2c(C)cc(C)[nH]c2=O)c1C)C1CCNCC1 ; Cl]

A mixture of tert-butyl 4-((4-(((4,6-dimethyl-2-oxo-1,2-dihydropyridin-3-yl)methyl)carbamoyl)-3-methylthiophen-2-yl)(ethyl)amino)piperidine-1-carboxylate (150 mg, 0.298 mmol) in 1 M HCl (5 mL, 5.00 mmol) was heated at reflux for 5 min, at which time the reaction mixture was evaporated. N-((4,6-dimethyl-2-oxo-1,2-dihydropyridin-3-yl)methyl)-5-(ethyl(piperidin-4-yl)amino)-4-methylthiophene-3-carboxamide (120 mg, 0.260 mmol, 87% yield) was isolated as its white hydrochloride salt. $^1$H NMR (400 MHz, methanol-$d_4$) δ 7.88 (s, 1H), 7.00 (s, 1H), 4.56 (s, 2H), 3.63 (q, J=7.07 Hz, 2H), 3.41 (td, J=3.38, 13.20 Hz, 2H), 3.14-3.24 (m, 1H), 3.05-3.10 (m, 2H), 2.62 (s, 3H), 2.52 (s, 3H), 2.29 (s, 3H), 2.12 (dd, J=2.02, 13.89 Hz, 2H), 1.62-1.83 (m, 2H), 1.20 (t, J=6.95 Hz, 3H). MS(ES) [M+H]$^+$ 403.4.

Example 13

N-((4,6-dimethyl-2-oxo-1,2-dihydropyridin-3-yl)methyl)-5-(1-(4-(dimethylamino)piperidin-1-yl)ethyl)thiophene-3-carboxamide

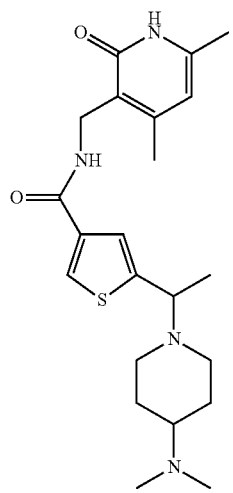 [SMILES: Cc1cc(C)c(CNC(=O)c2csc(C(C)N3CCC(N(C)C)CC3)c2)c(=O)[nH]1]

(a) 5-Acetyl-N-((4,6-dimethyl-2-oxo-1,2-dihydropyridin-3-yl)methyl)thiophene-3-carboxamide

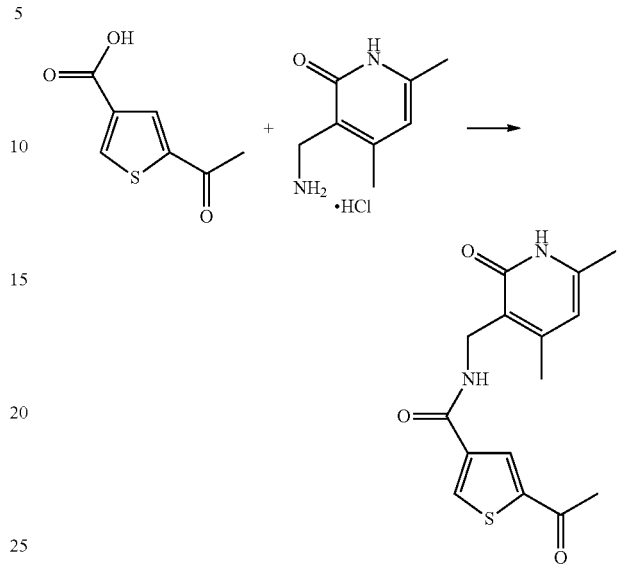

A mixture of 5-acetylthiophene-3-carboxylic acid (300 mg, 1.763 mmol), 3-(aminomethyl)-4,6-dimethylpyridin-2(1H)-one hydrochloride (399 mg, 2.115 mmol), HOAt (360 mg, 2.64 mmol), EDC (507 mg, 2.64 mmol) and NMM (0.581 mL, 5.29 mmol) in DMSO (5 mL) was stirred at RT overnight. LCMS analysis indicated complete conversion, so the reaction mixture was poured into water (100 mL), stirred for 30 min, then filtered and washed with water (50 mL). The residue was dried in vacuo for 2 h, then in a vacuum oven overnight to afford 5-acetyl-N-((4,6-dimethyl-2-oxo-1,2-dihydropyridin-3-yl)methyl)thiophene-3-carboxamide (481 mg, 90%) as a pale beige solid. MS(ES) [M+H]$^+$ 305.

(b) N-((4,6-dimethyl-2-oxo-1,2-dihydropyridin-3-yl)methyl)-5-(1-(4-(dimethylamino)piperidin-1-yl)ethyl)thiophene-3-carboxamide

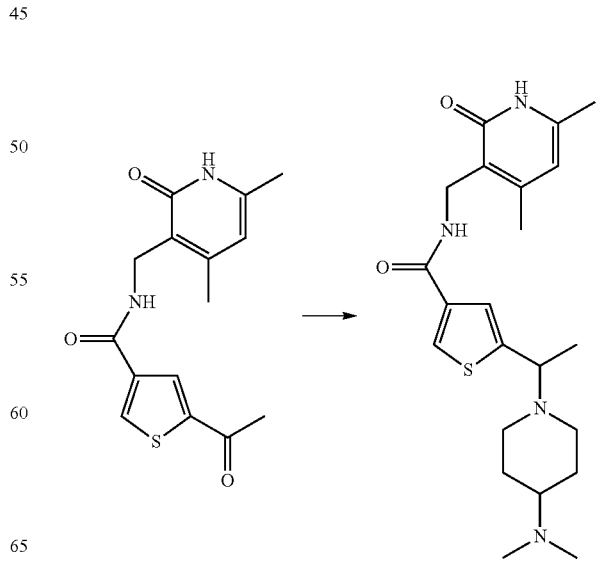

To a solution of 5-acetyl-N-((4,6-dimethyl-2-oxo-1,2-dihydropyridin-3-yl)methyl)thiophene-3-carboxamide (176 mg, 0.578 mmol) in THF (10 mL) was added N,N-dimethylpiperidin-4-amine (222 mg, 1.735 mmol) and Ti(OCH(CH$_3$)$_2$)$_4$ (0.508 mL, 1.735 mmol). The reaction was heated at reflux for 48 h. The reaction was allowed to cool to RT, then NaBH$_4$ (65.6 mg, 1.735 mmol) was added and the reaction was stirred at RT for 2 h. MeOH (1 mL) was added, followed by an additional portion of NaBH$_4$ (65.6 mg, 1.735 mmol) and the reaction mixture was stirred for an additional hour. The reaction was poured into water (50 mL) and saturated aqueous NaHCO$_3$ (50 mL), then extracted with EtOAc (3×100 mL). The combined organics were filtered, concentrated and the residue purified by reverse phase HPLC (Gilson instrument, Trilution software, Waters SunFire Prep C18 OBD 5 uM, 19×50 mm column, using 5-30% CH$_3$CN in water with 0.1% TFA) and then concentrated. The residue was dissolved in MeOH and passed through a Silicycle(carbonate) cartridge (1 g) to afford N-((4,6-dimethyl-2-oxo-1,2-dihydropyridin-3-yl)methyl)-5-(1-(4-(dimethylamino)piperidin-1-yl)ethyl)thiophene-3-carboxamide (26 mg, 10.79% yield) as a white solid. $^1$H NMR (400 MHz, DMSO-d$_6$) δ 11.44 (s, 1H), 8.07 (br. s., 1H), 7.99 (d, J=1.26 Hz, 1H), 7.29 (s, 1H), 5.86 (s, 1H), 4.24 (d, J=4.80 Hz, 2H), 3.81-3.94 (m, 1H), 2.83 (br. s., 1H), 2.69-2.77 (m, 1H), 2.16 (s, 3H), 2.13 (s, 6H), 2.11 (s, 3H), 2.07-2.10 (m, 1H), 1.90-2.02 (m, 2H), 1.64-1.77 (m, 2H), 1.20-1.40 (m, 5H). MS(ES) [M+H]$^+$ 417.

Example 14

N-[(4,6-dimethyl-2-oxo-1,2-dihydro-3-pyridinyl)methyl]-5-[ethyl(tetrahydro-2H-pyran-4-yl)amino]-1,4-dimethyl-1H-pyrazole-3-carboxamide

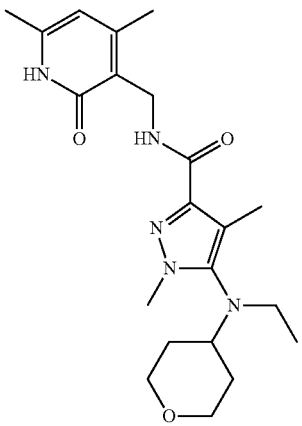 [SMILES: CCN(c1c(C)c(C(=O)NCc2c(C)cc(C)[nH]c2=O)nn1C)C1CCOCC1]

a) Potassium 3-cyano-1-ethoxy-1-oxobut-2-en-2-olate

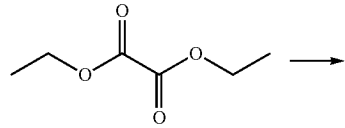

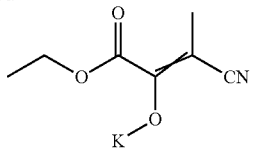

To a 20 mL microwave vial was added 576 mg of KOEt and EtOH (12 mL). After all of the KOEt dissolved, diethyl oxalate (928 μl, 6.84 mmol) was added (precipitate immediately formed). To the mixture was added propiononitrile (0.522 μl, 6.84 mmol) and the microwave vial was capped and heated at 120° C. for 16 h. This was repeated for 7 other reaction vials. The contents of all eight vials were combined and filtered. The filtrate was concentrated to give 3.87 g of crude potassium 3-cyano-1-ethoxy-1-oxobut-2-en-2-olate.

b) Ethyl 5-amino-1,4-dimethyl-1H-pyrazole-3-carboxylate

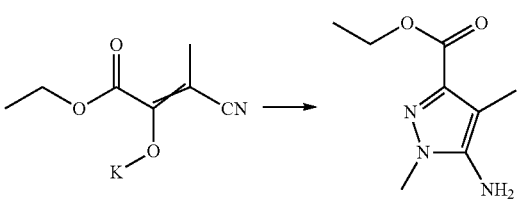

A solution of potassium 3-cyano-1-ethoxy-1-oxobut-2-en-2-olate (3.87 g, 20.03 mmol), methylhydrazine (1.054 mL, 20.03 mmol) and 1 M HCl (0.608 mL, 20.03 mmol) in EtOH (40 mL) was stirred at RT for 16 h. The mixture was concentrated and saturated NaHCO$_3$ was added until basic. The mixture was extracted with EtOAc and the combined extracts were combined and washed with brine, dried over MgSO$_4$, filtered and concentrated to give ethyl 5-amino-1,4-dimethyl-1H-pyrazole-3-carboxylate (930 mg, 25%) as a brown solid. $^1$H NMR (400 MHz, CDCl$_3$) δ 1.40 (t, J=7.07 Hz, 3H) 2.16 (s, 3H) 3.18-3.53 (m, 2H) 3.77 (s, 3H) 4.39 (q, J=7.07 Hz, 2H). MS(ES) [M+H]$^+$ 184.0.

c) Ethyl 5-[ethyl(tetrahydro-2H-pyran-4-yl)amino]-1,4-dimethyl-1H-pyrazole-3-carboxylate

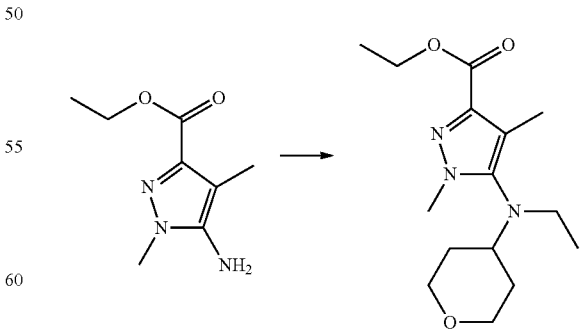

A solution of ethyl 5-amino-1,4-dimethyl-1H-pyrazole-3-carboxylate (516 mg, 2.82 mmol) and dihydro-2H-pyran-4(3H)-one (310 mg, 3.10 mmol) in DCE (25 mL) and AcOH (0.322 mL, 5.63 mmol) was stirred at RT for 20 min. To the solution was added portionwise NaBH(OAc)₃ (2388 mg, 11.27 mmol) and the mixture was stirred for 90 min. Acetaldehyde (0.191 mL, 3.38 mmol) was added and the reaction was stirred for 16 h, at which time it was quenched with NaHCO₃ and extracted with DCM. The organic layer was dried over MgSO₄, filtered and concentrated. The residue was purified via flash column chromatography (0% to 50% EtOAc:Hex; 50 g-HP-silica gel column) to give ethyl 5-[ethyl(tetrahydro-2H-pyran-4-yl)amino]-1,4-dimethyl-1H-pyrazole-3-carboxylate (590 mg, 70.9%). ¹H NMR (400 MHz, CDCl₃) δ 0.93 (t, J=7.07 Hz, 3H) 1.38-1.56 (m, 5H) 2.25 (s, 3H) 3.12 (q, J=7.07 Hz, 2H) 3.21 (tt, J=10.99, 4.04 Hz, 1H) 3.37 (td, J=11.81, 1.39 Hz, 2H) 3.77 (s, 3H) 3.90-4.05 (m, 2H) 4.40 (q, 2H). MS(ES) [M+H]⁺ 296.2.

d) 5-[Ethyl(tetrahydro-2H-pyran-4-yl)amino]-1,4-dimethyl-1H-pyrazole-3-carboxylic acid

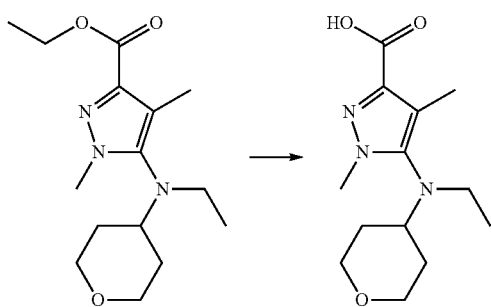 [SMILES: CCOC(=O)c1nn(C)c(N(CC)C2CCOCC2)c1C ; CCN(c1c(C)c(C(=O)O)nn1C)C1CCOCC1]

A solution of ethyl 5-(ethyl(tetrahydro-2H-pyran-4-yl)amino)-1,4-dimethyl-1H-pyrazole-3-carboxylate (580 mg, 1.964 mmol) and 1 M NaOH (2.356 mL, 2.356 mmol) in water (20 mL) and EtOH (20 mL) was heated at reflux for 2 h. The reaction mixture was concentrated and acidified by addition of 1 N HCl, then extracted with DCM, dried over MgSO₄, filtered and concentrated to give 5-[ethyl(tetrahydro-2H-pyran-4-yl)amino]-1,4-dimethyl-1H-pyrazole-3-carboxylic acid (523 mg, 100%) as a white solid. ¹H NMR (400 MHz, CDCl₃) δ 0.95 (t, 3H) 1.31-2.00 (m, 4H) 2.27 (s, 3H) 3.13 (q, J=7.07 Hz, 2H) 3.18-3.29 (m, 1H) 3.39 (td, J=11.87, 2.02 Hz, 2H) 3.79 (s, 3H) 3.99 (d, J=10.86 Hz, 2H). MS(ES) [M+H]⁺ 268.1.

e) N-[(4,6-dimethyl-2-oxo-1,2-dihydro-3-pyridinyl)methyl]-5-[ethyl(tetrahydro-2H-pyran-4-yl)amino]-1,4-dimethyl-1H-pyrazole-3-carboxamide

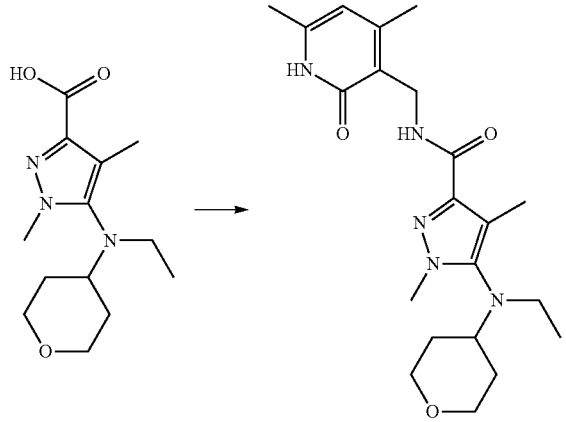 [SMILES: CCN(c1c(C)c(C(=O)O)nn1C)C1CCOCC1 ; CCN(c1c(C)c(C(=O)NCc2c(C)cc(C)[nH]c2=O)nn1C)C1CCOCC1]

5-(Ethyl(tetrahydro-2H-pyran-4-yl)amino)-1,4-dimethyl-1H-pyrazole-3-carboxylic acid (208 mg, 0.778 mmol), 3-(aminomethyl)-4,6-dimethyl-2(1H)-pyridinone (176 mg, 0.934 mmol), HOAt (212 mg, 1.556 mmol), EDC (298 mg, 1.556 mmol) and NMM (0.342 mL, 3.11 mmol) were added to DMSO (10 mL) and the mixture was stirred at RT for 16 h. Water was added and the mixture was extracted with DCM. Combined DCM extracts were washed with water, dried over MgSO₄, filtered and concentrated. The residue was purified via flash column chromatography (0% to 100% EtOAc:Hex; then 0% to 20% MeOH:DCM; 10 g-HP-silica gel column) to give N-[(4,6-dimethyl-2-oxo-1,2-dihydro-3-pyridinyl)methyl]-5-[ethyl(tetrahydro-2H-pyran-4-yl)amino]-1,4-dimethyl-1H-pyrazole-3-carboxamide (240 mg, 77%). ¹H NMR (400 MHz, CDCl₃) δ 0.90 (t, J=7.20 Hz, 6H) 1.32-1.58 (m, 4H) 2.29 (s, 6H) 2.37 (s, 6H) 2.39 (s, 6H) 3.09 (q, J=7.07 Hz, 4H) 3.18 (tt, J=10.99, 4.04 Hz, 2H) 3.35 (t, J=11.37 Hz, 3H) 3.64 (s, 5H) 3.94 (d, J=9.85 Hz, 3H) 4.52 (d, J=6.06 Hz, 3H) 5.93 (s, 1H) 7.91 (t, J=6.06 Hz, 1H) 12.97 (br. s., 1H). MS(ES) [M+H]⁺ 402.3.

Example 15

5-(Ethyl(tetrahydro-2H-pyran-4-yl)amino)-4-methyl-N-((6-methyl-2-oxo-4-(trifluoromethyl)-1,2-dihydropyridin-3-yl)methyl)thiophene-3-carboxamide

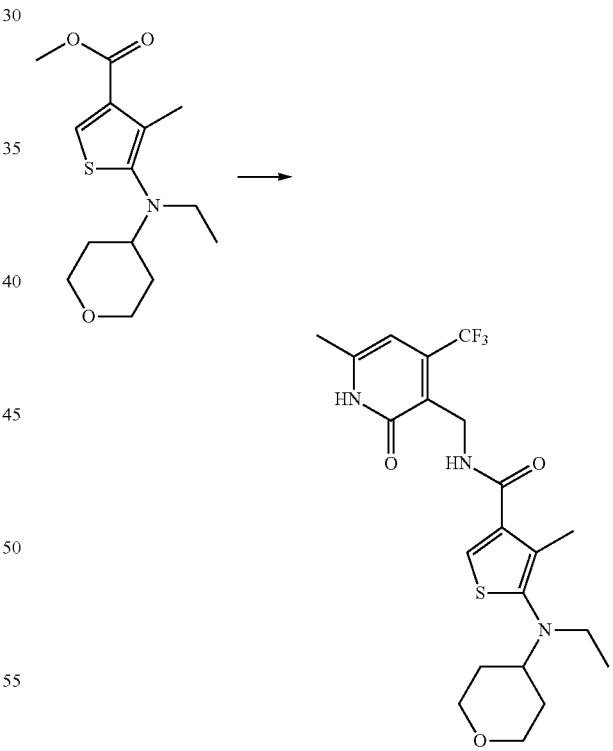

Following the general procedure of Example 6, but substituting 3-(aminomethyl)-6-methyl-4-(trifluoromethyl)pyridin-2(1H)-one for 3-(aminomethyl)-4,6-dimethylpyridin-2(1H)-one the title material was synthesized (30 mg, 11%) as a tan solid. ¹H NMR (400 MHz, DMSO-d₆) δ 12.22 (br.s., 1H) 8.55 (br. s., 1H) 7.57 (s, 1H) 6.18 (s, 1H) 4.30 (d, J=3.79 Hz, 2H) 3.83 (dd, J=11.37, 2.53 Hz, 2H) 3.22-3.27 (m, 2H) 2.90-2.96 (m, 3H) 2.20 (s, 3H) 2.15 (s, 3H) 1.69 (dd, J=12.25, 1.89 Hz, 2H) 1.39 (td, J=11.87, 7.83 Hz, 2H) 0.85-0.89 (m, 3H). MS(ES) [M+H]+ 458.2.

Example 16

5-(((trans)-4-(Dimethylamino)cyclohexyl)(ethyl)amino)-4-methyl-N-((6-methyl-2-oxo-4-propyl-1,2-dihydropyridin-3-yl)methyl)thiophene-3-carboxamide

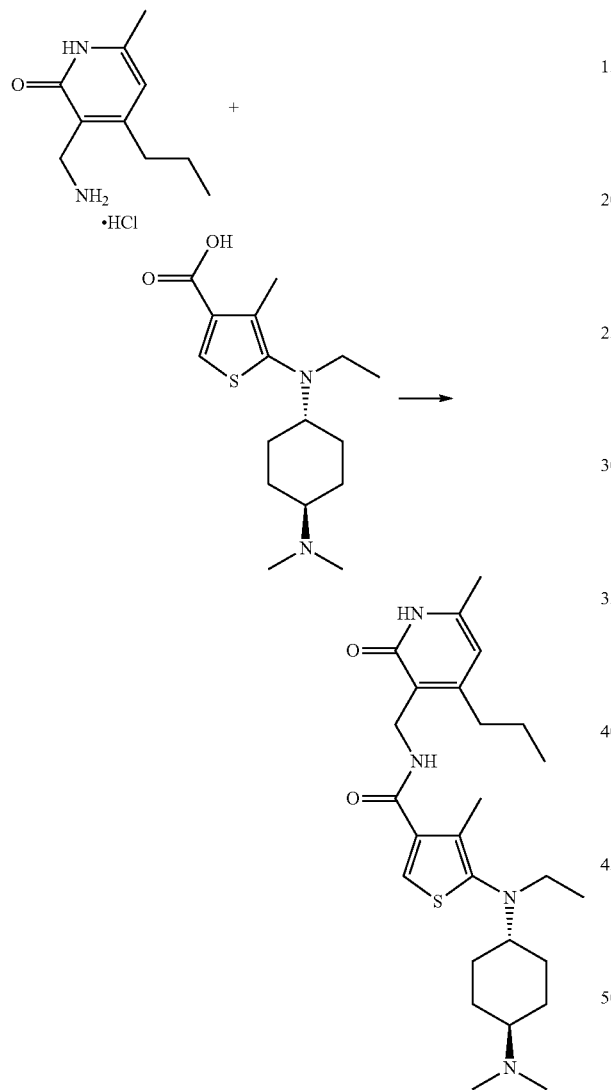

A reaction vessel was charged with the following as solids: 5-(((trans)-4-(dimethylamino)cyclohexyl)(ethyl)amino)-4-methylthiophene-3-carboxylic acid (0.174 g, 0.280 mmol), HOAt (0.046 g, 0.336 mmol), EDC (0.064 g, 0.336 mmol), and 3-(aminomethyl)-6-methyl-4-propylpyridin-2(1H)-one hydrochloride (0.079 g, 0.364 mmol). DMSO (3.0 mL) was added, followed by NMM (0.185 mL, 1.681 mmol). The mixture was stirred at RT for 4 h, at which time it was diluted with water (30 mL), cooled with an ice bath, and stirred for 15 min. Solids precipitated. The pH was adjusted to 10.9 with the addition of concentrated NH$_4$OH, then extracted with DCM/MeOH/NH$_4$OH-90/10/1 (3×35 mL). The combined organics were washed with brine, dried over MgSO$_4$, filtered and concentrated in vacuo. The residue was dissolved in DCM, pre-absorbed onto silica gel, and purified by flash column chromatography (4 g silica column; Gradient of B: 8-95%; A:DCM, B: 90/10/1 of DCM/MeOH/NH$_4$OH) to give 5-(((trans)-4-(dimethylamino)cyclohexyl)(ethyl)amino)-4-methyl-N-((6-methyl-2-oxo-4-propyl-1,2-dihydropyridin-3-yl)methyl)thiophene-3-carboxamide (85 mg, 0.176 mmol, 62.9% yield) as a white solid. $^1$H NMR (400 MHz, DMSO-d$_6$) δ 11.49 (br. s., 1H), 7.92 (t, J=5.1 Hz, 1H), 7.59 (s, 1H), 5.88 (s, 1H), 4.24 (d, J=5.1 Hz, 2H), 2.90 (q, J=7.0 Hz, 2H), 2.61-2.72 (m, 1H), 2.47 (d, J=7.8 Hz, 1H), 2.08-2.15 (m, 12H), 1.95-2.04 (m, 1H), 1.85 (d, J=9.9 Hz, 2H), 1.76 (d, J=9.9 Hz, 2H), 1.43-1.56 (m, 2H), 1.11-1.27 (m, 4H), 1.11 (s, 1H), 0.84 (t, J=7.1 Hz, 3H), 0.89 (t, J=7.3 Hz, 3H). MS(ES) [M+H]+ 473.3.

Example 17

5-(((trans)-4-(Dimethylamino)cyclohexyl)(ethyl)amino)-4-methyl-N-((4-methyl-2-oxo-6-(trifluoromethyl)-1,2-dihydropyridin-3-yl)methyl)thiophene-3-carboxamide

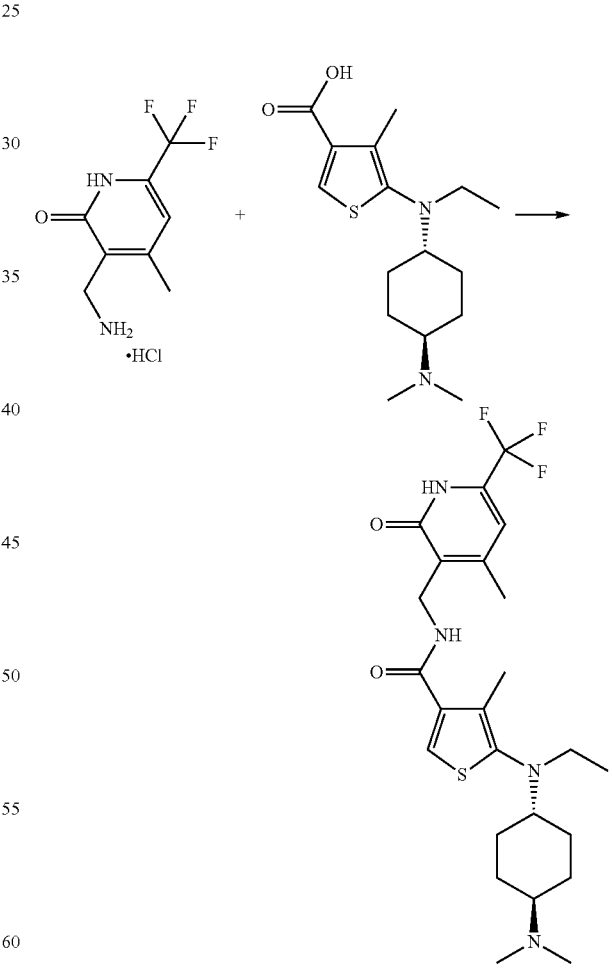

A reaction vessel was charged with the following as solids: 5-(((trans)-4-(dimethylamino)cyclohexyl)(ethyl)amino)-4-methylthiophene-3-carboxylic acid (170 g, 0.274 mmol), HOAt (0.045 g, 0.329 mmol), EDC (0.063 g, 0.329 mmol), and 3-(aminomethyl)-4-methyl-6-(trifluoromethyl)

pyridin-2(1H)-one hydrochloride (0.086 g, 0.356 mmol). DMSO (3.0 mL) was added, followed by NMM (0.181 mL, 1.643 mmol) and the reaction was stirred at RT for 20 h. The stirred reaction mixture was slowly diluted with water (~12 mL) and then placed into a freezer for 30 min. The pH was adjusted to 9.1 with concentrated NH$_4$OH and filtered. The solids were collected, washed with a small amount of water, and air dried for 15 min. The residue was dissolved in DCM/MeOH. Silcia gel was added and the mixture was concentrated in vacuo to give a free flowing solid. Purification by flash column chromatography (4 g silica column; Gradient of B: 8-100%; A:DCM, B: 90/10/1 of DCM/MeOH/NH$_4$OH) provided 5-(((trans)-4-(dimethylamino)cyclohexyl)(ethyl)amino)-4-methyl-N-((4-methyl-2-oxo-6-(trifluoromethyl)-1,2-dihydropyridin-3-yl)methyl)thiophene-3-carboxamide (58 mg, 0.111 mmol, 40.4% yield) as a white solid following trituration with TBME. $^1$H NMR (400 MHz, DMSO-d$_6$) δ 11.81 (br. s., 1H), 8.24 (t, J=4.9 Hz, 1H), 7.61 (s, 1H), 7.17 (s, 1H), 4.37 (d, J=4.8 Hz, 2H), 2.91 (q, J=6.9 Hz, 2H), 2.61-2.71 (m, 1H), 2.42 (s, 3H), 2.10-2.16 (m, 9H), 2.04 (br. s., 1H), 1.84 (br. s., 2H), 1.78 (br. s., 2H), 1.11-1.21 (m, 4H), 0.85 (t, J=7.1 Hz, 3H). MS(ES) [M+H]$^+$ 473.3.

Example 18

5-(((trans)-4-(Dimethylamino)cyclohexyl)(ethyl)amino)-N-((4-methoxy-6-methyl-2-oxo-1,2-dihydropyridin-3-yl)methyl)-4-methylthiophene-3-carboxamide

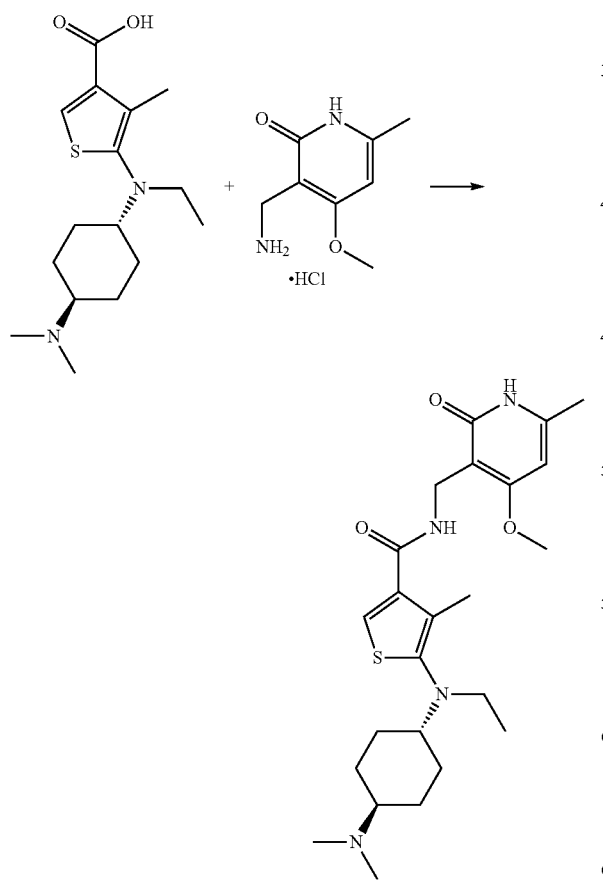

A reaction vessel was charged with the following solids: 5-((4-(dimethylamino)cyclohexyl)(ethyl)amino)-4-methyl-thiophene-3-carboxylic acid (0.24 g, 0.387 mmol), HOAt (0.063 g, 0.464 mmol), EDC (0.089 g, 0.464 mmol) and 3-(aminomethyl)-4-methoxy-6-methylpyridin-2(1H)-one hydrochloride (0.095 g, 0.464 mmol). The mixture was diluted with DMF (5 mL), followed by NMM (0.170 mL, 1.546 mmol). The reaction mixture was stirred at RT until the reaction was complete (by LCMS). The mixture was diluted with water (50 mL) and basified to pH 11 with concentrated NH$_4$OH, at which time it was stirred for 5 min and extracted with DCM (3×40 mL). The combined organics were dried over MgSO$_4$, filtered, and concentrated. The residue was dissolved in DCM and purified by flash column chromatography (12 g silica column; Gradient of B: 8-100%; A:DCM. B: 90/10/1 of DCM/MeOH/NH$_4$OH) to give 5-(((trans)-4-(dimethylamino)cyclohexyl)(ethyl)amino)-N-((4-methoxy-6-methyl-2-oxo-1,2-dihydropyridin-3-yl)methyl)-4-methylthiophene-3-carboxamide (57 mg, 0.118 mmol, 30.4% yield) as a solid (from TBME). $^1$H NMR (400 MHz, DMSO-d$_6$) δ 11.46 (br. s., 1H), 7.79 (t, J=4.5 Hz, 1H), 7.51-7.61 (m, 1H), 6.11 (s, 1H), 4.17 (d, J=4.5 Hz, 2H), 3.80 (s, 3H), 2.91 (q, J=7.1 Hz, 2H), 2.60-2.74 (m, 1H), 2.17-2.22 (m, 3H), 2.06-2.15 (m, 9H), 2.00 (td, J=10.7, 3.3 Hz, 1H), 1.86 (d, J=10.4 Hz, 2H), 1.76 (d, J=10.4 Hz, 2H), 1.07-1.26 (m, 4H), 0.85 (t, J=7.1 Hz, 3H). MS(ES) [M+H]$^+$ 461.

Example 19

2-Bromo-N-((4,6-dimethyl-2-oxo-1,2-dihydropyridin-3-yl)methyl)-5-(ethyl(tetrahydro-2H-pyran-4-yl)amino)-4-methylthiophene-3-carboxamide

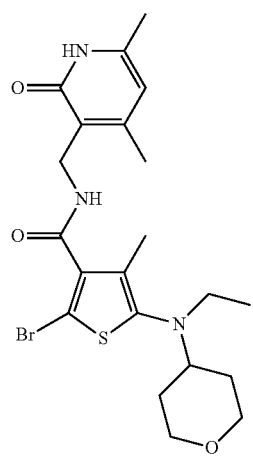 [SMILES: CCN(c1sc(Br)c(C(=O)NCc2c(C)cc(C)[nH]c2=O)c1C)C1CCOCC1]

a) 2-Bromo-5-(ethyl(tetrahydro-2H-pyran-4-yl)amino)-4-methylthiophene-3-carboxylic Acid)

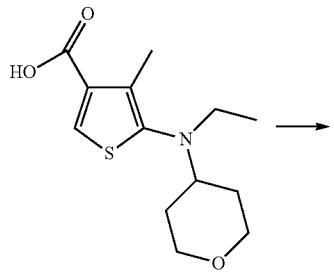

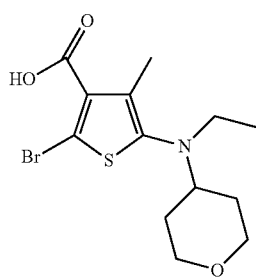

A solution of 5-(ethyl(tetrahydro-2H-pyran-4-yl)amino)-4-methylthiophene-3-carboxylic acid (0.580 g, 2.153 mmol) in DMF (5 mL) was treated with NBS (0.383 g, 2.153 mmol) and stirred under argon at RT for 10 min. The reaction was diluted with water (100 mL) and the resulting precipitate was filtered, washed with water and dried under vacuum to afford 2-bromo-5-(ethyl(tetrahydro-2H-pyran-4-yl)amino)-4-methylthiophene-3-carboxylic acid (0.808 g, 1.856 mmol, 86% yield) as a dark tar. $^1$H NMR (400 MHz, DMSO-$d_6$) δ 13.19 (s, 1H) 3.79-3.89 (m, 2H) 3.22-3.32 (m, 2H) 2.91-3.02 (m, 2H) 2.57 (s, 1H) 2.15 (s, 3H) 1.65-1.76 (m, 2H) 1.30-1.47 (m, 2H) 0.90 (t, J=7.07 Hz, 3H). MS(ES) [M+H]$^+$ 348, 350.

b) 2-Bromo-N-((4,6-dimethyl-2-oxo-1,2-dihydro-pyridin-3-yl)methyl)-5-(ethyl(tetrahydro-2H-pyran-4-yl)amino)-4-methylthiophene-3-carboxamide

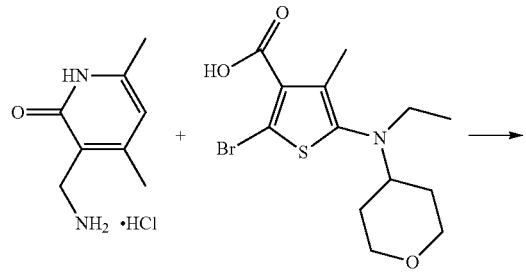

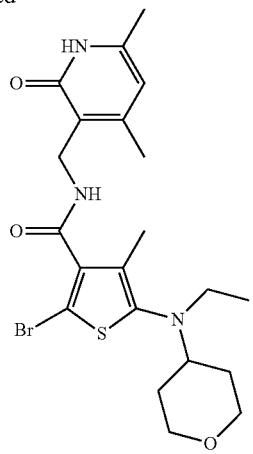

2-Bromo-5-(ethyl(tetrahydro-2H-pyran-4-yl)amino)-4-methylthiophene-3-carboxylic acid (0.136 g, 0.391 mmol), 3-(aminomethyl)-4,6-dimethylpyridin-2(1H)-one hydrochloride (0.081 g, 0.430 mmol), EDC (0.090 g, 0.469 mmol), and HOAt (0.064 g, 0.469 mmol) were combined in DMF (3 mL) and NMM (0.172 mL, 1.562 mmol). The reaction vessel was flushed with argon, sealed and stirred at RT for 2 h. The reaction was diluted with water (25 mL) and extracted with DCM (2×20 mL). The organics were washed with water and dried over MgSO$_4$. The resulting solution was concentrated to a thick orange tar and purified using an ISCO Combiflash Rf (liquid load) on 12 g silica using a gradient of CHCl$_3$: MeOH w/1% NH$_4$OH (0-5%). The product fractions were combined and concentrated to an oil that was evaporated from CHCl$_3$ to afford 2-bromo-N-((4,6-dimethyl-2-oxo-1,2-dihydropyridin-3-yl)methyl)-5-(ethyl (tetrahydro-2H-pyran-4-yl)amino)-4-methylthiophene-3-carboxamide (0.109 g, 0.217 mmol, 55.5% yield) as a tan solid. $^1$H NMR (400 MHz, CDCl$_3$) δ 12.64 (br. s., 1H) 7.11-7.23 (m, 1H) 5.98 (s, 1H) 4.57 (d, J=5.81 Hz, 2H) 3.90-4.03 (m, 2H) 3.28-3.42 (m, 2H) 2.83-2.99 (m, 3H) 2.40 (s, 3H) 2.29 (s, 3H) 2.12 (s, 3H) 1.69-1.80 (m, 2H) 1.44-1.65 (m, 2H) 0.97 (t, J=7.07 Hz, 3H). MS(ES) [M+H]$^+$ 482, 484.

Example 20 tert-Butyl 4-((4-(((4,6-dimethyl-2-oxo-1,2-dihydro-pyridin-3-yl)methyl)carbamoyl)-3-methylthiophen-2-yl)(hydroxy)methyl)piperidine-1-carboxylate

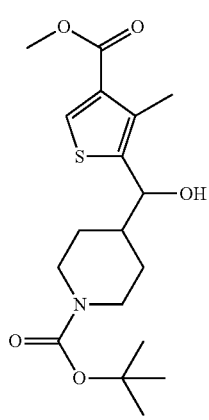 [SMILES: COC(=O)c1csc(C(O)C2CCN(C(=O)OC(C)(C)C)CC2)c1C]

a) Methyl 4-methylthiophene-3-carboxylate

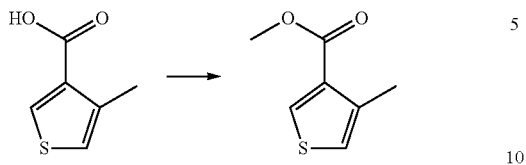

To MeOH (100 mL) with stirring at 0° C. in an ice bath was added slowly down the side of the flask SOCl$_2$ (10 ml, 137 mmol). The flask was rinsed down with MeOH and stirred for 15 min. 4-Methylthiophene-3-carboxylic acid (5.0 g, 35.2 mmol) was added and the reaction was allowed to warm to RT and stirred overnight. The reaction heated at reflux for 4 h, at which time it was allowed to cool to RT. The reaction was evaporated under vacuum, taken up in EtOAc, washed with saturated NaHCO$_3$, brine, dried over Na$_2$SO$_4$, filtered, and evaporated to dryness to give methyl 4-methylthiophene-3-carboxylate (4.68 g, 30.0 mmol, 85% yield) as a light brown oil. $^1$H NMR (400 MHz, CDCl$_3$) δ 8.10 (d, J=3.5 Hz, 1H), 6.95 (dd, J=1.1, 3.4 Hz, 1H), 3.87 (s, 3H), 2.49 (d, J=1.0 Hz, 3H). MS(ES) [M+H]$^+$ 156.9.

b) Methyl 5-iodo-4-methylthiophene-3-carboxylate

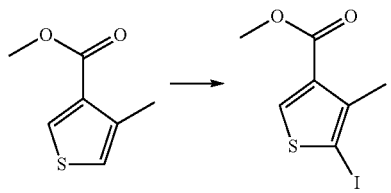

To a solution of methyl 4-methylthiophene-3-carboxylate (1.0 g, 6.40 mmol) in DMF (25 mL) was added NIS (2.5 g, 11.11 mmol). The reaction mixture was heated at 100° C. for 24 h, at which time it was allowed to cool to RT and evaporated to dryness under vacuum (to remove most of the DMF). The residue was taken up in EtOAc, washed with water, brine, dried over Na$_2$SO$_4$, filtered and evaporated to dryness. Purification by silica gel chromatography (Analogix, SF25-60 g, 0 to 10% EtOAc in hexanes) gave methyl 5-iodo-4-methylthiophene-3-carboxylate (0.86 g, 3.05 mmol, 47.6% yield) as an off-white solid. $^1$H NMR (400 MHz, CDCl$_3$) δ 8.26 (s, 1H), 3.87 (s, 3H), 2.47 (s, 3H). MS(ES) [M+H]$^+$ 282.9.

c) tert-Butyl 4-(hydroxy(4-(methoxycarbonyl)-3-methylthiophen-2-yl)methyl)piperidine-1-carboxylate

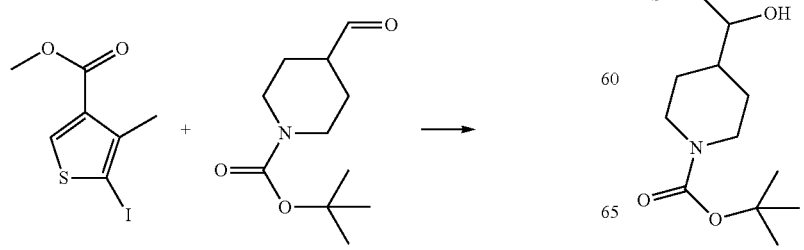

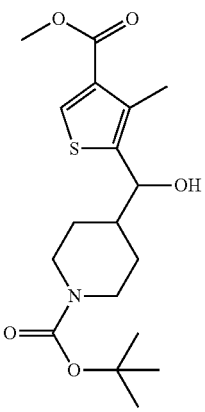

To a cooled (−78° C.) solution of methyl 5-iodo-4-methylthiophene-3-carboxylate (1.0 g, 3.54 mmol) in THF (20 mL) under nitrogen was added dropwise 1.3 N isopropylmagnesium chloride lithium chloride complex in THF (3.0 mL, 3.90 mmol). The reaction was maintained for 1 h, at which time a solution of N-Boc-4-piperidinecarboxaldehyde (1.0 g, 4.69 mmol) in THF (5 mL) was added. The reaction was maintained at −78° C. for 30 min, at which time it was quenched with 1 N HCl (5 mL) and allowed to warm to RT. The reaction was diluted with water, extracted with EtOAc, washed with brine, dried over Na$_2$SO$_4$, filtered and evaporated to dryness. Purification by silica gel chromatography (Analogix, SF25-60 g, 10 to 50% EtOAc in hexanes) afforded tert-butyl 4-(hydroxy(4-(methoxycarbonyl)-3-methylthiophen-2-yl)methyl)piperidine-1-carboxylate (0.84 g, 2.273 mmol, 64.1% yield) as a white foam. $^1$H NMR (400 MHz, CDCl$_3$) δ 8.07 (s, 1H), 4.77 (dd, J=3.0, 8.1 Hz, 1H), 4.27-4.01 (m, 2H), 3.86 (s, 3H), 2.76-2.55 (m, 2H), 2.41 (s, 3H), 2.14 (d, J=3.0 Hz, 1H), 2.08 (d, J=12.9 Hz, 1H), 1.87-1.73 (m, J=3.7, 3.7, 3.7, 7.9, 7.9, 11.7 Hz, 1H), 1.48 (br. s., 1H), 1.47 (s, 9H), 1.40-1.25 (m, 2H), 1.24-1.11 (m, 1H). MS(ES) [M+H]$^+$ 252.1 (-Boc —H$_2$O), [M+Na]$^+$ 392.2.

d) tert-Butyl 4-((4-(((4,6-dimethyl-2-oxo-1,2-dihydropyridin-3-yl)methyl)carbamoyl)-3-methylthiophen-2-yl)(hydroxy)methyl)piperidine-1-carboxylate

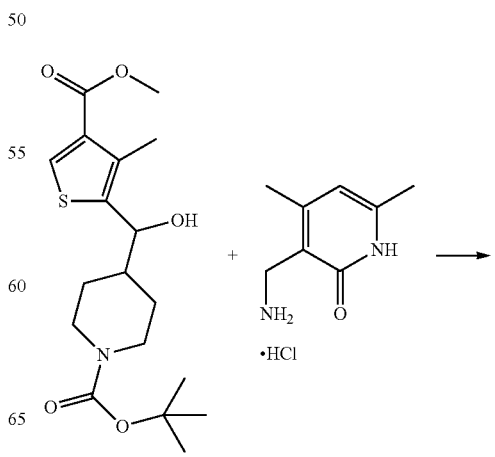

91

-continued

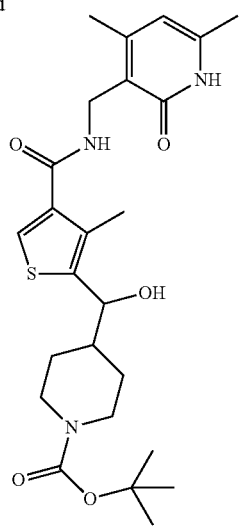

To a solution of tert-butyl 4-(hydroxy(4-(methoxycarbonyl)-3-methylthiophen-2-yl)methyl)piperidine-1-carboxylate (0.83 g, 2.246 mmol) in MeOH (25 mL) was added 1 N NaOH (5 mL, 5.00 mmol). The reaction was heated at 70° C. for 4 h, at which time it was concentrated under vacuum, acidified with 1 N HCl (5.0 mL), extracted with DCM, dried over MgSO$_4$, filtered and concentrated under vacuum.

To the above residue was added 3-(aminomethyl)-4,6-dimethylpyridin-2(1H)-one hydrochloride (0.45 g, 2.385 mmol), HOAt (0.31 g, 2.278 mmol) and DCM (25 mL). The resultant suspension was broken up with a stir rod and then NMM (270 μL, 2.456 mmol) was added, followed by EDC free base (0.42 g, 2.71 mmol). The reaction was stirred overnight. The suspension was filtered free of insolubles and rinsed with a small volume of DCM. The clear filtrate was concentrated under vacuum and purified by silica gel chromatography (Analogix, SF25-60 g, 2 to 10% (5% NH$_4$OH/MeOH) in DCM). The residue was triturated with 10% MeOH/H$_2$O, filtered and dried under vacuum to give tert-butyl 4-((4-(((4,6-dimethyl-2-oxo-1,2-dihydropyridin-3-yl)methyl)carbamoyl)-3-methylthiophen-2-yl)(hydroxy)methyl)piperidine-1-carboxylate (0.82 g, 1.675 mmol, 74.6% yield) as a white solid. $^1$H NMR (400 MHz, CDCl$_3$) δ 11.48 (br. s., 1H), 7.98 (t, J=5.1 Hz, 1H), 7.73 (s, 1H), 5.86 (s, 1H), 5.61 (d, J=3.8 Hz, 1H), 4.60 (dd, J=3.3, 7.1 Hz, 1H), 4.29-4.16 (m, 2H), 4.02-3.85 (m, 2H), 2.70-2.54 (m, 2H), 2.21 (s, 3H), 2.17 (s, 3H), 2.11 (s, 3H), 1.82 (d, J=12.9 Hz, 1H), 1.67-1.55 (m, 1H), 1.38 (s, 9H), 1.28 (d, J=11.9 Hz, 1H), 1.19-1.01 (m, J=3.8, 12.4, 12.4, 12.4, 12.4 Hz, 2H). MS(ES) [M+H]$^+$ 490.3.

92

Example 21

N-((4,6-dimethyl-2-oxo-1,2-dihydropyridin-3-yl)methyl)-5-(hydroxy(piperidin-4-yl)methyl)-4-methylthiophene-3-carboxamide To tert-butyl 4-((4-(((4,6-dimethyl-2-oxo-1,2-dihydropyridin-3-yl)methyl)carbamoyl)-3-methylthiophen-2-yl)(hydroxy)methyl)piperidine-1-carboxylate (750 mg, 1.532 mmol) was added 4 N HCl in 1,4-dioxane (15 mL, 494 mmol) and MeOH (2 mL). The reaction was stirred at RT for 30 min and then evaporated to dryness under vacuum. The remaining mixture was basified with 1 N Na$_2$CO$_3$, extracted with 10% MeOH in DCM (2×), washed with brine, dried over Na$_2$SO$_4$, filtered and concentrated under vacuum. The residue was purified by silica gel chromatography (Analogix SF25-60 g, 20 to 100% (5% NH$_4$OH/MeOH) in DCM). The fractions containing product were combined, evaporated to dryness, triturated with Et$_2$O, filtered and dried under vacuum to give N-((4,6-dimethyl-2-oxo-1,2-dihydropyridin-3-yl)methyl)-5-(hydroxy(piperidin-4-yl)methyl)-4-methylthiophene-3-carboxamide (47 mg, 0.121 mmol, 7.88% yield) as a white solid. $^1$H NMR (400 MHz, DMSO-d$_6$) δ 7.98 (t, J=4.9 Hz, 3H), 7.71 (s, 1H), 5.86 (s, 1H), 5.52 (br. s., 1H), 4.55 (d, J=7.1 Hz, 1H), 4.29-4.15 (m, 2H), 3.02-2.79 (m, 2H), 2.43-2.28 (m, 2H), 2.20 (s, 3H), 2.17 (s, 3H), 2.11 (s, 3H), 1.88-1.62 (m, 2H), 1.57-1.46 (m, 1H), 1.28-1.18 (m, 1H), 1.17-1.01 (m, 2H). MS(ES) [M+H]$^+$ 390.1.

Example 22

N-((4,6-Dimethyl-2-oxo-1,2-dihydropyridin-3-yl)methyl)-4-methyl-5-(1-(tetrahydro-2H-pyran-4-yl)pyrrolidin-2-yl)thiophene-3-carboxamide

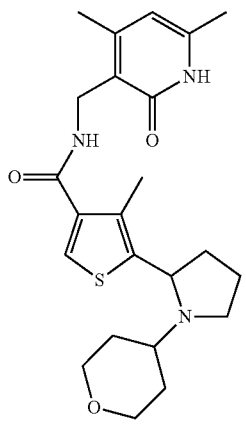 [SMILES: Cc1cc(C)c(CNC(=O)c2csc(C3CCCN3C3CCOCC3)c2C)c(=O)[nH]1]

a) Methyl 5-(4-chlorobutanol)-4-methylthiophene-3-carboxylate

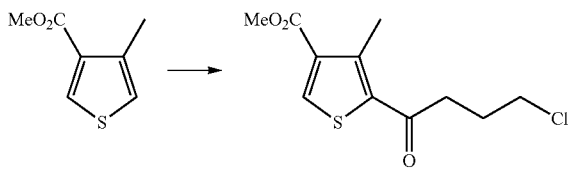

To a solution of methyl 4-methylthiophene-3-carboxylate (1.2 g, 7.68 mmol) in nitromethane (20 mL) were added 4-chlorobutanoyl chloride (0.946 mL, 8.45 mmol) and Zn(OTf)$_2$ (0.279 g, 0.768 mmol), and the mixture was stirred at RT for 20 h. The reaction mixture was diluted with EtOAc and treated with 10% NaHCO$_3$ aqueous solution. The organic layer was collected, dried over Na$_2$SO$_4$ and concentrated. The residue was purified using column chromatography (silica gel, 0 to 60% EtOAc/hexanes) to give methyl 5-(4-chlorobutanoyl)-4-methylthiophene-3-carboxylate (850 mg) as a white solid. $^1$H NMR (400 MHz, CDCl$_3$) δ 1.63 (s, 3H), 2.24 (quin, J=6.57 Hz, 2H), 2.84 (s, 3H), 3.09 (t, J=6.95 Hz, 2H), 3.69 (t, J=6.19 Hz, 2H), 3.90 (s, 3H), 8.25 (s, 1H). MS(ES) [M+H]$^+$ 261.0.

b) Methyl 4-methyl-5-(1-(tetrahydro-2H-pyran-4-yl)pyrrolidin-2-yl)thiophene-3-carboxylate

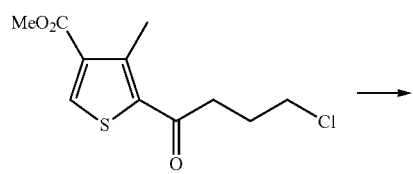

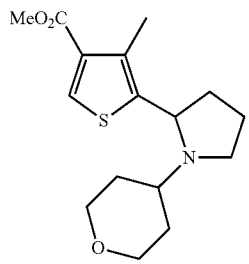

To a solution of methyl 5-(4-chlorobutanoyl)-4-methyl-thiophene-3-carboxylate (180 mg, 0.690 mmol) in MeOH (3 mL) were added tetrahydro-2H-pyran-4-amine (419 mg, 4.14 mmol) and AcOH (0.040 mL, 0.690 mmol). The mixture was stirred at RT for 1 h, at which time NaBH$_3$CN (130 mg, 2.071 mmol) was added. The mixture was heated at reflux for 18 h, at which time it was quenched with water, neutralized with 10% aqueous NaHCO$_3$ and extracted with EtOAc (3×). The extract was dried over Na$_2$SO$_4$ and concentrated. The residue was purified using column chromatography (silica gel, 0 to 60% EtOAc/hexanes) to give methyl 4-methyl-5-(1-(tetrahydro-2H-pyran-4-yl)pyrrolidin-2-yl)thiophene-3-carboxylate (41 mg) as a pale yellow solid. $^1$H NMR (600 MHz, CDCl$_3$) δ 1.72-1.92 (m, 2H), 1.99-2.18 (m, 2H), 2.30-2.98 (m, 7H), 3.01-3.59 (m, 4H), 3.73-3.96 (m, 3H), 4.12 (d, J=6.80 Hz, 3H), 4.65 (br. s., 1H), 8.23 (br. s., 1H). MS(ES) [M+H]$^+$ 310.1.

c) 4-Methyl-5-(1-(tetrahydro-2H-pyran-4-yl)pyrrolidin-2-yl)thiophene-3-carboxylic acid

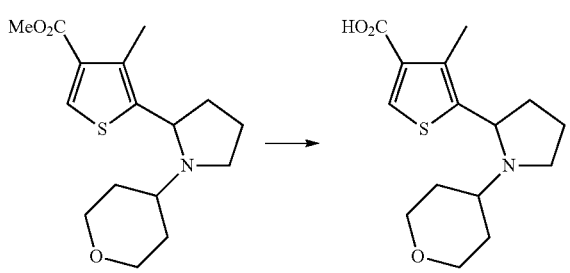 [SMILES: COC(=O)c1csc(C2CCCN2C2CCOCC2)c1C ; Cc1c(C(=O)O)csc1C1CCCN1C1CCOCC1]

To a solution of methyl 4-methyl-5-(1-(tetrahydro-2H-pyran-4-yl)pyrrolidin-2-yl)thiophene-3-carboxylate (40 mg, 0.129 mmol) in MeOH (2 mL) was added NaOH (0.032 mL, 0.129 mmol), and the mixture was stirred at RT for 20 h. The mixture was purified using reverse-phase HPLC to give 4-methyl-5-(1-(tetrahydro-2H-pyran-4-yl)pyrrolidin-2-yl)thiophene-3-carboxylic acid (30 mg) as a pale yellow solid. $^1$H NMR (400 MHz, methanol-d$_4$) δ 1.60-1.80 (m, 3H), 1.83-2.16 (m, 4H), 2.34-2.49 (m, 4H), 2.97-3.11 (m, 2H), 3.88-4.07 (m, 2H), 4.68 (t, J=7.33 Hz, 1H), 8.16 (s, 1H). MS(ES) [M+H]$^+$ 296.1.

d) N-((4,6-Dimethyl-2-oxo-1,2-dihydropyridin-3-yl)methyl)-4-methyl-5-(1-(tetrahydro-2H-pyran-4-yl)pyrrolidin-2-yl)thiophene-3-carboxamide

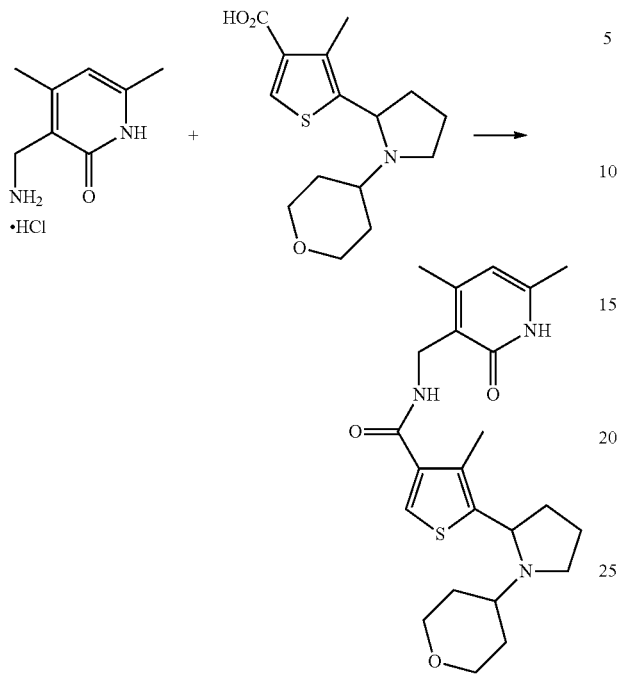

To a solution of 4-methyl-5-(1-(tetrahydro-2H-pyran-4-yl)pyrrolidin-2-yl)thiophene-3-carboxylic acid (30 mg, 0.102 mmol) in DMSO (2 mL) were added 3-(aminomethyl)-4,6-dimethylpyridin-2(1H)-one hydrochloride (24.91 mg, 0.132 mmol), NMM (0.067 mL, 0.609 mmol), HOAt (27.6 mg, 0.203 mmol), and EDC (38.9 mg, 0.203 mmol), and the mixture was stirred at RT for 18 h. The reaction mixture was purified using reverse-phase HPLC. The fractions containing the product were combined, treated with 1 N HCl and concentrated to give N-((4,6-dimethyl-2-oxo-1,2-dihydropyridin-3-yl)methyl)-4-methyl-5-(1-(tetrahydro-2H-pyran-4-yl)pyrrolidin-2-yl)thiophene-3-carboxamide (17 mg) as an off-white solid. $^1$H NMR (400 MHz, methanol-d$_4$) δ 1.76-1.90 (m, 3H), 2.03 (m, 1H), 2.23-2.33 (m, 3H), 2.40-2.59 (m, 6H), 2.60-2.67 (m, 1H), 3.38-3.60 (m, 4H), 3.64-3.76 (m, 1H), 3.92-4.13 (m, 2H), 5.18-5.31 (m, 1H), 6.86 (s, 1H), 8.17 (s, 1H). MS(ES) [M+H]$^+$ 430.2.

Example 23

N-((4,6-dimethyl-2-oxo-1,2-dihydropyridin-3-yl)methyl)-4-methyl-5-(1-(piperidin-4-yl)-1H-pyrazol-4-yl)thiophene-3-carboxamide

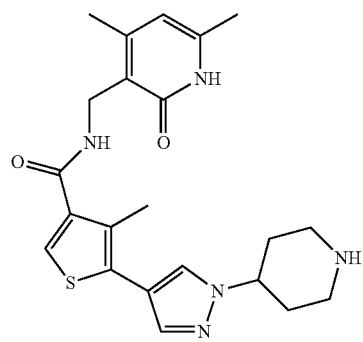 [SMILES: Cc1cc(C)c(CNC(=O)c2csc(-c3cnn(C4CCNCC4)c3)c2C)c(=O)[nH]1]

a) tert-Butyl 4-(4-(4-(methoxycarbonyl)-3-methylthiophen-2-yl)-1H-pyrazol-1-yl)piperidine-1-carboxylate

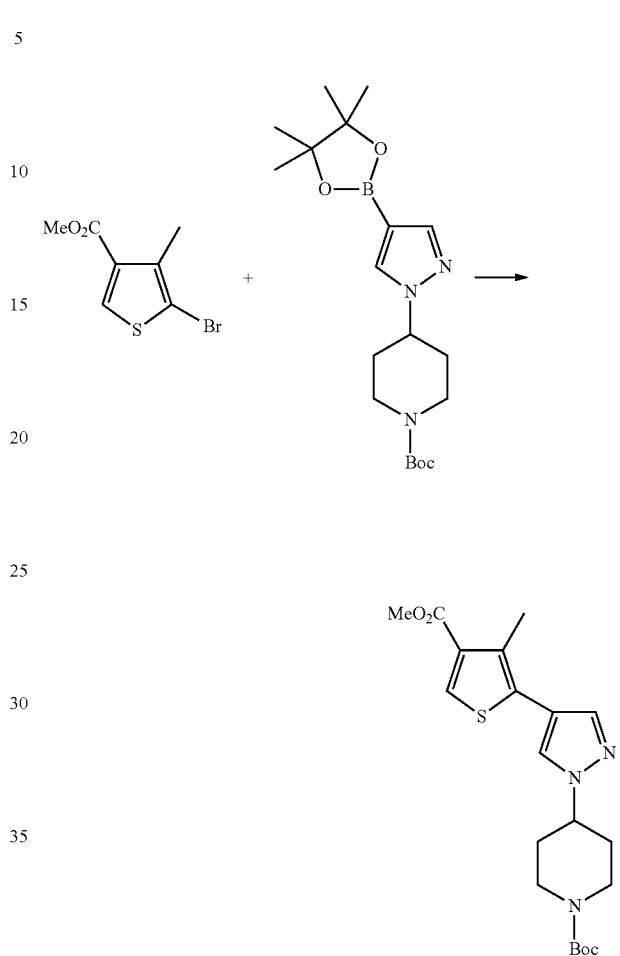

To a 10-mL microwave tube were added methyl 5-bromo-4-methylthiophene-3-carboxylate (150 mg, 0.638 mmol), tert-butyl 4-(4-(4,4,5,5-tetramethyl-1,3,2-dioxaborolan-2-yl)-1H-pyrazol-1-yl)piperidine-1-carboxylate (313 mg, 0.829 mmol), DMF (4 mL), and 2 M Na$_2$CO$_3$ aqueous solution (1.436 mL, 2.87 mmol), and the mixture was degassed for 5 min by bubbling N$_2$. Pd(PPh$_3$)$_4$ (73.7 mg, 0.064 mmol) was added and the tube was sealed. The mixture was heated at 80° C. under microwave conditions for 90 min. The mixture was cooled, diluted with water, and extracted with EtOAc (3×). The extract was dried over Na$_2$SO$_4$ and concentrated. The residue was purified using column chromatography (silica gel, 0 to 100% EtOAc/hexanes) to give tert-butyl 4-(4-(4-(methoxycarbonyl)-3-methylthiophen-2-yl)-1H-pyrazol-1-yl)piperidine-1-carboxylate (240 mg) as a pale yellow solid. $^1$H NMR (400 MHz, CDCl$_3$) δ 1.45-1.54 (s, 9H), 1.97 (qd, J=12.25, 4.42 Hz, 2H), 2.20 (dd, J=12.13, 2.02 Hz, 2H), 2.45-2.56 (m, 3H), 2.93 (m, 2H), 3.85-3.91 (m, 3H), 4.24-4.42 (m, 3H), 7.53-7.60 (m, 1H), 7.65 (s, 1H), 7.95-8.05 (m, 1H). MS(ES) [M+H]$^+$ 406.2.

b) 5-(1-(1-(tert-Butoxycarbonyl)piperidin-4-yl)-1H-pyrazol-4-yl)-4-methylthiophene-3-carboxylic acid

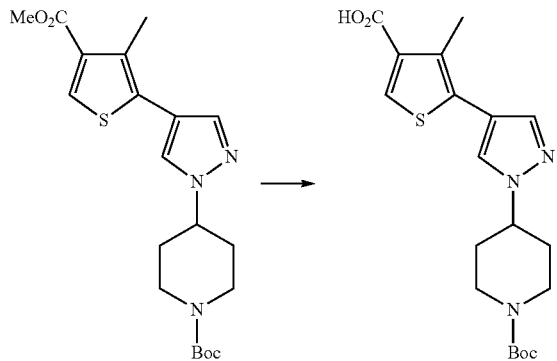 [SMILES: COC(=O)c1csc(-c2cnn(C3CCN(C(=O)OC(C)(C)C)CC3)c2)c1C ; Cc1c(C(=O)O)csc1-c1cnn(C2CCN(C(=O)OC(C)(C)C)CC2)c1]

To a solution of tert-butyl 4-(4-(4-(methoxycarbonyl)-3-methylthiophen-2-yl)-1H-pyrazol-1-yl)piperidine-1-carboxylate (240 mg, 0.592 mmol) in MeOH (4 mL) was added 4 M NaOH (0.740 mL, 2.96 mmol), and the mixture was stirred at RT for 18 h. The mixture was concentrated to removed MeOH and the residue was acidified using 1 N HCl and extracted with EtOAc (3×). The extract was dried over Na$_2$SO$_4$ and concentrated. The residue was dried under vacuum to give 5-(1-(1-(tert-butoxycarbonyl)piperidin-4-yl)-1H-pyrazol-4-yl)-4-methylthiophene-3-carboxylic acid (195 mg) as an off-white solid. $^1$H NMR (400 MHz, CDCl$_3$) δ 1.47-1.57 (m, 9H), 1.98 (qd, J=12.25, 4.42 Hz, 2H), 2.16-2.26 (m, 2H), 2.51 (s, 3H), 2.93 (br. s., 2H), 4.21-4.43 (m, 3H), 7.57 (s, 1H), 7.67 (s, 1H), 8.17 (s, 1H). MS(ES) [M+H]$^+$ 392.1.

c) tert-Butyl 4-(4-(4-(((4,6-dimethyl-2-oxo-1,2-dihydropyridin-3-yl)methyl)carbamoyl)-3-methylthiophen-2-yl)-1H-pyrazol-1-yl)piperidine-1-carboxylate

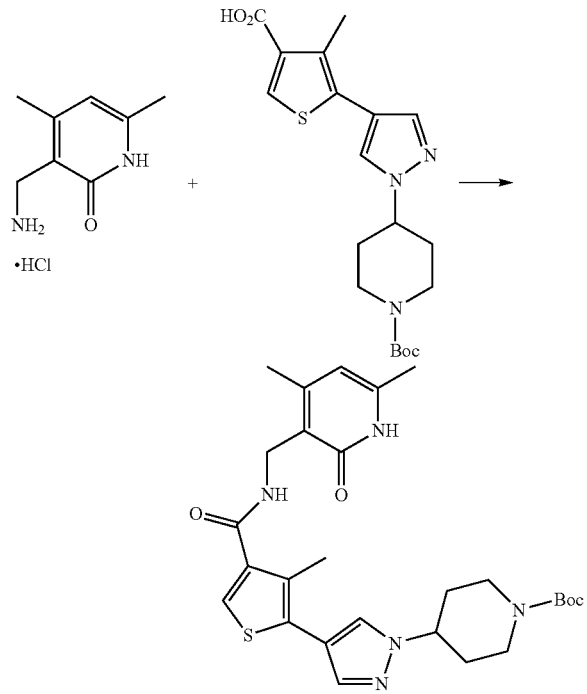

To a solution of 5-(1-(1-(tert-butoxycarbonyl)piperidin-4-yl)-1H-pyrazol-4-yl)-4-methylthiophene-3-carboxylic acid (187 mg, 0.478 mmol) in DMSO (3 mL) were added 3-(aminomethyl)-4,6-dimethylpyridin-2(1H)-one hydrochloride (117 mg, 0.621 mmol), NMM (0.263 mL, 2.388 mmol), EDC (183 mg, 0.955 mmol), and HOAt (130 mg, 0.955 mmol), and the mixture was stirred at RT for 18 h. The reaction mixture was quenched with water. The precipitate was collected by filtration and dried under vacuum to give tert-butyl 4-(4-(4-(((4,6-dimethyl-2-oxo-1,2-dihydropyridin-3-yl)methyl)carbamoyl)-3-methylthiophen-2-yl)-1H-pyrazol-1-yl)piperidine-1-carboxylate (240 mg) as an off-white solid. $^1$H NMR (400 MHz, DMSO-d$_6$) δ 1.42 (s, 9H), 1.82 (qd, J=12.21, 4.55 Hz, 2H), 2.01 (m, 2H), 2.12 (s, 3H), 2.18 (s, 3H), 2.30 (s, 3H), 2.83-3.03 (m, 2H), 4.04 (m, 2H), 4.25 (d, J=5.05 Hz, 2H), 4.34-4.49 (m, 1H), 5.87 (s, 1H), 7.63 (s, 1H), 7.70 (s, 1H), 8.00-8.15 (m, 2H). MS(ES) [M+H]$^+$ 526.4.

d) N-((4,6-Dimethyl-2-oxo-1,2-dihydropyridin-3-yl)methyl)-4-methyl-5-(1-(piperidin-4-yl)-1H-pyrazol-4-yl)thiophene-3-carboxamide

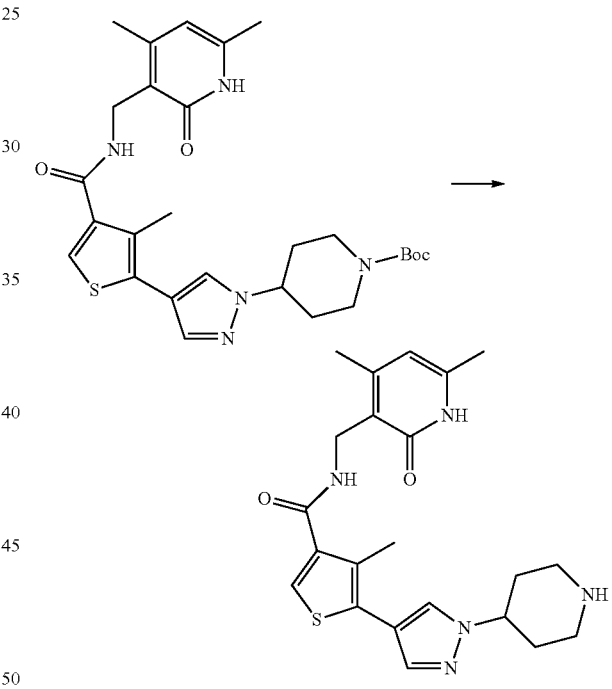

To a suspension of tert-butyl 4-(4-(4-(((4,6-dimethyl-2-oxo-1,2-dihydropyridin-3-yl)methyl)carbamoyl)-3-methylthiophen-2-yl)-1H-pyrazol-1-yl)piperidine-1-carboxylate (45 mg, 0.086 mmol) in 1,4-dioxane (1 mL) was added 4 M HCl in 1,4-dioxane (0.5 mL, 2.000 mmol), and the mixture was stirred at RT for 1 h. The mixture was concentrated and the residue was purified using reverse-phase HPLC. The fractions containing the product were combined, treated with 1 N HCl and concentrated to give N-((4,6-dimethyl-2-oxo-1,2-dihydropyridin-3-yl)methyl)-4-methyl-5-(1-(piperidin-4-yl)-1H-pyrazol-4-yl)thiophene-3-carboxamide (32 mg) as an off-white solid. $^1$H NMR (400 MHz, DMSO-d$_6$) 2.09-2.27 (m, 10H), 2.29-2.33 (m, 3H), 2.98-3.13 (m, 2H), 3.33-3.44 (m, 2H), 4.26 (d, J=4.55 Hz, 2H), 4.54 (tt, J=9.95, 4.96 Hz, 1H), 5.94 (s, 1H), 7.69 (s, 1H), 7.75 (s, 1H), 8.03 (s, 1H), 8.13-8.26 (m, 1H). MS(ES) [M+H]$^+$ 426.2.

Example 24 tert-Butyl 3-(4-(((4,6-dimethyl-2-oxo-1,2-dihydro-pyridin-3-yl)methyl)carbamoyl)-3-methylthiophen-2-yl)pyrrolidine-1-carboxylate a) tert-Butyl 3-(4-(methoxycarbonyl)-3-methylthiophen-2-yl)-2,5-dihydro-1H-pyrrole-1-carboxylate

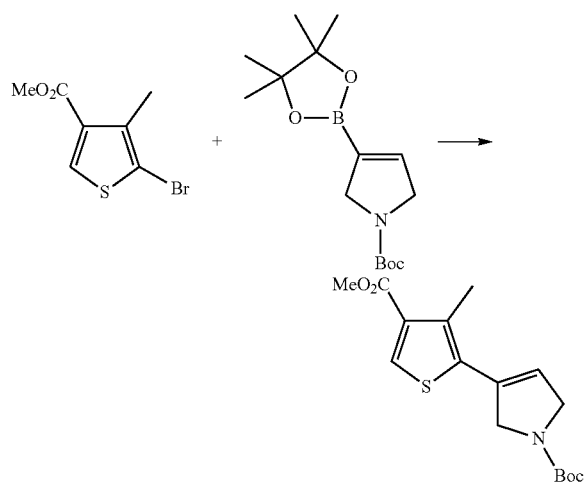

To a 30-mL microwave tube were added methyl 5-bromo-4-methylthiophene-3-carboxylate (500 mg, 2.127 mmol), tert-butyl 3-(4,4,5,5-tetramethyl-1,3,2-dioxaborolan-2-yl)-2,5-dihydro-1H-pyrrole-1-carboxylate (816 mg, 2.76 mmol), DMF (14 mL), and 2 M Na$_2$CO$_3$ (4.79 mL, 9.57 mmol), and the mixture was degassed for 5 min by bubbling N$_2$. Pd(PPh$_3$)$_4$ (246 mg, 0.213 mmol) was added and the tube was sealed. The mixture was heated at 80° C. under microwave conditions for 90 min. The mixture was cooled, diluted with water, and extracted with EtOAc (3×). The combined extracts were dried over Na$_2$SO$_4$ and concentrated. The residue was purified using column chromatography (silica gel, 0 to 60% EtOAc/hexanes) to give tert-butyl 3-(4-(methoxycarbonyl)-3-methylthiophen-2-yl)-2,5-dihydro-1H-pyrrole-1-carboxylate (650 mg) as a white solid. $^1$H NMR (400 MHz, CDCl$_3$) δ 1.52 (s, 9H), 2.55 (s, 3H), 3.87 (s, 3H), 4.25-4.57 (m, 4H), 5.95 (m, 1H), 8.02 (s, 1H). MS(ES) [M+H]$^+$ 346.2.

b) tert-Butyl 3-(4-(methoxycarbonyl)-3-methylthiophen-2-yl)pyrrolidine-1-carboxylate

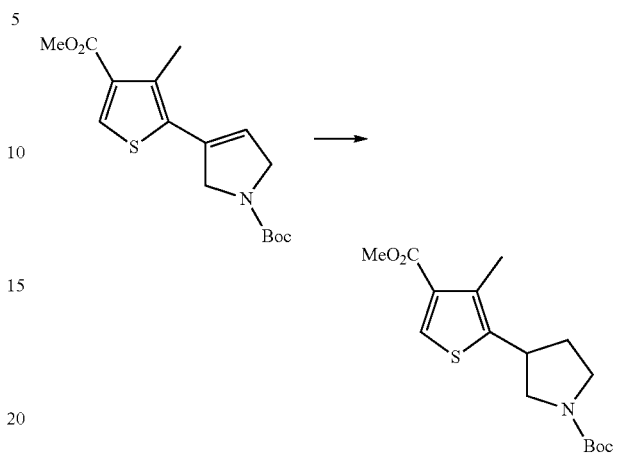

A solution of tert-butyl 3-(4-(methoxycarbonyl)-3-methylthiophen-2-yl)-2,5-dihydro-1H-pyrrole-1-carboxylate (520 mg, 1.608 mmol) in MeOH (50 mL) was hydrogenated on an H-Cube at 60 bar and 35° C. using 10% Pd/C (171 mg, 1.608 mmol) for 20 h. The reaction mixture was concentrated to give tert-butyl 3-(4-(methoxycarbonyl)-3-methylthiophen-2-yl)pyrrolidine-1-carboxylate (510 mg) as pale yellow oil. $^1$H NMR (400 MHz, CDCl$_3$) δ 1.41-1.55 (m, 9H), 2.01 (br. s., 1H), 2.29 (d, J=1.52 Hz, 1H), 2.44 (s, 3H), 3.10-3.70 (m, 5H), 3.86 (s, 3H), 7.93-8.02 (m, 1H). MS(ES) [M+H]$^+$ 348.1.

c) 5-(1-(tert-Butoxycarbonyl)pyrrolidin-3-yl)-4-methylthiophene-3-carboxylic acid

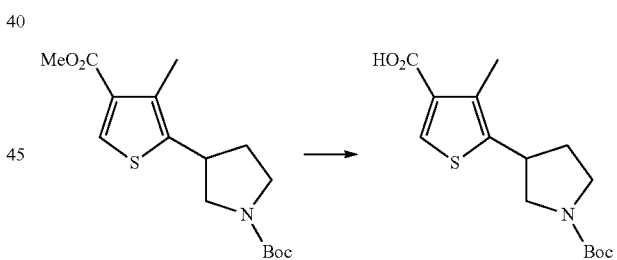

To a solution of tert-butyl 3-(4-(methoxycarbonyl)-3-methylthiophen-2-yl)pyrrolidine-1-carboxylate (510 mg, 1.567 mmol) in MeOH (8 mL) was added 4 M NaOH (1.959 mL, 7.84 mmol), and the mixture was stirred at RT for 20 h. The mixture was concentrated. The residue was treated with water, acidified using 1 N HCl and extracted with EtOAc (3×). The combined extracts were dried over Na$_2$SO$_4$ and concentrated. The residue was dried under vacuum to give 5-(1-(tert-butoxycarbonyl)pyrrolidin-3-yl)-4-methylthiophene-3-carboxylic acid (460 mg) as a pale brown solid. $^1$H NMR (400 MHz, CDCl$_3$) δ 1.40-1.63 (m, 9H), 1.93-2.08 (m, 1H), 2.25-2.40 (m, 1H), 2.45 (br. s., 3H), 3.18-3.37 (m, 1H), 3.38-3.52 (m, 1H), 3.54-3.99 (m, 3H), 8.13 (s, 1H). MS(ES) [M+H]$^+$ 311.9.

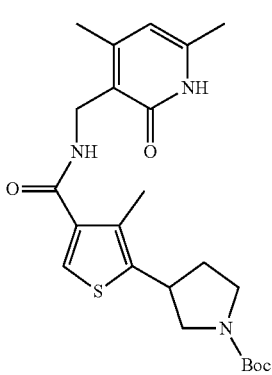 [SMILES: Cc1cc(C)c(CNC(=O)c2csc(C3CCN(C(=O)OC(C)(C)C)C3)c2C)c(=O)[nH]1]

101 d) tert-Butyl 3-(4-(((4,6-dimethyl-2-oxo-1,2-dihydropyridin-3-yl)methyl)carbamoyl)-3-methylthiophen-2-yl)pyrrolidine-1-carboxylate

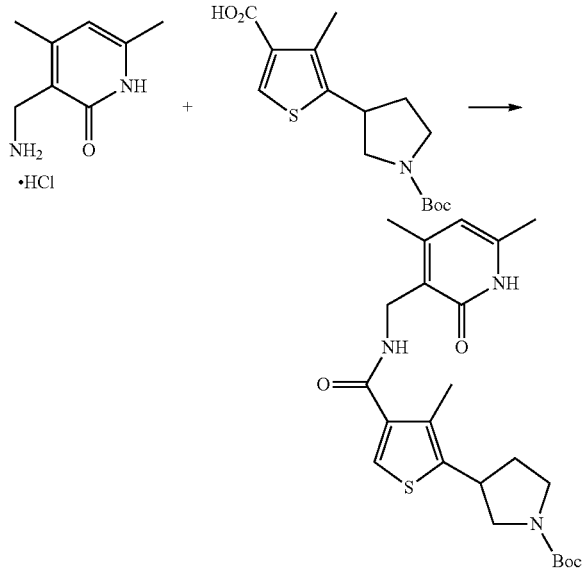

To a solution of 5-(1-(tert-butoxycarbonyl)pyrrolidin-3-yl)-4-methylthiophene-3-carboxylic acid (450 mg, 1.445 mmol) in DMSO (4 mL) were added 3-(aminomethyl)-4,6-dimethylpyridin-2(1H)-one hydrochloride (354 mg, 1.879 mmol), NMM (0.794 mL, 7.23 mmol), HOAt (393 mg, 2.89 mmol) and EDC (554 mg, 2.89 mmol) and the mixture was stirred at RT for 18 h. The mixture was quenched with water and the resultant precipitate was collected by filtration and dried under vacuum to give tert-butyl 3-(4-(((4,6-dimethyl-2-oxo-1,2-dihydropyridin-3-yl)methyl)carbamoyl)-3-methylthiophen-2-yl)pyrrolidine-1-carboxylate (590 mg) as an off-white solid. $^1$H NMR (400 MHz, DMSO-$d_6$) δ 1.41 (d, 9H), 1.75-1.92 (m, 1H), 2.07-2.29 (m, 10H), 3.02-3.15 (m, 1H), 3.46 (m, 1H), 3.60-3.82 (m, 2H), 4.23 (d, J=5.05 Hz, 2H), 5.86 (s, 1H), 7.67 (s, 1H), 8.02 (t, J=4.93 Hz, 1H). MS(ES) [M+H]$^+$ 446.2.

Example 25

N-((4,6-Dimethyl-2-oxo-1,2-dihydropyridin-3-yl)methyl)-4-methyl-5-(2-methylpyrrolidin-1-yl)thiophene-3-carboxamide

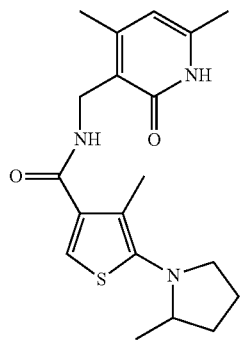 [SMILES: Cc1cc(C)c(CNC(=O)c2csc(N3CCCC3C)c2C)c(=O)[nH]1]

102 a) Methyl 4-methyl-5-(2-methylpyrrolidin-1-yl)thiophene-3-carboxylate

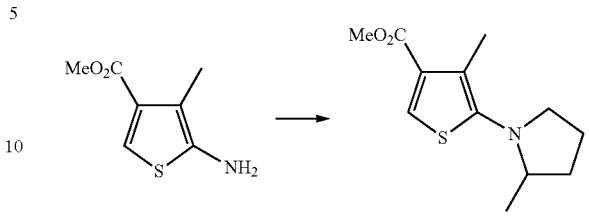

To a solution of methyl 5-amino-4-methylthiophene-3-carboxylate (100 mg, 0.584 mmol) in MeOH (3 mL) were added 5-chloropentan-2-one (0.802 mL, 7.01 mmol), AcOH (0.067 mL, 1.168 mmol), and NaBH$_3$CN (184 mg, 2.92 mmol), and the mixture was heated at reflux for 4 h. The mixture was concentrated and the residue was treated with water, neutralized using 10% aqueous NaHCO$_3$ and extracted with EtOAc (3×). The combined extracts were dried over Na$_2$SO$_4$ and concentrated. The residue was purified using column chromatography (silica gel, 0 to 60% EtOAc/hexanes) to give methyl 4-methyl-5-(2-methylpyrrolidin-1-yl)thiophene-3-carboxylate (110 mg) as a pale yellow oil. $^1$H NMR (400 MHz, CDCl$_3$) δ 1.03-1.11 (m, 3H), 1.52-1.70 (m, 1H), 1.80-2.02 (m, 2H), 2.08-2.19 (m, 1H), 2.29-2.41 (m, 3H), 2.78-2.93 (m, 1H), 3.16-3.30 (m, 1H), 3.43 (ddd, J=9.09, 7.83, 5.05 Hz, 1H), 3.79-3.90 (m, 3H), 4.14 (q, 2H), 7.72 (s, 1H). MS(ES) [M+H]$^+$ 240.0.

b) 4-Methyl-5-(2-methylpyrrolidin-1-yl)thiophene-3-carboxylic acid

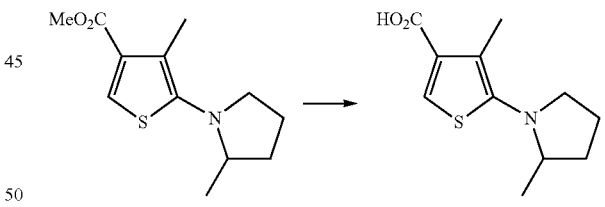

To a solution of methyl 4-methyl-5-(2-methylpyrrolidin-1-yl)thiophene-3-carboxylate (110 mg, 0.460 mmol) in MeOH (3 mL) was added 4 M NaOH (0.575 mL, 2.298 mmol), and the mixture was heated at 40° C. for 18 h. The mixture was purified using reverse-phase HPLC to give 4-methyl-5-(2-methylpyrrolidin-1-yl)thiophene-3-carboxylic acid (72 mg) as a pale yellow solid. $^1$H NMR (400 MHz, methanol-$d_4$) δ 1.06 (d, 3H), 1.52-1.69 (m, 1H), 1.83-2.05 (m, 2H), 2.09-2.24 (m, 1H), 2.27-2.34 (m, 3H), 2.85 (td, J=8.72, 7.07 Hz, 1H), 3.15-3.28 (m, 1H), 3.43 (ddd, J=9.09, 7.83, 5.05 Hz, 1H), 7.86 (s, 1H). MS(ES) [M+H]$^+$ 225.9.

c) N-((4,6-Dimethyl-2-oxo-1,2-dihydropyridin-3-yl)methyl)-4-methyl-5-(2-methylpyrrolidin-1-yl)thiophene-3-carboxamide

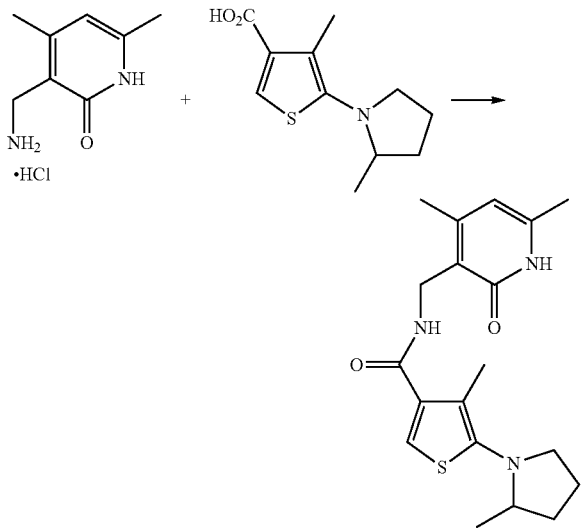

To a solution of 4-methyl-5-(2-methylpyrrolidin-1-yl)thiophene-3-carboxylic acid (68 mg, 0.302 mmol) in DMSO (2 mL) were added 3-(aminomethyl)-4,6-dimethylpyridin-2 (1H)-one hydrochloride (74.0 mg, 0.392 mmol), NMM (0.199 mL, 1.811 mmol), EDC (116 mg, 0.604 mmol) and HOAt (82 mg, 0.604 mmol), and the mixture was stirred at RT for 18 h. The reaction mixture was purified using reverse-phase HPLC to give N-((4,6-dimethyl-2-oxo-1,2-dihydropyridin-3-yl)methyl)-4-methyl-5-(2-methylpyrrolidin-1-yl)thiophene-3-carboxamide (41 mg) as an off-white solid. $^1$H NMR (400 MHz, DMSO-$d_6$) δ 0.99 (d, 3H), 1.44-1.60 (m, 1H), 1.77-1.96 (m, 2H), 2.04-2.22 (m, 10H), 2.70-2.82 (m, 1H), 3.07-3.22 (m, 1H), 3.30-3.44 (m, 1H), 4.23 (d, J=5.31 Hz, 2H), 5.86 (s, 1H), 7.34-7.52 (m, 1H), 7.94 (t, J=4.93 Hz, 1H) 11.48 (s, 1H). MS(ES) [M+H]$^+$ 360.2.

Example 26

N-((4,6-dimethyl-2-oxo-1,2-dihydropyridin-3-yl)methyl)-4-methyl-5-(1-morpholinoethyl)thiophene-3-carboxamide

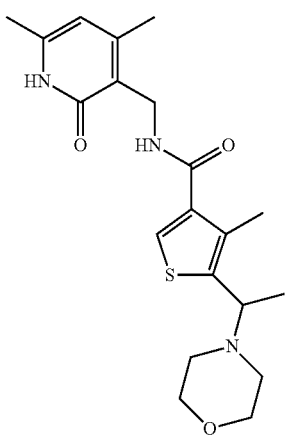 [SMILES: Cc1cc(C)c(CNC(=O)c2csc(C(C)N3CCOCC3)c2C)c(=O)[nH]1]

a) Methyl 4-methylthiophene-3-carboxylate

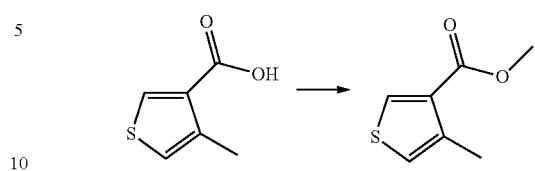

To a 250 mL round bottom flask were added 4-methylthiophene-3-carboxylic acid (5.0 g, 35.2 mmol) and MeOH (75 mL), followed by H$_2$SO$_4$ (9.37 mL, 176 mmol) dropwise. The mixture was heated at 72° C. for 4 h. The reaction was allowed to cool, diluted with EtOAc/Et$_2$O (1/2) and extracted with 1 N HCl/brine (1/2). The organics were dried with Na$_2$SO$_4$, filtered and evaporated to give methyl 4-methylthiophene-3-carboxylate (4.3 g, 27.5 mmol, 78% yield) as a tan oil. $^1$H NMR (400 MHz, CDCl$_3$) δ 8.10 (d, J=3.28 Hz, 1H) 6.95 (dd, J=3.41, 1.14 Hz, 1H) 3.87 (s, 3H) 2.49 (s, 3H). MS(ES) [M+H]$^+$ 156.9.

b) Methyl 5-acetyl-4-methylthiophene-3-carboxylate

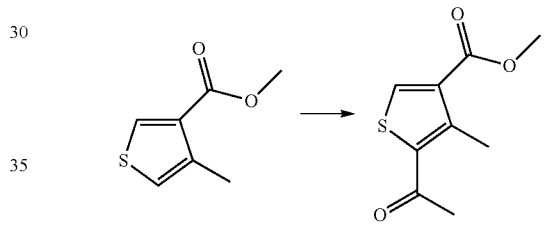

A mixture of methyl 4-methylthiophene-3-carboxylate (0.5 g, 3.20 mmol), nitromethane (5 mL), In(OTf)$_3$ (0.090 g, 0.160 mmol), LiClO$_4$ (0.409 g, 3.84 mmol) and Ac$_2$O (0.302 mL, 3.20 mmol) was heated at 50° C. for 40 min. Water was added to the reaction and the solution was separated. The water was extracted with DCM and the organics were washed with brine, dried with Na$_2$SO$_4$, filtered and evaporated to give methyl 5-acetyl-4-methylthiophene-3-carboxylate (549 mg, 2.63 mmol, 82% yield) as a pale yellow solid. $^1$H NMR (400 MHz, CDCl$_3$) δ 8.57 (s, 1H) 3.81 (s, 3H) 2.71 (s, 3H) 2.55 (s, 3H). MS(ES) [M+H]$^+$ 198.9.

c) Methyl 5-(1-hydroxyethyl)-4-methylthiophene-3-carboxylate

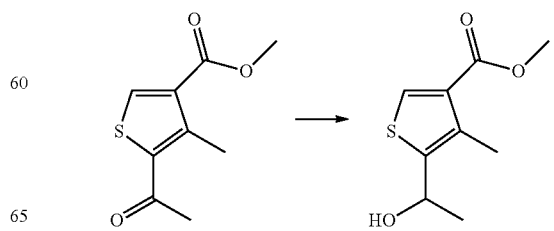

To a cooled (0° C.) solution of methyl 5-acetyl-4-methylthiophene-3-carboxylate (300 mg, 1.513 mmol) in THF (15 mL) was added NaBH₄ (34.4 mg, 0.908 mmol). The reaction was allowed to warm to RT and was stirred for 25 h. The reaction was quenched with water and extracted with EtOAc. The combined organics were evaporated. Purification by silica gel chromatography (Varian 971FP, 0-30% EtOAc/hexanes, SF25-40 g, 15 min) provided methyl 5-(1-hydroxyethyl)-4-methylthiophene-3-carboxylate (250 mg, 1.236 mmol, 82% yield) as a clear oil. $^1$H NMR (400 MHz, CDCl₃) δ 8.02 (s, 1H) 5.23-5.30 (m, 1H) 3.86 (s, 3H) 2.44 (s, 3H) 1.97 (br. s., 1H) 1.58 (d, J=6.32 Hz, 3H). MS(ES) [M+H]⁺ 182.9, 200.9.

d) Methyl 4-methyl-5-(1-morpholinoethyl)thiophene-3-carboxylate

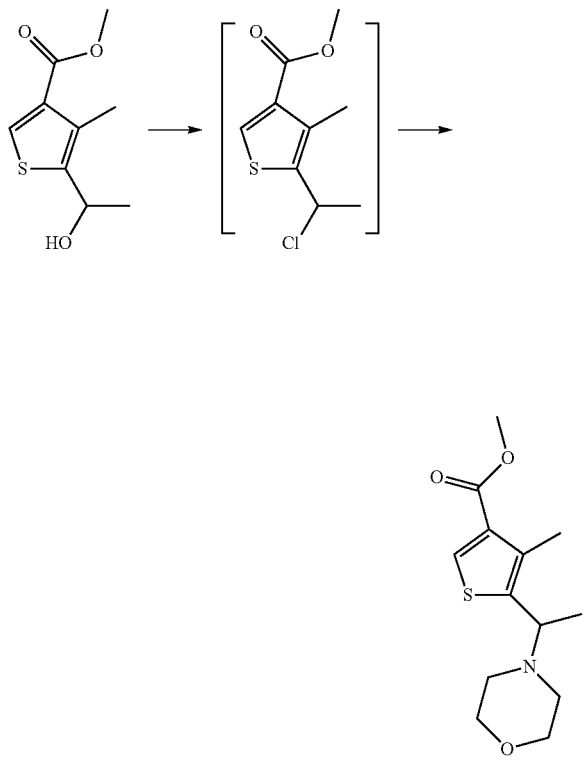

To a solution of methyl 5-(1-hydroxyethyl)-4-methylthiophene-3-carboxylate (190 mg, 0.949 mmol) in DCM (5 mL) was added SOCl₂ (1.898 mL, 3.80 mmol). The reaction was stirred at RT for 4 h. The mixture was evaporated and evaporated again from DCM. A solution of morpholine (0.331 mL, 3.80 mmol) in CH₃CN (5.00 mL) was added to the crude evaporated material. The reaction was stirred at 65° C. for 1 h, at which time it was allowed to cool to RT and was stirred overnight. The reaction was evaporated and the residue was suspended in EtOAc. A solid formed and was filtered. The filtrate was evaporated. Purification by reverse phase Gilson HPLC (2-40% CH₃CN/water+0.1% TFA, YMC ODS-A C18 Column 75×30 mm ID S-5 um, 12 nM Column 5 min) provided methyl 4-methyl-5-(1-morpholinoethyl) thiophene-3-carboxylate (180 mg, 0.668 mmol, 70.4% yield) as a clear oil after isolation and extraction into 20% MeOH/EtOAc from saturated aqueous NaHCO₃. $^1$H NMR (400 MHz, DMSO-d₆) δ 8.18 (s, 1H) 3.72-3.79 (m, 4H) 3.55 (t, J=4.67 Hz, 4H) 2.42-2.49 (m, 2H) 2.31-2.38 (m, 5H) 1.28 (d, J=6.57 Hz, 3H) H). MS(ES) [M+H]⁺ 270.0.

e) N-((4,6-dimethyl-2-oxo-1,2-dihydropyridin-3-yl)methyl)-4-methyl-5-(1-morpholinoethyl)thiophene-3-carboxamide

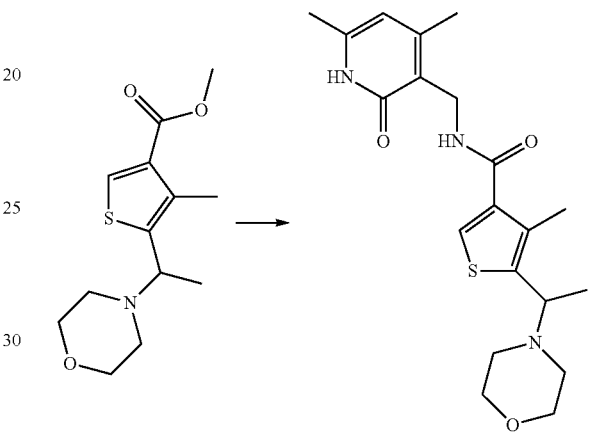

A mixture of methyl 4-methyl-5-(1-morpholinoethyl) thiophene-3-carboxylate (180 mg, 0.668 mmol), MeOH (5 mL), and 5 N NaOH (1.337 mL, 6.68 mmol) was heated at 45° C. overnight. The reaction was allowed to cool to RT and neutralized with 6 N HCl (1.114 mL, 6.68 mmol). The reaction mixture was evaporated and evaporated again from DCM.

To a solution of the crude residue in DMSO (5.00 mL) was added NMM (0.367 mL, 3.34 mmol) and 3-(aminomethyl)-4,6-dimethylpyridin-2(1)-one (153 mg, 1.002 mmol), followed by EDC (192 mg, 1.002 mmol), HOBT (154 mg, 1.002 mmol) and more NMM (0.367 mL, 3.34 mmol). The reaction stirred at RT for 3 h. Purification by reverse phase HPLC (5-55% CH₃CN/water+0.1% TFA, YMC ODS-A C18 Column 75×30 mm ID S-5 um, 12 nM Column 6 min) provided the desired crude product, which was isolated by extracting the desired clean fractions with 10% MeOH/EtOAc from saturated aqueous NaHCO₃, evaporating the organics, and filtering from 2 mL 10% MeOH/water to give N-((4,6-dimethyl-2-oxo-1,2-dihydropyridin-3-yl)methyl)-4-methyl-5-(1-morpholinoethyl)thiophene-3-carboxamide (65 mg, 0.159 mmol, 23.72% yield) as a solid. $^1$H NMR (400 MHz, DMSO-d₆) δ 11.47 (br. s., 1H) 7.98 (t, J=5.05 Hz, 1H) 7.70 (s, 1H) 5.86 (s, 1H) 4.23 (d, J=5.05 Hz, 2H) 3.71 (d, J=6.57 Hz, 1H) 3.54 (t, J=4.55 Hz, 4H) 2.31-2.48 (m, 4H) 2.24 (s, 3H) 2.17 (s, 3H) 2.11 (s, 3H) 1.26 (d, J=6.57 Hz, 3H). MS(ES) [M+H]⁺ 390.2.

Example 27

N-((4,6-dimethyl-2-oxo-1,2-dihydropyridin-3-yl)methyl)-5-(1-(4-(dimethylamino)piperidin-1-yl)ethyl)-4-methylthiophene-3-carboxamide hydrochloride

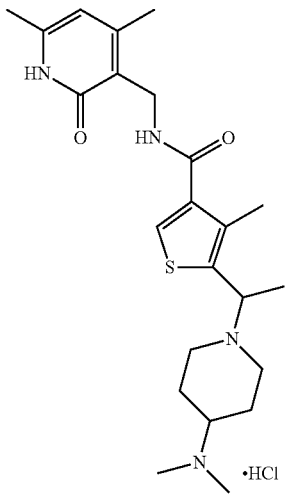 [SMILES: Cc1cc(C)c(CNC(=O)c2csc(C(C)N3CCC(N(C)C)CC3)c2C)c(=O)[nH]1 ; Cl]

Following the general procedures of Example 26, but substituting N,N-dimethylpiperidin-4-amine for morpholine in Step d, N-((4,6-dimethyl-2-oxo-1,2-dihydropyridin-3-yl)methyl)-5-(1-(4-(dimethylamino)piperidin-1-yl)ethyl)-4-methylthiophene-3-carboxamide (50 mg, 0.098 mmol, 34.0% yield) was isolated as its hydrochloride salt. $^1$H NMR (400 MHz, DMSO-$d_6$) δ 1.73 (d, J=6.57 Hz, 3H) 2.11 (s, 3H) 2.15-2.28 (m, 7H) 2.34 (s, 3H) 2.62-2.69 (m, 6H) 2.76-2.84 (m, 1H) 2.85-2.95 (m, 1H) 3.33 (br. s., 1H) 3.42 (d, J=11.12 Hz, 1H) 3.78 (br. s., 1H) 4.18-4.32 (m, 2H) 4.93 (d, J=5.56 Hz, 1H) 5.88 (s, 1H) 8.06 (s, 1H) 8.14 (t, J=4.93 Hz, 1H) 11.55 (br. s., 1H). MS(ES) [M+H]$^+$ 216.1, 431.3.

Example 28

N-((4,6-dimethyl-2-oxo-1,2-dihydropyridin-3-yl)methyl)-5-(1-(4-(dimethylamino)piperidin-1-yl)propyl)-4-methylthiophene-3-carboxamide

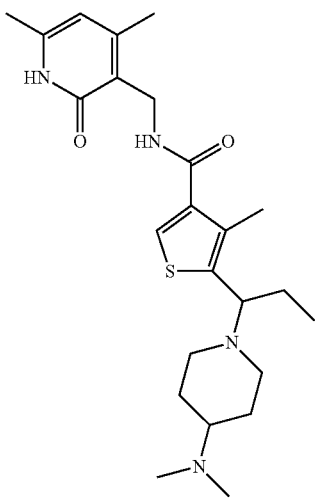 [SMILES: CCC(c1scc(C(=O)NCc2c(C)cc(C)[nH]c2=O)c1C)N1CCC(N(C)C)CC1]

Following the general procedure of Example 26, but substituting propionic anhydride for Ac$_2$O in Step b and N,N-dimethylpiperidin-4-amine for morpholine in Step d, N-((4,6-dimethyl-2-oxo-1,2-dihydropyridin-3-yl)methyl)-5-(1-(4-(dimethylamino)piperidin-1-yl)ethyl)-4-methylthiophene-3-carboxamide (65 mg, 0.139 mmol, 25.04% yield) was isolated as a pale yellow solid. $^1$H NMR (400 MHz, DMSO-$d_6$) δ 11.47 (br. s., 1H) 7.99 (t, J=5.05 Hz, 1H) 7.72 (s, 1H) 5.86 (s, 1H) 4.23 (d, J=5.05 Hz, 2H) 3.66 (dd, J=8.84, 5.31 Hz, 1H) 2.96-3.01 (m, 1H) 2.76-2.82 (m, 1H) 2.23 (s, 3H) 2.18 (s, 3H) 2.11 (s, 9H) 1.85-1.97 (m, 4H) 1.63-1.72 (m, 2H) 1.49-1.56 (m, 1H) 1.20-1.39 (m, 2H) 0.73 (t, J=7.33 Hz, 3H). MS(ES) [M+H]$^+$ 445.3.

Example 29

N-((4,6-dimethyl-2-oxo-1,2-dihydropyridin-3-yl)methyl)-4-methyl-5-(1-morpholinopropyl)thiophene-3-carboxamide

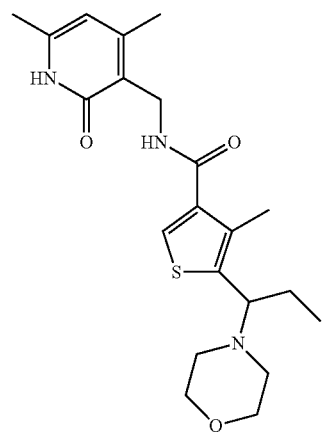 [SMILES: CCC(c1scc(C(=O)NCc2c(C)cc(C)[nH]c2=O)c1C)N1CCOCC1]

Following the general procedure of Example 13, N-((4,6-dimethyl-2-oxo-1,2-dihydropyridin-3-yl)methyl)-4-methyl-5-(1-morpholinopropyl)thiophene-3-carboxamide (75 mg, 0.177 mmol, 20.85% yield) was isolated as a pale yellow solid. $^1$H NMR (400 MHz, DMSO-$d_6$) δ 11.47 (br. s., 1H) 8.00 (t, J=5.05 Hz, 1H) 7.75 (s, 1H) 5.86 (s, 1H) 4.23 (d, J=5.05 Hz, 2H) 3.61 (dd, J=9.09, 4.80 Hz, 1H) 3.50-3.57 (m, 4H) 2.41-2.48 (m, 2H) 2.29-2.35 (m, 2H) 2.24 (s, 3H) 2.18 (s, 3H) 2.11 (s, 3H) 1.93 (ddd, J=13.07, 7.39, 5.05 Hz, 1H) 1.49 (ddd, J=13.39, 8.97, 7.45 Hz, 1H) 0.72 (t, J=7.33 Hz, 3H). MS(ES) [M+H]$^+$ 404.2.

Example 30

N-((4,6-Dimethyl-2-oxo-1,2-dihydropyridin-3-yl)methyl)-5-(ethyl(tetrahydro-2H-pyran-4-yl)amino)thiophene-2-carboxamide

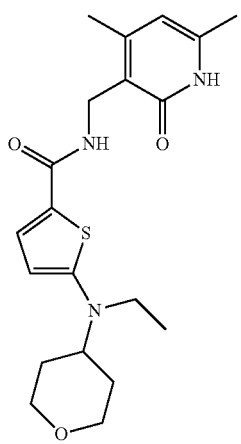 [SMILES: CCN(c1ccc(C(=O)NCc2c(C)cc(C)[nH]c2=O)s1)C1CCOCC1]

a) Methyl 5-((tetrahydro-2H-pyran-4-yl)amino)thiophene-2-carboxylate

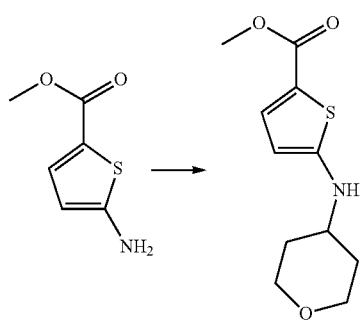

To a solution of methyl 5-aminothiophene-2-carboxylate (4.5 g, 28.6 mmol) in DCM (80 mL) was added dihydro-2H-pyran-4(3H)-one (2.64 mL, 28.6 mmol), AcOH (1.639 mL, 28.6 mmol), and NaBH(OAc)$_3$ (8.49 g, 40.1 mmol). The mixture was stirred at RT for 18 h and then quenched with saturated aqueous NaHCO$_3$. The layers were separated and the aqueous layer was extracted with DCM. The combined organic layer was washed with brine, then dried over Na$_2$SO$_4$, filtered, and concentrated. The crude was purified by silica gel chromatography (Biotage SNAP 100 g, 10-50% EtOAc/hexanes, Rf 0.50 (50% EtOAc/hexanes)) to provide methyl 5-((tetrahydro-2H-pyran-4-yl)amino)thiophene-2-carboxylate (4.80 g, 70%). $^1$H NMR (400 MHz, CDCl$_3$) δ 1.49-1.62 (m, 2H), 2.08-2.16 (m, 2H), 3.35-3.46 (m, 1H), 3.51 (td, J=11.62, 2.02 Hz, 2H), 3.84 (s, 3H), 3.98-4.07 (m, 2H), 4.33-4.51 (m, 1H), 5.97 (d, J=4.29 Hz, 1H), 7.51 (d, J=4.04 Hz, 1H). MS(ES) [M+H]$^+$ 241.9.

b) Methyl 5-(ethyl(tetrahydro-2H-pyran-4-yl)amino)thiophene-2-carboxylate

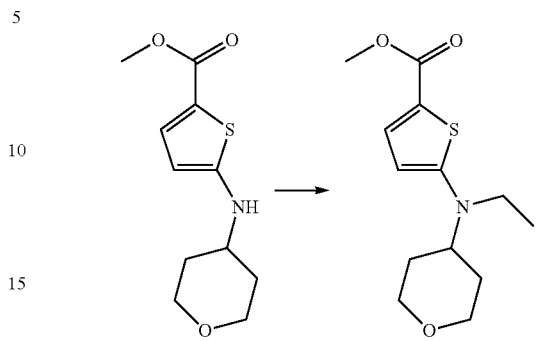

To a solution of methyl 5-((tetrahydro-2H-pyran-4-yl)amino)thiophene-2-carboxylate (2.8 g, 11.6 mmol) in DCM (40 mL) was added acetaldehyde (1.965 mL, 34.8 mmol), AcOH (0.664 mL, 11.6 mmol), and NaBH(OAc)$_3$ (4.92 g, 23.2 mmol). The mixture was stirred at RT for 66 h, then quenched with saturated aqueous NaHCO$_3$. The layers were separated and the aqueous layer was extracted with DCM. The combined organic layer was washed with brine, dried over Na$_2$SO$_4$, filtered, and concentrated. The crude was purified by silica gel chromatography (Biotage SNAP 100 g, 0-40% EtOAc/hexanes, Rf 0.38 (25% EtOAc/hexanes)) to provide methyl 5-(ethyl(tetrahydro-2H-pyran-4-yl)amino)thiophene-2-carboxylate (2.27 g, 73%). $^1$H NMR (400 MHz, methanol-d$_4$) δ 1.24 (t, J=7.07 Hz, 3H), 1.80-1.93 (m, 4H), 3.41 (q, J=7.07 Hz, 2H), 3.48-3.57 (m, 2H), 3.69-3.77 (m, 1H), 3.79 (s, 3H), 4.01-4.10 (m, 2H), 6.01 (d, J=4.29 Hz, 1H), 7.54 (d, J=4.55 Hz, 1H). MS(ES) [M+H]$^+$ 270.4.

c) 5-(ethyl(tetrahydro-2H-pyran-4-yl)amino)thiophene-2-carboxylic acid

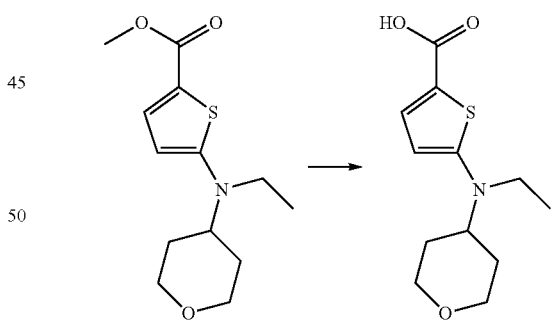

To a solution of methyl 5-(ethyl(tetrahydro-2H-pyran-4-yl)amino)thiophene-2-carboxylate (810 mg, 3.01 mmol) in THF (18 mL) was added LiOH (9.02 mL, 9.02 mmol). The mixture was stirred at RT for 16 h and then stirred at 80° C. for 18 h. After concentration, the residue was suspended in water and acidified with 6 M HCl. 2-Methyltetrahydrofuran was added to the acidified mixture and the layers were separated. The organic layer was dried over Na$_2$SO$_4$, filtered, and concentrated to provide 5-(ethyl(tetrahydro-2H-pyran-4-yl)amino)thiophene-2-carboxylic acid (600 mg, 78%). $^1$H NMR (400 MHz, DMSO-d$_6$) δ 1.13 (t, J=6.95 Hz, 3H), 1.65-1.81 (m, 4H), 3.29-3.34 (m, 2H), 3.37-3.47 (m, 2H), 3.61-3.73 (m, 1H), 3.87-4.01 (m, 2H), 5.99 (d, J=4.29 Hz, 1H), 7.41 (d, J=4.29 Hz, 1H), 12.00 (br. s., 1H). MS(ES) [M+H]+ 255.9.

d) N-((4,6-dimethyl-2-oxo-1,2-dihydropyridin-3-yl)methyl)-5-(ethyl(tetrahydro-2H-pyran-4-yl)amino)thiophene-2-carboxamide

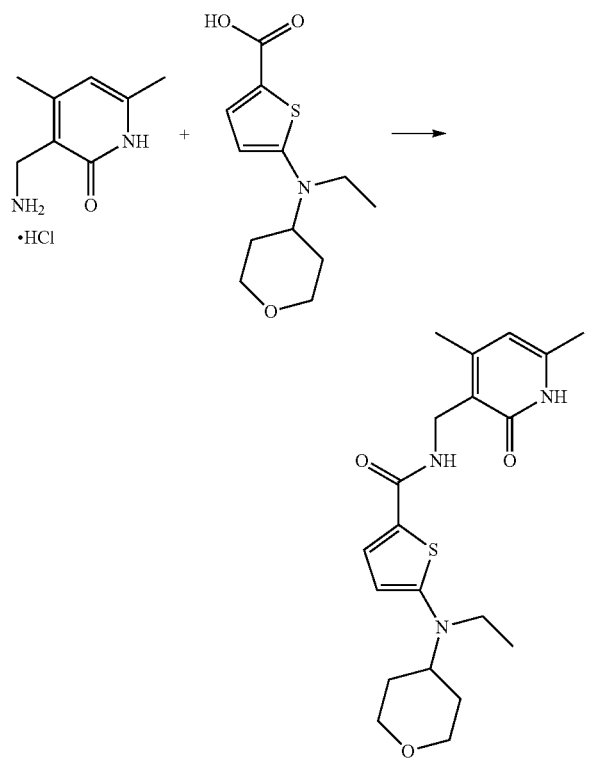

To a solution of 5-(ethyl(tetrahydro-2H-pyran-4-yl)amino)thiophene-2-carboxylic acid (100 mg, 0.39 mmol) in THF (9 mL) was added 3-(aminomethyl)-4,6-dimethylpyridin-2(1H)-one hydrochloride (73.6 mg, 0.39 mmol), DIPEA (0.136 mL, 0.78 mmol), EDC (90 mg, 0.47 mmol), and HOBt (72.0 mg, 0.47 mmol). The mixture was stirred at RT for 16 h and then concentrated. The residue was dissolved in DMSO and purified by reversed-phase HPLC [Phenomenex Luna 5 m C18, 50×30 mm, 10-90% CH3CN (0.1% TFA)/water (0.1% TFA)]). The fractions containing the desired product were combined and passed through a PL-HCO3 MP SPE cartridge. The eluate was partially concentrated to precipitate the product which was filtered and rinsed with water to provide N-((4,6-dimethyl-2-oxo-1,2-dihydropyridin-3-yl)methyl)-5-(ethyl(tetrahydro-2H-pyran-4-yl)amino)thiophene-2-carboxamide (50 mg, 33%). $^1$H NMR (400 MHz, methanol-d$_4$) δ 1.22 (t, J=7.07 Hz, 3H), 1.79-1.88 (m, 4H), 2.26 (s, 3H), 2.36 (s, 3H), 3.35-3.41 (m, 2H), 3.46-3.57 (m, 2H), 3.64-3.77 (m, 1H), 4.01-4.08 (m, 2H), 4.43 (s, 2H), 5.93 (d, J=4.29 Hz, 1H), 6.12 (s, 1H), 7.39 (d, 1H). MS(ES) [M+H]+ 390.3.

Example 31

5-(Ethyl(tetrahydro-2H-pyran-4-yl)amino)-4-methyl-N-((1,4,6-trimethyl-2-oxo-1,2-dihydropyridin-3-yl)methyl)thiophene-3-carboxamide

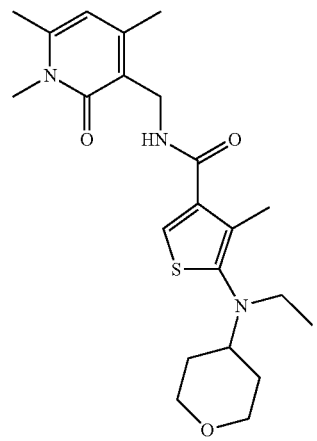 [SMILES: CCN(c1scc(C(=O)NCc2c(C)cc(C)n(C)c2=O)c1C)C1CCOCC1]

To a mixture of 5-(ethyl(tetrahydro-2H-pyran-4-yl)amino)-4-methylthiophene-3-carboxylic acid (0.10 g, 0.334 mmol), HOAt (0.055 g, 0.401 mmol), EDC (0.077 g, 0.401 mmol), and 3-(aminomethyl)-1,4,6-trimethylpyridin-2(1H)-one hydrochloride (0.074 g, 0.368 mmol) in DMF (3 mL) was added NMM (0.147 mL, 1.337 mmol) via syringe. The reaction mixture was stirred at RT for 3 days, at which time it was diluted with water (50 mL). Concentrated NH4OH (1 mL) was added and the mixture was stirred for 15 min, then placed into a freezer for 20 min. The solids were filtered, washed with water, air-dried for 5 min, and dried in a vacuum oven for 4 h to give 5-(ethyl(tetrahydro-2H-pyran-4-yl)amino)-4-methyl-N-((1,4,6-trimethyl-2-oxo-1,2-dihydropyridin-3-yl)methyl)thiophene-3-carboxamide (105 mg, 0.246 mmol, 73.8% yield). $^1$H NMR (400 MHz, DMSO-d$_6$) δ 0.86 (t, J=7.07 Hz, 3H) 1.38 (qd, J=12.00, 4.42 Hz, 2H) 1.61-1.74 (m, 2H) 2.14 (s, 3H) 2.20 (s, 3H) 2.30 (s, 3H) 2.86-2.97 (m, 3H) 3.20-3.29 (m, 2H) 3.41 (s, 3H) 3.82 (dd, J=11.62, 2.53 Hz, 2H) 4.26 (d, J=5.05 Hz, 2H) 6.02 (s, 1H) 7.65 (s, 1H) 7.95 (t, J=5.18 Hz, 1H). MS(ES) [M+H]+ 418.2.

Example 32

5-(((trans)-4-(Dimethylamino)cyclohexyl)(ethyl)amino)-4-methyl-N-((1,4,6-trimethyl-2-oxo-1,2-dihydropyridin-3-yl)methyl)thiophene-3-carboxamide

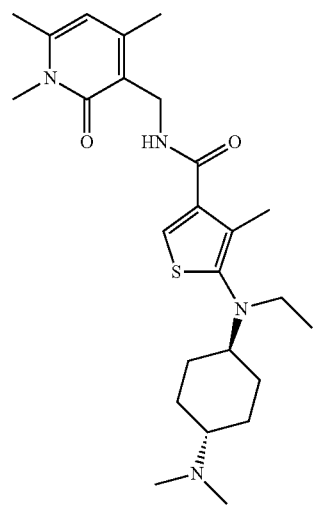 [SMILES: CCN(c1scc(C(=O)NCc2c(C)cc(C)n(C)c2=O)c1C)[C@H]1CC[C@H](N(C)C)CC1]

To a mixture of 5-((4-(dimethylamino)cyclohexyl)(ethyl)amino)-4-methylthiophene-3-carboxylic acid (0.24 g, 0.387 mmol), HOAt (0.063 g, 0.464 mmol), EDC (0.089 g, 0.464 mmol), and 3-(aminomethyl)-1,4,6-trimethylpyridin-2(1H)-one hydrochloride (0.086 g, 0.425 mmol) in DMF (5 mL) was added NMM (0.170 mL, 1.546 mmol) via syringe. The reaction mixture was stirred at RT overnight, at which time it was diluted with water (50 mL) and basified to pH 11 with concentrated NH$_4$OH. The mixture was stirred for 5 min and extracted with DCM (3×40 mL). The combined organics were dried over MgSO$_4$, filtered, and concentrated in vacuo. The resultant residue was dried under vacuum for 2 h, at which time it was dissolved in a small amount of DCM. Silica gel was added and the mixture dried under vacuum for 1 h. Purification of the residue (12 g Isco silica column; Gradient B: 8-95%, A:DCM, B: 90/10/1 of DCM/MeOH/NH$_4$OH) gave a yellow solid (131 mg; mixture of trans/cis isomers).

The residue was further purified by preparative HPLC (Gilson; Sunfire 30×75 mm column; Gradient B: 10-45%, A: water+0.1% TFA, B: CH$_3$CN+0.1% TFA). The resultant residue was dissolved in DCM and treated with 90/10/1 DCM/MeOH/NH$_4$OH and silca gel. The solvent was removed in vacuo to give a free flowing solid, which was purified by column chromatography (4 g Isco silica column; Gradient B: 25-100%, A: DCM, B: 90/10/1 of DCM/MeOH/NH$_4$OH) to afford 5-(((trans)-4-(dimethylamino)cyclohexyl)(ethyl)amino)-4-methyl-N-((1,4,6-trimethyl-2-oxo-1,2-dihydropyridin-3-yl)methyl)thiophene-3-carboxamide (53 mg, 0.113 mmol, 29.3% yield). $^1$H NMR (400 MHz, DMSO-d$_6$) δ 0.85 (t, J=7.07 Hz, 3H) 1.12-1.27 (m, 4H) 1.74-1.82 (m, 2H) 1.82-1.91 (m, 2H) 2.09-2.22 (m, 13H) 2.30 (s, 3H) 2.67 (br. s., 1H) 2.90 (q, J=7.07 Hz, 2H) 3.41 (s, 3H) 4.26 (d, J=5.31 Hz, 2H) 6.02 (s, 1H) 7.61 (s, 1H) 7.92 (t, J=5.18 Hz, 1H). MS(ES) [M+H]$^+$ 459.3. Additional NMR data were consistent with the assigned structure (trans isomer). The corresponding cis isomer was not isolated.

Example 33

(E)-N-((4,6-Dimethyl-2-oxo-1,2-dihydropyridin-3-yl)methyl)-4-methyl-5-(1-(piperidin-4-yl)prop-1-en-1-yl)thiophene-3-carboxamide

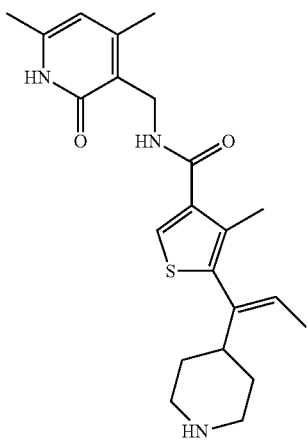 [SMILES: C/C=C(/c1scc(C(=O)NCc2c(C)cc(C)[nH]c2=O)c1C)C1CCNCC1]

a) Methyl 5-iodo-4-methylthiophene-3-carboxylate

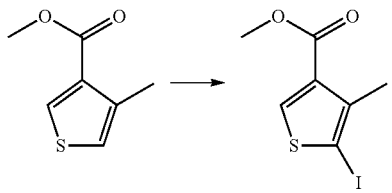

To a solution of methyl 4-methylthiophene-3-carboxylate (1.0 g, 6.40 mmol) in DMF (25 mL) was added NIS (2.5 g, 11.11 mmol). The reaction was stirred at 100° C. for 24 h. The reaction was evaporated to dryness under vacuum to remove most of the DMF. The remaining residue was taken up in EtOAc, washed with water and brine, dried over Na$_2$SO$_4$, filtered and evaporated to dryness. Purification by silica gel chromatography (Analogix, SF25-60 g, 0 to 10% EtOAc in hexanes) provided methyl 5-iodo-4-methylthiophene-3-carboxylate (0.86 g, 3.05 mmol, 47.6% yield) as an off-white solid. $^1$H NMR (400 MHz, CDCl$_3$) δ 8.26 (s, 1H), 3.87 (s, 3H), 2.47 (s, 3H). MS(ES) [M+H]$^+$282.9.

b) tert-Butyl 4-(hydroxy(4-(methoxycarbonyl)-3-methylthiophen-2-yl)methyl)piperidine-1-carboxylate

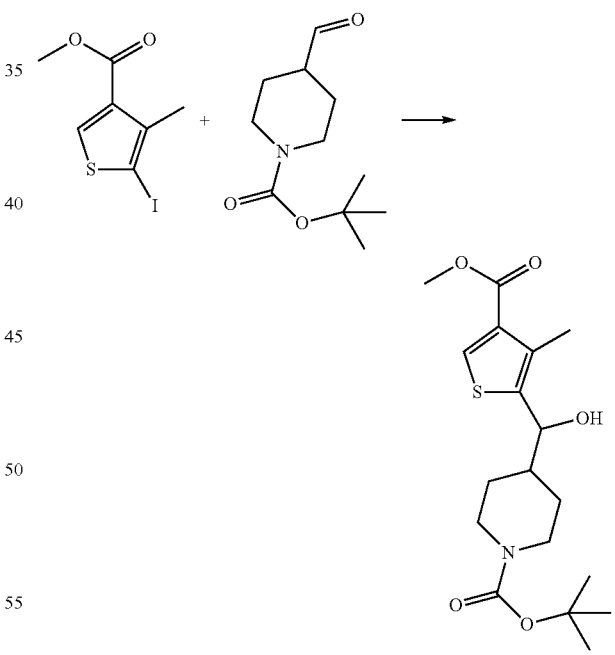

To a cooled (−78° C.) solution of methyl 5-iodo-4-methylthiophene-3-carboxylate (1.0 g, 3.54 mmol) in THF (20 mL) under nitrogen was added dropwise isopropylmagnesium chloride lithium chloride complex 1.3 N in THF (3.0 mL, 3.90 mmol). The reaction was stirred for 1 h, at which time was added a solution of N-Boc-4-piperidinecarboxaldehyde (1.0 g, 4.69 mmol) in THF (5 mL). The reaction was maintained at −78° C. for 30 min, at which time it was quenched with 1 N HCl (5 mL) and allowed to warm to RT.

The reaction was diluted with water, extracted with EtOAc, washed with brine, dried over Na$_2$SO$_4$, filtered and evaporated to dryness. Purification by silica gel chromatography (Analogix, SF25-60 g, 10 to 50% EtOAc in hexanes) gave tert-butyl 4-(hydroxy(4-(methoxycarbonyl)-3-methylthiophen-2-yl)methyl)piperidine-1-carboxylate (0.84 g, 2.273 mmol, 64.1% yield) as a white foam. $^1$H NMR (400 MHz, CDCl$_3$) δ 8.07 (s, 1H), 4.77 (dd, J=3.0, 8.1 Hz, 1H), 4.27-4.01 (m, 2H), 3.86 (s, 3H), 2.76-2.55 (m, 2H), 2.41 (s, 3H), 2.14 (d, J=3.0 Hz, 1H), 2.08 (d, J=12.9 Hz, 1H), 1.87-1.73 (m, J=3.7, 3.7, 3.7, 7.9, 7.9, 11.7 Hz, 1H), 1.48 (br. s., 1H), 1.47 (s, 9H), 1.40-1.25 (m, 2H), 1.24-1.11 (m, 1H). MS(ES) [M+H]$^+$ 252.1 (-Boc, —H$_2$O), [M+Na]$^+$ 392.2.

c) tert-Butyl 4-(4-(methoxycarbonyl)-3-methylthiophene-2-carbonyl)piperidine-1-carboxylate

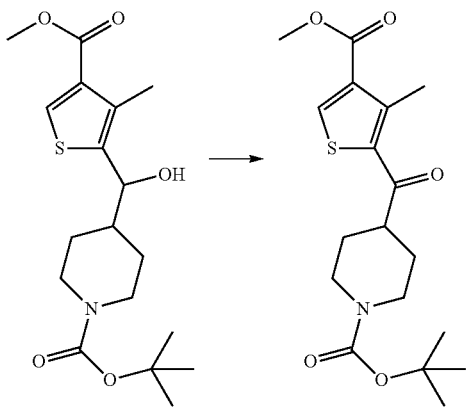 [SMILES: COC(=O)c1csc(C(O)C2CCN(C(=O)OC(C)(C)C)CC2)c1C ; COC(=O)c1csc(C(=O)C2CCN(C(=O)OC(C)(C)C)CC2)c1C]

To a cooled (0° C.) solution of tert-butyl 4-(hydroxy(4-(methoxycarbonyl)-3-methylthiophen-2-yl)methyl)piperidine-1-carboxylate (1.7 g, 4.60 mmol) and pyridine (0.75 mL, 9.27 mmol) in DCM (40 mL) was added Dess-Martin periodinane (2.0 g, 4.72 mmol) portionwise over 30 min. The reaction was allowed to warm to RT and was stirred for 4 h. The reaction was concentrated under vacuum, taken up in EtOAc, and treated with an aqueous solution of sodium thiosulfate pentahydrate (9.0 g, 36.3 mmol) and saturated NaHCO$_3$ (50 mL). The suspension was stirred until nearly homogeneous (30 min) and filtered through a pad of Celite®. The EtOAc phase was removed, washed with brine, dried over Na$_2$SO$_4$, filtered and evaporated to dryness under vacuum. Purification by silica gel chromatography (Analogix SF25-60 g, 10 to 40% EtOAc in hexanes) gave tert-butyl 4-(4-(methoxycarbonyl)-3-methylthiophene-2-carbonyl)piperidine-1-carboxylate (1.05 g, 44.1% yield) as a clear oil. $^1$H NMR (400 MHz, CDCl$_3$) δ 8.24 (s, 1H), 4.19 (br. s., 2H), 3.90 (s, 3H), 3.09 (tt, J=3.8, 11.1 Hz, 1H), 2.92-2.85 (m, 2H), 2.82 (s, 3H), 1.88 (d, J=12.4 Hz, 2H), 1.80-1.68 (m, 2H), 1.49 (s, 9H). MS(ES) [M+H]$^+$ [M+Na]$^+$ 390.0, 312.0 (-isobutylene).

d) (E)-tert-Butyl 4-(1-(4-(methoxycarbonyl)-3-methylthiophen-2-yl)prop-1-en-1-yl)piperidine-1-carboxylate

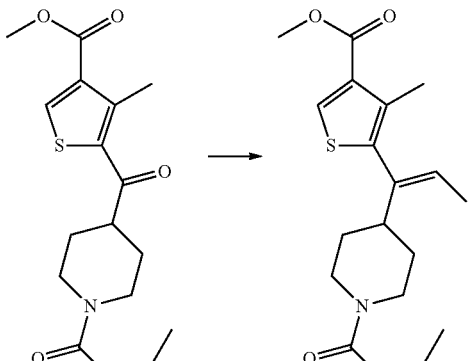

To a cooled (0° C.) solution of ethyltriphenylphosphonium bromide (1.2 g, 3.23 mmol) in THF (10 mL) under nitrogen was added dropwise a solution of potassium tert-butoxide (1 N in THF, 3.2 mL, 3.20 mmol). The reaction was allowed to warm to RT and was stirred for 1 h, at which time it was cooled to −78° C. To the now bright orange reaction was added a solution of tert-butyl 4-(4-(methoxycarbonyl)-3-methylthiophene-2-carbonyl)piperidine-1-carboxylate (1.0 g, 2.72 mmol) in THF (5 mL). The reaction was allowed to warm to RT and was stirred overnight. The reaction was evaporated to dryness under vacuum, taken up with EtOAc, washed with water and brine, dried over Na$_2$SO$_4$, filtered and concentrated under vacuum. Purification by silica gel chromatography (Analogix, 10 to 40% EtOAc in hexanes) furnished (E)-tert-butyl 4-(1-(4-(methoxycarbonyl)-3-methylthiophen-2-yl)prop-1-en-1-yl)piperidine-1-carboxylate (0.37 g, 0.975 mmol, 35.8% yield) as a clear oil (contaminated with ~10% of the Z olefin isomer). $^1$H NMR (400 MHz, CDCl$_3$) δ 8.08 (s, 1H), 5.83-5.74 (m, 1H), 4.14 (br. s., 2H), 3.87 (s, 3H), 2.72-2.63 (m, 2H), 2.24 (s, 3H), 1.71 (d, J=11.9 Hz, 2H), 1.48 (dd, J=1.0, 6.6 Hz, 3H), 1.46 (s, 9H), 1.35 (d, J=10.9 Hz, 2H). MS(ES) [M+H]$^+$ 324.1 (-isobutylene), [M+Na]$^+$ 402.0.

e) (E)-tert-Butyl 4-(1-(4-(((4,6-dimethyl-2-oxo-1,2-dihydropyridin-3-yl)methyl)carbamoyl)-3-methylthiophen-2-yl)prop-1-en-1-yl)piperidine-1-carboxylate

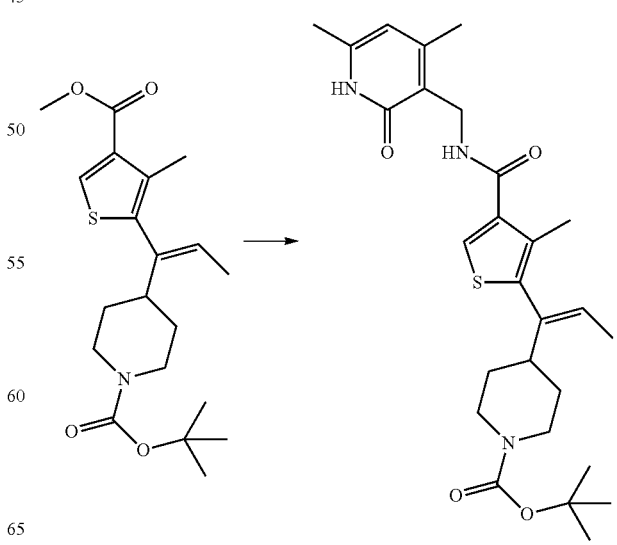

117

To a solution of (E)-tert-butyl 4-(1-(4-(methoxycarbonyl)-3-methylthiophen-2-yl)prop-1-en-1-yl)piperidine-1-carboxylate (0.36 g, 0.949 mmol) in MeOH (15 mL) was added 1 N NaOH (3 mL, 3.00 mmol). The reaction was stirred at 70° C. for 4 h, at which time it was concentrated under vacuum, acidified with 1 N HCl (3.0 mL), extracted with DCM, dried over MgSO₄, filtered, and concentrated under vacuum.

To the resultant residue was added 3-(aminomethyl)-4,6-dimethylpyridin-2(1H)-one hydrochloride (200 mg, 1.060 mmol), HOAt (130 mg, 0.955 mmol) and DCM (15 mL). The suspension was broken up with a stir rod. To the stirring suspension was added NMM (120 µL, 1.091 mmol) followed by EDC free base (180 mg, 1.159 mmol). The reaction was stirred overnight, at which time the suspension was filtered free of insolubles and rinsed with a small volume of DCM. The clear filtrate was concentrated under vacuum and purified by silica gel chromatography (Analogix, SF25-60 g, 2 to 10% EtOH in EtOAc). The solid residue was triturated with 10% MeOH/H₂O, filtered and dried under vacuum to give (E)-tert-butyl 4-(1-(4-(((4,6-dimethyl-2-oxo-1,2-dihydropyridin-3-yl)methyl)carbamoyl)-3-methylthiophen-2-yl)prop-1-en-1-yl)piperidine-1-carboxylate (360 mg, 0.720 mmol, 76% yield) as a white solid (contaminated with ~10% of the Z olefin isomer). ¹H NMR (400 MHz, DMSO-d₆) δ 11.49 (br. s., 1H), 8.04 (t, J=5.1 Hz, 1H), 7.85 (s, 1H), 5.87 (s, 1H), 5.76 (q, J=6.3 Hz, 1H), 4.24 (d, J=5.1 Hz, 2H), 3.96 (d, J=11.1 Hz, 2H), 2.65 (br. s., 2H), 2.27-2.20 (m, 1H), 2.19 (s, 3H), 2.12 (s, 3H), 2.06 (s, 3H), 1.62 (d, J=12.4 Hz, 2H), 1.40 (d, J=6.3 Hz, 3H), 1.37 (s, 9H), 1.17 (dq, J=4.3, 12.4 Hz, 2H). MS(ES) [M+H]⁺ 500.2.

f) (E)-N-((4,6-Dimethyl-2-oxo-1,2-dihydropyridin-3-yl)methyl)-4-methyl-5-(1-(piperidin-4-yl)prop-1-en-1-yl)thiophene-3-carboxamide

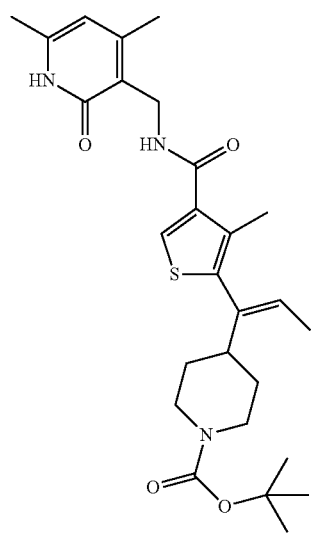

118

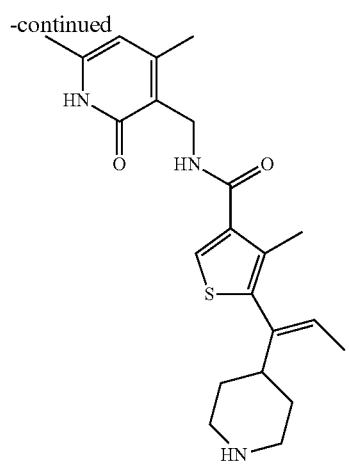

To (E)-tert-butyl 4-(1-(4-(((4,6-dimethyl-2-oxo-1,2-dihydropyridin-3-yl)methyl)carbamoyl)-3-methylthiophen-2-yl)prop-1-en-1-yl)piperidine-1-carboxylate (300 mg, 0.600 mmol) was added 4 N HCl in 1,4-dioxane (15 mL, 494 mmol) and MeOH (2 mL). The reaction was stirred at RT for 30 min, at which time it was evaporated to dryness under vacuum. The remaining material was basified with 1 N Na₂CO₃, extracted with 10% MeOH in DCM (2×), washed with brine, dried over Na₂SO₄, filtered and concentrated under vacuum. The residue was purified by silica gel chromatography (Analogix SF25-40 g, 10 to 30% (5% NH₄OH/MeOH) in DCM). The resultant solid was triturated with Et₂O/pet. ether and dried under vacuum to give (E)-N-((4,6-dimethyl-2-oxo-1,2-dihydropyridin-3-yl)methyl)-4-methyl-5-(1-(piperidin-4-yl)prop-1-en-1-yl)thiophene-3-carboxamide (230 mg, 0.576 mmol, 96% yield) as a white solid (contaminated with ~10% of the Z olefin isomer). ¹H NMR (400 MHz, DMSO-d₆) δ 8.05 (t, J=4.8 Hz, 1H), 7.86 (s, 1H), 5.87 (s, 1H), 5.77-5.71 (m, 3H), 4.24 (d, J=5.1 Hz, 2H), 3.03 (d, J=12.4 Hz, 2H), 2.61-2.53 (m, 2H), 2.26-2.20 (m, 1H), 2.19 (s, 3H), 2.12 (s, 3H), 2.06 (s, 3H), 1.63 (d, J=12.4 Hz, 2H), 1.41 (d, J=6.8 Hz, 3H), 1.32 (dt, J=9.0, 12.3 Hz, 2H). MS(ES) [M+H]⁺ 400.1.

Example 34 tert-Butyl ((trans)-4-((E)-1-(4-(((4,6-dimethyl-2-oxo-1,2-dihydropyridin-3-yl)methyl)carbamoyl)-3-methylthiophen-2-yl)prop-1-en-1-yl)cyclohexyl)carbamate

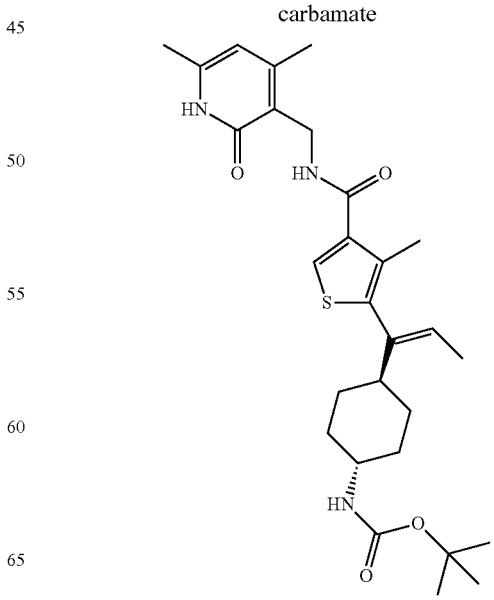

a) Methyl 5-(((trans)-4-((tert-butoxycarbonyl)amino)cyclohexyl)(hydroxy)methyl)-4-methylthiophene-3-carboxylate

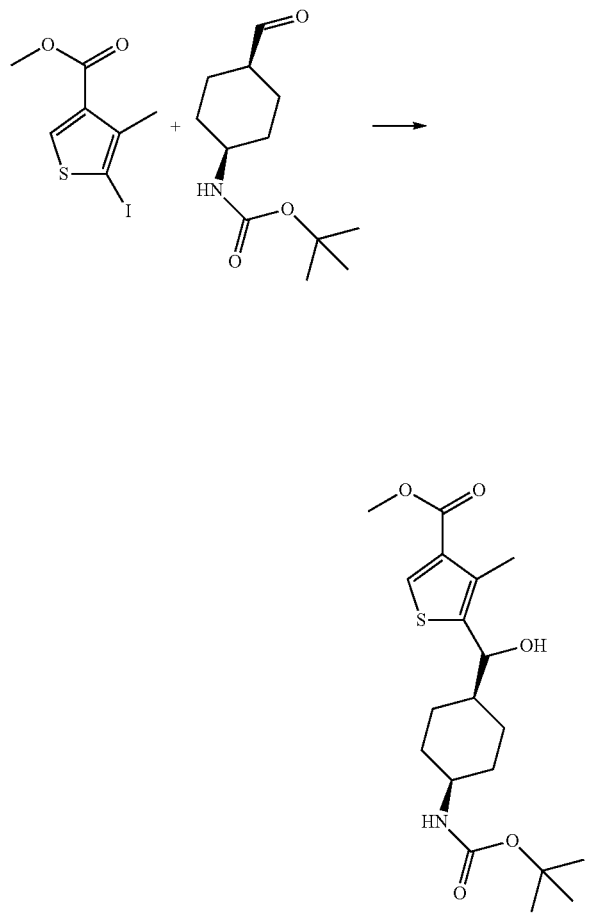

To a cooled (−78° C.) solution of methyl 5-iodo-4-methylthiophene-3-carboxylate (2.0 g, 7.09 mmol) in THF (25 mL) at under nitrogen was added dropwise isopropylmagnesium chloride lithium chloride complex 1.3 N in THF (6.0 mL, 7.80 mmol). The reaction was stirred for 1 h, at which time was added a solution of tert-butyl ((trans)-4-formylcyclohexyl)carbamate (2.0 g, 8.80 mmol) in THF (5 mL). The reaction was maintained at −78° C. for 45 min, at which time it was quenched with 1 N HCl (10 mL) and allowed to warm to RT. The reaction was diluted with water, extracted with EtOAc, washed with brine, dried over Na$_2$SO$_4$, filtered and evaporated to dryness. Purification by silica gel chromatography (Analogix, SF25-60 g, 15 to 40% EtOAc in hexanes) furnished methyl 5-(((trans)-4-((tert-butoxycarbonyl)amino)cyclohexyl)(hydroxy)methyl)-4-methylthiophene-3-carboxylate (0.78 g, 2.034 mmol, 28.7% yield) as a white solid foam. $^1$H NMR (400 MHz, CDCl$_3$) δ 8.06 (s, 1H), 4.74 (d, J=7.8 Hz, 1H), 4.38 (d, J=6.1 Hz, 1H), 3.86 (s, 3H), 3.39 (br. s., 1H), 2.41 (s, 3H), 2.25-2.15 (m, 1H), 2.14-2.03 (m, 2H), 2.03-1.93 (m, 1H), 1.69-1.56 (m, 2H), 1.45 (s, 9H), 1.25-0.98 (m, 4H). MS(ES) [M+H]$^+$ 266.0 (-Boc, —H$_2$O), [M+Na]$^+$ 406.1.

b) Methyl 5-((trans)-4-((tert-butoxycarbonyl)amino)cyclohexanecarbonyl)-4-methylthiophene-3-carboxylate

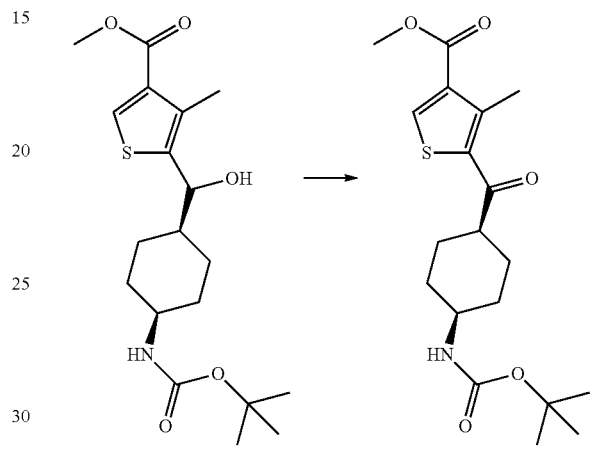

To a cooled (0° C.) solution of methyl 5-(((trans)-4-((tert-butoxycarbonyl)amino)cyclohexyl)(hydroxy)methyl)-4-methylthiophene-3-carboxylate (2.1 g, 5.48 mmol) and pyridine (0.9 mL, 11.13 mmol) in DCM (50 mL) with was added Dess-Martin periodinane (2.5 g, 5.89 mmol) portionwise over 30 min. The reaction was allowed to warm to RT and stirred for 4 h, at which time it was concentrated under vacuum, taken up in EtOAc, and treated with an aqueous solution of sodium thiosulfate pentahydrate (10.0 g, 40.3 mmol) and saturated NaHCO$_3$ (50 mL). The suspension was stirred until nearly homogeneous (30 min), at which time it was filtered through a pad of Celite®. The EtOAc phase was removed, washed with brine, dried over Na$_2$SO$_4$, filtered and evaporated to dryness under vacuum. The residue was purified by silica gel chromatography (Isco RediSep Rf Gold column, 0 to 5% EtOAc in DCM). The resultant solid was triturated with 10% EtOAc in hexanes and dried under vacuum to give methyl 5-((trans)-4-((tert-butoxycarbonyl)amino)cyclohexanecarbonyl)-4-methylthiophene-3-carboxylate (1.07 g, 2.80 mmol, 51.2% yield) as a white solid. $^1$H NMR (400 MHz, CDCl$_3$) δ 8.22 (s, 1H), 4.43 (d, J=5.3 Hz, 1H), 3.89 (s, 3H), 3.48 (br. s., 1H), 2.89 (tt, J=3.4, 11.8 Hz, 1H), 2.81 (s, 3H), 2.16 (d, J=10.1 Hz, 2H), 2.00 (d, J=13.4 Hz, 2H), 1.73-1.62 (m, 2H), 1.47 (s, 9H), 1.29-1.17 (m, 2H). MS(ES) [M+H]$^+$ 326.0 (-isobutylene), [M+Na]$^+$ 404.1.

c1) Methyl 5-((E)-1-((trans)-4-((tert-butoxycarbonyl)amino)cyclohexyl)prop-1-en-1-yl)-4-methylthiophene-3-carboxylate

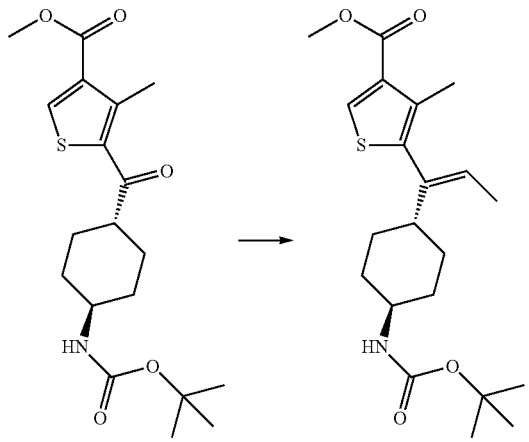 [SMILES: COC(=O)c1csc(C(=O)[C@H]2CC[C@H](NC(=O)OC(C)(C)C)CC2)c1C ; C/C=C(/c1scc(C(=O)OC)c1C)[C@H]1CC[C@H](NC(=O)OC(C)(C)C)CC1]

To a cooled (0° C.) solution of ethyltriphenylphosphonium bromide (1.2 g, 3.23 mmol) in THF (10 mL) under nitrogen was added dropwise a solution of potassium tert-butoxide (1 N in THF, 3.0 mL, 3.00 mmol). The reaction was allowed to warm to RT and stirred for 1 h, at which time it was cooled to −78° C. To the bright orange reaction was added a solution of methyl 5-((trans)-4-((tert-butoxycarbonyl)amino)cyclohexanecarbonyl)-4-methylthiophene-3-carboxylate (1.0 g, 2.62 mmol) in THF (5 mL). The reaction was stirred for 1 h at −78° C., allowed to warm to 0° C. in an ice bath, stirred for 1 h, and allowed to slowly warm to RT overnight. The reaction was evaporated to dryness under vacuum, taken up in EtOAc, washed with aqueous NH$_4$Cl and brine, dried over Na$_2$SO$_4$, filtered and concentrated under vacuum. Purification by silica gel chromatography ((Isco RediSep Rf Gold 80 g, 10 to 40% EtOAc in hexanes) provided methyl 5-((E)-1-((trans)-4-((tert-butoxycarbonyl)amino)cyclohexyl)prop-1-en-1-yl)-4-methylthiophene-3-carboxylate (480 mg, 1.220 mmol, 46.5% yield) as a clear oil (contaminated with ~10% Z olefin isomer). $^1$H NMR (400 MHz, CDCl$_3$) δ 8.06 (s, 1H), 5.80-5.72 (m, 1H), 4.36 (br. s., 1H), 3.87 (s, 3H), 3.35 (br. s., 1H), 2.23 (s, 3H), 2.04 (d, J=11.6 Hz, 2H), 1.85-1.78 (m, 2H), 1.66 (d, J=11.6 Hz, 1H), 1.45 (s, 9H), 1.37-1.23 (m, 2H), 1.17-1.04 (m, 2H). MS(ES) [M+H]$^+$-Boc 294.1, [M+H]$^+$-Boc+Na$^+$ 306.1, [M+H]$^+$-isobutylene 338.1, [M+Na]$^+$ 416.1.

c2) Alternatively, the Title Compound May be Prepared by the Following Procedure

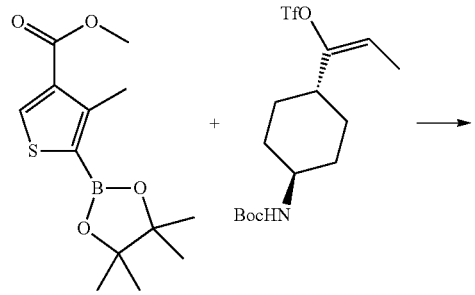

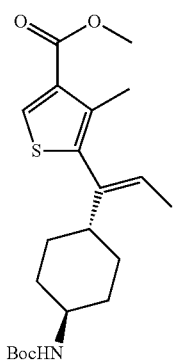

A solution of methyl 4-methyl-5-(4,4,5,5-tetramethyl-1,3,2-dioxaborolan-2-yl)thiophene-3-carboxylate (3.5 g, 12.40 mmol), (E)-1-((trans)-4-((tert-butoxycarbonyl)amino)cyclohexyl)prop-1-en-1-yl trifluoromethanesulfonate (4.81 g, 12.40 mmol), and NaHCO$_3$ (3.13 g, 37.2 mmol) in 1,4-dioxane (80 mL) and water (20 mL) was deggased (N$_2$). To the solution was added Pd(PPh$_3$)$_4$ (0.717 g, 0.620 mmol). The reaction was heated at 60° C. for 2 h, at which time it was diluted with EtOAc (30 mL). The organics were washed with brine, dried over MgSO$_4$, filtered and evaporated. The residue was purified by column chromatography (7% EtOAc:hexanes) to give methyl 5-((E)-1-((trans)-4-((tert-butoxycarbonyl)amino)cyclohexyl)prop-1-en-1-yl)-4-methylthiophene-3-carboxylate (3.6 g, 8.69 mmol, 70.1% yield). $^1$H NMR (400 MHz, CDCl3) δ 8.06 (s, 1H), 5.68-5.88 (m, 1H), 4.35 (br. s., 1H), 3.80-3.91 (m, 3H), 3.36 (br. s., 1H), 2.23 (s, 3H), 1.98-2.12 (m, 3H), 1.76-1.87 (m, 2H), 1.62 (br. s., 1H), 1.41-1.50 (m, 9H), 1.23-1.37 (m, 3H), 1.02-1.18 (m, 2H). MS(ES) [M+H]$^+$ 200.9. MS(ES) [M+Na]$^+$ 416.1.

d) tert-Butyl ((trans)-4-((E)-1-(4-(((4,6-dimethyl-2-oxo-1,2-dihydropyridin-3-yl)methyl)carbamoyl)-3-methylthiophen-2-yl)prop-1-en-1-yl)cyclohexyl)carbamate

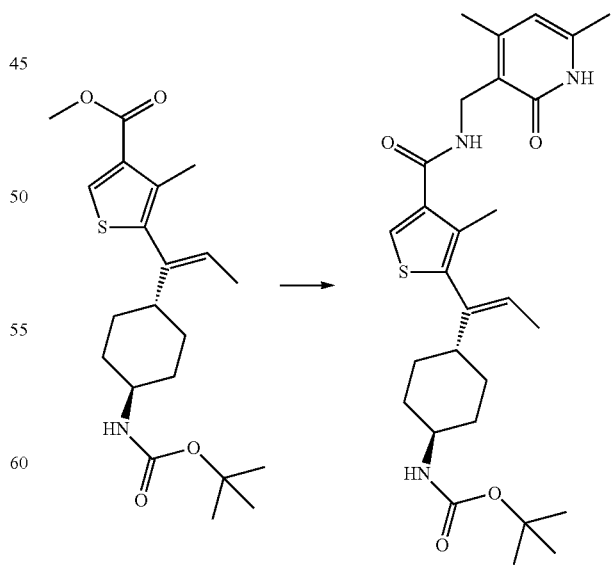

To a solution of methyl 5-((E)-1-((trans)-4-((tert-butoxycarbonyl)amino)cyclohexyl)prop-1-en-1-yl)-4-methylthiophene-3-carboxylate (470 mg, 1.194 mmol) in MeOH (25 mL) was added 1 N NaOH (4.0 mL, 4.00 mmol). The reaction was heated at reflux for 6 h, at which time it was concentrated under vacuum, acidified with 1 N HCl (4.0 mL), extracted with DCM, dried over MgSO$_4$, filtered and concentrated under vacuum.

To the residue was added 3-(aminomethyl)-4,6-dimethylpyridin-2(1H)-one hydrochloride (250 mg, 1.325 mmol), HOAt (170 mg, 1.249 mmol) and DCM (25.00 mL). The suspension was broken up with a stir rod. To the stirring suspension was added NMM (150 μL, 1.364 mmol), followed by EDC free base (220 mg, 1.417 mmol). The reaction was stirred overnight, at which time the suspension was filtered free of insolubles and rinsed with a small volume of DCM. The clear filtrate was concentrated under vacuum and purified by silica gel chromatography (Analogix, Isco RediSep Rf Gold 80 g, 2 to 10% EtOH in EtOAc). The resultant solid was triturated with 10% MeOH/H$_2$O, filtered and dried under vacuum to give tert-butyl ((trans)-4-((E)-1-(4-(((4,6-dimethyl-2-oxo-1,2-dihydropyridin-3-yl)methyl)carbamoyl)-3-methylthiophen-2-yl)prop-1-en-1-yl)cyclohexyl)carbamate (430 mg, 0.837 mmol, 70.1% yield) as a white solid (contaminated with ~13% of the Z olefin isomer). $^1$H NMR (400 MHz, DMSO-d$_6$) δ 11.48 (s, 1H), 8.05-8.02 (m, 1H), 7.83 (s, 1H), 6.69 (d, J=8.1 Hz, 1H), 5.87 (s, 1H), 5.73 (q, J=6.6 Hz, 1H), 4.24 (d, J=5.1 Hz, 2H), 3.10 (br. s., 1H), 2.19 (s, 3H), 2.11 (s, 3H), 2.05 (s, 3H), 1.96 (br. s., 1H), 1.76 (d, J=7.1 Hz, 2H), 1.72-1.66 (m, 2H), 1.40-1.37 (m, 3H), 1.36 (s, 9H), 1.23-1.09 (m, 4H). MS(ES) [M+H]$^+$ 514.3.

Example 35

5-((E)-1-((trans)-4-Aminocyclohexyl)prop-1-en-1-yl)-N-((4,6-dimethyl-2-oxo-1,2-dihydropyridin-3-yl)methyl)-4-methylthiophene-3-carboxamide

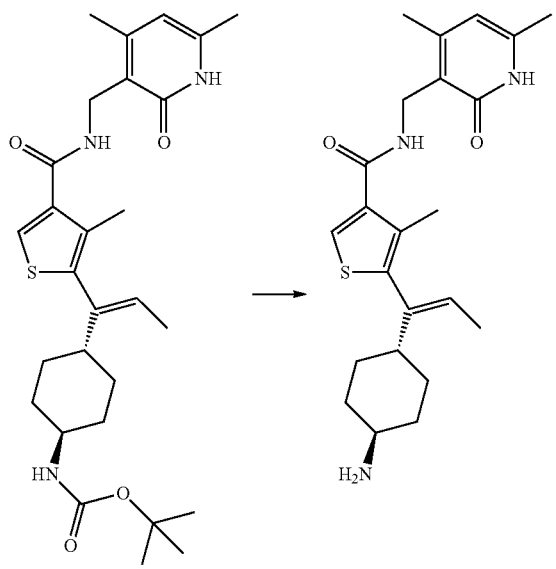 [SMILES: C/C=C(/c1scc(C(=O)NCc2c(C)cc(C)[nH]c2=O)c1C)[C@H]1CC[C@H](NC(=O)OC(C)(C)C)CC1 ; C/C=C(/c1scc(C(=O)NCc2c(C)cc(C)[nH]c2=O)c1C)[C@H]1CC[C@H](N)CC1]

To tert-butyl ((trans)-4-((E)-1-(4-(((4,6-dimethyl-2-oxo-1,2-dihydropyridin-3-yl)methyl)carbamoyl)-3-methylthiophen-2-yl)prop-1-en-1-yl)cyclohexyl)carbamate (390 mg, 0.759 mmol) in MeOH (1 mL) was added 4 N HCl in 1,4-dioxane (20 mL, 80 mmol). The reaction was stirred for 45 min, at which time it was evaporated to dryness under vacuum. The resultant solid was dissolved in MeOH (5 mL), basified with 1 N Na$_2$CO$_3$ (3 mL) and evaporated to dryness under vacuum. The residue was triturated with 10% MeOH in DCM, filtered free of insoluble materials, rinsed with 10% MeOH in DCM and concentrated under vacuum. The residue was purified by silica gel chromatography (Analogix, SF25-40 g, 10 to 25% (5% NH$_4$OH/MeOH) in DCM). The pure fractions were combined, evaporated to dryness, triturated with Et$_2$O/pet. ether, filtered and dried under vacuum to give 5-((E)-1-((trans)-4-aminocyclohexyl)prop-1-en-1-yl)-N-((4,6-dimethyl-2-oxo-1,2-dihydropyridin-3-yl)methyl)-4-methylthiophene-3-carboxamide (310 mg, 0.750 mmol, 99% yield) as a white solid. $^1$H NMR (400 MHz, DMSO-d$_6$) δ 8.04 (t, J=4.8 Hz, 1H), 7.82 (s, 1H), 5.87 (s, 1H), 5.72 (q, J=6.5 Hz, 1H), 4.24 (d, J=4.8 Hz, 2H), 2.45-2.36 (m, 1H), 2.19 (s, 3H), 2.11 (s, 3H), 2.05 (s, 3H), 1.98 (t, J=11.7 Hz, 1H), 1.81-1.70 (m, 2H), 1.65 (d, J=12.1 Hz, 2H), 1.38 (d, J=6.6 Hz, 3H), 1.22-1.07 (m, 2H), 1.06-0.91 (m, 2H). MS(ES) [M+H]$^+$ 414.1.

Example 36

N-((4,6-dimethyl-2-oxo-1,2-dihydropyridin-3-yl)methyl)-5-((E)-1-((trans)-4-(dimethylamino)cyclohexyl)prop-1-en-1-yl)-4-methylthiophene-3-carboxamide

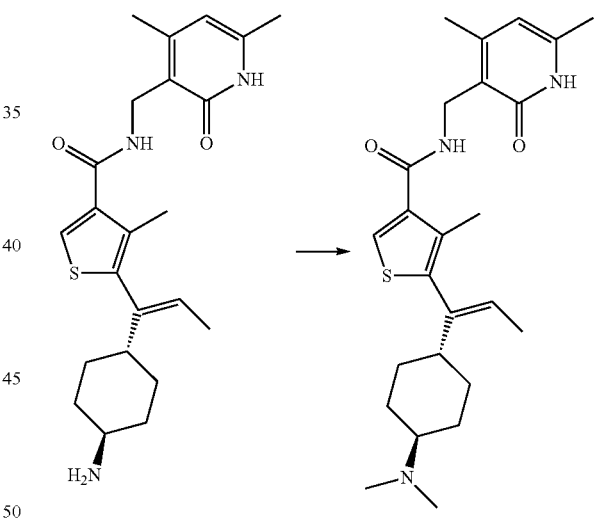

To a solution of 5-((E)-1-((trans)-4-aminocyclohexyl)prop-1-en-1-yl)-N-((4,6-dimethyl-2-oxo-1,2-dihydropyridin-3-yl)methyl)-4-methylthiophene-3-carboxamide (300 mg, 0.725 mmol) in MeOH (15 mL) was added formaldehyde (37 wt % in water, 0.7 mL, 9.40 mmol). The reaction was stirred for 15 min, at which time NaBH$_3$CN (100 mg, 1.591 mmol) was added. The reaction was stirred overnight, at which time it was evaporated to dryness under vacuum. The residue was purified by silica gel chromatography (Analogix, SF25-40 g, 10 to 50% (5% NH$_4$OH/EtOH) in EtOAc). The pure fractions were combined, evaporated to dryness, triturated with DCM/hexanes, filtered and dried under vacuum to give N-((4,6-dimethyl-2-oxo-1,2-dihydropyridin-3-yl)methyl)-5-((E)-1-((trans)-4-(dimethylamino)cyclohexyl)prop-1-en-1-yl)-4-methylthiophene-3-carboxamide (200 mg, 0.453 mmol, 62.4% yield) as a white solid.

¹H NMR (400 MHz, DMSO-d₆) δ 11.49 (br. s., 1H), 8.04 (t, J=4.9 Hz, 1H), 7.84 (s, 1H), 5.87 (s, 1H), 5.74 (q, J=6.6 Hz, 1H), 4.24 (d, J=5.1 Hz, 2H), 2.43-2.35 (m, 1H), 2.31 (s, 6H), 2.19 (s, 3H), 2.12 (s, 3H), 2.05 (s, 3H), 2.04-2.00 (m, 1H), 1.84 (d, J=9.9 Hz, 2H), 1.80-1.71 (m, 2H), 1.39 (d, J=6.6 Hz, 3H), 1.30-1.10 (m, 4H). MS(ES) [M+H]⁺ 442.2.

Example 37

5-(((trans)-4-Aminocyclohexyl)(hydroxy)methyl)-N-((4,6-dimethyl-2-oxo-1,2-dihydropyridin-3-yl)methyl)-4-methylthiophene-3-carboxamide

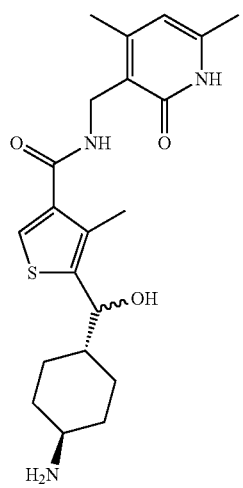 [SMILES: Cc1cc(C)c(CNC(=O)c2csc(C(O)[C@H]3CC[C@H](N)CC3)c2C)c(=O)[nH]1]

a) tert-Butyl ((trans)-4-((4-(((4,6-dimethyl-2-oxo-1,2-dihydropyridin-3-yl)methyl)carbamoyl)-3-methyl-thiophen-2-yl)(hydroxy)methyl)cyclohexyl)carbamate

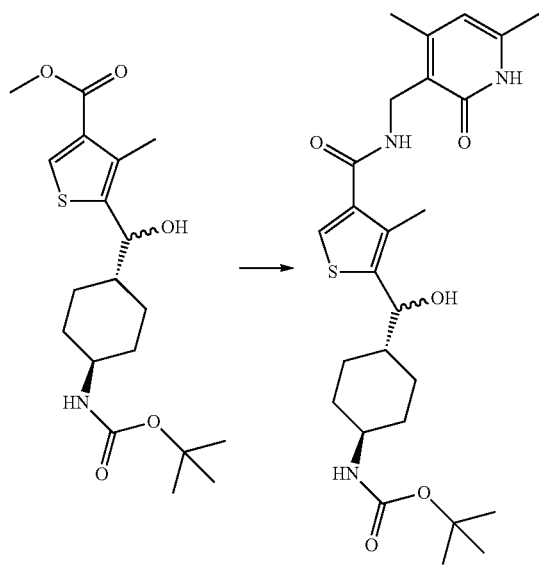 [SMILES: COC(=O)c1csc(C(O)[C@H]2CC[C@H](NC(=O)OC(C)(C)C)CC2)c1C ; Cc1cc(C)c(CNC(=O)c2csc(C(O)[C@H]3CC[C@H](NC(=O)OC(C)(C)C)CC3)c2C)c(=O)[nH]1]

To a solution of methyl 5-(((trans)-4-((tert-butoxycarbonyl)amino)cyclohexyl)(hydroxy)methyl)-4-methylthiophene-3-carboxylate (0.77 g, 2.008 mmol) in MeOH (25 mL) was added 1 N NaOH (5 mL, 5.00 mmol). The reaction was heated at 70° C. for 4 h, at which time it was concentrated under vacuum. The residue was acidified with 1 N HCl (5.0 mL), extracted with DCM, dried over MgSO₄, filtered and concentrated under vacuum.

To the resultant material was added 3-(aminomethyl)-4,6-dimethylpyridin-2(1)-one hydrochloride (0.4 g, 2.120 mmol), HOAt (0.3 g, 2.204 mmol) and DCM (25 mL). The suspension was broken up with a stir rod and to the suspension was added NMM (0.235 mL, 2.137 mmol), followed by EDC free base (0.4 g, 2.58 mmol). The reaction was stirred overnight, at which time the suspension was filtered free of insolubles and rinsed with a small volume of DCM. The clear filtrate was concentrated under vacuum and purified by silica gel chromatography (Analogix, SF25-60 g, 2 to 10% EtOH in EtOAc). The pure fractions were combined and evaporated to dryness under vacuum. The resultant solid was triturated with 5% MeOH/H₂O, filtered and dried under vacuum to give tert-butyl ((trans)-4-((4-(((4,6-dimethyl-2-oxo-1,2-dihydropyridin-3-yl)methyl)carbamoyl)-3-methyl-thiophen-2-yl)(hydroxy)methyl)cyclohexyl)carbamate (0.64 g, 1.271 mmol, 63.3% yield) as a white solid. ¹H NMR (400 MHz, DMSO-d₆) δ 11.48 (s, 1H), 7.98 (t, J=5.1 Hz, 1H), 7.71 (s, 1H), 6.65 (d, J=7.8 Hz, 1H), 5.86 (s, 1H), 5.50 (d, J=4.0 Hz, 1H), 4.53 (dd, J=4.2, 6.7 Hz, 1H), 4.31-4.14 (m, 2H), 3.11 (br. s., 1H), 2.19 (s, 3H), 2.17 (s, 3H), 2.11 (s, 3H), 1.95 (br. s., 1H), 1.77 (br. S., 1H), 1.71 (br. S., 1H), 1.36 (s, 9H), 1.33 (br. S., 1H), 1.12-0.97 (m, 4H). MS(ES) [M+H]⁺ 504.3.

b) 5-(((trans)-4-Aminocyclohexyl)(hydroxy)methyl)-N-((4,6-dimethyl-2-oxo-1,2-dihydropyridin-3-yl)methyl)-4-methylthiophene-3-carboxamide

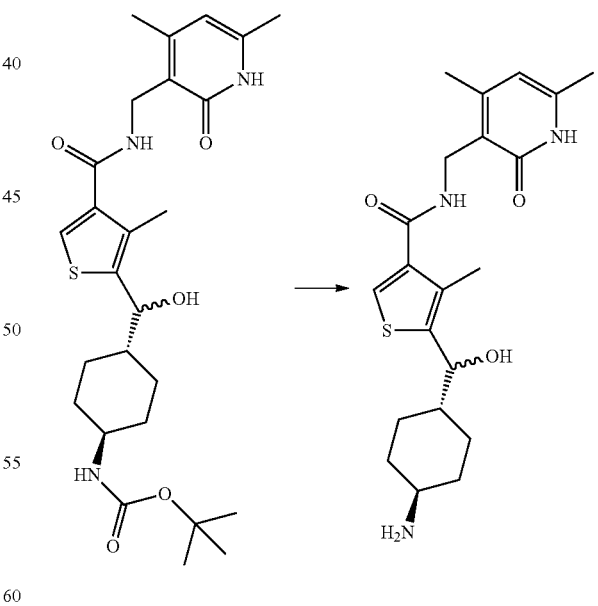

To tert-butyl ((trans)-4-((4-(((4,6-dimethyl-2-oxo-2-dihydropyridin-3-yl)methyl)carbamoyl)-3-methylthiophen-2-yl)(hydroxy)methyl)cyclohexyl)carbamate (600 mg, 1.191 mmol) was added 4 N HCl in 1,4-dioxane (20 mL, 80 mmol) and 6 N HCl (1 mL) to keep the reaction in solution. The reaction was stirred for 30 min, at which time it was evaporated to dryness under vacuum, triturated with Et₂O, filtered, and dried under vacuum to give 5-(((trans)-4-aminocyclohexyl)(hydroxy)methyl)-N-((4,6-dimethyl-2-oxo-1,2-dihydropyridin-3-yl)methyl)-4-methylthiophene-3-carboxamide hydrochloride (550 mg, 1.188 mmol, 100% yield) as a white solid. The HCl salt (500 mg) was converted to the free base with 1 N Na$_2$CO$_3$, extracted with 10% MeOH/DCM (3×), dried over Na$_2$SO$_4$, filtered, and concentrated under vacuum. The residue was purified by silica gel chromatography (Analogix, SF25-40 g, 10 to 60% (5% NH$_4$OH/MeOH) in DCM). The pure fractions were combined and evaporated to dryness. The resultant residue was triturated with Et$_2$O, filtered, washed with hexanes and dried under vacuum to give 5-(((trans)-4-aminocyclohexyl)(hydroxy)methyl)-N-((4,6-dimethyl-2-oxo-1,2-dihydropyridin-3-yl)methyl)-4-methylthiophene-3-carboxamide (168 mg, 0.396 mmol, 33.2% yield) as a white solid. $^1$H NMR (400 MHz, DMSO-d$_6$) δ 7.98 (t, J=4.9 Hz, 1H), 7.70 (s, 1H), 5.86 (s, 1H), 5.48 (br. s., 1H), 4.53 (d, J=6.8 Hz, 1H), 4.31-4.11 (m, 2H), 3.34 (br. s., 2H), 2.41 (t, J=10.6 Hz, 1H), 2.19 (s, 3H), 2.17 (s, 3H), 2.11 (s, 3H), 1.91 (d, J=12.9 Hz, 1H), 1.83-1.62 (m, 2H), 1.42-1.26 (m, 2H), 1.07-0.79 (m, 4H). MS(ES) [M+H]$^+$ 404.1.

Example 38

N-((4,6-dimethyl-2-oxo-1,2-dihydropyridin-3-yl)methyl)-5-(((trans)-4-(dimethylamino)cyclohexyl)(hydroxy)methyl)-4-methylthiophene-3-carboxamide

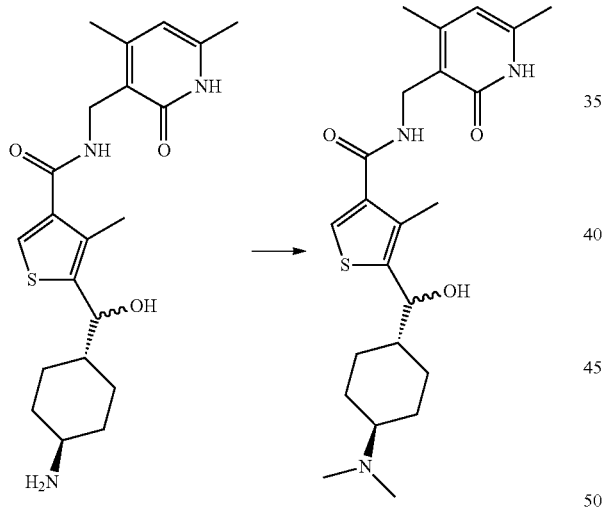

To a mixture of 5-(((trans)-4-aminocyclohexyl)(hydroxy)methyl)-N-((4,6-dimethyl-2-oxo-1,2-dihydropyridin-3-yl)methyl)-4-methylthiophene-3-carboxamide hydrochloride (490 mg, 1.114 mmol) and NaOAc (100 mg, 1.219 mmol) in MeOH (25 mL) was added formaldehyde (37 wt % in water, 1.0 mL, 13.43 mmol). The reaction was stirred for 15 min, at which time NaBH$_3$CN (150 mg, 2.387 mmol) was added. The reaction stirred overnight, at which time it was quenched with 6 N HCl (2 mL), stirred for 30 min and evaporated to dryness under vacuum. The residue was basified with 1 N Na$_2$CO$_3$, extracted with DCM (3×), dried over Na$_2$SO$_4$, filtered and concentrated under vacuum. Purification by silica gel chromatography (Analogix, SF25-40 g, 10 to 30% (5% NH$_4$OH/MeOH) in DCM) furnished N-((4,6-dimethyl-2-oxo-1,2-dihydropyridin-3-yl)methyl)-5-(((trans)-4-(dimethylamino)cyclohexyl)(hydroxy)methyl)-4-methylthiophene-3-carboxamide (136 mg, 0.315 mmol, 28.3% yield) as a white solid. $^1$H NMR (400 MHz, DMSO-d$_6$) δ 11.48 (br. s., 1H), 7.98 (br. s., 1H), 7.70 (s, 1H), 5.86 (s, 1H), 5.49 (d, J=3.3 Hz, 1H), 4.53 (br. s., 1H), 4.22 (br. s., 2H), 2.19 (br. s., 3H), 2.17 (br. s., 3H), 2.13 (br. s., 6H), 2.11 (br. s., 3H), 2.01 (br. s., 1H), 1.84-1.69 (m, 2H), 1.39 (br. s., 2H), 1.13-0.94 (m, 4H). MS(ES) [M+H]$^+$ 432.2.

Example 39 tert-Butyl 4-(1-(4-(((4,6-dimethyl-2-oxo-1,2-dihydropyridin-3-yl)methyl)carbamoyl)-3-methylthiophen-2-yl)propyl)piperidine-1-carboxylate

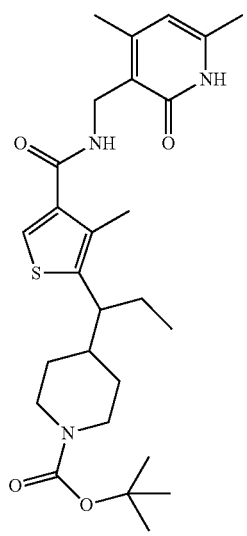 [SMILES: CCC(c1scc(C(=O)NCc2c(C)cc(C)[nH]c2=O)c1C)C1CCN(C(=O)OC(C)(C)C)CC1]

a) tert-Butyl 4-(1-(4-(methoxycarbonyl)-3-methylthiophen-2-yl)propyl)piperidine-1-carboxylate

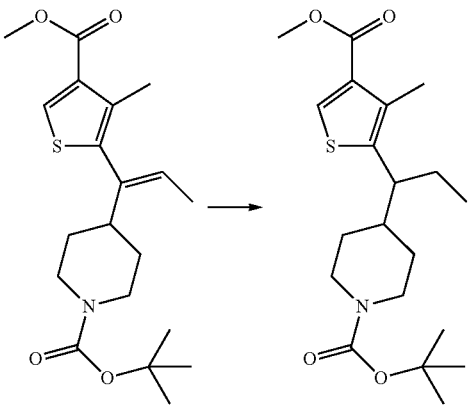 [SMILES: C/C=C(/c1scc(C(=O)OC)c1C)C1CCN(C(=O)OC(C)(C)C)CC1 ; CCC(c1scc(C(=O)OC)c1C)C1CCN(C(=O)OC(C)(C)C)CC1]

To 10% Pd/C (activated, dry) (2.0 g, 1.879 mmol) under N$_2$ was carefully added isopropanol (5 mL) to wet the catalyst. A solution of (E)-tert-butyl 4-(1-(4-(methoxycarbonyl)-3-methylthiophen-2-yl)prop-1-en-1-yl)piperidine-1-carboxylate (900 mg, 2.371 mmol) in MeOH (25 mL) was added and the flask fitted with two balloons of H2. The reaction was stirred for 3 days, at which time it was carefully filtered through a pad of Celite® and rinsed with MeOH. The filtrate was evaporated to dryness under vacuum to give tert-butyl 4-(1-(4-(methoxycarbonyl)-3-methylthiophen-2-yl)propyl)piperidine-1-carboxylate (720 mg, 1.887 mmol, 80% yield) as a clear oil (contaminated with ~11% of the ethyl ester). $^1$H NMR (400 MHz, CHLOROFORM-d) δ 8.01 (s, 1H), 4.21-3.98 (m, 2H), 3.85 (s, 3H), 2.77-2.51 (m, 3H), 2.36 (s, 3H), 1.99-1.87 (m, 2H), 1.59-1.53 (m, 1H), 1.46 (s, 9H), 1.22-1.06 (m, 2H), 0.77 (t, J=7.3 Hz, 3H). MS(ES) [M+H]$^+$ 326.1 (-isobutylene), [M+Na]$^+$ 404.1.

b) tert-Butyl 4-(1-(4-(((4,6-dimethyl-2-oxo-1,2-dihydropyridin-3-yl)methyl)carbamoyl)-3-methylthiophen-2-yl)propyl)piperidine-1-carboxylate

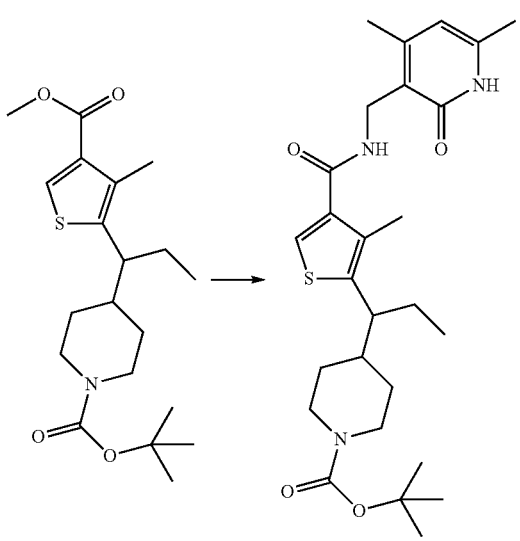 [SMILES: CCC(c1scc(C(=O)OC)c1C)C1CCN(C(=O)OC(C)(C)C)CC1 ; CCC(c1scc(C(=O)NCc2c(C)cc(C)[nH]c2=O)c1C)C1CCN(C(=O)OC(C)(C)C)CC1]

To a solution of tert-butyl 4-(1-(4-(methoxycarbonyl)-3-methylthiophen-2-yl)propyl)piperidine-1-carboxylate (710 mg, 1.861 mmol) in MeOH (25 mL) was added 1 N NaOH (5.0 mL, 5.00 mmol). The reaction was heated at 70° C. for 18 h, at which time the MeOH was removed under reduced pressure. The mixture was acidified with 1 N HCl (5.0 mL). The precipitate was filtered off, washed with cold water and dried under vacuum to give a white solid.

To the white solid was added 3-(aminomethyl)-4,6-dimethylpyridin-2(1H)-one hydrochloride (370 mg, 1.961 mmol), HOAt (260 mg, 1.910 mmol) and DCM (25 mL). The suspension was broken up with a stir rod. To the stirring suspension was added NMM (220 μL, 2.001 mmol), followed by EDC free base (320 mg, 2.061 mmol). The reaction was stirred overnight, at which time it was purified by silica gel chromatography (Isco RediSep Rf Gold 80 g, 2 to 10% EtOH in EtOAc). The fractions containing product were combined and evaporated to dryness under vacuum. The residue was triturated with 10% MeOH/H$_2$O, filtered and dried under vacuum to give tert-butyl 4-(1-(4-(((4,6-dimethyl-2-oxo-1,2-dihydropyridin-3-yl)methyl)carbamoyl)-3-methylthiophen-2-yl)propyl)piperidine-1-carboxylate (840 mg, 1.674 mmol, 90% yield) as a white solid. $^1$H NMR (400 MHz, DMSO-d$_6$) δ 11.48 (s, 1H), 7.99 (t, J=4.9 Hz, 1H), 7.70 (s, 1H), 5.86 (s, 1H), 4.23 (d, J=5.1 Hz, 2H), 4.00-3.82 (m, 2H), 2.77-2.70 (m, 2H), 2.18 (s, 6H), 2.11 (s, 3H), 1.90-1.79 (m, 2H), 1.56-1.47 (m, 1H), 1.37 (s, 9H), 1.40-1.30 (m, 2H), 1.08-0.91 (m, 2H), 0.70 (t, J=7.2 Hz, 3H). MS(ES) [M+H]$^+$ 502.2.

Example 40

N-((4,6-Dimethyl-2-oxo-1,2-dihydropyridin-3-yl)methyl)-4-methyl-5-(1-(piperidin-4-yl)propyl)thiophene-3-carboxamide

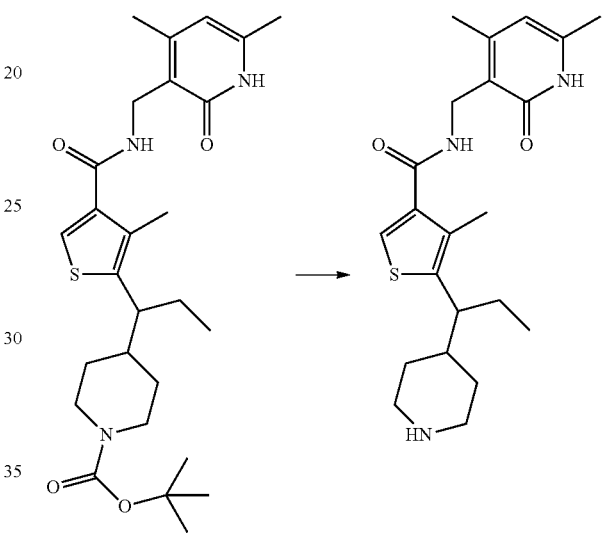

To tert-butyl 4-(1-(4-(((4,6-dimethyl-2-oxo-1,2-dihydropyridin-3-yl)methyl)carbamoyl)-3-methylthiophen-2-yl)propyl)piperidine-1-carboxylate (790 mg, 1.575 mmol) in MeOH (1 mL) was added 4 N HCl in 1,4-dioxane (20 mL, 80 mmol). The reaction was stirred for 45 min, at which time it was evaporated to dryness under vacuum. The residue was basified with 1 N Na$_2$CO$_3$, extracted with 10% MeOH in DCM (2×), dried over Na$_2$SO$_4$, filtered and concentrated under vacuum. The residue was purified by silica gel chromatography (Analogix SF25-40 g, 10 to 35% (5% NH$_4$OH/MeOH) in DCM). The pure fractions were combined, evaporated to dryness, triturated with Et$_2$O/pet. ether, filtered and dried under vacuum to give N-((4,6-dimethyl-2-oxo-1,2-dihydropyridin-3-yl)methyl)-4-methyl-5-(1-(piperidin-4-yl)propyl)thiophene-3-carboxamide (600 mg, 1.494 mmol, 95% yield) as a white solid. $^1$H NMR (400 MHz, DMSO-d$_6$) δ 7.98 (t, J=4.9 Hz, 1H), 7.68 (s, 1H), 5.86 (s, 1H), 4.23 (d, J=5.1 Hz, 2H), 3.34 (br. s., 2H), 2.91 (d, J=11.6 Hz, 1H), 2.82 (d, J=11.9 Hz, 1H), 2.73-2.63 (m, 1H), 2.43-2.34 (m, 1H), 2.29 (t, J=11.1 Hz, 1H), 2.18 (s, 6H), 2.11 (s, 3H), 1.86 (ddd, J=3.9, 7.3, 13.5 Hz, 1H), 1.76 (d, J=12.1 Hz, 1H), 1.49-1.30 (m, 2H), 1.27 (d, J=12.9 Hz, 1H), 1.07-0.92 (m, 2H), 0.70 (t, J=7.2 Hz, 3H). MS(ES) [M+H]$^+$ 402.1.

Example 41

(S)-(−)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide

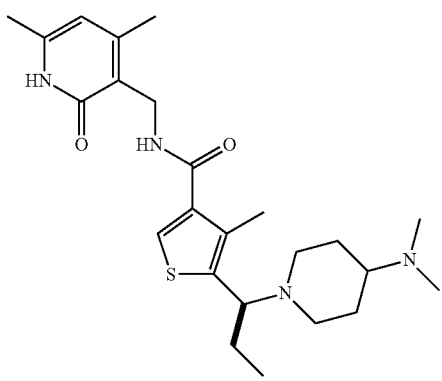

a) Methyl 4-methylthiophene-3-carboxylate

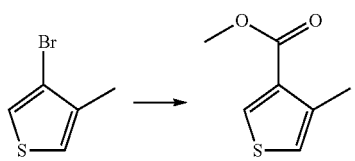

To a solution of 3-bromo-4-methylthiophene (25 g, 141 mmol) in THF (50 mL) under nitrogen at RT was added isopropylmagnesium chloride lithium chloride complex (1.3 N in THF, 120 mL, 156 mmol) dropwise. The reaction was stirred overnight for 24 h. The reaction was cooled to −78° C. (acetone, $CO_2$) and treated with methyl chloroformate (12 mL, 155 mmol) in one portion. The reaction was allowed to warm slowly to RT and stirred overnight. The reaction was concentrated under vacuum to remove most of the THF and diluted with EtOAc (200 mL). The solution was added to saturated $NaHCO_3$ (300 mL) and stirred for 60 min (the aqueous phase contained a white suspension). The mixture was transferred to a separatory funnel. The lower aqueous phase containing the white suspension was removed and the EtOAc phase washed with brine, dried over $Na_2SO_4$, filtered and concentrated under vacuum. The product was short path distilled under vacuum (3 to 2 mm Hg). Main fraction distilled at 55-65° C. (oil bath 75-90° C.). The forerun and main fractions were collected. The main fraction gave the product methyl 4-methylthiophene-3-carboxylate (15.3 g, 98 mmol, 69.4% yield) as a clear liquid (94% pure by LCMS). The forerun (3.2 g, 20.48 mmol, 14.5%) was 88% pure by LCMS. The remaining dark brown oil did not have any detectable product by LCMS: MS(ES) [M+H]⁺156.8.

b) Methyl 4-methyl-5-propionylthiophene-3-carboxylate

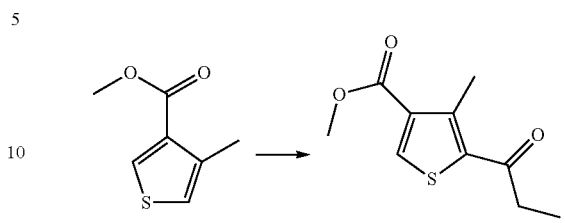

A 250 mL round bottom flask was purged with $N_2$ and kept under inert atmosphere. The reaction flask was charged with methyl 4-methylthiophene-3-carboxylate (9.99 g, 64.0 mmol) as a solution in nitromethane (118 mL). To the reaction were added propionic anhydride (9.84 mL, 77 mmol), lithium perchlorate (8.17 g, 77 mmol), and indium (III) trifluoromethanesulfonate (0.844 g, 3.20 mmol). The mixture was heated at 50° C. for 2 h, at which time it was quenched with water (100 mL). The layers were separated and the aqueous extracted with DCM (100 mL). The combined organics were washed with brine (20 mL), dried over $Na_2SO_4$, and concentrated. The residue was further dried under high vacuum overnight to give methyl 4-methyl-5-propionylthiophene-3-carboxylate (11.99 g, 56.5 mmol, 88% yield) as a light grey/brown solid. ¹H NMR (400 MHz, DMSO-$d_6$) δ 8.56 (s, 1H), 3.81 (s, 3H), 2.94 (q, J=7.16 Hz, 2H), 2.71 (s, 3H), 1.05-1.11 (m, 3H). LCMS [M+H]⁺ 212.9. HPLC (Agilent 1100 Series, 5-95% MeCN/$H_2O$ with 0.1% TFA in each, 5 min) showed >99% purity, rt 3.05 min, UV 254 nm.

c) Methyl 5-(1-hydroxypropyl)-4-methylthiophene-3-carboxylate

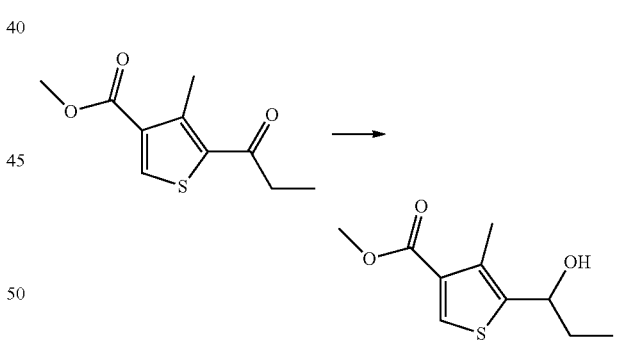

A 1 L round bottom flask was purged with $N_2$, then charged with methyl 4-methyl-5-propionylthiophene-3-carboxylate (11.99 g, 56.5 mmol), and THF (565 mL). The reaction was equipped with a magnetic stir bar, rubber septa and $N_2$ line. Under inert atmosphere the reaction was stirred at 0° C. for 20 min, at which time was added $NaBH_4$ (1.069 g, 28.2 mmol) in 4 equal portions in 3 min intervals. The reaction was kept under $N_2$ and stirred overnight while the ice-bath was allowed to slowly warm to RT. After 16 h, LCMS showed 28% conversion. Additional $NaBH_4$ (0.759 g, 20.05 mmol) was added and the reaction continued to stir at RT. After 3 h, LCMS showed little to no change in reaction progression. Another portion of $NaBH_4$ (0.759 g, 20.05 mmol) was added and the reaction continued to stir at RT. After 3 h, LCMS showed 42% conversion. A final portion of NaBH$_4$ (0.759 g, 20.05 mmol) was added and the reaction continued to stir at RT overnight. After 16 h, LCMS showed 92% conversion. The reaction was quenched with water (200 mL) and stirred at RT until bubbling slowed. The product was extracted with EtOAc (200 mL). The organic layer was washed with brine (2×25 mL), dried over Na$_2$SO$_4$, filtered and concentrated in vacuo. The residue was purified by column chromatography (200 g SiO$_2$ column, 150 mL/min, 100% Hex 2 min, 0-30% 18 min, 257 nm) to give methyl 5-(1-hydroxypropyl)-4-methylthiophene-3-carboxylate as a translucent light-golden-yellow oil. (9.94 g, 45.5 mmol, 80% yield) $^1$H NMR (400 MHz, DMSO-d$_6$) δ 8.15 (s, 1H), 5.62 (d, J=4.04 Hz, 1H), 4.80 (ddd, J=4.17, 5.75, 7.01 Hz, 1H), 3.72-3.78 (m, 3H), 2.30 (s, 3H), 1.54-1.73 (m, 2H), 0.82-0.90 (m, 3H). MS(ES) [M+H]$^+$196.9.

d) (S)-(+)-Methyl 5-(1-(4-(dimethylamino)piperidin-1-yl)propyl)-4-methylthiophene-3-carboxylate

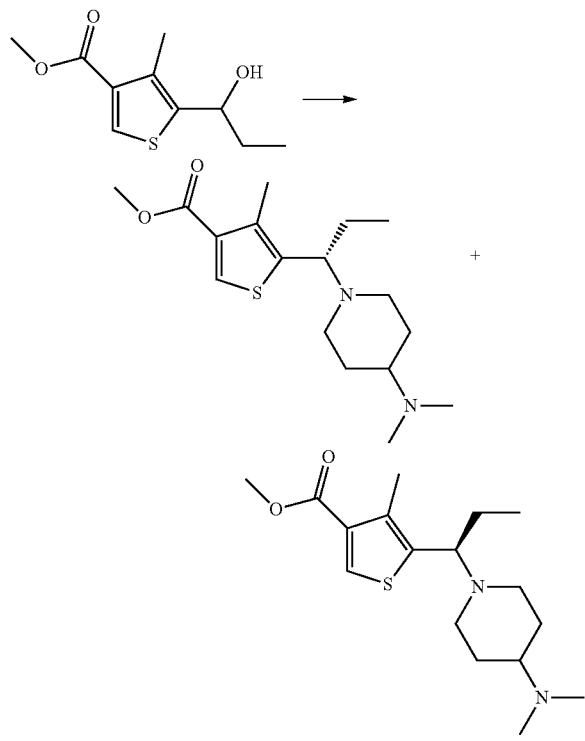

To a 250 mL round bottom flask purged with N$_2$, methyl 5-(1-hydroxypropyl)-4-methylthiophene-3-carboxylate (9.94 g, 46.4 mmol) was added as a solution in DCM (60 mL). The reaction was kept under positive N$_2$ pressure and cooled in an ice. Thionyl chloride (4.37 mL, 60.3 mmol) was added slowly as a solution in DCM (20.89 mL, 325 mmol) and the reaction stirred at 0° C. for 10 min, at which time the ice-bath was removed and the reaction maintained at RT for 3 h. The reaction was concentrated in vacuo and the residue evaporated from DCM (2×60 mL). Under inert atmosphere, the residue was dissolved with CH$_3$CN (60.6 mL, 1160 mmol) and cooled to 0° C. The reaction was maintained at 0° C. for 30 min, at which time a solution of N,N-dimethylpiperidin-4-amine (21.83 mL, 186 mmol) in CH$_3$CN (10 mL) was added in 2 portions. The reaction was stirred at 0° C. for 1 h, then at RT for 3 days. Excess dimethylaminopiperidine-HCl salt was removed by filtration and the reaction was concentrated. The residue was triturated with EtOAc (200 mL) and a yellow solid formed. The solid was treated with CH$_3$CN (50 mL) and 3 N HCl in cyclopropyl methyl ether (30 mL). The remaining solid was collected and washed with CH$_3$CN (2×20 mL) and Et$_2$O (20 mL). The combined organics were concentrated. The residue was dissolved in EtOAc, washed with saturated NaHCO$_3$ (5 mL) in water (100 mL) and brine (20 mL). The organic layer was dried over Na$_2$SO$_4$, filtered and concentrated. The residue was passed thru a plug of silica with EtOAc/hexanes and concentrated. The residue was dissolved in EtOAc (200 mL) and washed with 0.5 N HCl (200 mL). The aqueous layer was diluted with water (30 mL), washed with EtOAc (2×100 mL), basified with 1 N Na$_2$CO$_3$ (120 mL), and extracted with EtOAc (3×70 mL). The combined organics were washed with brine (20 mL), dried over Na$_2$SO$_4$, filtered and concentrated to yield (±)-methyl 5-(1-(4-(dimethylamino)piperidin-1-yl)propyl)-4-methylthiophene-3-carboxylate (9.3 g, 28.6 mmol, 61.7% yield) as a light-brown translucent oil. $^1$H NMR (400 MHz, DMSO-d$_6$) δ 8.20 (s, 1H), 3.76 (s, 3H), 3.70 (dd, J=5.31, 8.84 Hz, 1H), 3.01 (d, J=9.09 Hz, 1H), 2.79 (dd, J=1.77, 11.12 Hz, 1H), 2.33 (s, 3H), 2.12 (s, 6H), 1.81-1.98 (m, 4H), 1.61-1.78 (m, 2H), 1.45-1.60 (m, 1H), 1.20-1.42 (m, 2H), 0.72 (t, J=7.33 Hz, 3H). MS(ES) [M+H]$^+$325.1.

The racemic mixture was resolved by preparative HPLC (Chiralpak AD-H, 5 microns, 50 mm×250 mm, 250 nm UV, 100 mL/min, 22° C., 0.1% isopropylamine in MeOH, isocratic) to afford (+)-methyl 5-(1-(4-(dimethylamino)piperidin-1-yl)propyl)-4-methylthiophene-3-carboxylate (4.36 g, >99.8% ee, +14.0°, 48%) and (−)-methyl 5-(1-(4-(dimethylamino)piperidin-1-yl)propyl)-4-methylthiophene-3-carboxylate (4.34 g, 99.0% ee, −14.2°, 48%) as light yellow oils.

Data for (+)-methyl 5-(1-(4-(dimethylamino)piperidin-1-yl)propyl)-4-methylthiophene-3-carboxylate: $^1$H NMR (400 MHz, DMSO-d$_6$) δ 8.21 (s, 1H), 3.76 (s, 3H), 3.70 (dd, J=5.18, 8.72 Hz, 1H), 3.01 (d, J=11.12 Hz, 1H), 2.79 (dd, J=2.02, 11.12 Hz, 1H), 2.33 (s, 3H), 2.12 (s, 6H), 1.83-2.00 (m, 4H), 1.61-1.76 (m, 2H), 1.55 (s, 1H), 1.18-1.42 (m, 2H), 0.72 (t, J=7.33 Hz, 3H). MS(ES) [M+H]$^+$ 325.1. [α]$_D$=+14.0° (MeOH, c=0.5, 21° C.).

Data for (−)-methyl 5-(1-(4-(dimethylamino)piperidin-1-yl)propyl)-4-methylthiophene-3-carboxylate: $^1$H NMR (400 MHz, DMSO-d$_6$) δ 8.21 (s, 1H), 3.76 (s, 3H), 3.70 (dd, J=5.05, 8.84 Hz, 1H), 2.96-3.06 (m, 1H), 2.74-2.83 (m, 1H), 2.33 (s, 3H), 2.12 (s, 6H), 1.84-1.98 (m, 4H), 1.66 (d, J=15.66 Hz, 2H), 1.46-1.60 (m, 1H), 1.18-1.43 (m, 2H), 0.72 (t, J=7.20 Hz, 3H). MS(ES) [M+H]$^+$=325.1. [α]$_D$=−14.2° (MeOH, c=0.5, 21° C.).

e) (S)-(−)-N-((4,6-Dimethyl-2-oxo-1,2-dihydropyridin-3-yl)methyl)-5-(1-(4-(dimethylamino)piperidin-1-yl)propyl)-4-methylthiophene-3-carboxamide

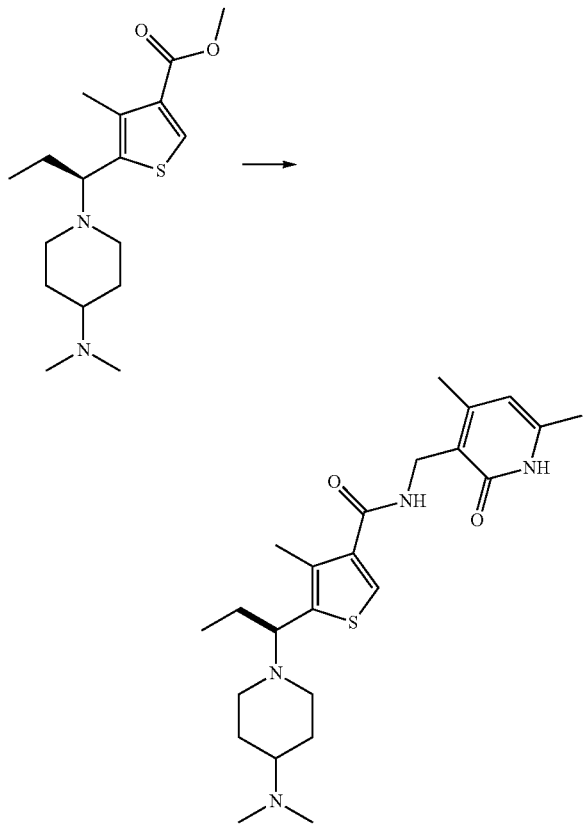

To a solution of (+)-methyl 5-(1-(4-(dimethylamino)piperidin-1-yl)propyl)-4-methylthiophene-3-carboxylate (4.36 g, 13.44 mmol) in MeOH (24.46 mL, 605 mmol) and THF (25.3 mL, 309 mmol) was added 8 M NaOH (10.08 mL, 81 mmol). The reaction was heated at 55° C. for 2 h, at which time the organic solvents were removed in vacuo. The remaining aqueous solution was diluted with water (20 mL) and cooled in an ice-bath with stirring. The cooled solution was acidified with 6 M HCl (13.55 mL, 81 mmol) to pH ~4.5. The water was removed in vacuo at 55° C. and the remaining solid was dried under high vacuum until consistent mass was obtained.

To a solution of the residue in DMF (50 mL) was added NMM (14.77 mL, 134 mmol) and HATU (7.66 g, 20.16 mmol). The reaction mixture was stirred for 10 min at RT, at which time 3-(aminomethyl)-4,6-dimethylpyridin-2(1H)-one hydrochloride (2.66 g, 14.11 mmol) was added. After the reaction was complete (by LCMS), it was poured into a stirred solution of saturated NaHCO₃ (37.5 mL) and water (112.5 mL). The aqueous solution was extracted with DCM (5×200 mL) and the combined organic layers were dried over Na₂SO₄, filtered and concentrated. The residue was dissolved in DCM (20 mL) and charged onto a pad of silica and purified by normal phase flash chromatography (330 g, ISCO® gold, 100 mL/min, A: DCM, B: 5% NH₄OH/MeOH, 0% B for 2 min, then 0-20% B over 25 min, hold 20% for 5 min) to give (S)-(−)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide as a white crystalline solid (2.83 g, 6.36 mmol, 47.3% yield, −0.017°). Note: the absolute stereochemistry was determined by vibrational circular dichroism (VCD) with a 92% confidence level. ¹H NMR (400 MHz, DMSO-d₆) δ 11.48 (s, 1H), 7.99 (t, J=4.93 Hz, 1H), 7.72 (s, 1H), 5.86 (s, 1H), 4.23 (d, J=5.05 Hz, 2H), 3.66 (dd, J=5.31, 8.84 Hz, 1H), 2.98 (d, J=10.36 Hz, 1H), 2.79 (d, J=11.37 Hz, 1H), 2.23 (s, 3H), 2.18 (s, 3H), 2.08-2.15 (m, 9H), 1.82-1.99 (m, 4H), 1.68 (t, J=13.89 Hz, 2H), 1.52 (dd, J=5.68, 7.96 Hz, 1H), 1.18-1.42 (m, 2H), 0.73 (t, J=7.33 Hz, 3H). MS(ES) [M+H]⁺ 445.2. [α]$_D$=−1.6° (EtOH, c=1.0, 23.2° C.).

Example 42

(R)-(+)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide

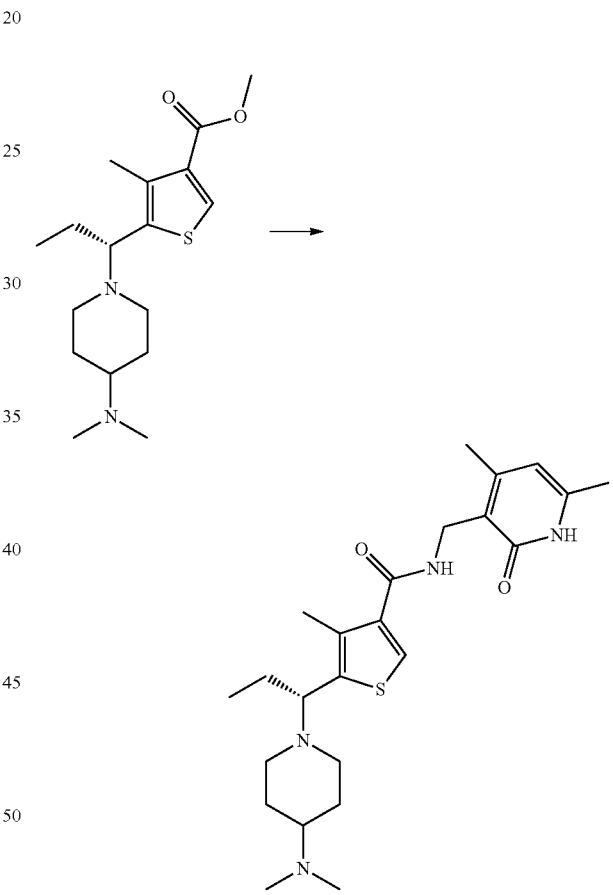

Following the general procedure of Example 41e, (−)-methyl 5-(1-(4-(dimethylamino)piperidin-1-yl)propyl)-4-methylthiophene-3-carboxylate was converted to (R)-(+)-N-((4,6-dimethyl-2-oxo-1,2-dihydropyridin-3-yl)methyl)-5-(1-(4-(dimethylamino)piperidin-1-yl)propyl)-4-methylthiophene-3-carboxamide (1.72 g, 3.86 mmol, 28.8% yield, +0.017°) as a white solid. Note: the absolute stereochemistry was determined by vibrational circular dichroism (VCD) with a 92% confidence level. ¹H NMR (400 MHz, DMSO-d₆) δ 11.48 (s, 1H), 7.99 (t, J=4.93 Hz, 1H), 7.72 (s, 1H), 5.86 (s, 1H), 4.23 (d, J=5.05 Hz, 2H), 3.66 (dd, J=5.31, 8.84 Hz, 1H), 2.98 (d, J=9.85 Hz, 1H), 2.79 (d, J=10.86 Hz, 1H), 2.23 (s, 3H), 2.18 (s, 3H), 2.07-2.14 (m, 9H), 1.80-1.99

(m, 4H), 1.60-1.75 (m, 2H), 1.52 (dd, J=5.94, 8.46 Hz, 1H), 1.18-1.41 (m, 2H), 0.73 (t, J=7.33 Hz, 3H). MS(ES) [M+H]+ 445.2. [α]$_D$=+1.6° (EtOH, c=1.0, 22.7° C.).

Example 43

5-(1-((trans)-4-Aminocyclohexyl)propyl)-N-((4,6-dimethyl-2-oxo-1,2-dihydropyridin-3-yl)methyl)-4-methylthiophene-3-carboxamide

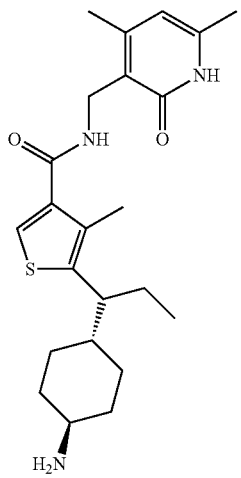 [SMILES: CCC(c1scc(C(=O)NCc2c(C)cc(C)[nH]c2=O)c1C)[C@H]1CC[C@H](N)CC1]

a1) Methyl 5-(1-((trans)-4-((tert-butoxycarbonyl)amino)cyclohexyl)propyl)-4-methylthiophene-3-carboxylate

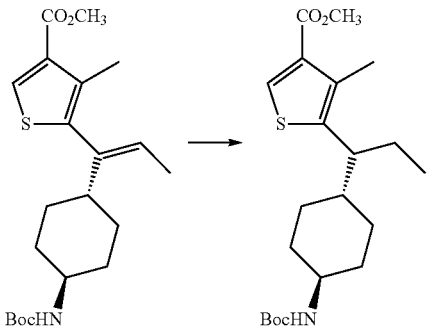 [SMILES: C/C=C(/c1scc(C(=O)OC)c1C)[C@H]1CC[C@H](NC(=O)OC(C)(C)C)CC1 ; CCC(c1scc(C(=O)OC)c1C)[C@H]1CC[C@H](NC(=O)OC(C)(C)C)CC1]

To 10% Pd/C (activated dry) (2.0 g, 1.879 mmol) in a 100 mL round bottom flask under N$_2$ was carefully added isopropanol (5 mL) to wet the catalyst. A solution of methyl 5-((E)-1-((trans)-4-((tert-butoxycarbonyl)amino)cyclohexyl)prop-1-en-1-yl)-4-methylthiophene-3-carboxylate (900 mg, 2.287 mmol) in MeOH (25 mL) was then added and two balloons of H2 were attached. The reaction was stirred for 3 days, at which time it was carefully filtered through a pad of Celite® and rinsed with MeOH. The filtrate was evaporated to dryness under vacuum and purified by silica gel chromatography (Analogix®, ISCO® RediSep Rf Gold 80 g, 5-25% EtOAc in hexanes) to give methyl 5-(1-((trans)-4-((tert-butoxycarbonyl)amino)cyclohexyl)propyl)-4-methylthiophene-3-carboxylate (480 mg, 1.213 mmol, 53.1% yield) as a white solid foam. The material was contaminated with ~20% of the cis-cyclohexane isomer (by $^1$H NMR). $^1$H NMR (major trans-isomer, 400 MHz, CDCl$_3$) δ 7.99 (s, 1H), 4.35 (br. s., 1H), 3.85 (s, 3H), 3.34 (br. s., 1H), 2.74-2.60 (m, 1H), 2.36 (s, 3H), 2.06-1.99 (m, 2H), 1.96-1.88 (m, 2H), 1.58-1.51 (m, 1H), 1.45 (s, 9H), 1.42-1.35 (m, 2H), 1.13-0.95 (m, 2H), 0.75 (t, J=7.3 Hz, 3H). MS(ES) [M+H]+-Boc 296.1, [M+H]+-Boc+Na+ 308.0, [M+H]+-isobutylene 340.1, M+Na+ 418.1.

a2) Alternatively, the Title Compound May be Prepared by the Following Procedure To 10% Pd/C (activated dry, 11.4 g, 107 mmol) in a 250 mL round bottom flask under N$_2$ was carefully added 1-propanol (20 mL) down the sides of the flask to wet the catalyst. A solution of methyl 5-(1-((trans)-4-((tert-butoxycarbonyl)amino)cyclohexyl)prop-1-en-1-yl)-4-methylthiophene-3-carboxylate (prepared by methods analogous to Example 34c2) (5.74 g, 14.59 mmol) in MeOH (100 mL) was added and two balloons of H2 were attached. The reaction was stirred for 3 days, filling the balloons periodically when low. The reaction was carefully filtered through a pad of Celite® and rinsed with MeOH. The filtrate was evaporated to dryness under vacuum and purified by silica gel chromatography (Analogix®, Isco® RediSep Rf Gold 120 g, 5 to 25% EtOAc in hexanes) to give methyl 5-(1-((trans)-4-((tert-butoxycarbonyl)amino)cyclohexyl)propyl)-4-methylthiophene-3-carboxylate (4.23 g, 10.69 mmol, 73.3% yield) as a white solid foam. $^1$H NMR shows >95% trans vs. cis cyclohexane regioisomer. $^1$H NMR (400 MHz, CDCl3) δ 7.92-8.09 (m, 1H), 4.35 (br. s., 1H), 3.79-3.92 (m, 3H), 3.34 (br. s., 1H), 2.68-2.82 (m, 1H), 2.28-2.41 (m, 3H), 1.86-2.12 (m, 5H), 1.34-1.49 (m, 11H), 0.93-1.14 (m, 4H), 0.63-0.81 (m, 3H). MS(ES) [M+H]+-Boc 296.1, [M+H]+-Boc+Na+ 308.1, [M+H]+-isobutylene 340.1, M+Na+ 418.2.

b) tert-Butyl ((trans)-4-(1-(4-(((4,6-dimethyl-2-oxo-1,2-dihydropyridin-3-yl)methyl)carbamoyl)-3-methylthiophen-2-yl)propyl)cyclohexyl)carbamate

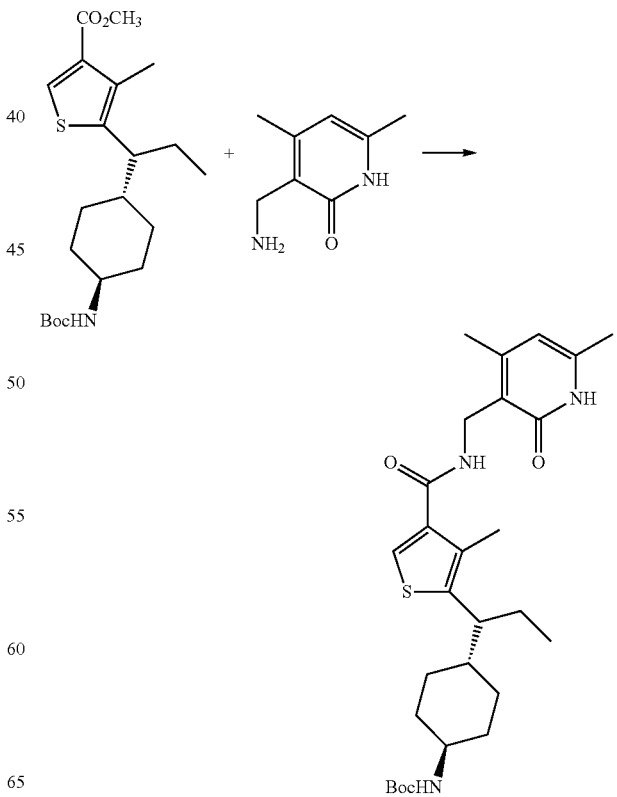

To a solution of methyl 5-(1-((trans)-4-((tert-butoxycarbonyl)amino)cyclohexyl)propyl)-4-methylthiophene-3-carboxylate (470 mg, 1.188 mmol) in MeOH (25 mL) was added 1 N NaOH (5.0 mL, 5.00 mmol). The reaction was heated at 70° C. for 18 h. The reaction was concentrated under vacuum to remove the MeOH and acidified with 1 N HCl (5.0 mL). The precipitate was extracted with DCM, dried over MgSO$_4$, filtered, and evaporated to dryness.

To the above residue was added 3-(aminomethyl)-4,6-dimethylpyridin-2(1H)-one hydrochloride (250 mg, 1.325 mmol), HOAt (170 mg, 1.249 mmol) and DCM (25 mL). The suspension was broken up with a stir rod. To the stirring suspension was added NMM (145 μL, 1.319 mmol), followed by EDC free base (220 mg, 1.417 mmol). The reaction was stirred overnight and purified directly by silica gel chromatography (ISCO® RediSep Rf Gold 80 g, 2-10% EtOH in EtOAc) to give tert-butyl ((trans)-4-(1-(4-(((4,6-dimethyl-2-oxo-1,2-dihydropyridin-3-yl)methyl)carbamoyl)-3-methylthiophen-2-yl)propyl)cyclohexyl)carbamate (520 mg, 1.008 mmol, 85% yield) as a white solid (mixture of enantiomers and contains ~20% of the cis-cyclohexane). $^1$H NMR (400 MHz, CDCl$_3$) δ 11.85 (br. s., 1H), 7.44-7.42 (m, 1H), 7.35 (d, J=5.1 Hz, 1H), 5.97 (s, 1H), 4.51 (d, J=5.8 Hz, 2H), 4.36 (d, J=6.6 Hz, 1H), 3.33 (br. s., 1H), 2.69-2.58 (m, 1H), 2.40 (s, 3H), 2.28 (s, 3H), 2.27 (s, 3H), 2.02 (m, 1H), 1.95-1.83 (m, 2H), 1.54 (m, 1H), 1.44 (s, 9H), 1.41-1.32 (m, 2H), 1.11-0.93 (m, 4H), 0.73 (t, J=7.3 Hz, 3H). MS(ES) [M+H]$^+$516.3.

c) 5-(1-((trans)-4-Aminocyclohexyl)propyl)-N-((4,6-dimethyl-2-oxo-1,2-dihydropyridin-3-yl)methyl)-4-methylthiophene-3-carboxamide

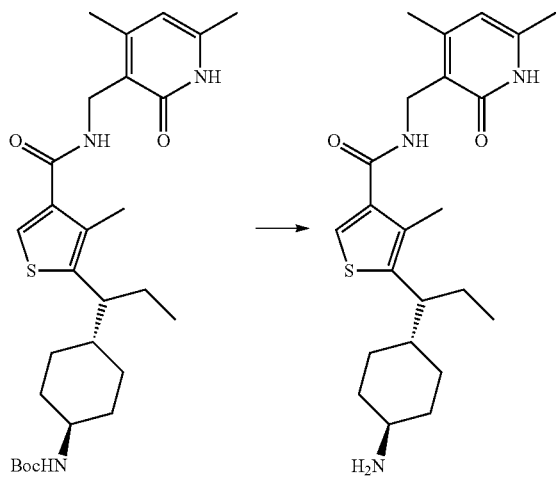 [SMILES: CCC(c1scc(C(=O)NCc2c(C)cc(C)[nH]c2=O)c1C)[C@H]1CC[C@H](NC(=O)OC(C)(C)C)CC1 ; CCC(c1scc(C(=O)NCc2c(C)cc(C)[nH]c2=O)c1C)[C@H]1CC[C@H](N)CC1]

To a solution of tert-butyl ((trans)-4-(1-(4-(((4,6-dimethyl-2-oxo-1,2-dihydropyridin-3-yl)methyl)carbamoyl)-3-methylthiophen-2-yl)propyl)cyclohexyl)carbamate (510 mg, 0.989 mmol) in MeOH (1 mL) was added 4 N HCl in 1,4-dioxane (20 mL, 80 mmol). The reaction was stirred for 45 min, at which time it was evaporated to dryness under vacuum. The remaining solid was dissolved in MeOH (10 mL), basified with 1 N Na$_2$CO$_3$ (2 mL), and evaporated to dryness under vacuum. The solids were triturated and extracted with 10% MeOH in DCM (2×25 mL), filtered and concentrated under vacuum. The residue was purified by silica gel chromatography (Analogix SF25-40 g, 10-35% (5% NH$_4$OH/MeOH) in DCM). The pure fractions were combined, evaporated to dryness, triturated with Et$_2$O/petroleum ether, filtered and dried under vacuum to give 5-(1-((trans)-4-aminocyclohexyl)propyl)-N-((4,6-dimethyl-2-oxo-1,2-dihydropyridin-3-yl)methyl)-4-methylthiophene-3-carboxamide (410 mg, 0.987 mmol, 100% yield) as a white solid (mixture of enantiomers and contains ~20% of the cis-cyclohexane). $^1$H NMR (400 MHz, DMSO-d$_6$) δ 7.99 (t, J=4.9 Hz, 1H), 7.67 (s, 1H), 5.86 (s, 1H), 4.23 (d, J=5.1 Hz, 2H), 2.71-2.60 (m, 1H), 2.41 (br. s., 1H), 2.18 (s, 3H), 2.17 (s, 3H), 2.11 (s, 3H), 1.91-1.79 (m, 2H), 1.68 (m, 1H), 1.47-1.22 (m, 4H), 1.03-0.81 (m, 4H), 0.68 (t, J=7.2 Hz, 3H). MS(ES) [M+H]$^+$ 416.2.

Examples 44-47

N-((4,6-Dimethyl-2-oxo-1,2-dihydropyridin-3-yl)methyl)-5-(1-((trans)-4-(dimethylamino)cyclohexyl)propyl)-4-methylthiophene-3-carboxamide and
N-((4,6-Dimethyl-2-oxo-1,2-dihydropyridin-3-yl)methyl)-5-(1-((cis)-4-(dimethylamino)cyclohexyl)propyl)-4-methylthiophene-3-carboxamide

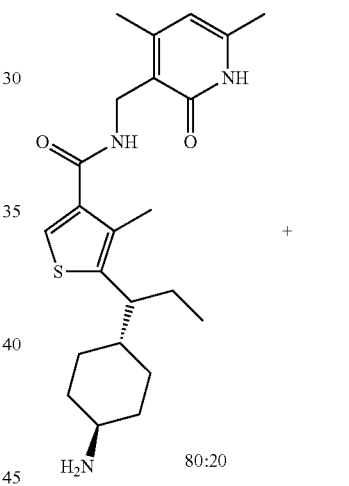

80:20

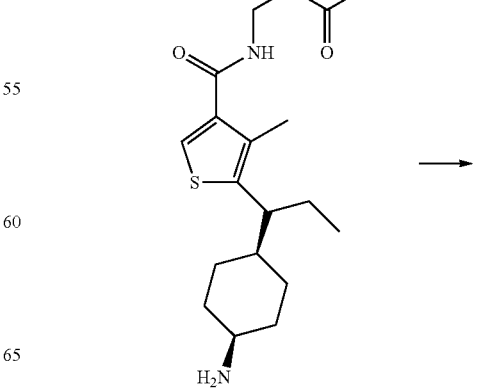

-continued

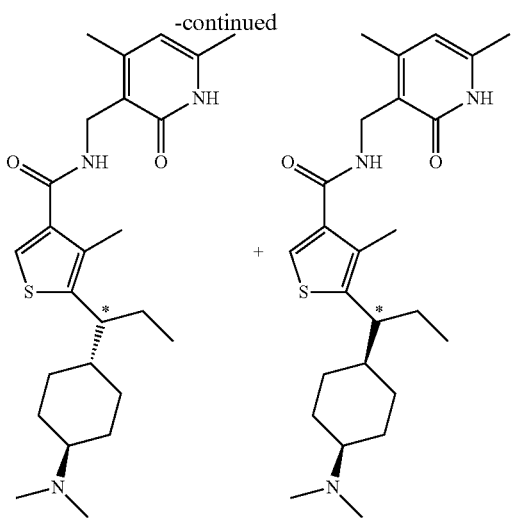

To a solution of 5-(1-((trans)-4-aminocyclohexyl)propyl)-N-((4,6-dimethyl-2-oxo-1,2-dihydropyridin-3-yl)methyl)-4-methylthiophene-3-carboxamide (400 mg, 0.962 mmol, mixture of enantiomers and contains ~20% of the cis-cyclohexane) in MeOH (15 mL) was added formaldehyde (37 wt % in water, 0.8 mL, 10.75 mmol). The reaction was stirred for 15 min, at which time NaBH$_3$CN (130 mg, 2.069 mmol) was added. The reaction mixture was stirred overnight, at which time it was evaporated to dryness under vacuum. The residue was purified by silica gel chromatography (Analogix, SF25-40 g, 10 to 35% (5% NH$_4$OH/MeOH) in DCM). The pure fractions were combined, evaporated to dryness, triturated with Et$_2$O/petroleum ether, filtered and dried under vacuum to give N-((4,6-dimethyl-2-oxo-1,2-dihydropyridin-3-yl)methyl)-5-(1-((trans)-4-(dimethylamino)cyclohexyl)propyl)-4-methylthiophene-3-carboxamide (240 mg, 0.541 mmol, 56.2% yield) as a white solid (mixture of enantiomers and contains ~20% of the cis-cyclohexane; 4 compounds total).

The mixture was resolved by chiral preparative HPLC (Chiralpak AD-H, 5 microns, 30 mm×250 mm, 300 nm UV, 45 mL/min, 22° C., 85:15:0.2 n-heptane:EtOH:isopropylamine, isocratic) to give all four purified compounds of unknown absolute configuration at C*.

Example 44

(−)-N-((4,6-Dimethyl-2-oxo-1,2-dihydropyridin-3-yl)methyl)-5-(1-((trans)-4-(dimethylamino)cyclohexyl)propyl)-4-methylthiophene-3-carboxamide

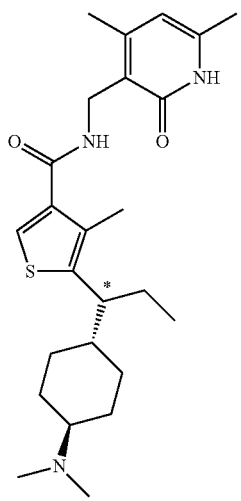 [SMILES: CCC(c1scc(C(=O)NCc2c(C)cc(C)[nH]c2=O)c1C)[C@H]1CC[C@H](N(C)C)CC1]

Obtained 63 mg (>99.8% ee): $^1$H NMR (400 MHz, DMSO-d$_6$) δ 11.48 (s, 1H), 7.99 (t, J=5.05 Hz, 1H), 7.67 (s, 1H), 5.86 (s, 1H), 4.22 (d, J=5.05 Hz, 2H), 2.62-2.76 (m, 1H), 2.18 (d, J=3.03 Hz, 6H), 2.11 (s, 9H), 1.91-2.05 (m, 2H), 1.76-1.89 (m, 2H), 1.71 (d, J=12.63 Hz, 1H), 1.49 (d, J=12.13 Hz, 1H), 1.21-1.40 (m, 2H), 0.83-1.15 (m, 4H), 0.69 (t, J=7.20 Hz, 3H). MS(ES) [M+H]$^+$ 444.2. [α]$_D$=−13.5° (MeOH, c=0.20, 22° C.). Unknown absolute configuration at C*.

Example 45

(+)-N-((4,6-Dimethyl-2-oxo-1,2-dihydropyridin-3-yl)methyl)-5-(1-((trans)-4-(dimethylamino)cyclohexyl)propyl)-4-methylthiophene-3-carboxamide

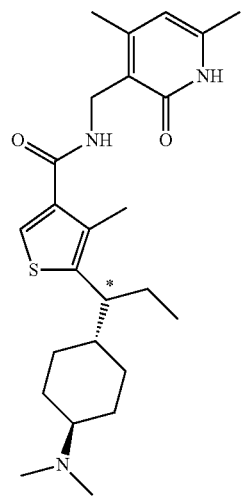

Obtained 64 mg (97.4% ee): $^1$H NMR (400 MHz, DMSO-d$_6$) δ 11.48 (br. s., 1H), 7.99 (t, J=4.93 Hz, 1H), 7.67 (s, 1H), 5.86 (s, 1H), 4.22 (d, J=5.05 Hz, 2H), 2.60-2.80 (m, 1H), 2.18 (d, J=3.03 Hz, 6H), 2.11 (s, 9H), 1.91-2.04 (m, 2H), 1.75-1.89 (m, 2H), 1.71 (d, J=12.63 Hz, 1H), 1.49 (d, J=12.63 Hz, 1H), 1.21-1.42 (m, 2H), 0.80-1.16 (m, 4H), 0.69 (t, J=7.20 Hz, 3H). MS(ES) [M+H]$^+$ 444.2. [α]$_D$=+13.0° (MeOH, c=0.20, 22° C.). Unknown absolute configuration at C*.

Example 46

(+)-N-((4,6-Dimethyl-2-oxo-1,2-dihydropyridin-3-yl)methyl)-5-(1-((cis)-4-(dimethylamino)cyclohexyl)propyl)-4-methylthiophene-3-carboxamide

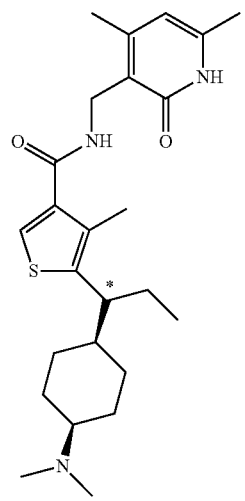

Obtained 21 mg (>99.8% ee): $^1$H NMR (400 MHz, DMSO-$d_6$) δ 11.45 (br. s., 1H), 7.97 (t, J=5.05 Hz, 1H), 7.68 (s, 1H), 5.86 (s, 1H), 4.23 (d, J=5.05 Hz, 2H), 2.72-2.87 (m, 1H), 2.19 (d, J=4.29 Hz, 6H), 2.12 (d, J=3.54 Hz, 9H), 1.98 (br. s., 1H), 1.88 (ddd, J=4.29, 7.39, 13.58 Hz, 1H), 1.74 (d, J=13.64 Hz, 1H), 1.46-1.67 (m, 3H), 1.40 (d, J=5.05 Hz, 1H), 1.19-1.33 (m, 4H), 1.14 (d, J=3.54 Hz, 1H), 0.68 (t, J=7.33 Hz, 3H). MS(ES) [M+H]$^+$ 444.2. $[α]_D$=+38.5° (MeOH, c=0.20, 22° C.). Unknown absolute configuration at C*.

Example 47

(−)-N-((4,6-Dimethyl-2-oxo-1,2-dihydropyridin-3-yl)methyl)-5-(1-((cis)-4-(dimethylamino)cyclohexyl)propyl)-4-methylthiophene-3-carboxamide

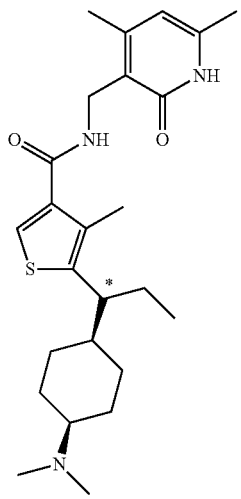 [SMILES: CCC(c1scc(C(=O)NCc2c(C)cc(C)[nH]c2=O)c1C)[C@H]1CC[C@@H](N(C)C)CC1]

Obtained 22 mg (99.2% ee): $^1$H NMR (400 MHz, DMSO-$d_6$) δ 11.48 (br. s., 1H), 7.99 (t, J=5.05 Hz, 1H), 7.68 (s, 1H), 5.86 (s, 1H), 4.22 (d, J=5.05 Hz, 2H), 2.78 (br. s., 1H), 2.19 (d, J=3.54 Hz, 6H), 2.11 (s, 9H), 1.83-2.00 (m, 2H), 1.74 (d, J=13.14 Hz, 1H), 1.45-1.67 (m, 4H), 1.17-1.42 (m, 5H), 0.68 (t, J=7.33 Hz, 3H). MS(ES) [M+H]$^+$ 444.2. $[α]_D$=−37.5° (MeOH, c=0.20, 22° C.). Unknown absolute configuration at C*.

Example 48

N-((4,6-dimethyl-2-oxo-1,2-dihydropyridin-3-yl)methyl)-4-methyl-5-(1-(piperidin-4-ylidene)propyl)thiophene-3-carboxamide

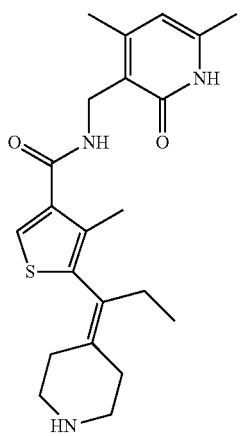 [SMILES: CCC(=C1CCNCC1)c1scc(C(=O)NCc2c(C)cc(C)[nH]c2=O)c1C]

a) tert-Butyl 4-(1-(4-(methoxycarbonyl)-3-methylthiophen-2-yl)propylidene)piperidine-1-carboxylate

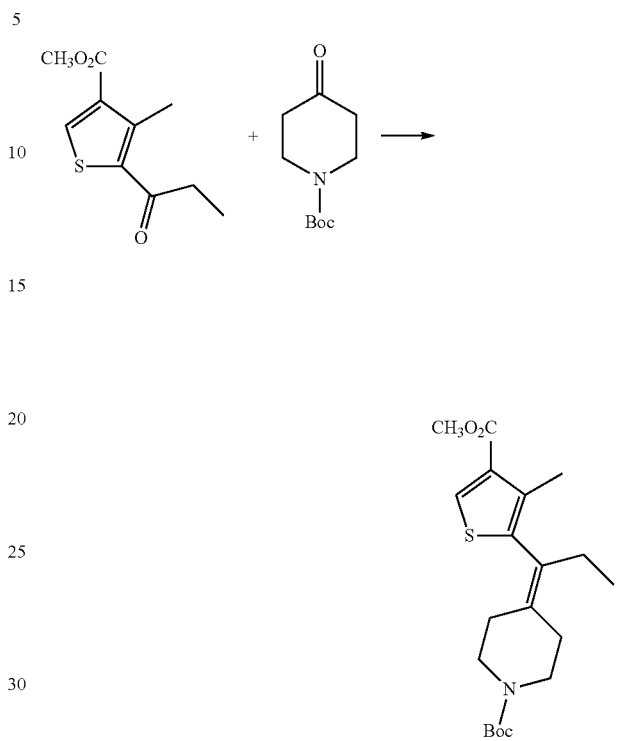

To a cooled (0° C.) suspension of zinc powder (2.1 g, 32.1 mmol) in THF (30 mL) under nitrogen was slowly added titanium(IV) chloride (1.7 mL, 15.51 mmol). The resulting black slurry was heated at reflux (70° C. oil bath) for 2 h. The reaction was rinsed down with fresh THF to enable stirring. A solution of methyl 4-methyl-5-propionylthiophene-3-carboxylate (0.5 g, 2.356 mmol), tert-butyl 4-oxopiperidine-1-carboxylate (1.5 g, 7.53 mmol) and pyridine (2.0 mL, 24.73 mmol) in THF (5 mL) was added and the heated at reflux for 3 days. The reaction was allowed to cool to RT and was quenched with saturated aq. NH$_4$C$_1$ (100 mL) and extracted with EtOAc (3×75 mL). The combined organics were filtered through a pad of Celite®, dried over Na$_2$SO$_4$, filtered and evaporated to dryness. The crude amine hydrochloride was taken up in DCM (30.0 mL) and treated with TEA (0.4 mL, 2.87 mmol) and Boc$_2$O (0.638 mL, 2.75 mmol). The reaction was maintained for 1 h, at which time it purified by silica gel chromatography (ISCO® RediSep Rf Gold 40 g, 5 to 30% EtOAc in hexanes) to give tert-butyl 4-(1-(4-(methoxycarbonyl)-3-methylthiophen-2-yl)propylidene)piperidine-1-carboxylate (0.36 g, 0.949 mmol, 40.3% yield) as a colorless oil. $^1$H NMR (400 MHz, CDCl$_3$) δ 8.04 (s, 1H), 3.86 (s, 3H), 3.51 (br. s., 2H), 3.34 (br. s., 2H), 2.44 (t, J=5.7 Hz, 2H), 2.35 (d, J=6.6 Hz, 2H), 2.25 (s, 3H), 2.02 (t, J=5.8 Hz, 2H), 1.48 (s, 9H), 0.95 (t, J=7.5 Hz, 3H). MS(ES) [M+H]$^+$-Boc 280.0, [M+H]$^+$-isobutylene 324.1, M+N$^+$ 402.1.

b) tert-Butyl 4-(1-(4-(((4,6-dimethyl-2-oxo-1,2-dihydropyridin-3-yl)methyl)carbamoyl)-3-methylthiophen-2-yl)propylidene)piperidine-1-carboxylate

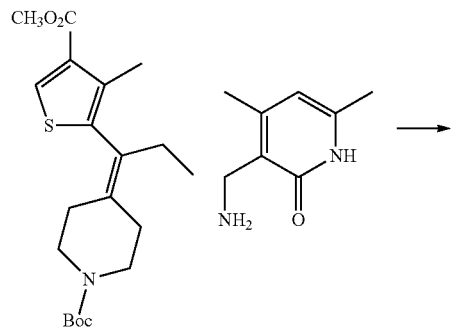

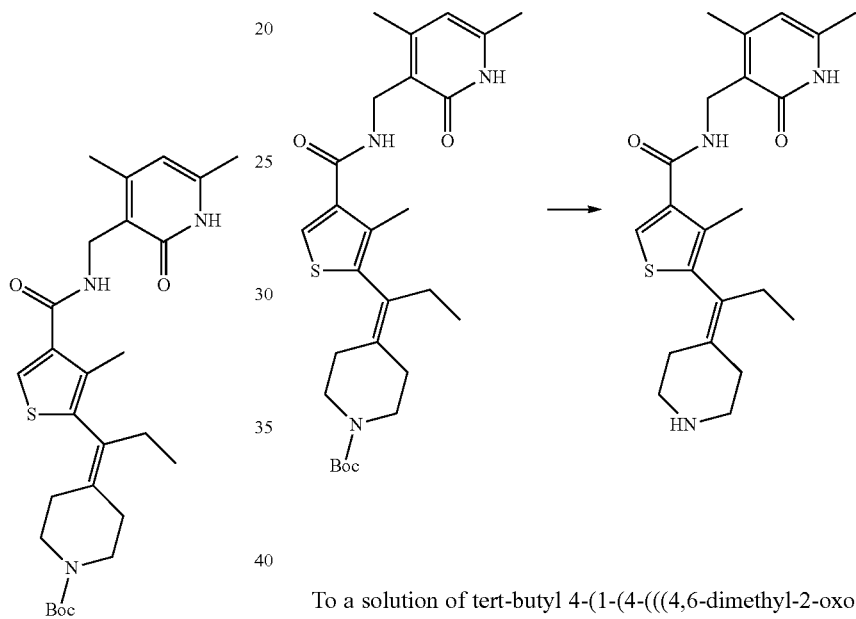

To a solution of tert-butyl 4-(1-(4-(methoxycarbonyl)-3-methylthiophen-2-yl)propylidene)piperidine-1-carboxylate (350 mg, 0.922 mmol) in MeOH (15 mL) was added 1 N NaOH (3.0 mL, 3.00 mmol). The reaction was heated at 70° C. for 18 h. The reaction was concentrated under vacuum to remove the MeOH and acidified with 1 N HCl (3.0 mL). The mixture was extracted with DCM, dried over MgSO$_4$, filtered, and dried under vacuum to a white solid.

To the above residue was added 3-(aminomethyl)-4,6-dimethylpyridin-2(1H)-one hydrochloride (190 mg, 1.007 mmol), HOAt (126 mg, 0.922 mmol), DCM (DCM) (20 mL) and NMM (111 μL, 1.010 mmol). The suspension was broken up with a stir rod. To the stirring suspension was added EDC free base (160 mg, 1.031 mmol). The reaction was stirred overnight. The reaction purified by silica gel chromatography (ISCO® RediSep Rf Gold 40 g, 2 to 10% EtOH in EtOAc). The fractions containing product were combined and evaporated to dryness under vacuum. The residue was triturated with cold 10% MeOH/H$_2$O, filtered and dried under vacuum to give tert-butyl 4-(1-(4-(((4,6-dimethyl-2-oxo-1,2-dihydropyridin-3-yl)methyl)carbamoyl)-3-methylthiophen-2-yl)propylidene)piperidine-1-carboxylate (380 mg, 0.761 mmol, 82% yield) as a white solid. $^1$H NMR (400 MHz, DMSO-d$_6$) δ 11.48 (br. s., 1H), 8.01 (t, J=5.1 Hz, 1H), 7.80 (s, 1H), 5.86 (s, 1H), 4.24 (d, J=5.1 Hz, 2H), 3.40 (br. s., 2H), 3.23 (br. s., 2H), 2.36 (t, J=5.7 Hz, 2H), 2.28 (d, J=7.1 Hz, 2H), 2.19 (s, 3H), 2.11 (s, 3H), 2.07 (s, 3H), 1.90 (t, J=5.7 Hz, 2H), 1.39 (s, 9H), 0.87 (t, J=7.5 Hz, 3H). MS(ES) [M+H]$^+$ 500.2.

c) N-((4,6-Dimethyl-2-oxo-1,2-dihydropyridin-3-yl)methyl)-4-methyl-5-(1-(piperidin-4-ylidene)propyl)thiophene-3-carboxamide To a solution of tert-butyl 4-(1-(4-(((4,6-dimethyl-2-oxo-1,2-dihydropyridin-3-yl)methyl)carbamoyl)-3-methylthiophen-2-yl)propylidene)piperidine-1-carboxylate (0.35 g, 0.700 mmol) in MeOH (2 mL) was added with stirring 4 N HCl in 1,4-dioxane (15 mL, 60.0 mmol). The reaction was stirred for 30 min, at which time it was evaporated to dryness under vacuum. The residue was basified with 1 N Na$_2$CO$_3$ (2 mL) and re-evaporated to dryness. The remaining solid was triturated with 20% MeOH in DCM (30 mL), filtered, and rinsed with fresh 20% MeOH in DCM (20 mL). The filtrate was concentrated under vacuum and purified by silica gel chromatography (ISCO® RediSep Rf Gold 40 g, 20 to 70% (5% NH$_4$OH/MeOH) in DCM. The purified residue was triturated with (1:1) Et$_2$O in petroleum ether to give N-((4,6-dimethyl-2-oxo-1,2-dihydropyridin-3-yl)methyl)-4-methyl-5-(1-(piperidin-4-ylidene)propyl)thiophene-3-carboxamide (245 mg, 0.613 mmol, 88% yield) as a white solid. $^1$H NMR (400 MHz, DMSO-d$_6$) δ 8.00 (t, J=4.9 Hz, 1H), 7.77 (s, 1H), 5.86 (s, 1H), 4.24 (d, J=5.1 Hz, 2H), 2.74 (br. s., 2H), 2.59 (br. s., 2H), 2.33-2.21 (m, 4H), 2.18 (s, 3H), 2.11 (s, 3H), 2.07 (s, 3H), 1.83 (t, J=5.2 Hz, 2H), 0.86 (t, J=7.6 Hz, 3H). MS(ES) [M+H]$^+$ 400.1.

Example 49

N-((4,6-dimethyl-2-oxo-1,2-dihydropyridin-3-yl)methyl)-4-methyl-5-(1-(piperidin-4-yl)vinyl)thiophene-3-carboxamide

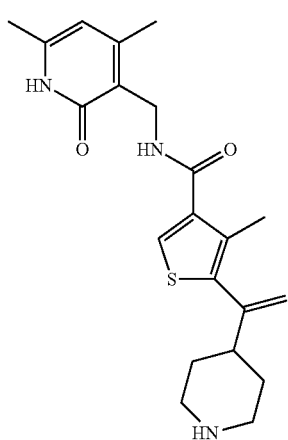 [SMILES: C=C(c1scc(C(=O)NCc2c(C)cc(C)[nH]c2=O)c1C)C1CCNCC1]

Following the general procedure of Example 33, N-((4,6-Dimethyl-2-oxo-1,2-dihydropyridin-3-yl)methyl)-4-methyl-5-(1-(piperidin-4-yl)vinyl thiophene-3-carboxamide was prepared. $^1$H NMR (400 MHz, DMSO-d$_6$) δ 1.26-1.33 (m, 1H) 1.48 (s, 1H) 1.68 (d, J=13.39 Hz, 2H) 2.09 (s, 3H) 2.30 (s, 3H) 2.36 s, 3H) 2.4-2.5 (m, 1H) 2.56-2.63 (m, 2H), 3.02-3.05 (m, 2H) 4.11-4.30 (m, 2H) 5.06 (s, 1H) 5.29 (s, 1H) 5.76 (s, 1H) 5.8 (s, 1H) 7.7 (s, 1H) 8.0 (m, 1H) 12.5 (m, 1H). MS(ES) [M+H]$^+$ 386.1.

Example 50

2-Bromo-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide hydrochloride

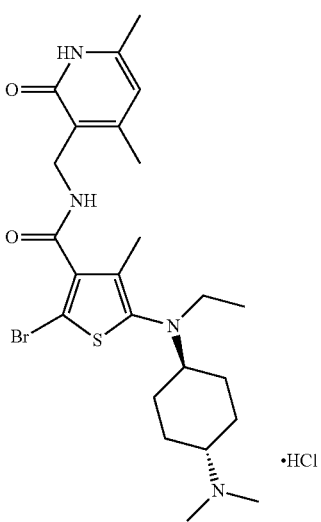 [SMILES: CCN(c1sc(Br)c(C(=O)NCc2c(C)cc(C)[nH]c2=O)c1C)[C@H]1CC[C@H](N(C)C)CC1 ; Cl]

a) Methyl 2-bromo-5-(((trans)-4-(dimethylamino)cyclohexyl)(ethyl)amino)-4-methylthiophene-3-carboxylate

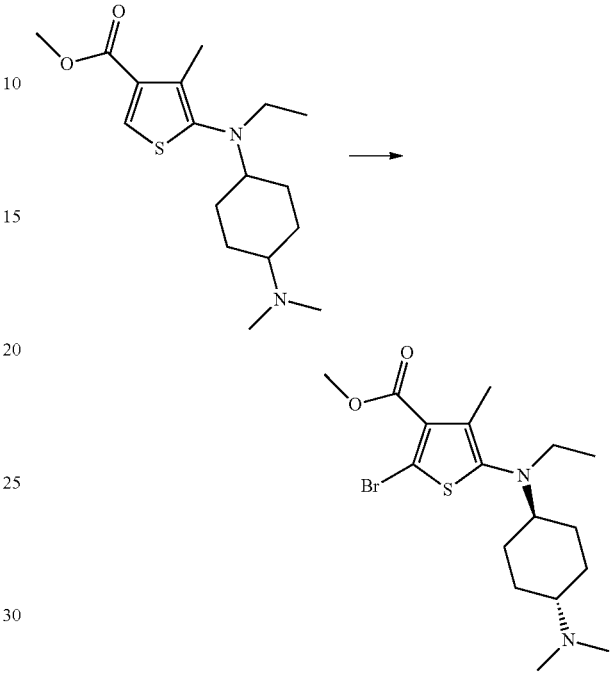

A solution of methyl 5-((4-(dimethylamino)cyclohexyl)(ethyl)amino)-4-methylthiophene-3-carboxylate (5.21 g, 16.06 mmol) in DMF (32 mL) was treated with NBS (4.00 g, 22.48 mmol) and stirred under argon at RT for 30 min. The reaction was diluted with water (10 mL) and saturated Na$_2$CO$_3$ solution (pH 9, 1 mL). The resulting suspension was extracted with EtOAc (3×75 mL). The organics were washed with water (50 mL), dried over MgSO$_4$ and concentrated onto silica. The material was purified on an ISCO® Combiflash Rf on 24 g silica using a gradient of CHCl$_3$:MeOH w/1% NH$_4$OH (0-15%). The product fractions were combined and concentrated to afford methyl 2-bromo-5-((4-(dimethylamino)cyclohexyl)(ethyl)amino)-4-methylthiophene-3-carboxylate (3.83 g) as a mixture of cis- and trans-cyclohexyl isomers. The mixture was then separated by HPLC (Chiralpak AD-H, 5 microns, 50 mm×250 mm, 97:3:0.1 CH$_3$CN:isopropylalcohol:isopropylamine, 100 mL/min) to afford ethyl 2-bromo-5-(((trans)-4-(dimethylamino)cyclohexyl)(ethyl)amino)-4-methylthiophene-3-carboxylate (2.64 g, 6.41 mmol, 39.9% yield) as an orange tar. $^1$H NMR (400 MHz, CDCl$_3$) δ 3.90 (s, 3H) 2.94 (q, J=7.07 Hz, 2H) 2.64-2.77 (m, 1H) 2.27 (s, 6H) 2.21 (s, 3H) 2.05-2.16 (m, 1H) 1.89-2.00 (m, 4H) 1.16-1.34 (m, 4H) 0.96 (t, J=7.07 Hz, 3H). MS(ES) [M+H]$^+$ 403, 405.

b) 2-Bromo-5-(((trans)-4-(dimethylamino)cyclohexyl)(ethyl)amino)-4-methylthiophene-3-carboxylic acid

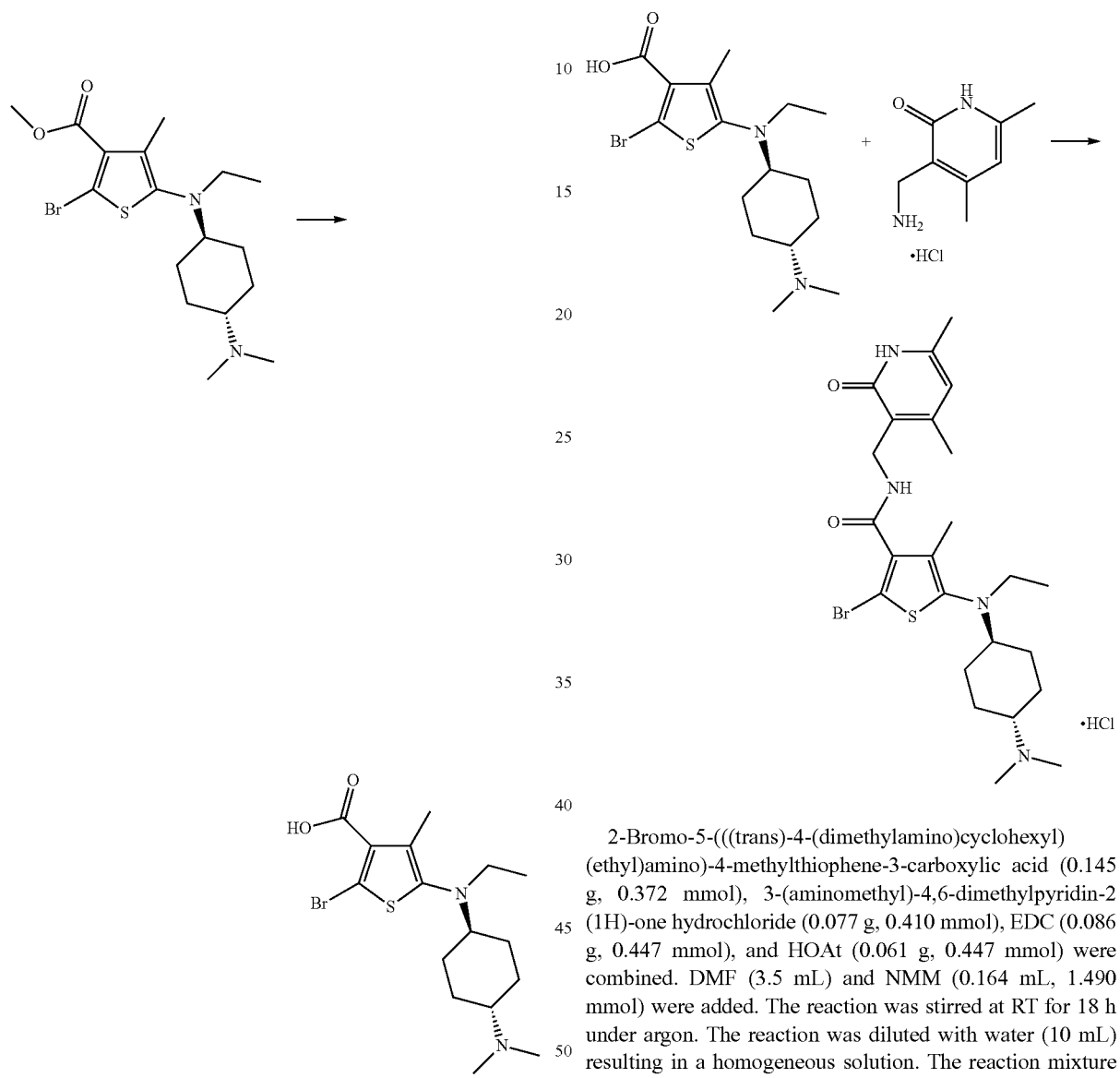

A solution of methyl 2-bromo-5-(((trans)-4-(dimethylamino)cyclohexyl)(ethyl)amino)-4-methylthiophene-3-carboxylate (0.150 g, 0.372 mmol) in MeOH (1.5 mL) and THF (0.300 mL) was treated with 6 M NaOH (0.310 mL, 1.859 mmol). The reaction was heated in a 45° C. oil bath for 18 h. The reaction was neutralized with 5 M HCl (0.372 mL, 1.859 mmol) and concentrated to dryness. MS(ES) [M+H]+ 389.

c) 2-Bromo-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide hydrochloride 2-Bromo-5-(((trans)-4-(dimethylamino)cyclohexyl)(ethyl)amino)-4-methylthiophene-3-carboxylic acid (0.145 g, 0.372 mmol), 3-(aminomethyl)-4,6-dimethylpyridin-2(1H)-one hydrochloride (0.077 g, 0.410 mmol), EDC (0.086 g, 0.447 mmol), and HOAt (0.061 g, 0.447 mmol) were combined. DMF (3.5 mL) and NMM (0.164 mL, 1.490 mmol) were added. The reaction was stirred at RT for 18 h under argon. The reaction was diluted with water (10 mL) resulting in a homogeneous solution. The reaction mixture was purified by RP-HPLC (Gilson®, 30×100, Varian Polaris C18, gradient of 5-95% MeCN in water with 0.1% formic acid). The product fractions were combined, treated with 5 M HCl (1 mL), and concentrated (co-evaporation with TBME) to afford 2-bromo-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide hydrochloride (0.178 g, 0.302 mmol, 81% yield) as a light orange solid. $^1$H NMR (400 MHz, DMSO-$d_6$) δ 10.33-10.47 (m, 1H) 8.19-8.29 (m, 1H) 5.89 (s, 1H) 4.26 (d, J=5.05 Hz, 2H) 2.98-3.07 (m, 1H) 2.89 (q, J=6.99 Hz, 2H) 2.70-2.80 (m, 1H) 2.62-2.65 (m, 6H) 2.19 (s, 3H) 2.12 (s, 3H) 1.99-2.06 (m, 2H) 1.94 (s, 3H) 1.89-1.97 (m, 2H) 1.38-1.52 (m, 2H) 1.18-1.33 (m, 2H) 0.90 (t, J=7.07 Hz, 3H). MS(ES) [M+H]+ 523, 525.

Example 51

2-Cyano-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide

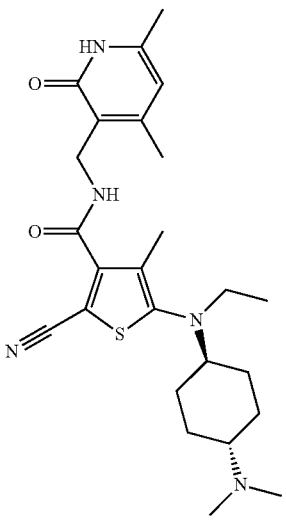 [SMILES: CCN(c1sc(C#N)c(C(=O)NCc2c(C)cc(C)[nH]c2=O)c1C)[C@H]1CC[C@H](N(C)C)CC1]

a) Methyl 2-cyano-5-(((trans)-4-(dimethylamino)cyclohexyl)(ethyl)amino)-4-methylthiophene-3-carboxylate

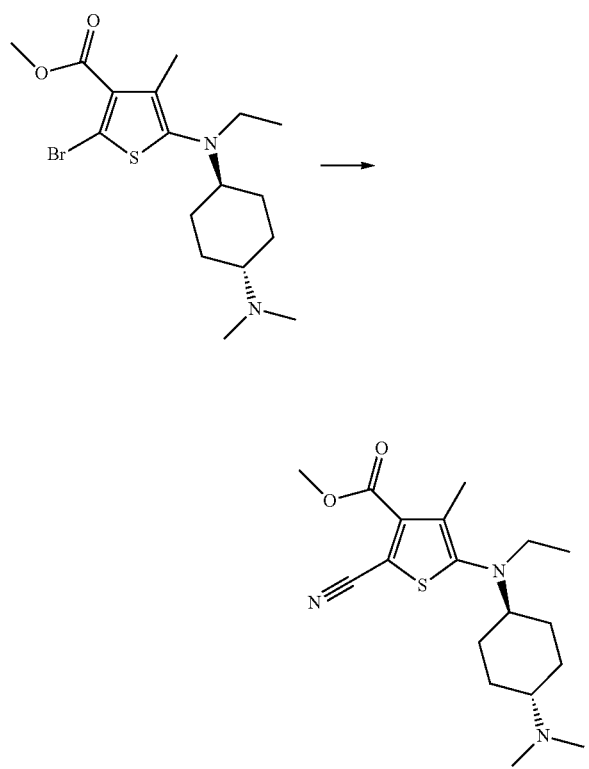

A solution of methyl 2-bromo-5-(((trans)-4-(dimethylamino)cyclohexyl)(ethyl)amino)-4-methylthiophene-3-carboxylate (0.240 g, 0.595 mmol) in DMF (3 mL) was treated with copper(I) cyanide (0.064 g, 0.714 mmol). The resulting tan mixture was heated at 130° C. under argon for 15 min, at which time it was allowed to cool to RT and diluted with water (8 mL). The heterogeneous mixture was stirred for 15 min and filtered. The solids were washed with water and heptanes to afford crude methyl 2-cyano-5-(((trans)-4-(dimethylamino)cyclohexyl)(ethyl)amino)-4-methylthiophene-3-carboxylate (0.167 g, 0.430 mmol, 72.3% yield) as a pale green solid. MS(ES) [M+H]+ 350.

b) 2-Cyano-5-(((trans)-4-(dimethylamino)cyclohexyl)(ethyl)amino)-4-methylthiophene-3-carboxylic acid

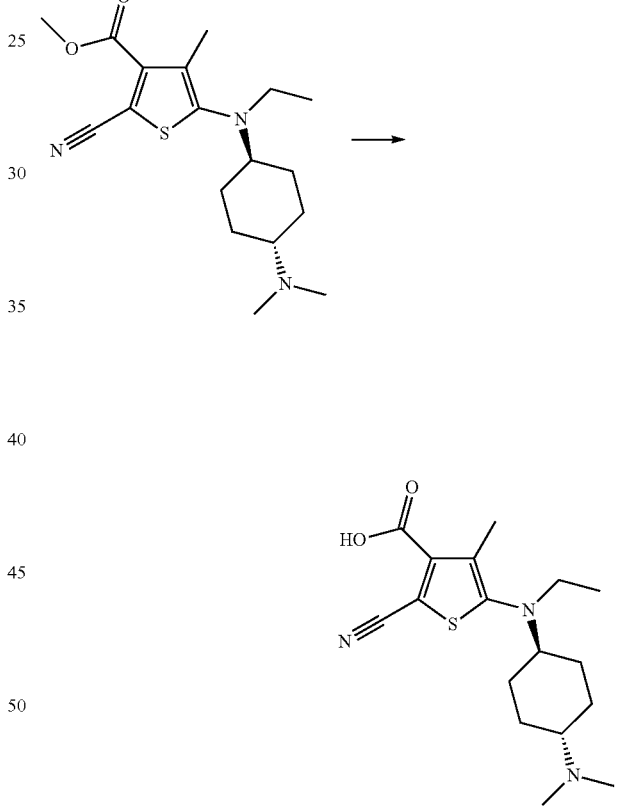

A solution of methyl 2-cyano-5-(((trans)-4-(dimethylamino)cyclohexyl)(ethyl)amino)-4-methylthiophene-3-carboxylate (0.067 g, 0.192 mmol) in MeOH (1.5 mL) and THF (0.300 mL) was treated with 6 M NaOH (0.160 mL, 0.959 mmol). The reaction was heated in a 45° C. oil bath for 18 h. The reaction was concentrated onto neutral alumina and purified on an ISCO® Combiflash Rf on 24 g basic alumina using a gradient of CHCl$_3$:MeOH w/1% NH$_4$OH (0-10%). The product containing fractions were combined and concentrated to give a gray residue. MS(ES) [M+H]+ 336.

c) 2-Cyano-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide hydrochloride

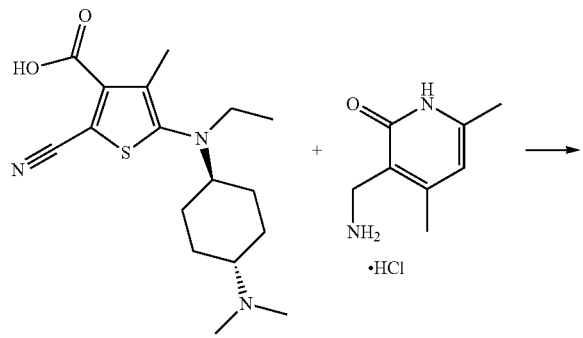

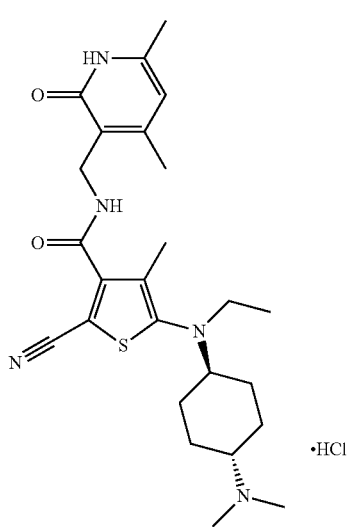

2-Cyano-N-((4,6-dimethyl-2-oxo-1,2-dihydropyridin-3-yl)methyl)-5-(((trans)-4-(dimethylamino)cyclohexyl)(ethyl)amino)-4-methylthiophene-3-carboxamide (0.034 g, 0.064 mmol, 34.0% yield) was obtained as its hydrochloride salt (orange solid) following the general procedure of Example 50c. $^1$H NMR (400 MHz, DMSO-$d_6$) δ 10.34 (br. s., 1H) 8.52-8.61 (m, 1H) 5.89 (s, 1H) 4.29 (d, J=4.80 Hz, 2H) 2.98-3.13 (m, 3H) 2.87-2.96 (m, 1H) 2.65 (d, J=5.05 Hz, 6H) 2.19 (s, 3H) 2.12 (s, 3H) 1.97-2.08 (m, 5H) 1.84-1.94 (m, 2H) 1.29-1.58 (m, 4H) 0.91-0.98 (m, 3H). MS(ES) [M+H]$^+$ 470.

Example 52

2-Bromo-5-(diethylamino)-N-((4,6-dimethyl-2-oxo-1,2-dihydropyridin-3-yl)methyl)-4-methylthiophene-3-carboxamide

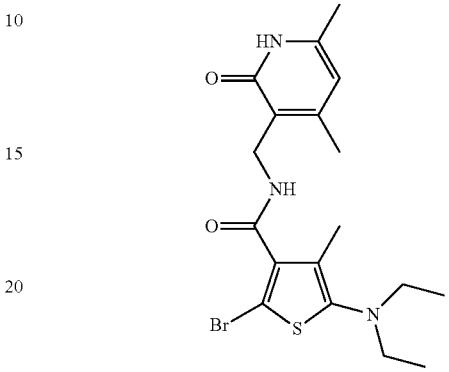

a) Methyl 5-(diethylamino)-4-methylthiophene-3-carboxylate

[Note: this procedure details the isolation of a minor byproduct from the reaction] To a solution of methyl 5-amino-4-methylthiophene-3-carboxylate (0.322 g, 1.881 mmol) and 4-(dimethylamino)cyclohexanone (0.33 mL, 2.243 mmol) in DCE (15 mL) under argon was added NaBH(OAc)$_3$ (1.196 g, 5.64 mmol), followed by AcOH (0.32 mL, 5.59 mmol). The reaction was stirred vigorously for 4.5 h (additional NaBH(OAc)$_3$ (0.399 g, 1.881 mmol) was added after 3 h). Acetaldehyde (0.159 mL, 2.82 mmol) was then added. After 15 min of stirring, the mixture was diluted with DCM (20 mL) and water (10 mL). The pH was adjusted to 7.5 with saturated NaHCO$_3$ and the biphasic solution was stirred at RT for 3 days. The organic phase was dried over MgSO$_4$ and concentrated onto silica. The material was purified on an ISCO® Combiflash Rf on 12 g silica using a gradient of CHCl$_3$:MeOH w/1% NH$_4$OH (0-10%). The minor byproduct containing fraction was combined and concentrated to afford methyl 5-(diethylamino)-4-methylthiophene-3-carboxylate (0.054 g, 0.226 mmol, 12% yield) as a light red oil. MS(ES) [M+H]$^+$ 228.

b) Methyl 2-bromo-5-(diethylamino)-4-methylthiophene-3-carboxylate

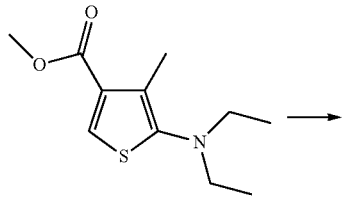

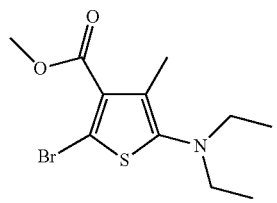

Methyl 2-bromo-5-(diethylamino)-4-methylthiophene-3-carboxylate (0.056 g, 0.174 mmol, 73.1% yield) was obtained as a dark tar following the procedure of Example 50a and was used without purification. $^1$H NMR (400 MHz, CDCl$_3$) δ 3.91 (s, 3H) 2.92 (q, J=7.16 Hz, 4H) 2.24 (s, 3H) 1.03 (t, J=7.20 Hz, 6H). MS(ES) [M+H]$^+$ 348, 350.

c) 2-Bromo-5-(diethylamino)-4-methylthiophene-3-carboxylic acid

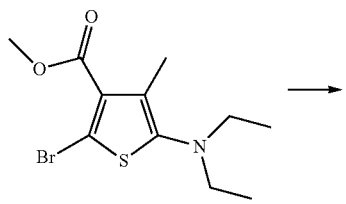

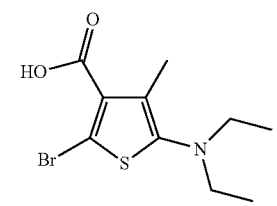

2-Bromo-5-(diethylamino)-4-methylthiophene-3-carboxylic acid (0.052 g, 0.169 mmol, 94% yield) was obtained as a light yellow solid following the procedure of Example 50b and was used without purification. MS(ES) [M+H]$^+$ 292, 294.

d) 2-Bromo-5-(diethylamino)-N-((4,6-dimethyl-2-oxo-1,2-dihydropyridin-3-yl)methyl)-4-methylthiophene-3-carboxamide

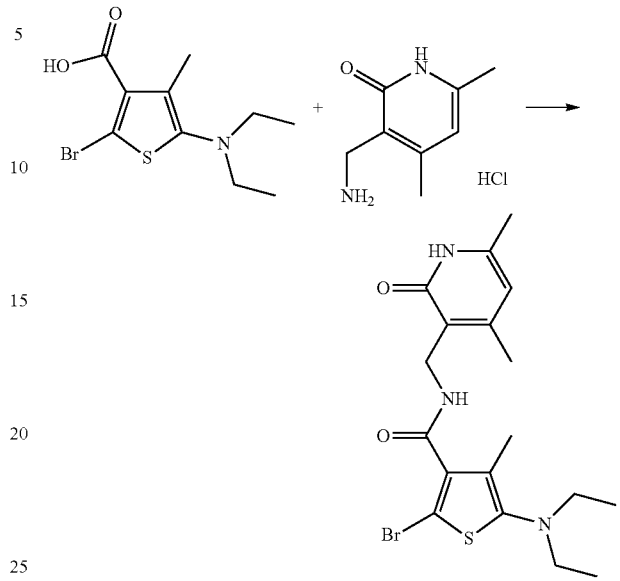

2-Bromo-5-(diethylamino)-4-methylthiophene-3-carboxylic acid (0.050 g, 0.171 mmol), 3-(aminomethyl)-4,6-dimethylpyridin-2(1H)-one hydrochloride (0.036 g, 0.188 mmol), EDC (0.039 g, 0.205 mmol), and HOAt (0.028 g, 0.205 mmol) were combined. DMF (2 mL) and NMM (0.075 mL, 0.684 mmol) were added. The reaction was stirred at RT under argon for 18 h. The reaction was diluted with water (15 mL). The resulting solids were filtered and washed with water to afford 2-bromo-5-(diethylamino)-N-((4,6-dimethyl-2-oxo-1,2-dihydropyridin-3-yl)methyl)-4-methylthiophene-3-carboxamide (0.019 g, 0.042 mmol, 24.74% yield) as an off-white solid. $^1$H NMR (400 MHz, DMSO-d$_6$) δ 11.48 (br. s., 1H) 8.13-8.33 (m, 1H) 5.86 (s, 1H) 4.25 (d, J=4.80 Hz, 2H) 2.84 (q, J=7.07 Hz, 4H) 2.19 (s, 3H) 2.11 (s, 3H) 1.95 (s, 3H) 0.95 (t, J=7.07 Hz, 6H) MS(ES) [M+H]$^+$ 426, 428.

Example 53

2-Chloro-N-((4,6-dimethyl-2-oxo-1,2-dihydropyridin-3-yl)methyl)-5-(ethyl(tetrahydro-2H-pyran-4-yl)amino)-4-methylthiophene-3-carboxamide

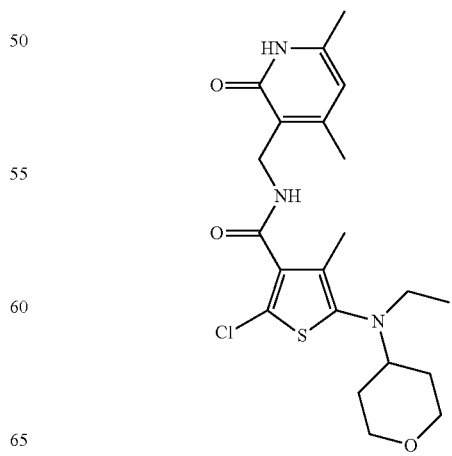

a) Methyl 2-chloro-5-(ethyl(tetrahydro-2H-pyran-4-yl)amino)-4-methylthiophene-3-carboxylate

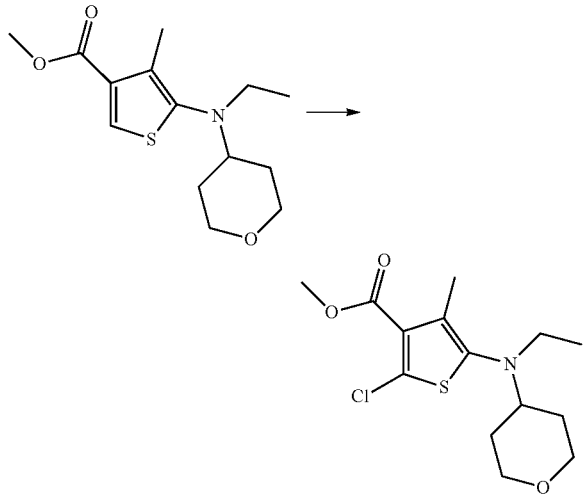

A solution of methyl 5-(ethyl(tetrahydro-2H-pyran-4-yl)amino)-4-methylthiophene-3-carboxylate (0.217 g, 0.766 mmol) in DMF (2 mL) was treated with NCS (0.143 g, 1.072 mmol) and stirred at RT under argon. Minimal reaction had occurred, so the mixture was heated at 95° C. for 10 min, at which time it was allowed to cool to RT, diluted with 20 mL water, and treated with 1 mL saturated Na$_2$CO$_3$ solution. The aqueous mixture was extracted with EtOAc (2×20 mL). The organics were concentrated onto silica. The material was purified on an ISCO® Combiflash Rf on 12 g silica using a gradient of EtOAc in heptanes (0-30%) to afford methyl 2-chloro-5-(ethyl(tetrahydro-2H-pyran-4-yl)amino)-4-methylthiophene-3-carboxylate (0.163 g, 0.472 mmol, 61.6% yield) as a light yellow oil. $^1$H NMR (400 MHz, CDCl$_3$) δ 3.95-4.04 (m, 2H) 3.91 (s, 3H) 3.31-3.43 (m, 2H) 2.88-3.03 (m, 3H) 2.25 (s, 3H) 1.74-1.83 (m, 2H) 1.53-1.68 (m, 2H) 1.00 (t, J=7.07 Hz, 3H). MS(ES) [M+H]$^+$ 318.

b) 2-Chloro-5-(ethyl(tetrahydro-2H-pyran-4-yl)amino)-4-methylthiophene-3-carboxylic acid

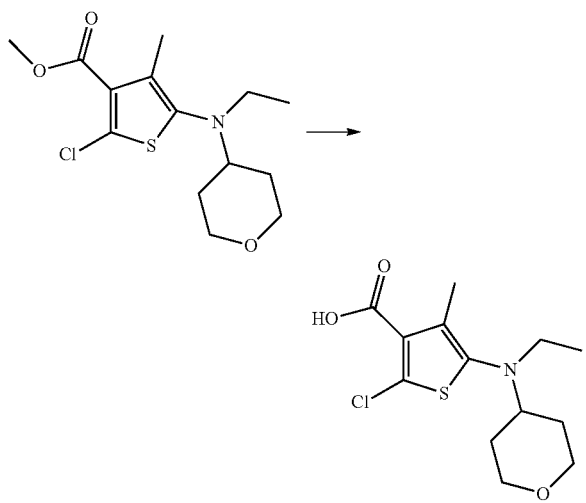

2-Chloro-5-(ethyl(tetrahydro-2H-pyran-4-yl)amino)-4-methylthiophene-3-carboxylic acid (0.156 g, 0.488 mmol, 95% yield) was obtained as a white solid following the general procedure of Example 50b and was used without purification. MS(ES) [M+H]$^+$ 304.

c) 2-Chloro-N-((4,6-dimethyl-2-oxo-1,2-dihydropyridin-3-yl)methyl)-5-(ethyl(tetrahydro-2H-pyran-4-yl)amino)-4-methylthiophene-3-carboxamide

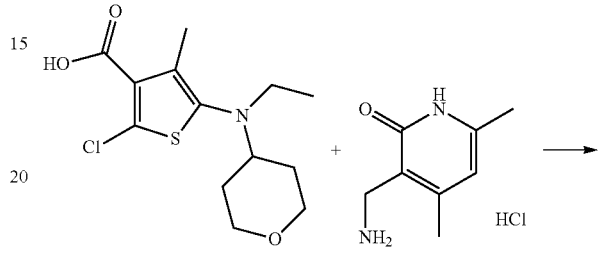

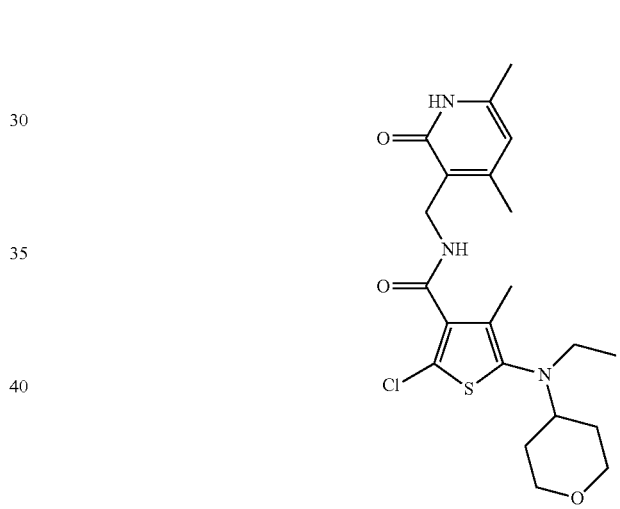

2-Chloro-5-(ethyl(tetrahydro-2H-pyran-4-yl)amino)-4-methylthiophene-3-carboxylic acid (0.152 g, 0.500 mmol), 3-(aminomethyl)-4,6-dimethylpyridin-2(1H)-one hydrochloride (0.104 g, 0.550 mmol), EDC (0.115 g, 0.600 mmol), and HOAt (0.082 g, 0.600 mmol) were combined. DMF (5 mL) and NMM (0.220 mL, 2.001 mmol) were added. The reaction was stirred at RT for 18 h under argon. The reaction was diluted with 25 mL water, stirred for 15 min, and filtered to afford 2-chloro-N-((4,6-dimethyl-2-oxo-1,2-dihydropyridin-3-yl)methyl)-5-(ethyl(tetrahydro-2H-pyran-4-yl)amino)-4-methylthiophene-3-carboxamide (0.099 g, 0.215 mmol, 42.9% yield) as a white solid. $^1$H NMR (400 MHz, DMSO-d$_6$) δ 11.50 (br. s., 1H) 8.29 (t, J=4.93 Hz, 1H) 5.86 (s, 1H) 4.25 (d, J=5.05 Hz, 2H) 3.78-3.88 (m, 2H) 3.20-3.30 (m, 2H) 2.83-2.97 (m, 3H) 2.18 (s, 3H) 2.11 (s, 3H) 1.94 (s, 3H) 1.63-1.75 (m, 2H) 1.31-1.47 (m, 2H) 0.90 (t, J=7.07 Hz, 3H). MS(ES) [M+H]$^+$ 438.

Example 54

N-((4,6-Dimethyl-2-oxo-1,2-dihydropyridin-3-yl)methyl)-5-(ethyl(tetrahydro-2H-pyran-4-yl)amino)-2,4-dimethylthiophene-3-carboxamide hydrochloride

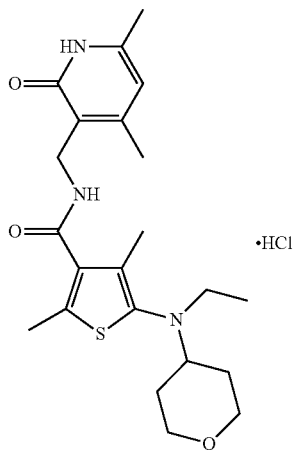 [SMILES: CCN(c1sc(C)c(C(=O)NCc2c(C)cc(C)[nH]c2=O)c1C)C1CCOCC1 ; Cl]

a) Methyl 2-bromo-5-(ethyl(tetrahydro-2H-pyran-4-yl)amino)-4-methylthiophene-3-carboxylate

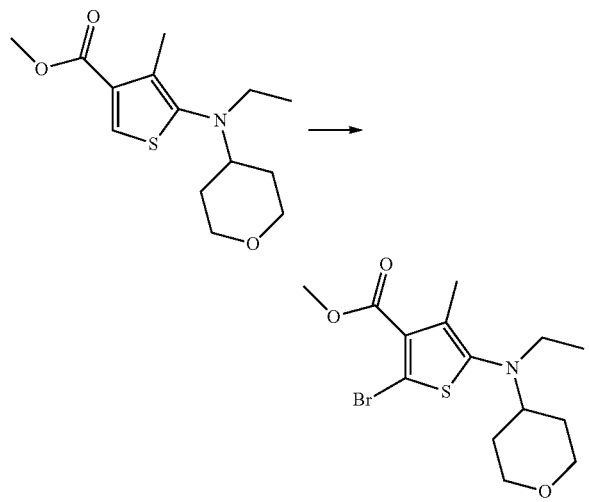

A solution of methyl 5-(ethyl(tetrahydro-2H-pyran-4-yl)amino)-4-methylthiophene-3-carboxylate (0.307 g, 1.083 mmol) in DMF (2 mL) was treated with NBS (0.270 g, 1.517 mmol) and stirred under argon at RT. After 15 min, the reaction was diluted with water (10 mL) and saturated Na$_2$CO$_3$ (1 mL, pH 9). The resulting suspension was extracted with EtOAc (2×25 mL). The organics were washed with water (50 mL), brine, dried over MgSO$_4$ and concentrated to a greenish tar. The material was purified on an ISCO® Combiflash Rf on 12 g silica using a gradient of heptane:EtOAc (0-30%) to afford methyl 2-bromo-5-(ethyl(tetrahydro-2H-pyran-4-yl)amino)-4-methylthiophene-3-carboxylate (0.258 g, 0.691 mmol, 63.8% yield) as an orange tar. $^1$H NMR (400 MHz, DMSO-d$_6$) δ 3.79-3.88 (m, 5H) 3.27 (m, J=11.70, 11.70, 1.90 Hz, 2H) 2.88-2.98 (m, 3H) 2.14 (s, 3H) 1.70 (m, J=12.40, 1.80 Hz, 2H) 1.38 (m, J=12.00, 12.00, 12.00, 4.50 Hz, 2H) 0.90 (t, J=7.07 Hz, 3H). MS(ES) [M+H]$^+$ 362, 364.

b) Methyl 5-(ethyl(tetrahydro-2H-pyran-4-yl)amino)-2,4-dimethylthiophene-3-carboxylate

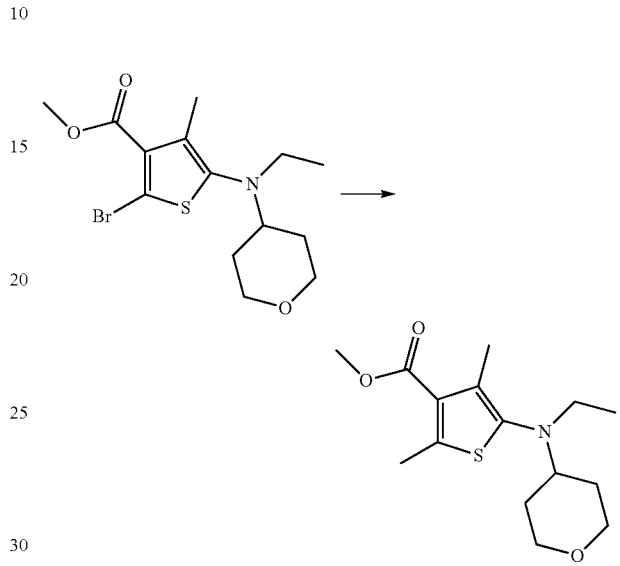

Methyl 2-bromo-5-(ethyl(tetrahydro-2H-pyran-4-yl)amino)-4-methylthiophene-3-carboxylate (0.258 g, 0.712 mmol), Cs$_2$CO$_3$ (0.464 g, 1.424 mmol) and PdCl$_2$(dppf)-DCM adduct (0.058 g, 0.071 mmol) in 1,4-dioxane (5 mL) and water (1.667 mL) was treated with 2,4,6-trimethyl-1,3,5,2,4,6-trioxatriborinane (0.149 mL, 1.068 mmol). The reaction vial was flushed with argon, sealed, and heated at 85° C. for 30 min. The reaction was allowed to cool to RT and the organic phase was concentrated onto silica. The material was purified on an ISCO® Combiflash Rf on 12 g silica using a gradient of EtOAc in heptanes (0-20%) to afford methyl 5-(ethyl(tetrahydro-2H-pyran-4-yl)amino)-2,4-dimethylthiophene-3-carboxylate (0.122 g, 0.345 mmol, 48.4% yield) as a clear oil. $^1$H NMR (400 MHz, CDCl$_3$) δ 3.98 (dd, J=12.00, 1.89 Hz, 2H) 3.86 (s, 3H) 3.37 (td, J=11.75, 1.77 Hz, 2H) 2.83-3.06 (m, 3H) 2.63 (s, 3H) 2.25 (s, 3H) 1.78 (dd, J=12.63, 1.77 Hz, 2H) 1.49-1.67 (m, 2H) 0.91-1.04 (m, 3H). MS(ES) [M+H]$^+$ 298.

c) 5-(Ethyl(tetrahydro-2H-pyran-4-yl)amino)-2,4-dimethylthiophene-3-carboxylic acid

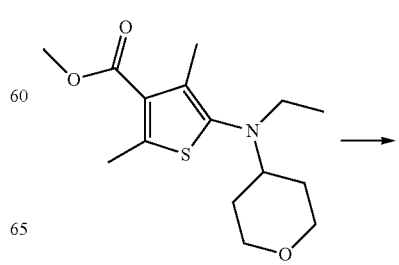

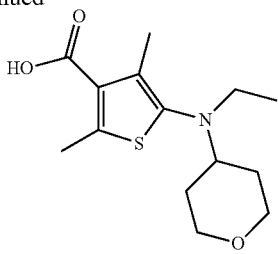

5-(Ethyl(tetrahydro-2H-pyran-4-yl)amino)-2,4-dimethyl-thiophene-3-carboxylic acid (0.116 g, 0.344 mmol, 84% yield) was obtained as a white solid following the general procedure of Example 50b and was used without purification. MS(ES) [M+H]$^+$ 284.

d) N-((4,6-Dimethyl-2-oxo-1,2-dihydropyridin-3-yl)methyl)-5-(ethyl(tetrahydro-2H-pyran-4-yl)amino)-2,4-dimethylthiophene-3-carboxamide hydrochloride

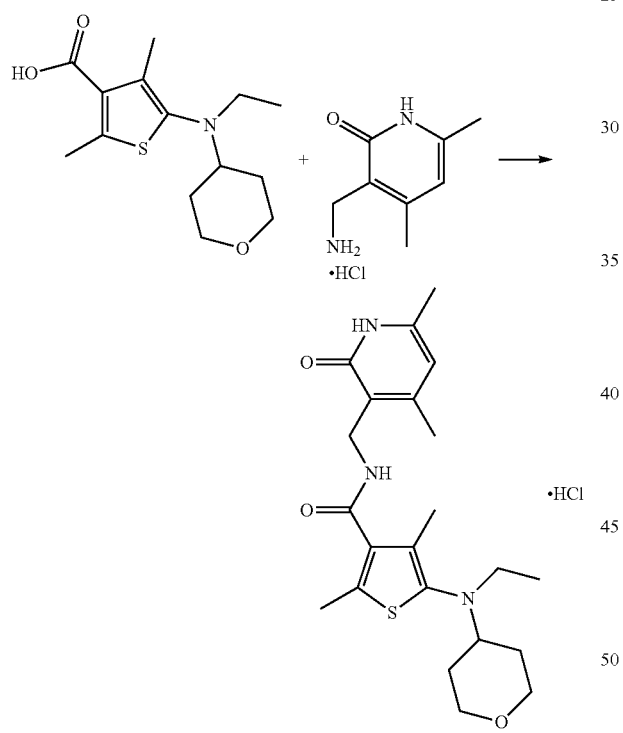

5-(Ethyl(tetrahydro-2H-pyran-4-yl)amino)-2,4-dimethyl-thiophene-3-carboxylic acid (0.116 g, 0.409 mmol), 3-(aminomethyl)-4,6-dimethylpyridin-2(1H)-one hydrochloride (0.085 g, 0.450 mmol), EDC (0.094 g, 0.491 mmol), and HOAt (0.067 g, 0.491 mmol) were combined. DMF (3 mL) and NMM (0.180 mL, 1.637 mmol) were added. The reaction was stirred at RT for 2 h under argon. The reaction was concentrated to a thick tar on a rotavap (60° C. bath temperature). The material was concentrated onto silica and purified on an ISCO® Combiflash Rf on 12 g silica using a gradient of CHCl$_3$:MeOH w/1% NH$_4$OH (0-15%). The product fractions were combined and concentrated to give a clear sticky tar. The residue was dissolved in 3 mL 50/50 MeOH/water with 2 drops TFA and purified by RP-HPLC (Gilson®, Sunfire C18 OBD 5 uM column, gradient of 5-55% MeCN in water with 0.1% TFA). The product fractions were combined, treated with 5M HCl (1 mL), and concentrated to afford N-((4,6-dimethyl-2-oxo-1,2-dihydropyridin-3-yl)methyl)-5-(ethyl(tetrahydro-2H-pyran-4-yl)amino)-2,4-dimethylthiophene-3-carboxamide (0.124 g, 0.259 mmol, 63.4% yield) as its hydrochloride salt (clear glassy solid that was dried to a white foam under hi-vac). $^1$H NMR (400 MHz, DMSO-d$_6$) δ 8.33 (s, 1H) 8.02 (t, J=5.05 Hz, 1H) 5.92 (s, 1H) 4.25 (d, J=4.80 Hz, 2H) 3.83 (dd, J=11.75, 2.40 Hz, 2H) 3.18-3.31 (m, 2H) 2.87 (d, J=6.82 Hz, 3H) 2.30 (s, 3H) 2.20 (s, 3H) 2.13 (s, 3H) 1.95 (s, 3H) 1.69 (d, J=10.86 Hz, 2H) 1.30-1.48 (m, 2H) 0.88 (t, J=7.07 Hz, 3H). MS(ES) [M+H]$^+$ 418.

Example 55

2-Cyano-N-((4,6-dimethyl-2-oxo-1,2-dihydropyridin-3-yl)methyl)-5-(ethyl(tetrahydro-2H-pyran-4-yl)amino)-4-methylthiophene-3-carboxamide hydrochloride

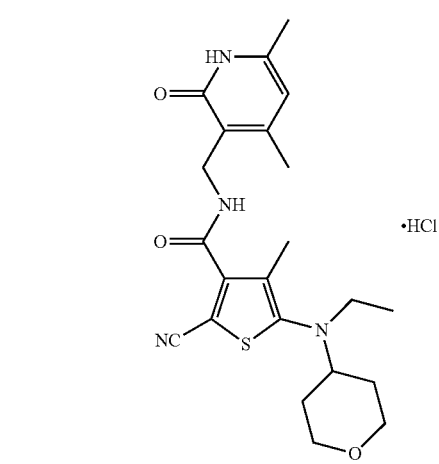 [SMILES: CCN(c1sc(C#N)c(C(=O)NCc2c(C)cc(C)[nH]c2=O)c1C)C1CCOCC1 ; Cl]

a) Methyl 2-cyano-5-(ethyl(tetrahydro-2H-pyran-4-yl)amino)-4-methylthiophene-3-carboxylate

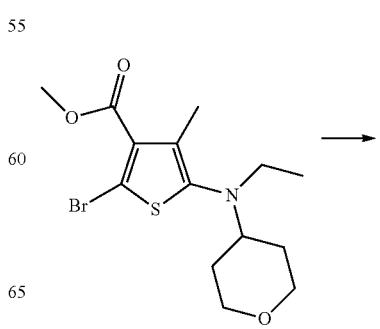

-continued

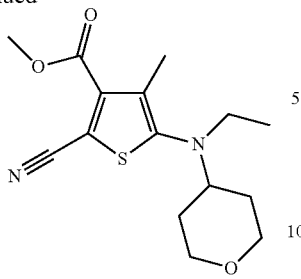

A solution of methyl 2-bromo-5-(ethyl(tetrahydro-2H-pyran-4-yl)amino)-4-methylthiophene-3-carboxylate (0.276 g, 0.762 mmol) in DMF (3 mL) was treated with copper(I) cyanide (0.082 g, 0.914 mmol). The resulting tan mixture was heated under argon at 130° C. for 30 min, at which time it was allowed to cool to RT and purified on an ISCO® Combiflash Rf on 24 g silica using a gradient of heptane: EtOAc (0-5%) to afford methyl 2-cyano-5-(ethyl(tetrahydro-2H-pyran-4-yl)amino)-4-methylthiophene-3-carboxylate (0.045 g, 0.131 mmol, 17.24% yield) as a crude red oil. MS(ES) [M+H]$^+$ 309.

b) 2-Cyano-5-(ethyl(tetrahydro-2H-pyran-4-yl)amino)-4-methylthiophene-3-carboxylic acid

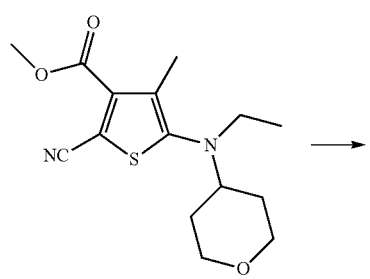

2-Cyano-5-(ethyl(tetrahydro-2H-pyran-4-yl)amino)-4-methylthiophene-3-carboxylic acid (0.043 g, 0.139 mmol, 95% yield) was obtained as a white solid following the general procedure of Example 50b and was used without purification. MS(ES) [M+H]$^+$ 295.

c) 2-Cyano-N-((4,6-dimethyl-2-oxo-1,2-dihydropyridin-3-yl)methyl)-5-(ethyl(tetrahydro-2H-pyran-4-yl)amino)-4-methylthiophene-3-carboxamide hydrochloride

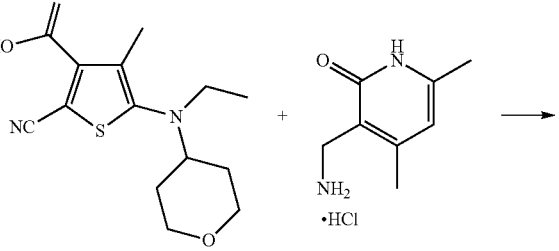

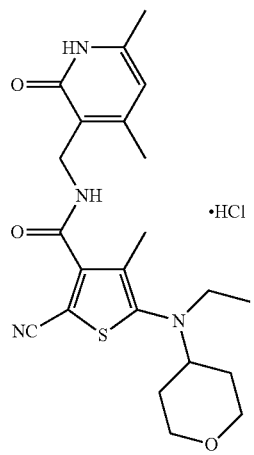

2-Cyano-5-(ethyl(tetrahydro-2H-pyran-4-yl)amino)-4-methylthiophene-3-carboxylic acid (0.041 g, 0.139 mmol), 3-(aminomethyl)-4,6-dimethylpyridin-2(1H)-one hydrochloride (0.029 g, 0.153 mmol), EDC (0.032 g, 0.167 mmol), and HOAt (0.023 g, 0.167 mmol) were combined. DMF (1.5 mL) and NMM (0.061 mL, 0.557 mmol) were added. The reaction was stirred at RT for 1 h under argon. The reaction was diluted with water (8 mL) and stirred for 5 min. The resulting heterogeneous mixture was concentrated onto Isolute® HM-N. The material was purified on an ISCO® Combiflash Rf on 30 g C18aq GOLD using a gradient of 0-100% MeOH in water with 0.1% formic acid. The product fraction was treated with 5 M HCl (1 mL) and concentrated to a yellow glassy solid. Evaporation from MeOH afforded 2-cyano-N-((4,6-dimethyl-2-oxo-1,2-dihydropyridin-3-yl)methyl)-5-(ethyl(tetrahydro-2H-pyran-4-yl)amino)-4-methylthiophene-3-carboxamide (0.039 g, 0.080 mmol, 57.2% yield) as its hydrochloride salt (light yellow solid). $^1$H NMR (400 MHz, DMSO-d$_6$) δ 11.57 (s, 1H) 8.57 (t, J=4.80 Hz, 1H) 5.90 (s, 1H) 4.29 (d, J=5.05 Hz, 2H) 3.85 (dd, J=11.24, 3.41 Hz, 2H) 3.22-3.32 (m, 2H) 2.97-3.13 (m, 3H) 2.19 (s, 3H) 2.12 (s, 3H) 2.01 (s, 3H) 1.68 (d, J=10.36 Hz, 2H) 1.50 (qd, J=12.00, 4.42 Hz, 2H) 0.94 (t, J=7.07 Hz, 3H). MS(ES) [M+H]$^+$ 429.

Example 56

N-((4,6-Dimethyl-2-oxo-1,2-dihydropyridin-3-yl)methyl)-5-(ethyl(tetrahydro-2H-pyran-4-yl)amino)-4-methyl-2-(4-methylpiperazin-1-yl)thiophene-3-carboxamide hydrochloride

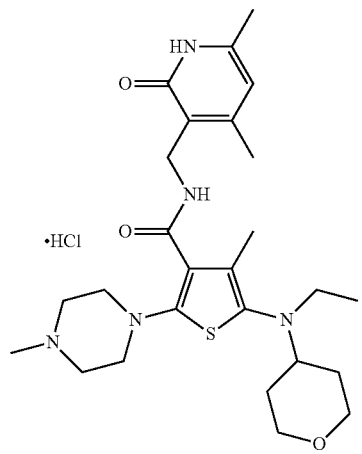 [SMILES: CCN(c1sc(N2CCN(C)CC2)c(C(=O)NCc2c(C)cc(C)[nH]c2=O)c1C)C1CCOCC1 ; Cl]

a) Methyl 5-(ethyl(tetrahydro-2H-pyran-4-yl)amino)-4-methyl-2-(4-methylpiperazin-1-yl)thiophene-3-carboxylate

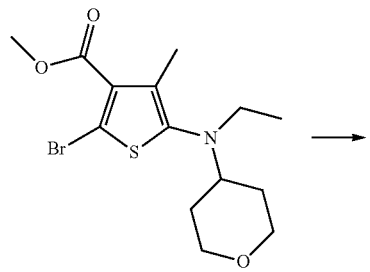

Methyl 2-bromo-5-(ethyl(tetrahydro-2H-pyran-4-yl)amino)-4-methylthiophene-3-carboxylate (0.169 g, 0.466 mmol), 1-methylpiperazine (0.078 mL, 0.700 mmol) and Cs$_2$CO$_3$ (0.228 g, 0.700 mmol) in 1,4-dioxane (5 mL) were degassed with bubbling argon for 10 min. Pd$_2$(dba)$_3$ (0.043 g, 0.047 mmol) and Xantphos (0.040 g, 0.070 mmol) were added. The reaction vial was sealed and heated overnight at 110° C. The reaction was allowed to cool to RT, concentrated onto Isolute® HM-N and purified on an ISCO® Combiflash Rf on 50 g C18aq Gold using a gradient of water: MeOH w/0.1% formic acid (0-60%). The product fraction was concentrated to afford methyl 5-(ethyl(tetrahydro-2H-pyran-4-yl)amino)-4-methyl-2-(4-methylpiperazin-1-yl)thiophene-3-carboxylate (0.039 g, 0.097 mmol, 20.82% yield) as a yellow oil. $^1$H NMR (400 MHz, methanol-d$_4$) δ 3.94 (dd, J=11.87, 2.27 Hz, 2H) 3.84 (s, 3H) 3.35-3.45 (m, 2H) 3.18-3.29 (m, 8H) 2.90-3.02 (m, 3H) 2.80 (s, 3H) 2.20 (s, 3H) 1.79 (dd, J=12.76, 1.64 Hz, 2H) 1.52 (qd, J=12.00, 4.42 Hz, 2H) 0.95 (t, J=7.07 Hz, 3H). MS(ES) [M+H]$^+$ 382.

b) 5-(Ethyl(tetrahydro-2H-pyran-4-yl)amino)-4-methyl-2-(4-methylpiperazin-1-yl)thiophene-3-carboxylic acid

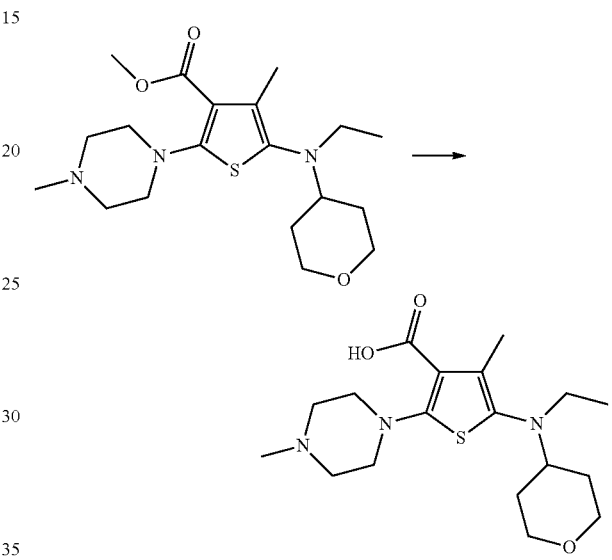

5-(Ethyl(tetrahydro-2H-pyran-4-yl)amino)-4-methyl-2-(4-methylpiperazin-1-yl)thiophene-3-carboxylic acid (0.037 g, 0.096 mmol, 94% yield) was obtained as a yellow solid following the general procedure of Example 50b and was used without purification. MS(ES) [M+H]$^+$ 368.

c) N-((4,6-Dimethyl-2-oxo-1,2-dihydropyridin-3-yl)methyl)-5-(ethyl(tetrahydro-2H-pyran-4-yl)amino)-4-methyl-2-(4-methylpiperazin-1-yl)thiophene-3-carboxamide hydrochloride

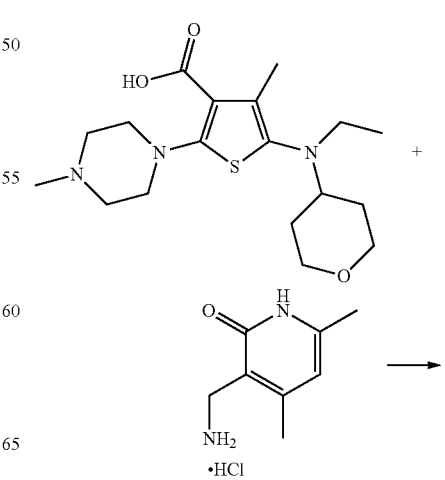

167

-continued

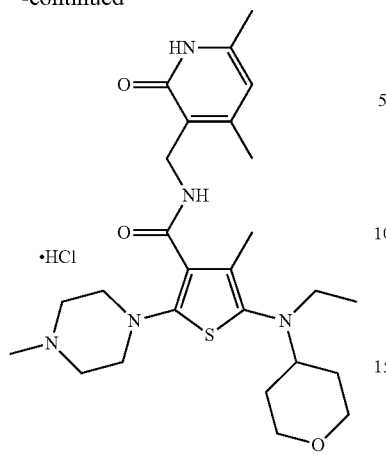

5-(Ethyl(tetrahydro-2H-pyran-4-yl)amino)-4-methyl-2-(4-methylpiperazin-1-yl)thiophene-3-carboxylic acid (0.037 g, 0.101 mmol), 3-(aminomethyl)-4,6-dimethylpyridin-2(1H)-one hydrochloride (0.021 g, 0.111 mmol), EDC (0.023 g, 0.121 mmol), and HOAt (0.016 g, 0.121 mmol) were combined. DMF (1.5 mL) and NMM (0.044 mL, 0.403 mmol) were added. The reaction was stirred at RT for 2 h under argon. The mixture was diluted with water (1.5 mL) and purified on an ISCO® Combiflash Rf on 30 g C18aq Gold using a gradient of water: MeOH w/0.1% formic acid (0-60%). The product fractions were combined and concentrated to a light pink glassy solid. The material was re-purified by RP-HPLC (Gilson®, 30×100 Varian Polaris C18, gradient of 10-90% MeCN in water with 0.1% formic acid). The product fractions were combined, treated with 1M HCl (1 mL), and concentrated to afford N-((4,6-dimethyl-2-oxo-1,2-dihydropyridin-3-yl)methyl)-5-(ethyl(tetrahydro-2H-pyran-4-yl)amino)-4-methyl-2-(4-methylpiperazin-1-yl)thiophene-3-carboxamide (0.009 g, 0.016 mmol, 16.28% yield) as its hydrochloride salt (clear glassy solid). $^1$H NMR (400 MHz, methanol-$d_4$) δ 6.14 (s, 1H) 4.47 (d, J=5.56 Hz, 2H) 3.93 (d, J=11.62 Hz, 2H) 3.37-3.44 (m, 3H) 3.03 (t, J=4.55 Hz, 4H) 2.85-2.99 (m, 6H) 2.60 (s, 3H) 2.37 (s, 3H) 2.28 (s, 3H) 2.22 (s, 3H) 1.78 (d, J=12.38 Hz, 2H) 1.41-1.64 (m, 2H) 0.94 (t, J=7.07 Hz, 3H). MS(ES) [M+H]$^+$ 502.

Example 57 tert-Butyl 3-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)pyrrolidine-1-carboxylate

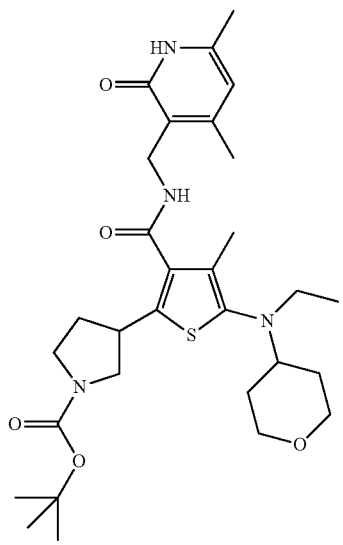 [SMILES: CCN(c1sc(C2CCN(C(=O)OC(C)(C)C)C2)c(C(=O)NCc2c(C)cc(C)[nH]c2=O)c1C)C1CCOCC1]

168 a) tert-Butyl 3-(5-(ethyl(tetrahydro-2H-pyran-4-yl)amino)-3-(methoxycarbonyl)-4-methylthiophen-2-yl)-2,5-dihydro-1H-pyrrole-1-carboxylate

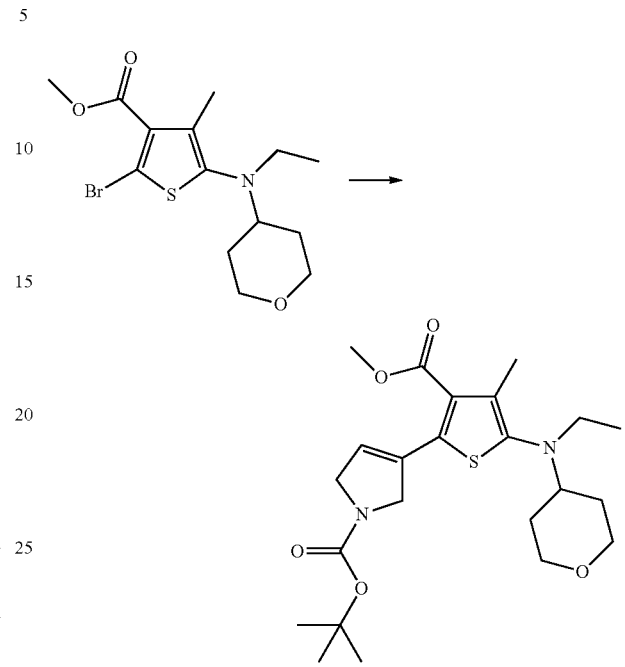

Methyl 2-bromo-5-(ethyl(tetrahydro-2H-pyran-4-yl)amino)-4-methylthiophene-3-carboxylate (0.191 g, 0.527 mmol), Cs$_2$CO$_3$ (0.344 g, 1.054 mmol) and PdCl$_2$(dppf)-DCM adduct (0.043 g, 0.053 mmol) in 1,4-dioxane (4 mL) and water (1.333 mL) were treated with tert-butyl 3-(4,4,5,5-tetramethyl-1,3,2-dioxaborolan-2-yl)-2,5-dihydro-1H-pyrrole-1-carboxylate (0.191 mL, 0.580 mmol). The reaction vial was flushed with argon, sealed, and heated at 85° C. for 60 min. The reaction was allowed to cool to RT. The material was concentrated onto Isolute® HM-N and purified on an ISCO® Combiflash Rf on 50 g C18aq Gold using a gradient of water: MeOH w/0.1% formic acid (0-100%). The product fraction was concentrated to afford tert-butyl 3-(5-(ethyl(tetrahydro-2H-pyran-4-yl)amino)-3-(methoxycarbonyl)-4-methylthiophen-2-yl)-2,5-dihydro-1H-pyrrole-1-carboxylate (0.195 g, 0.411 mmol, 78% yield) as a light orange oil. MS(ES) [M+H]$^+$ 451.

b) tert-Butyl 3-(5-(ethyl(tetrahydro-2H-pyran-4-yl)amino)-3-(methoxycarbonyl)-4-methylthiophen-2-yl)pyrrolidine-1-carboxylate

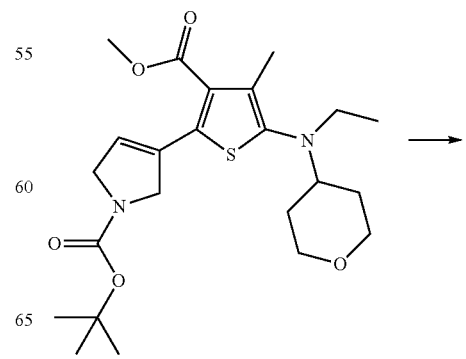

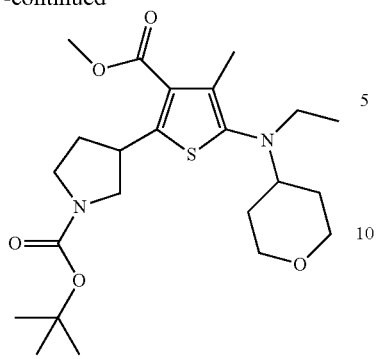

A solution of tert-butyl 3-(5-(ethyl(tetrahydro-2H-pyran-4-yl)amino)-3-(methoxycarbonyl)-4-methylthiophen-2-yl)-2,5-dihydro-1H-pyrrole-1-carboxylate (0.150 g, 0.333 mmol) in MeOH (7.5 mL) at RT was reduced overnight under an atmosphere of H2 with catalytic 20% palladium hydroxide on carbon (Degussa type) (0.023 g, 0.033 mmol). The following morning, the material was concentrated onto Isolute® HM-N and purified on an ISCO® Combiflash Rf on 50 g C18aq Gold using a gradient of water: MeOH w/0.1% formic acid (0-100%). The product fractions were concentrated to afford tert-butyl 3-(5-(ethyl(tetrahydro-2H-pyran-4-yl)amino)-3-(methoxycarbonyl)-4-methylthiophen-2-yl)pyrrolidine-1-carboxylate (0.115 g, 0.229 mmol, 68.7% yield) as a light yellow oil. MS(ES) [M+H]$^+$ 453.

c) 2-(1-(tert-butoxycarbonyl)pyrrolidin-3-yl)-5-(ethyl(tetrahydro-2H-pyran-4-yl)amino)-4-methylthiophene-3-carboxylic acid

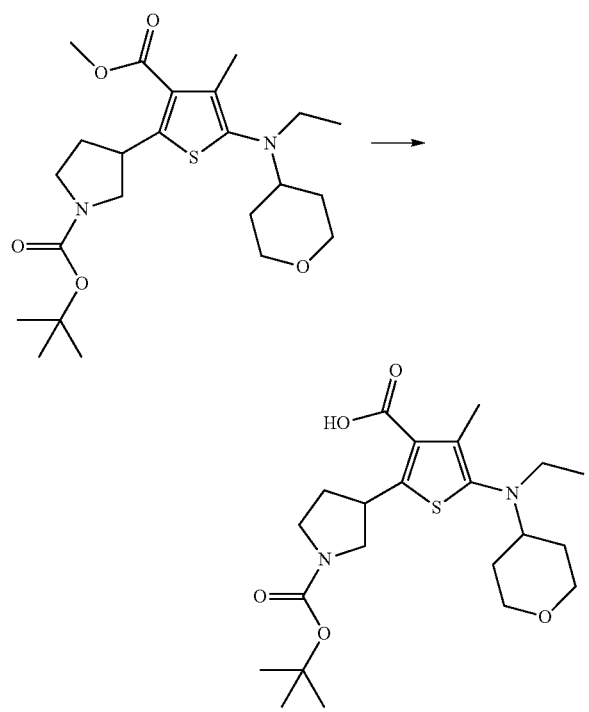

2-(1-(tert-Butoxycarbonyl)pyrrolidin-3-yl)-5-(ethyl(tetrahydro-2H-pyran-4-yl)amino)-4-methylthiophene-3-carboxylic acid (0.111 g, 0.240 mmol, 95% yield) was obtained as a yellow solid following the general procedure of Example 50b and was used without purification. MS(ES) [M+H]$^+$ 439.

d) tert-Butyl 3-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)pyrrolidine-1-carboxylate

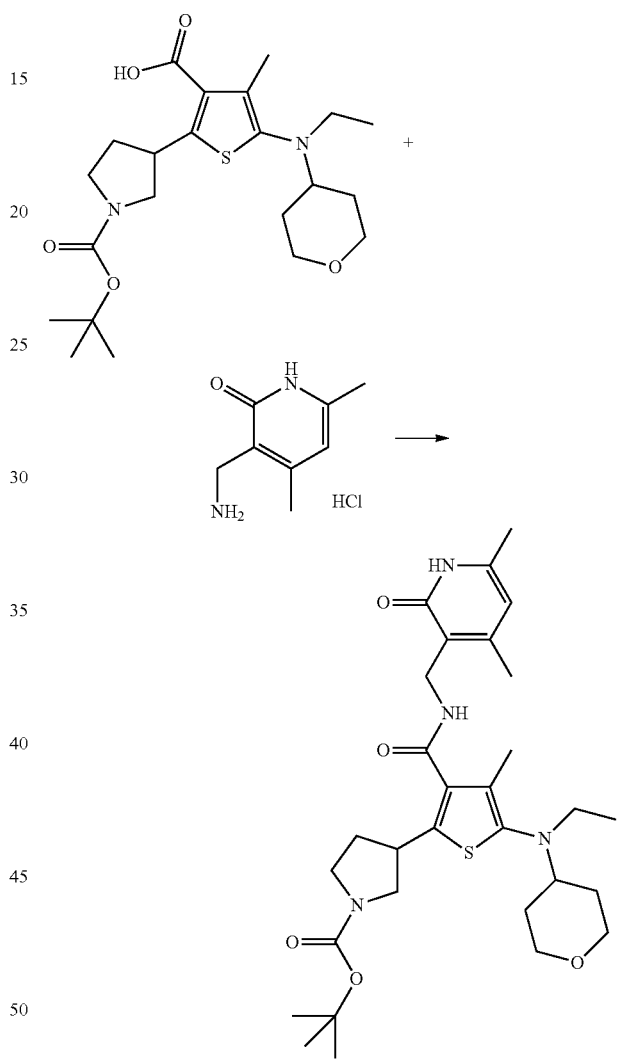

2-(1-(tert-butoxycarbonyl)pyrrolidin-3-yl)-5-(ethyl(tetrahydro-2H-pyran-4-yl)amino)-4-methylthiophene-3-carboxylic acid (0.111 g, 0.253 mmol), 3-(aminomethyl)-4,6-dimethylpyridin-2(1H)-one hydrochloride (0.053 g, 0.278 mmol), EDC (0.058 g, 0.304 mmol), and HOAt (0.041 g, 0.304 mmol) were combined. DMF (3 mL) and NMM (0.111 mL, 1.012 mmol) were added. The reaction was stirred at RT overnight under argon. The mixture was diluted with 10 mL water and purified on an ISCO® Combiflash Rf on 50 g C18aq Gold using a gradient of water: MeOH w/0.1% formic acid (0-35%). Product fractions were combined, concentrated, and re-concentrated from MeOH to afford tert-butyl 3-(3-(((4,6-dimethyl-2-oxo-1,2-dihydropyridin-3-yl)methyl)carbamoyl)-5-(ethyl(tetrahydro-2H- pyran-4-yl)amino)-4-methylthiophen-2-yl)pyrrolidine-1-carboxylate (0.073 g, 0.121 mmol, 47.8% yield) as a light yellow foam. $^1$H NMR (400 MHz, DMSO-$d_6$) δ 11.50 (s, 1H) 8.10 (t, J=4.93 Hz, 1H) 5.85 (s, 1H) 4.23 (d, J=5.05 Hz, 2H) 3.83 (d, J=9.09 Hz, 2H) 3.62-3.72 (m, 1H) 3.53-3.61 (m, 1H) 3.37-3.47 (m, 1H) 3.14-3.29 (m, 3H) 3.00-3.10 (m, 1H) 2.83-2.95 (m, 3H) 2.19 (s, 3H) 2.14 (br. s., 1H) 2.10 (s, 3H) 1.92 (s, 3H) 1.74-1.86 (m, 1H) 1.68 (d, J=12.63 Hz, 2H) 1.32-1.47 (m, 11H) 0.88 (t, J=6.95 Hz, 3H). MS(ES) [M+H]$^+$ 573.

Example 58

N-((4,6-Dimethyl-2-oxo-1,2-dihydropyridin-3-yl)methyl)-5-(ethyl(tetrahydro-2H-pyran-4-yl)amino)-4-methyl-2-(pyrrolidin-3-yl)thiophene-3-carboxamide hydrochloride

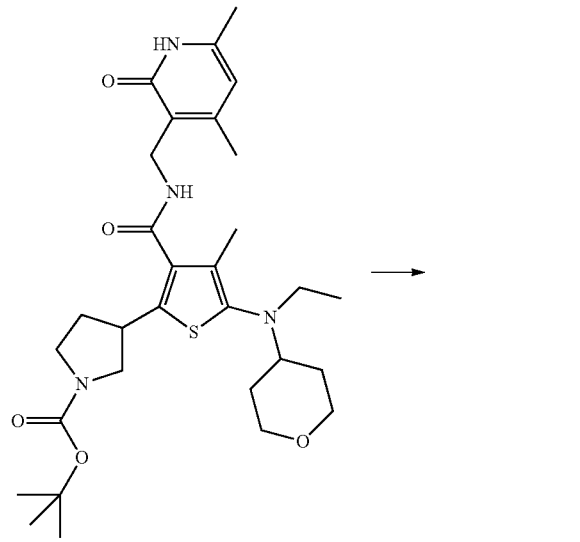

A solution of tert-butyl 3-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)pyrrolidine-1-carboxylate (0.063 g, 0.110 mmol) in 1,4-dioxane (3 mL) was treated with 4 M HCl in dioxanes (0.1 mL, 0.400 mmol) and stirred at RT. After 3 days, the reaction was concentrated to afford N-((4,6-dimethyl-2-oxo-1,2-dihydropyridin-3-yl)methyl)-5-(ethyl(tetrahydro-2H-pyran-4-yl)amino)-4-methyl-2-(pyrrolidin-3-yl)thiophene-3-carboxamide (0.051 g, 0.095 mmol, 87% yield) as its hydrochloride salt (off-white solid). $^1$H NMR (400 MHz, methanol-$d_4$) δ 6.60 (s, 1H) 4.53 (s, 2H) 3.89-4.04 (m, 3H) 3.75 (dd, J=11.49, 8.21 Hz, 1H) 3.56 (ddd, J=11.62, 8.59, 2.78 Hz, 1H) 3.37-3.45 (m, 3H) 3.01-3.19 (m, 4H) 2.45-2.56 (m, 4H) 2.41 (s, 3H) 1.99-2.18 (m, 4H) 1.82 (d, J=12.38 Hz, 2H) 1.50-1.62 (m, 2H) 0.98 (t, J=6.95 Hz, 3H). MS(ES) [M+H]$^+$ 473.

Example 59 tert-Butyl 4-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)piperidine-1-carboxylate

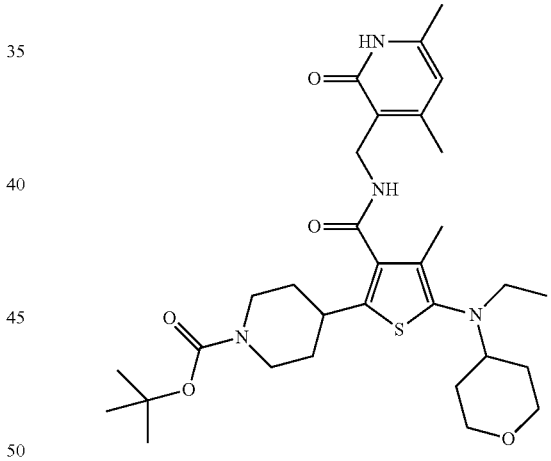

tert-Butyl 4-(3-(((4,6-dimethyl-2-oxo-1,2-dihydropyridin-3-yl)methyl)carbamoyl)-5-(ethyl(tetrahydro-2H-pyran-4-yl)amino)-4-methylthiophen-2-yl)piperidine-1-carboxylate (0.360 g, 0.583 mmol, 64.5% yield) was prepared following the general procedure of Example 57 and was isolated as an off-white solid. $^1$H NMR (400 MHz, DMSO-$d_6$) δ 11.48 (s, 1H) 8.00 (t, J=5.05 Hz, 1H) 5.86 (s, 1H) 4.22 (d, J=5.05 Hz, 2H) 3.96 (d, J=10.36 Hz, 2H) 3.83 (d, J=8.59 Hz, 2H) 3.25 (t, J=10.86 Hz, 2H) 3.02-3.14 (m, 1H) 2.83-2.94 (m, 3H) 2.58-2.65 (m, 1H) 2.21 (s, 3H) 2.11 (s, 3H) 1.92 (s, 3H) 1.79 (d, J=11.37 Hz, 2H) 1.67 (d, J=10.61 Hz, 2H) 1.35-1.47 (m, 12H) 1.19-1.33 (m, 2H) 0.87 (t, J=6.95 Hz, 3H). MS(ES) [M+H]$^+$ 587.

Example 60

N-((4,6-Dimethyl-2-oxo-1,2-dihydropyridin-3-yl)methyl)-5-(ethyl(tetrahydro-2H-pyran-4-yl)amino)-4-methyl-2-(piperidin-4-yl)thiophene-3-carboxamide hydrochloride

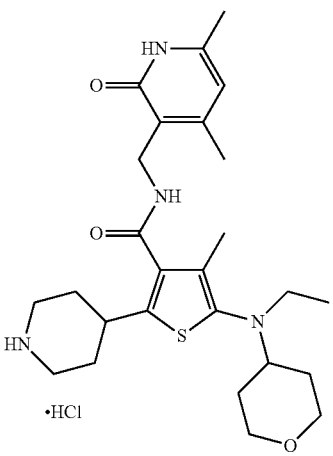 [SMILES: CCN(c1sc(C2CCNCC2)c(C(=O)NCc2c(C)cc(C)[nH]c2=O)c1C)C1CCOCC1 ; Cl]

N-((4,6-Dimethyl-2-oxo-1,2-dihydropyridin-3-yl)methyl)-5-(ethyl(tetrahydro-2H-pyran-4-yl)amino)-4-methyl-2-(piperidin-4-yl)thiophene-3-carboxamide (0.177 g, 0.346 mmol, 60.5% yield) was prepared following the general procedure of Example 58 and was isolated as a light pink foam. $^1$H NMR (400 MHz, methanol-$d_4$) δ 6.12 (s, 1H) 4.44 (s, 2H) 3.92 (dd, J=12.00, 2.40 Hz, 2H) 3.39-3.49 (m, 2H) 3.34-3.39 (m, 3H) 3.07 (td, J=13.07, 2.91 Hz, 2H) 2.92-3.02 (m, 3H) 2.38 (s, 3H) 2.27 (s, 3H) 2.14 (d, J=13.89 Hz, 2H) 2.03 (s, 3H) 1.73-1.94 (m, 4H) 1.47-1.60 (m, 2H) 0.94 (t, J=7.07 Hz, 3H). MS(ES) [M+H]$^+$ 487.

Example 61

N-((4,6-Dimethyl-2-oxo-1,2-dihydropyridin-3-yl)methyl)-5-(ethyl(tetrahydro-2H-pyran-4-yl)amino)-4-methyl-2-(1-methyl-1,2,3,6-tetrahydropyridin-4-yl)thiophene-3-carboxamide

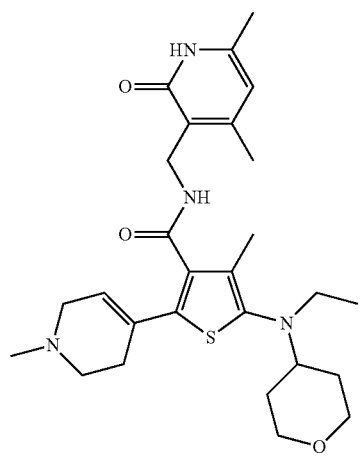 [SMILES: CCN(c1sc(C2=CCN(C)CC2)c(C(=O)NCc2c(C)cc(C)[nH]c2=O)c1C)C1CCOCC1]

N-((4,6-Dimethyl-2-oxo-1,2-dihydropyridin-3-yl)methyl)-5-(ethyl(tetrahydro-2H-pyran-4-yl)amino)-4-methyl-2-(1-methyl-1,2,3,6-tetrahydropyridin-4-yl)thiophene-3-carboxamide (0.104 g, 0.198 mmol, 47.8% yield) was prepared following the general procedure of Example 57 and was isolated as a light yellow foam. $^1$H NMR (400 MHz, DMSO-$d_6$) δ 8.16 (s, 1H) 8.04 (t, J=5.18 Hz, 1H) 5.86 (s, 1H) 5.81 (m, J=3.50, 3.50 Hz, 1H) 4.20 (d, J=5.05 Hz, 2H) 3.83 (dd, J=11.37, 2.78 Hz, 2H) 3.25 (t, J=10.86 Hz, 2H) 2.82-2.98 (m, 5H) 2.38-2.45 (m, 2H) 2.30 (br. s., 2H) 2.23 (s, 3H) 2.20 (s, 3H) 2.11 (s, 3H) 1.90 (s, 3H) 1.69 (d, J=10.86 Hz, 2H) 1.41 (qd, J=12.04, 4.29 Hz, 2H) 0.89 (t, J=6.95 Hz, 3H). MS(ES) [M+H]$^+$ 499.

Example 62

N-((4,6-Dimethyl-2-oxo-1,2-dihydropyridin-3-yl)methyl)-5-(ethyl(tetrahydro-2H-pyran-4-yl)amino)-4-methyl-2-(1-(methylsulfonyl)pyrrolidin-3-yl)thiophene-3-carboxamide

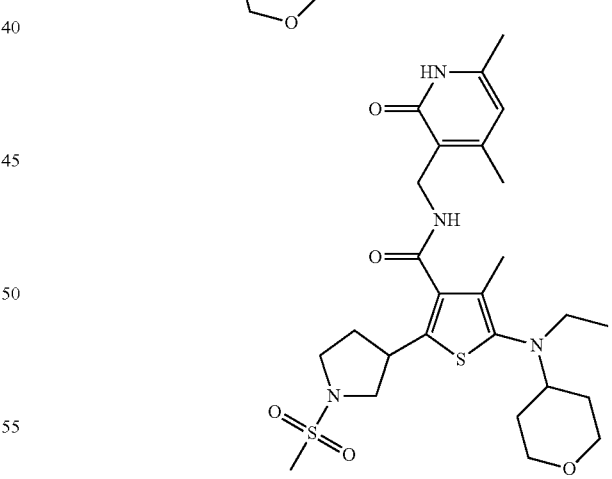

A slurry of N-((4,6-dimethyl-2-oxo-1,2-dihydropyridin-3-yl)methyl)-5-(ethyl(tetrahydro-2H-pyran-4-yl)amino)-4-methyl-2-(pyrrolidin-3-yl)thiophene-3-carboxamide hydrochloride (0.051 g, 0.100 mmol) in CHCl$_3$ (2 mL) was treated with TEA (60 μL, 0.430 mmol). After 1 minute of stirring, the homogeneous tan solution was treated with methanesulfonyl chloride (9 μL, 0.115 mmol) and maintained at RT under argon for 30 min. The reaction solution was purified on an ISCO® Combiflash Rf on 12 g silica using a gradient of heptane: (3/1) EtOAc/EtOH w/1% NH₄OH). The product fraction was concentrated to afford a clear oil. Trituration with MeOH afforded N-((4,6-dimethyl-2-oxo-1,2-dihydropyridin-3-yl)methyl)-5-(ethyl(tetrahydro-2H-pyran-4-yl)amino)-4-methyl-2-(1-(methylsulfonyl)pyrrolidin-3-yl)thiophene-3-carboxamide (0.032 g, 0.055 mmol, 55.1% yield) as a white solid. $^1$H NMR (400 MHz, methanol-d₄) δ 6.11 (s, 1H) 4.45 (d, J=2.53 Hz, 2H) 3.93 (dd, J=12.00, 2.15 Hz, 2H) 3.80 (tt, J=9.66, 7.14 Hz, 1H) 3.59-3.69 (m, 1H) 3.54 (ddd, J=9.92, 8.27, 2.78 Hz, 1H) 3.35-3.43 (m, 3H) 3.16 (t, J=9.47 Hz, 1H) 2.93-3.04 (m, 3H) 2.89 (s, 3H) 2.40 (s, 3H) 2.33 (dtd, J=12.60, 6.52, 6.52, 2.91 Hz, 1H) 2.26 (s, 3H) 2.04 (s, 3H) 1.97-2.02 (m, 1H) 1.79 (dt, J=12.76, 1.96 Hz, 2H) 1.47-1.61 (m, 2H) 0.95 (t, J=7.07 Hz, 3H). MS(ES) [M+H]⁺ 551.

Example 63

N-((4,6-Dimethyl-2-oxo-1,2-dihydropyridin-3-yl)methyl)-5-(ethyl(tetrahydro-2H-pyran-4-yl)amino)-4-methyl-2-(1-(methylsulfonyl)piperidin-4-yl)thiophene-3-carboxamide

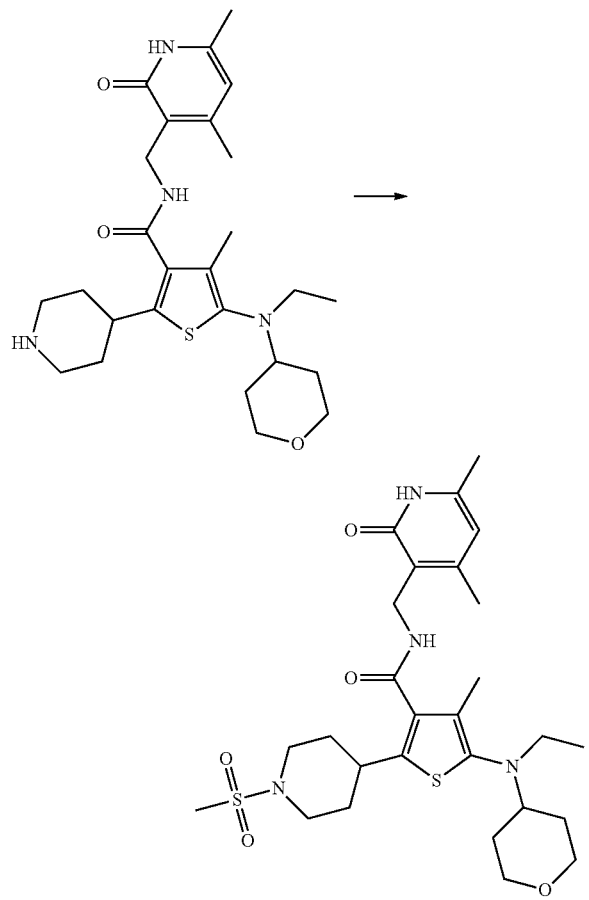

N-((4,6-Dimethyl-2-oxo-1,2-dihydropyridin-3-yl)methyl)-5-(ethyl(tetrahydro-2H-pyran-4-yl)amino)-4-methyl-2-(1-(methylsulfonyl)piperidin-4-yl)thiophene-3-carboxamide (0.026 g, 0.044 mmol, 42.6% yield) was prepared following the general procedure of Example 62 and was isolated as a white solid. $^1$H NMR (400 MHz, methanol-d₄) δ 6.11 (s, 1H) 4.44 (s, 2H) 3.93 (d, J=8.08 Hz, 2H) 3.75 (d, J=12.13 Hz, 2H) 3.36-3.43 (m, 2H) 3.00-3.13 (m, 1H) 2.92-2.99 (m, 3H) 2.86 (s, 3H) 2.64-2.78 (m, 2H) 2.40 (s, 3H) 2.26 (s, 3H) 1.93-2.08 (m, 5H) 1.78 (d, J=12.13 Hz, 2H) 1.45-1.71 (m, 4H) 0.94 (t, J=7.07 Hz, 3H). MS(ES) [M+H]⁺ 565.

Example 64

N-((4,6-dimethyl-2-oxo-1,2-dihydropyridin-3-yl)methyl)-5-(ethyl((trans)-4-(ethyl(methyl)amino)cyclohexyl)amino)-4-methylthiophene-3-carboxamide

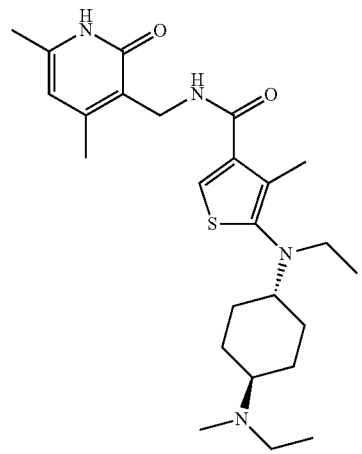 [SMILES: CCN(C)[C@H]1CC[C@H](N(CC)c2scc(C(=O)NCc3c(C)cc(C)[nH]c3=O)c2C)CC1]

a) Methyl 5-((4-((tert-butoxycarbonyl)(methyl)amino)cyclohexyl)(ethyl)amino)-4-methylthiophene-3-carboxylate

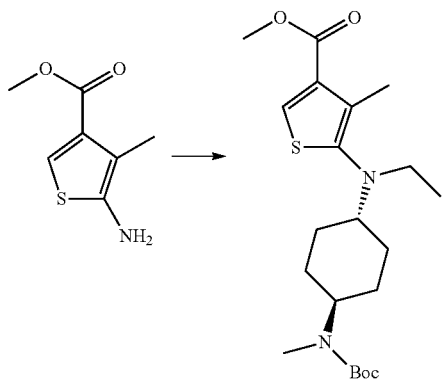

A solution of methyl 5-amino-4-methylthiophene-3-carboxylate (160 mg, 0.934 mmol), tert-butyl methyl(4-oxocyclohexyl)carbamate (255 mg, 1.121 mmol) and AcOH (0.053 mL, 0.934 mmol) in DCE (6 mL) was stirred for 30 min at RT. NaBH(OAc)₃ (792 mg, 3.74 mmol) was added and the solution was stirred for 1 h. Acetaldehyde (0.079 mL, 1.402 mmol) was added and the solution was stirred for 1 h. The reaction was quenched with water (5 mL) and 1 M Na₂CO₃ (5 mL). The mixture was diluted with DCM (40 mL) and the layers were separated. The organic layer was washed with brine, dried over MgSO₄, filtered and evaporated. The residue was purified by column chromatography (10% EtAOc:hexane) to give methyl 5-((4-((tert-butoxycarbonyl)(methyl)amino)cyclohexyl) (ethyl)amino)-4-methylthiophene-3-carboxylate (203 mg, 0.470 mmol, 50.3% yield) as colorless oil (7:3 mixture of cis- and trans-isomers). $^1$H NMR (400 MHz, CDCl$_3$) δ 7.94 (d, J=16.42 Hz, 1H), 3.86 (s, 4H), 2.87-3.05 (m, 2H), 2.63-2.83 (m, 4H), 2.34 (s, 2H), 2.00 (d, J=7.58 Hz, 2H), 1.57-1.86 (m, 3H), 1.43-1.51 (m, 11H), 0.86-1.05 (m, 3H). MS(ES) [M+H]$^+$ 411.2.

b) 5-(Ethyl((trans)-4-(ethyl(methyl)amino)cyclohexyl)amino)-4-methylthiophene-3-carboxylic acid

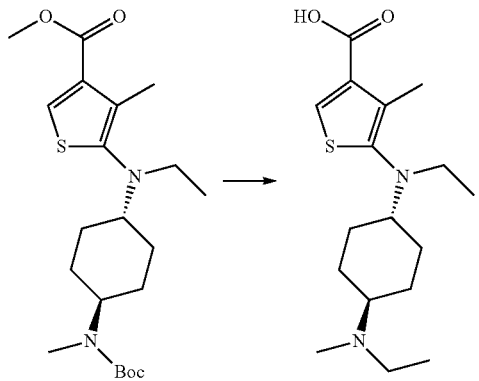 [SMILES: CCN(c1scc(C(=O)OC)c1C)[C@H]1CC[C@H](N(C)C(=O)OC(C)(C)C)CC1 ; CCN(C)[C@H]1CC[C@H](N(CC)c2scc(C(=O)O)c2C)CC1]

To a solution of methyl 5-((4-((tert-butoxycarbonyl)(methyl)amino)cyclohexyl)(ethyl)amino)-4-methylthiophene-3-carboxylate (203 mg, 0.494 mmol) in DCM (5 mL) was added TFA (2.5 mL). The reaction was stirred for 1 h, at which time it was evaporated. The residue was partitioned between EtOAc (30 mL) and 1 M Na$_2$CO$_3$ (20 mL). The organic layer was washed with brine, dried over MgSO$_4$, filtered and evaporated.

To a solution of the residue in acetone (7.5 mL) was added potassium carbonate (205 mg, 1.483 mmol) and iodoethane (0.034 mL, 0.544 mmol). The reaction was stirred overnight at RT, at which time it was filtered and evaporated.

To a solution of the residue in MeOH (10 mL) was added 5 M NaOH (0.494 mL, 2.472 mmol). The reaction was heated at 45° C. for 24 h, at which time 6 M HCl (0.5 mL) was added. The mixture was concentrated and the residue was purified by preparative HPLC (12 to 25% AcCN:H$_2$O with 0.1% formic acid modifier) to give 5-(ethyl((trans)-4-(ethyl(methyl)amino)cyclohexyl)amino)-4-methylthiophene-3-carboxylic acid (80 mg, 0.231 mmol, 46.7% yield) as an oil. $^1$H NMR (400 MHz, methanol-d$_4$) δ 7.97 (s, 1H), 3.15-3.28 (m, 3H), 3.05 (q, J=7.07 Hz, 2H), 2.83-2.94 (m, 1H), 2.78 (s, 3H), 2.31 (s, 3H), 2.00-2.21 (m, 4H), 1.61 (dq, J=2.53, 12.38 Hz, 2H), 1.38-1.51 (m, 2H), 1.34 (t, J=7.20 Hz, 3H), 0.96 (t, J=7.07 Hz, 3H). MS(ES) [M+H]$^+$ 325.2.

c) N-((4,6-dimethyl-2-oxo-1,2-dihydropyridin-3-yl)methyl)-5-(ethyl((trans)-4-(ethyl(methyl)amino)cyclohexyl)amino)-4-methylthiophene-3-carboxamide

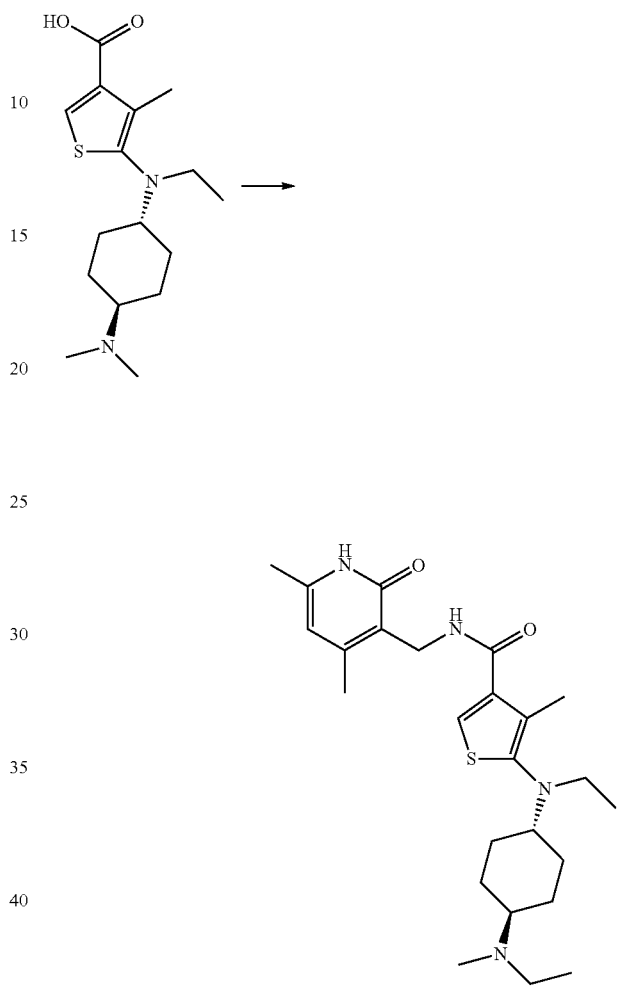

To a suspension of 5-(ethyl((trans)-4-(ethyl(methyl)amino)cyclohexyl)amino)-4-methylthiophene-3-carboxylic acid (80 mg, 0.247 mmol) in DMF (5 mL) was added EDC (56.7 mg, 0.296 mmol), followed by HOAt (40.3 mg, 0.296 mmol) and 3-(aminomethyl)-4,6-dimethylpyridin-2(1H)-one hydrochloride (55.8 mg, 0.296 mmol). After 5 minutes, NMM (0.108 mL, 0.986 mmol) was added and the reaction mixture was stirred for 4 h.

Water (1 mL) was added and the reaction mixture was purified directly by preparative HPLC (5 to 30% AcCN:water with 0.1% formic acid) to give N-((4,6-dimethyl-2-oxo-1,2-dihydropyridin-3-yl)methyl)-5-(ethyl((trans)-4-(ethyl(methyl)amino)cyclohexyl)amino)-4-methylthiophene-3-carboxamide (30 mg, 0.062 mmol, 25.2% yield) as white foam. $^1$H NMR (400 MHz, methanol-d$_4$) δ 7.56 (s, 1H), 6.13 (s, 1H), 4.45 (s, 2H), 3.11-3.26 (m, 3H), 3.02 (q, J=6.91 Hz, 2H), 2.86 (tt, J=3.47, 11.56 Hz, 1H), 2.76 (s, 3H), 2.37 (s, 3H), 2.26 (s, 3H), 2.21 (s, 3H), 2.01-2.18 (m, 4H), 1.52-1.66 (m, 2H), 1.37-1.51 (m, 2H), 1.32 (t, J=7.33 Hz, 3H), 0.95 (t, J=7.07 Hz, 3H). MS(ES) [M+H]$^+$ 459.3.

Example 65

Ethyl (4-(((4,6-dimethyl-2-oxo-1,2-dihydropyridin-3-yl)methyl)carbamoyl)-3-methylthiophen-2-yl)(ethyl)carbamate

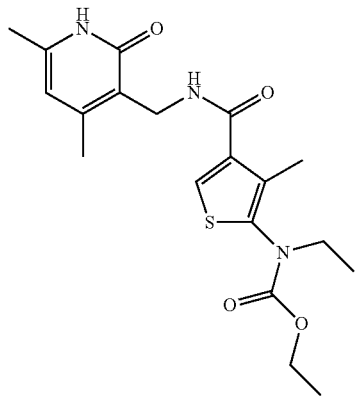 [SMILES: CCOC(=O)N(CC)c1scc(C(=O)NCc2c(C)cc(C)[nH]c2=O)c1C]

a) 5-((Ethoxycarbonyl)(ethyl)amino)-4-methylthiophene-3-carboxylic acid

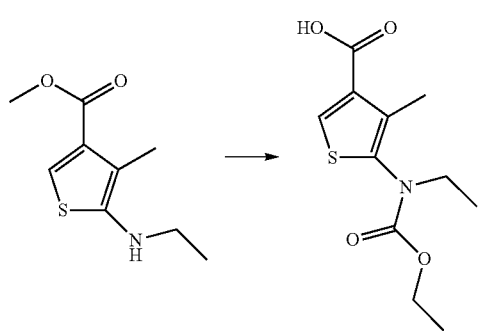 [SMILES: CCNc1scc(C(=O)OC)c1C ; CCOC(=O)N(CC)c1scc(C(=O)O)c1C]

To a solution of methyl 5-(ethylamino)-4-methylthiophene-3-carboxylate (100 mg, 0.502 mmol) in CHCl$_3$ (10 mL) was added ethyl chloroformate (0.241 mL, 2.509 mmol). The reaction was maintained overnight, at which time it was concentrated. The residue was purified by column chromatography (10% EtAOc:Hexane).

To a solution of the purified residue in MeOH (5 mL) was added 1 M NaOH (2 mL, 2.0 mmol). The reaction was stirred overnight, at which time it was neutralized with 6 M HCl and evaporated to give 5-((ethoxycarbonyl)(ethyl)amino)-4-methylthiophene-3-carboxylic acid (100 mg, 0.194 mmol, 38.7% yield), contaminated with NaCl (assumed 50 w/w %). $^1$H NMR (400 MHz, DMSO-d$_6$) δ ppm 0.99-1.22 (m, 6H) 2.09-2.16 (m, 3H) 3.55 (q, J=7.07 Hz, 3H) 4.06 (br. s., 2H) 8.13 (s, 1H) 12.69 (br. s., 1H). MS(ES) [M+H]$^+$ 258.0.

b) Ethyl (4-(((4,6-dimethyl-2-oxo-1,2-dihydropyridin-3-yl)methyl)carbamoyl)-3-methylthiophen-2-yl)(ethyl)carbamate

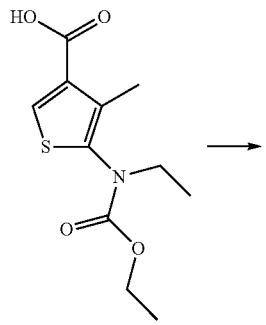

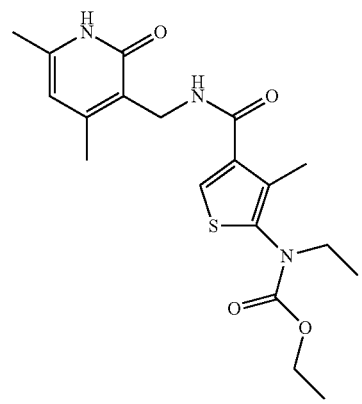

To a suspension of 5-((Ethoxycarbonyl)(ethyl)amino)-4-methylthiophene-3-carboxylic acid (50 mg, 0.194 mmol) (mixture with NaCl, assumed 50 w/w %) in DMF (5 mL) was added 3-(aminomethyl)-4,6-dimethylpyridin-2(1H)-one (32.5 mg, 0.214 mmol), EDC (44.7 mg, 0.233 mmol) and HOAt (31.7 mg, 0.233 mmol). The reaction mixture was stirred for 30 min, at which time NMM (0.085 mL, 0.777 mmol) was added. The reaction mixture was heated at 40° C. for 1 h. Water (2 mL) was added and the reaction mixture was purified by preparative HPLC (5 to 70% AcCN:H$_2$O with 0.1% formic acid) to give ethyl (4-(((4,6-dimethyl-2-oxo-1,2-dihydropyridin-3-yl)methyl)carbamoyl)-3-methylthiophen-2-yl)(ethyl)carbamate (35 mg, 0.085 mmol, 43.7% yield) as white solid. $^1$H NMR (400 MHz, methanol-d$_4$) δ ppm 1.18 (t, J=7.07 Hz, 6H) 2.15 (s, 3H) 2.26 (s, 3H) 2.37 (s, 3H) 3.64 (q, J=7.07 Hz, 2H) 4.14 (br. s., 2H) 4.39-4.53 (m, 2H) 6.13 (s, 1H) 7.66 (s, 1H). MS(ES) [M+H]$^+$ 392.1.

Example 66

N-((4,6-dimethyl-2-oxo-1,2-dihydropyridin-3-yl)methyl)-5-(ethyl(1-isopropylpiperidin-4-yl)amino)-4-methylthiophene-3-carboxamide

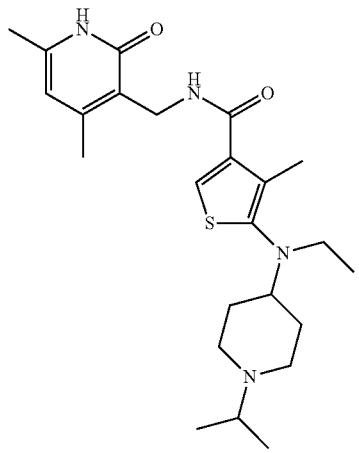 [SMILES: CCN(c1scc(C(=O)NCc2c(C)cc(C)[nH]c2=O)c1C)C1CCN(C(C)C)CC1]

a) Methyl 5-(ethyl(1-isopropylpiperidin-4-yl)amino)-4-methylthiophene-3-carboxylate

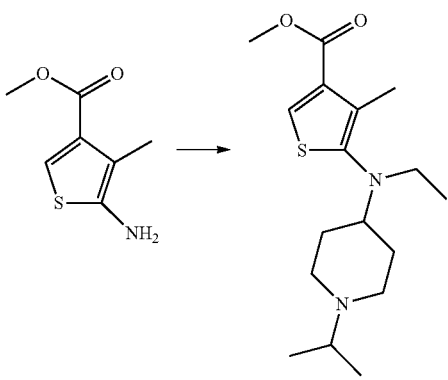

Following the general procedure described in Example 64a using 1-isopropylpiperidin-4-one, methyl 5-(ethyl(1-isopropylpiperidin-4-yl)amino)-4-methylthiophene-3-carboxylate (70.2% yield) was prepared as white solid. $^1$H NMR (400 MHz, methanol-$d_4$) δ 8.07 (s, 1H), 3.84 (s, 3H), 2.98-3.29 (m, 6H), 2.78 (t, J=11.62 Hz, 2H), 2.33 (s, 3H), 2.07 (d, J=13.14 Hz, 2H), 1.65-1.84 (m, 2H), 1.25 (d, J=6.82 Hz, 6H), 0.97 (t, J=7.07 Hz, 3H). MS(ES) [M+H]$^+$ 325.1.

b) N-((4,6-dimethyl-2-oxo-1,2-dihydropyridin-3-yl)methyl)-5-(ethyl(1-isopropylpiperidin-4-yl)amino)-4-methylthiophene-3-carboxamide

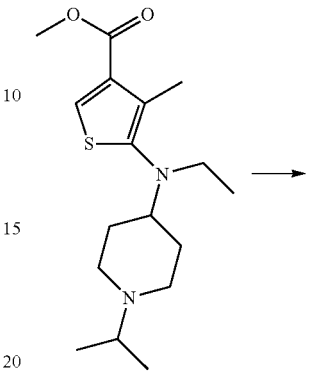

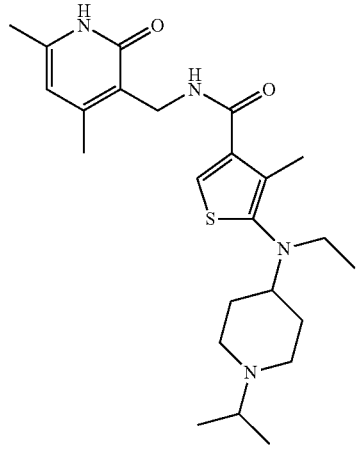

To a solution of methyl 5-(ethyl(1-isopropylpiperidin-4-yl)amino)-4-methylthiophene-3-carboxylate (280 mg, 0.863 mmol) in MeOH (8 mL) was added 6 M NaOH (1 mL, 6.0 mmol). The reaction mixture was heated at 45° C. overnight, at which time 6 M HCl (1 mL) was added and the mixture was concentrated.

To a suspension of the resultant solid in DMF (5 mL) was added 3-(aminomethyl)-4,6-dimethylpyridin-2(1H)-one (144 mg, 0.949 mmol), EDC (199 mg, 1.035 mmol) and HOAt (141 mg, 1.035 mmol). The reaction mixture was stirred for 30 min, at which time NMM (0.379 mL, 3.45 mmol) was added. The reaction mixture was heated at 40° C. for 1 h. The reaction mixture was purified directly by preparative HPLC (5-40% AcCN:H$_2$O with 0.1% formic acid as modifier) to give N-((4,6-dimethyl-2-oxo-1,2-dihydropyridin-3-yl)methyl)-5-(ethyl(1-isopropylpiperidin-4-yl)amino)-4-methylthiophene-3-carboxamide (156 mg, 0.305 mmol, 35.4% yield) as white solid $^1$H NMR (400 MHz, methanol-$d_4$) δ 7.62 (s, 1H), 6.13 (s, 1H), 4.44 (s, 2H), 3.40-3.56 (m, 3H), 2.90-3.20 (m, 5H), 2.37 (s, 3H), 2.26 (d, J=6.06 Hz, 6H), 2.15 (d, J=12.13 Hz, 2H), 1.82 (br. s., 1H), 1.34 (d, J=6.82 Hz, 6H), 0.97 (t, J=7.07 Hz, 3H). MS(ES) [M+H]$^+$ 445.2.

Example 67

N-((4,6-dimethyl-2-oxo-1,2-dihydropyridin-3-yl)methyl)-5-(ethyl(3-fluoropiperidin-4-yl)amino)-4-methylthiophene-3-carboxamide

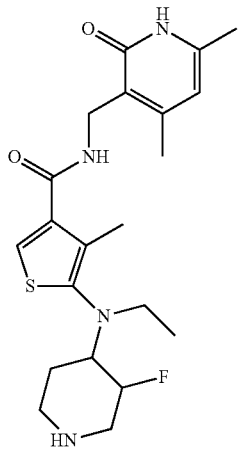 [SMILES: CCN(c1scc(C(=O)NCc2c(C)cc(C)[nH]c2=O)c1C)C1CCNCC1F]

a) tert-Butyl 4-(ethyl(4-(methoxycarbonyl)-3-methylthiophen-2-yl)amino)-3-fluoropiperidine-1-carboxylate

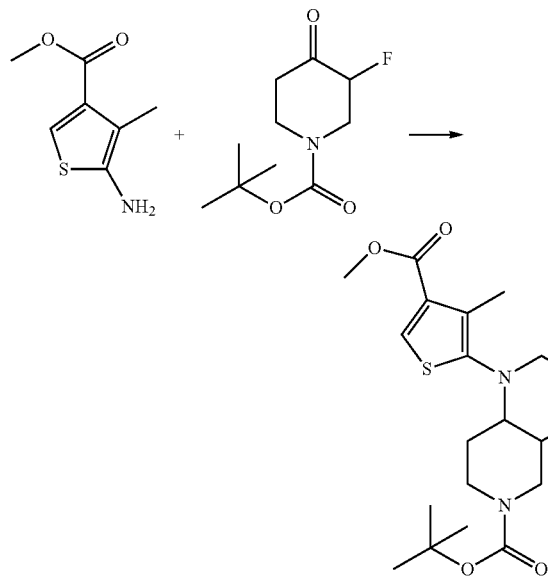

Following the general reductive amination procedure described in Example 64a, tert-butyl 4-(ethyl(4-(methoxycarbonyl)-3-methylthiophen-2-yl)amino)-3-fluoropiperidine-1-carboxylate (728 mg, 51%) was prepared as an oily residue. $^1$H NMR (DMSO-d6) δ: 8.11 (s, 1H), 4.59-5.03 (m, 1H), 4.16 (br. s., 1H), 4.00 (br. s., 1H), 3.76 (s, 3H), 2.91-3.11 (m, 3H), 2.80 (br. s., 1H), 2.67 (dd, J=3.8, 1.8 Hz, 1H), 2.22 (s, 3H), 1.50-1.71 (m, 2H), 1.37 (s, 8H), 0.80-0.90 (m, 4H). MS(ES) [M+H]$^+$ 401.

b) 5-((1-(tert-Butoxycarbonyl)-3-fluoropiperidin-4-yl)(ethyl)amino)-4-methylthiophene-3-carboxylic acid

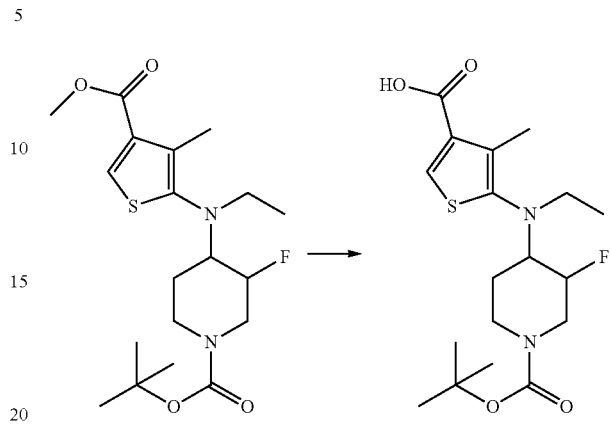

Following the general saponification procedure described in Example 64a in Example 64a, 5-((1-(tert-butoxycarbonyl)-3-fluoropiperidin-4-yl)(ethyl)amino)-4-methylthiophene-3-carboxylic acid (1.3 g) was prepared. MS(ES) [M+H]$^+$ 387.

c) tert-Butyl 4-((4-(((4,6-dimethyl-2-oxo-1,2-dihydropyridin-3-yl)methyl)carbamoyl)-3-methylthiophen-2-yl)(ethyl)amino)-3-fluoropiperidine-1-carboxylate

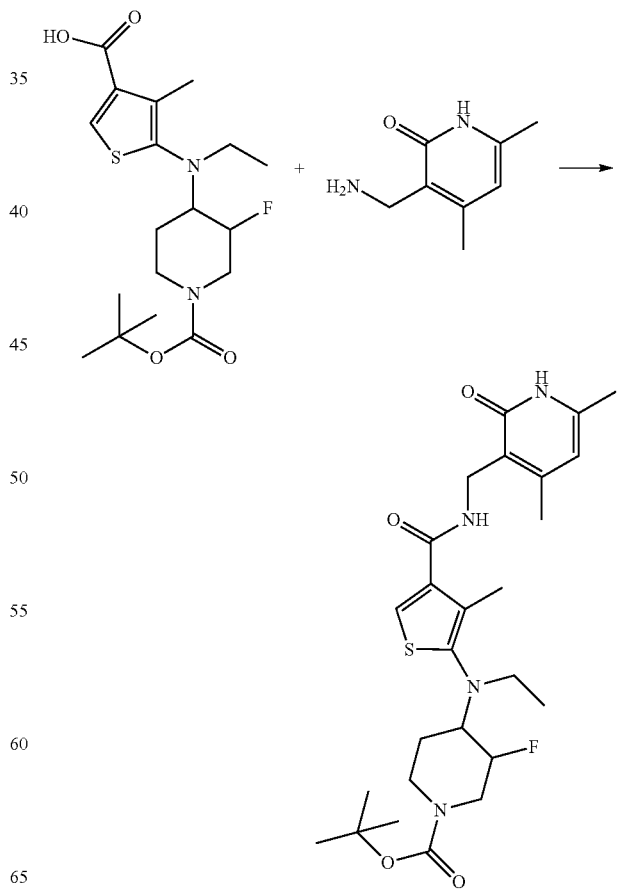

Following the general coupling procedure described in Example 64c, tert-butyl 4-((4-(((4,6-dimethyl-2-oxo-1,2-dihydropyridin-3-yl)methyl)carbamoyl)-3-methylthiophen-2-yl)(ethyl)amino)-3-fluoropiperidine-1-carboxylate (848 mg, 92%) was prepared. $^1$H NMR (DMSO-d6) δ: 11.49 (s, 1H), 7.96 (t, J=5.1 Hz, 1H), 7.65 (s, 1H), 5.86 (s, 1H), 4.91 (br. s., 1H), 4.78 (br. s., 1H), 4.22 (d, J=5.3 Hz, 3H), 4.00 (br. s., 1H), 2.86-3.09 (m, 4H), 2.73 (s, 1H), 2.08-2.21 (m, 9H), 1.56-1.71 (m, 2H), 1.30-1.45 (m, 9H), 0.86 (t, J=7.1 Hz, 3H). MS(ES) [M+H]$^+$ 521.

d) N-((4,6-Dimethyl-2-oxo-1,2-dihydropyridin-3-yl)methyl)-5-(ethyl(3-fluoropiperidin-4-yl)amino)-4-methylthiophene-3-carboxamide

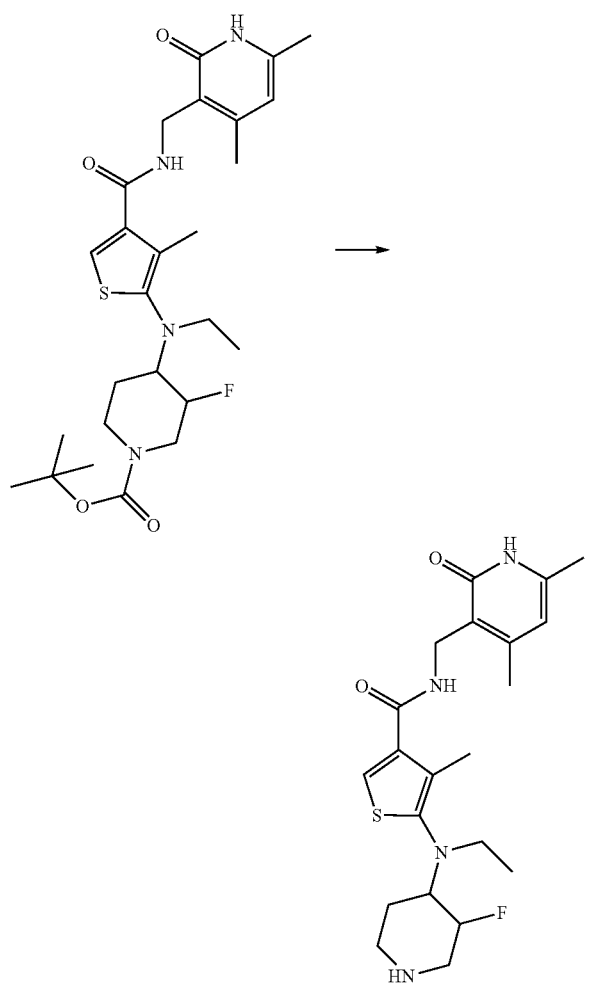

Following the general Boc-deprotection procedure described within and purification by flash chromatography (DCM: 90/10/1 DCM/MeOH/NH$_4$OH), N-((4,6-dimethyl-2-oxo-1,2-dihydropyridin-3-yl)methyl)-5-(ethyl(3-fluoropiperidin-4-yl)amino)-4-methylthiophene-3-carboxamide (264 mg, 78%) was prepared. $^1$H NMR (DMSO-d6) δ: 11.49 (br. s., 1H), 7.95 (t, J=5.1 Hz, 1H), 7.60-7.67 (m, 1H), 5.86 (s, 1H), 4.77 (br. s., 1H), 4.22 (d, J=5.1 Hz, 2H), 2.96-3.07 (m, 3H), 2.76-2.95 (m, 2H), 2.55-2.67 (m, 1H), 2.25-2.47 (m, 1H), 2.06-2.21 (m, 9H), 1.60 (qd, J=12.3, 4.2 Hz, 1H), 1.44-1.52 (m, 1H), 0.86 (t, J=7.1 Hz, 3H). MS(ES) [M+H]$^+$ 421.

Example 68

N-((4,6-dimethyl-2-oxo-1,2-dihydropyridin-3-yl)methyl)-4-methyl-5-(2-(piperidin-4-yl)pyrrolidin-1-yl)thiophene-3-carboxamide hydrochloride

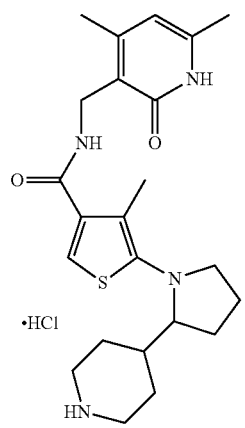 [SMILES: Cc1cc(C)c(CNC(=O)c2csc(N3CCCC3C3CCNCC3)c2C)c(=O)[nH]1 ; Cl]

a) Benzyl 4-(1-hydroxypent-4-en-1-yl)piperidine-1-carboxylate

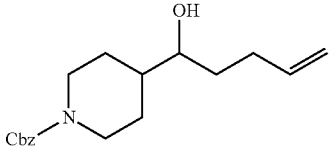 [SMILES: C=CCCC(O)C1CCN(C(=O)OCc2ccccc2)CC1]

To a cooled (−78° C.) solution of benzyl 4-formylpiperidine-1-carboxylate (2.3 g, 9.30 mmol) in THF (70 mL) was added but-3-en-1-ylmagnesium bromide, 0.5M in THF (37.2 mL, 18.60 mmol) dropwise over 20 min. The mixture was stirred at −78° C. for 2 h. The reaction mixture was quenched with saturated NH$_4$C$_1$ aqueous solution and extracted with EtOAc (3×). The extract was dried over Na$_2$SO$_4$ and concentrated. The residue was purified using column chromatography (silica gel, 0 to 80% EtOAc/hexanes) to give benzyl 4-(1-hydroxypent-4-en-1-yl)piperidine-1-carboxylate (1.21 g) as a pale yellow oil. $^1$H NMR (400 MHz, CDCl$_3$) δ 1.17-1.89 (m, 9H), 2.08-2.38 (m, 2H), 2.76 (br. s., 2H), 3.39-3.50 (m, 1H), 4.26 (br. s., 2H), 4.93-5.21 (m, 5H), 5.86 (ddt, J=17.05, 10.23, 6.69, 6.69 Hz, 1H), 7.31-7.46 (m, 5H). MS(ES) [M+H]$^+$ 304.1.

b) Benzyl 4-(1-bromopent-4-en-1-yl)piperidine-1-carboxylate

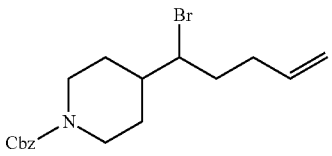 [SMILES: C=CCCC(Br)C1CCN(C(=O)OCc2ccccc2)CC1]

To a cooled (0° C.) solution of benzyl 4-(1-hydroxypent-4-en-1-yl)piperidine-1-carboxylate (850 mg, 2.80 mmol) and carbon tetrabromide (1208 mg, 3.64 mmol) in THF (16 mL) was added triphenylphosphine (955 mg, 3.64 mmol) portionwise. The mixture was stirred at RT for 5 h. The mixture was filtered and the filtrate was concentrated. The residue was purified using column chromatography (silica gel, 0 to 60% EtOAc/hexanes) to give benzyl 4-(1-bromopent-4-en-1-yl)piperidine-1-carboxylate (402 mg) as a colorless oil. $^1$H NMR (400 MHz, CDCl$_3$) δ 1.37-1.55 (m, 1H), 1.68-2.03 (m, 5H), 2.21 (dq, J=15.16, 7.49 Hz, 1H), 2.33-2.46 (m, 1H), 2.78 (br. s., 2H), 3.89-4.05 (m, 1H), 4.98-5.23 (m, 4H), 5.79 (m, 1H), 7.30-7.47 (m, 5H). MS(ES) [M+H]$^+$ 366.0, 368.0.

c) Benzyl 4-(1-bromo-4-oxobutyl)piperidine-1-carboxylate

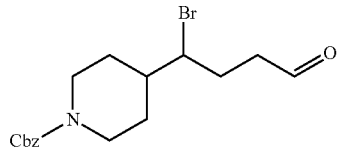 [SMILES: O=CCCC(Br)C1CCN(C(=O)OCc2ccccc2)CC1]

To a solution of benzyl 4-(1-bromopent-4-en-1-yl)piperidine-1-carboxylate (400 mg, 1.092 mmol) in acetone (3 mL) and water (0.667 mL) were added NMO (154 mg, 1.310 mmol) and osmium tetroxide and 2.5% in t-BuOH (0.055 mL, 4.37 μmol). The mixture was stirred at RT for 18 h. The reaction was diluted with EtOAc and washed with water. The organic layer was dried over Na$_2$SO$_4$ and concentrated. The residue was treated with THF (6 mL) and water (3 mL), and sodium periodate (467 mg, 2.184 mmol) was added. The reaction mixture was stirred at RT for 1.5 h. The reaction mixture was quenched with water and extracted with EtOAc (3×). The extract was dried over Na$_2$SO$_4$ and concentrated to give benzyl 4-(1-bromo-4-oxobutyl)piperidine-1-carboxylate (360 mg) as pale yellow oil. $^1$H NMR (400 MHz, CDCl$_3$) δ 1.39-1.57 (m, 1H), 1.69-1.94 (m, 2H), 1.99-2.11 (m, 1H), 2.16-2.32 (m, 1H), 2.69-2.91 (m, 4H), 3.91-4.06 (m, 1H), 4.21-4.45 (m, 2H), 5.15 (s, 2H), 7.31-7.44 (m, 5H), 9.81-9.90 (m, 1H). MS(ES) [M+H]$^+$ 368.0, 370.0.

d) Benzyl 4-(1-(4-(methoxycarbonyl)-3-methylthiophen-2-yl)pyrrolidin-2-yl)piperidine-1-carboxylate

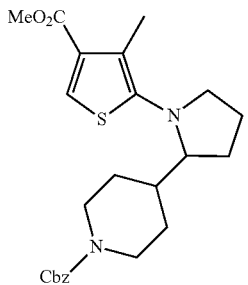 [SMILES: COC(=O)c1csc(N2CCCC2C2CCN(C(=O)OCc3ccccc3)CC2)c1C]

To a solution of methyl 5-amino-4-methylthiophene-3-carboxylate (150 mg, 0.876 mmol) in MeOH (8 mL) were added benzyl 4-(1-bromo-4-oxobutyl)piperidine-1-carboxylate (355 mg, 0.964 mmol) and AcOH (0.050 mL, 0.876 mmol). The mixture was stirred at RT for 30 min. NaBH$_3$CN (138 mg, 2.190 mmol) was added and the mixture was heated at reflux for 1 h. The mixture was quenched with water and extracted with EtOAc (3×). The extract was dried over Na$_2$SO$_4$ and concentrated. The residue was purified using column chromatography (silica gel, 0 to 60% EtOAc/hexanes) to give benzyl 4-(1-(4-(methoxycarbonyl)-3-methylthiophen-2-yl)pyrrolidin-2-yl)piperidine-1-carboxylate (203 mg) as pale yellow solid. $^1$H NMR (400 MHz, CDCl$_3$) δ 1.10-1.32 (m, 2H) 1.52-2.04 (m, 7H) 2.30-2.37 (m, 3H) 2.56-2.86 (m, 3H) 3.18-3.32 (m, 1H) 3.42 (dt, J=9.28, 5.72 Hz, 1H) 3.83-3.88 (m, 3H) 4.22 (br. s., 2H) 5.13 (s, 2H) 7.29-7.46 (m, 5H) 7.70-7.81 (m, 1H). MS(ES) [M+H]$^+$ 443.2.

e) tert-Butyl 4-(1-(4-(methoxycarbonyl)-3-methylthiophen-2-yl)pyrrolidin-2-yl)piperidine-1-carboxylate

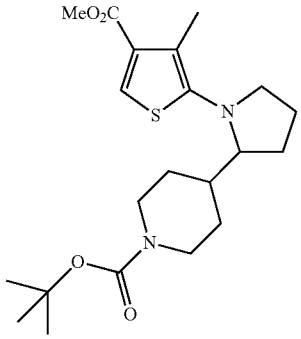 [SMILES: COC(=O)c1csc(N2CCCC2C2CCN(C(=O)OC(C)(C)C)CC2)c1C]

To a solution of benzyl 4-(1-(4-(methoxycarbonyl)-3-methylthiophen-2-yl)pyrrolidin-2-yl)piperidine-1-carboxylate (200 mg, 0.452 mmol) in DCM (5 mL) was added 33% HBr in AcOH (0.744 mL, 4.52 mmol). The mixture was stirred at RT for 5 h. The mixture was concentrated and the residue was treated with 10% NaHCO$_3$ and extracted with EtOAc. The extract was dried over Na$_2$SO$_4$ and concentrated.

To a solution of the oily residue in DCM (5 mL) was added TEA (0.189 mL, 1.356 mmol) and Boc$_2$O (0.210 mL, 0.904 mmol). The mixture was stirred at RT for 6 h, quenched with 10% NaHCO$_3$ and extracted with EtOAc (3×). The extract was dried over Na$_2$SO$_4$ and concentrated. The residue was purified using column chromatography (silica gel, 0 to 60% EtOAc/hexanes) to give tert-butyl 4-(1-(4-(methoxycarbonyl)-3-methylthiophen-2-yl)pyrrolidin-2-yl)piperidine-1-carboxylate (120 mg) as a colorless oil. $^1$H NMR (400 MHz, CDCl$_3$) δ 1.09-1.32 (m, 3H), 1.41-2.04 (m, 21H), 2.33 (s, 3H), 2.46-2.66 (m, 2H), 2.78 (dt, J=9.16, 7.42 Hz, 1H), 3.16-3.29 (m, 1H), 3.42 (dt, J=9.35, 5.68 Hz, 1H), 3.85 (s, 3H), 4.14 (q, J=7.16 Hz, 1H), 7.76 (s, 1H). MS(ES) [M+H]$^+$ 409.1.

f) 5-(2-(1-(tert-Butoxycarbonyl)piperidin-4-yl)pyrrolidin-1-yl)-4-methylthiophene-3-carboxylic acid

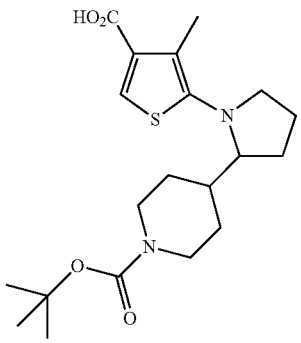 [SMILES: Cc1c(C(=O)O)csc1N1CCCC1C1CCN(C(=O)OC(C)(C)C)CC1]

To a solution of tert-butyl 4-(1-(4-(methoxycarbonyl)-3-methylthiophen-2-yl)pyrrolidin-2-yl)piperidine-1-carboxylate (120 mg, 0.294 mmol) in MeOH (3 mL) was added 8 M NaOH (0.184 mL, 1.469 mmol). The mixture was heated at 60° C. for 18 h. The mixture was concentrated to remove the MeOH. The residue was treated with water and acidified using 1 N HCl. The precipitate was collected by filtration and dried under vacuum to give 5-(2-(1-(tert-butoxycarbonyl)piperidin-4-yl)pyrrolidin-1-yl)-4-methylthiophene-3-carboxylic acid (110 mg) as an off-white solid. $^1$H NMR (400 MHz, CDCl$_3$) δ 1.11-1.30 (m, 1H), 1.41-2.05 (m, 20H), 2.35 (s, 3H), 2.50-2.67 (m, 2H), 2.74-2.90 (m, 1H), 3.19-3.31 (m, 1H), 3.45 (dt, J=9.22, 5.62 Hz, 1H), 7.91 (s, 1H). MS(ES) [M+H]$^+$ 395.1.

g) tert-Butyl 4-(1-(4-(((4,6-dimethyl-2-oxo-1,2-dihydropyridin-3-yl)methyl)carbamoyl)-3-methylthiophen-2-yl)pyrrolidin-2-yl)piperidine-1-carboxylate

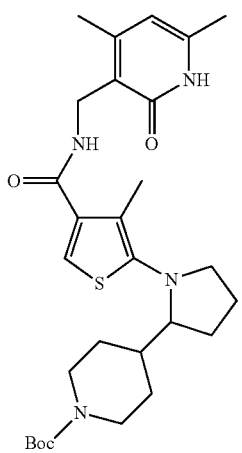 [SMILES: Cc1cc(C)c(CNC(=O)c2csc(N3CCCC3C3CCN(C(=O)OC(C)(C)C)CC3)c2C)c(=O)[nH]1]

To a solution of 5-(2-(1-(tert-butoxycarbonyl)piperidin-4-yl)pyrrolidin-1-yl)-4-methylthiophene-3-carboxylic acid (110 mg, 0.279 mmol) in DMSO (3 mL) were added 3-(aminomethyl)-4,6-dimethylpyridin-2(1H)-one hydrochloride (68.4 mg, 0.362 mmol), NMM (0.184 mL, 1.673 mmol), EDC (107 mg, 0.558 mmol) and HOAt (76 mg, 0.558 mmol). The mixture was stirred at RT for 18 h. The reaction mixture was quenched with water. The precipitate was collected by filtration, washed with water, and dried under vacuum to give tert-butyl 4-(1-(4-(((4,6-dimethyl-2-oxo-1,2-dihydropyridin-3-yl)methyl)carbamoyl)-3-methylthiophen-2-yl)pyrrolidin-2-yl)piperidine-1-carboxylate (120 mg) as an off-white solid. $^1$H NMR (400 MHz, CDCl$_3$) δ 1.10-1.23 (m, 1H), 1.41-2.02 (m, 20H), 2.27 (m, 6H), 2.40 (s, 3H), 2.49-2.67 (m, 2H), 2.70-2.83 (m, 1H), 3.16-3.27 (m, 1H), 3.40 (dt, J=9.16, 5.65 Hz, 1H), 4.47-4.56 (m, 2H), 5.95 (s, 1H), 7.19-7.36 (m, 3H). MS(ES) [M+H]$^+$ 529.2.

h) N-((4,6-Dimethyl-2-oxo-1,2-dihydropyridin-3-yl)methyl)-4-methyl-5-(2-(piperidin-4-yl)pyrrolidin-1-yl)thiophene-3-carboxamide hydrochloride

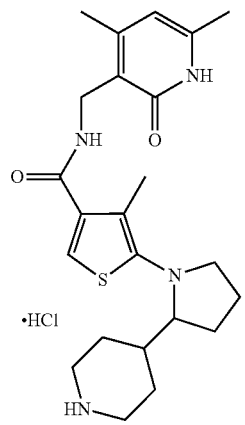 [SMILES: Cc1cc(C)c(CNC(=O)c2csc(N3CCCC3C3CCNCC3)c2C)c(=O)[nH]1 ; Cl]

To a suspension of tert-butyl 4-(1-(4-(((4,6-dimethyl-2-oxo-1,2-dihydropyridin-3-yl)methyl)carbamoyl)-3-methylthiophen-2-yl)pyrrolidin-2-yl)piperidine-1-carboxylate (120 mg, 0.227 mmol) in 1,4-dioxane (3 mL) was added 4 N HCl in dioxanes (1 mL, 4.00 mmol). The mixture was stirred at RT for 3 h. The mixture was concentrated and the residue was purified using reverse-phase HPLC. The fractions containing the product were combined, treated with 1 N HCl, and concentrated to give N-((4,6-dimethyl-2-oxo-1,2-dihydropyridin-3-yl)methyl)-4-methyl-5-(2-(piperidin-4-yl)pyrrolidin-1-yl)thiophene-3-carboxamide (55 mg) as its hydrochloride salt (pale brown solid). $^1$H NMR (400 MHz, DMSO-d$_6$) δ 1.34-1.52 (m, 2H) 1.60-2.01 (m, 8H) 2.13-2.34 (m, 9H) 2.63-2.83 (m, 3H) 3.12-3.41 (m, 4H) 4.18-4.33 (m, 2H) 5.67-5.85 (m, 1H) 6.06-6.15 (m, 1H) 7.54 (s, 1H) 8.33 (br. s., 1H) 8.67-9.02 (m, 2H). MS(ES) [M+H]$^+$ 429.2.

Example 69

5-([2,4'-Bipiperidin]-1-yl)-N-((4,6-dimethyl-2-oxo-1,2-dihydropyridin-3-yl)methyl)-4-methylthiophene-3-carboxamide hydrochloride

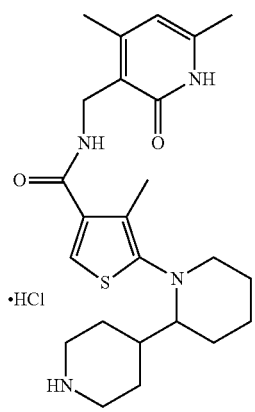 [SMILES: Cl ; Cc1cc(C)c(CNC(=O)c2csc(N3CCCCC3C3CCNCC3)c2C)c(=O)[nH]1]

a) tert-Butyl 4-(1-hydroxyhex-5-en-1-yl)piperidine-1-carboxylate

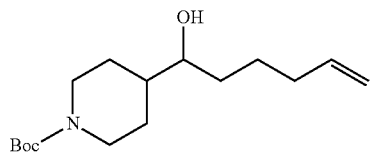 [SMILES: C=CCCCC(O)C1CCN(C(=O)OC(C)(C)C)CC1]

To a cooled (−78° C.) solution of tert-butyl 4-formylpiperidine-1-carboxylate (1 g, 4.69 mmol) in THF (20 mL) was added pent-4-en-1-ylmagnesium bromide (11.25 mL, 5.63 mmol) dropwise over 10 min. The mixture was maintained at −78° C. for 2 h. The reaction mixture was quenched with saturated NH₄Cl aqueous solution and extracted with EtOAc (3×). The extract was dried over Na₂SO₄ and concentrated. The residue was purified using column chromatography (silica gel, 0 to 80% EtOAc/hexanes) to give tert-butyl 4-(1-hydroxyhex-5-en-1-yl)piperidine-1-carboxylate (780 mg) as a pale yellow oil. $^1$H NMR (400 MHz, CDCl$_3$) δ 1.14-1.87 (m, 18H), 2.02-2.21 (m, 2H), 2.67 (m, 2H), 3.31-3.50 (m, 1H), 4.02-4.29 (m, 2H), 4.92-5.12 (m, 2H), 5.83 (ddt, J=16.99, 10.29, 6.57, 6.57 Hz, 1H). MS(ES) [M+H]$^+$ 284.2.

b) tert-Butyl 4-(1-bromohex-5-en-1-yl)piperidine-1-carboxylate

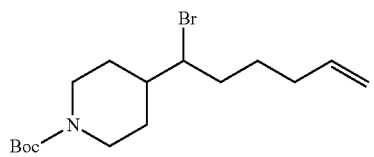 [SMILES: C=CCCCC(Br)C1CCN(C(=O)OC(C)(C)C)CC1]

To a cooled (0° C.) solution of tert-butyl 4-(1-hydroxyhex-5-en-1-yl)piperidine-1-carboxylate (770 mg, 2.72 mmol) and carbon tetrabromide (1171 mg, 3.53 mmol) in THF (12 mL) was added triphenylphosphine (926 mg, 3.53 mmol) portionwise. The mixture was stirred at RT for 18 h. The mixture was filtered and the filtrate was concentrated. The residue was purified using column chromatography (silica gel, 0 to 60% EtOAc/hexanes) to give tert-butyl 4-(1-bromohex-5-en-1-yl)piperidine-1-carboxylate (540 mg) as a colorless oil. $^1$H NMR (400 MHz, CDCl$_3$) δ 1.25-2.30 (m, 20H), 2.69 (br. s., 1H), 3.33-3.54 (m, 1H), 4.19 (br. s., 1H), 4.93-5.07 (m, 2H), 5.70-5.97 (m, 1H). MS(ES) [M+H]$^+$ 346.1, 348.1.

c) tert-Butyl 4-(1-bromo-5-oxopentyl)piperidine-1-carboxylate

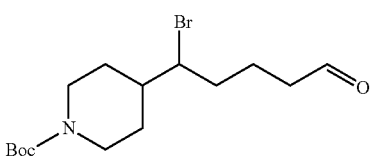 [SMILES: CC(C)(C)OC(=O)N1CCC(C(Br)CCCC=O)CC1]

To a solution of tert-butyl 4-(1-bromohex-5-en-1-yl)piperidine-1-carboxylate (530 mg, 1.530 mmol) in acetone (8 mL) and water (0.9 mL) were added NMO (215 mg, 1.837 mmol) and osmium tetroxide (2.5% in t-BuOH, 0.077 mL, 6.12 μmol). The mixture was stirred at RT for 18 h. The reaction was diluted with EtOAc and washed with water. The organic layer was dried over Na₂SO₄ and concentrated. The residue was treated with THF (6 mL) and water (3 mL). Sodium periodate (655 mg, 3.06 mmol) was added. The reaction mixture was stirred at RT for 1.5 h. The reaction mixture was quenched with water and extracted with EtOAc (3×). The extract was dried over Na₂SO₄ and concentrated to give tert-butyl 4-(1-bromo-5-oxopentyl)piperidine-1-carboxylate (480 mg) as a pale yellow oil. MS(ES) [M+Na]$^+$ 370.1, 372.1.

d) tert-Butyl 1-(4-(methoxycarbonyl)-3-methylthiophen-2-yl)-[2,4'-bipiperidine]-1'-carboxylate

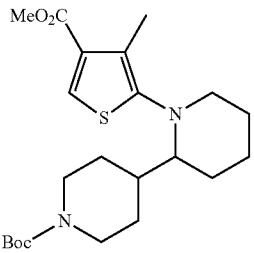 [SMILES: COC(=O)c1csc(N2CCCCC2C2CCN(C(=O)OC(C)(C)C)CC2)c1C]

To a solution of methyl 5-amino-4-methylthiophene-3-carboxylate (120 mg, 0.701 mmol) in MeOH (4 mL) were added tert-butyl 4-(1-bromo-5-oxopentyl)piperidine-1-carboxylate (269 mg, 0.771 mmol) and AcOH (0.040 mL, 0.701 mmol). The mixture was stirred at RT for 30 min. NaBH₃CN (176 mg, 2.80 mmol) was added and the mixture was heated at 65° C. for 7 h. The mixture was quenched with water and extracted with EtOAc (3×). The extract was dried over Na₂SO₄ and concentrated. The residue was purified using column chromatography (silica gel, 0 to 60% EtOAc/hexanes) to give tert-butyl 1-(4-(methoxycarbonyl)-3-methylthiophen-2-yl)-[2,4'-bipiperidine]-1'-carboxylate (84 mg) as a pale yellow oil. $^1$H NMR (400 MHz, CDCl$_3$) δ 1.09-1.87 (m, 20H), 2.28-2.73 (m, 8H), 3.02 (m, 1H), 3.86 (m, 4H), 4.76-4.79 (m, 1H), 7.91 (s, 1H). MS(ES) [M+H]$^+$ 423.2.

e) 5-(1'-(tert-Butoxycarbonyl)-[2,4'-bipiperidin]-1-yl)-4-methylthiophene-3-carboxylic acid

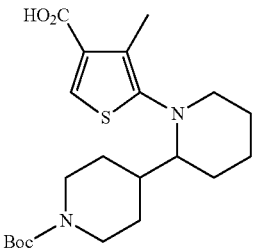 [SMILES: Cc1c(C(=O)O)csc1N1CCCCC1C1CCN(C(=O)OC(C)(C)C)CC1]

To a solution of tert-butyl 1-(4-(methoxycarbonyl)-3-methylthiophen-2-yl)-[2,4'-bipiperidine]-1'-carboxylate (56 mg, 0.133 mmol) in MeOH (3 mL) was added NaOH (0.166 mL, 0.663 mmol). The mixture was heated at 40° C. for 18 h. The mixture was concentrated to remove the MeOH. The remaining aqueous solution was acidified using 1 N HCl and the precipitate was collected by filtration and dried under vacuum to give 5-(1'-(tert-butoxycarbonyl)-[2,4'-bipiperidin]-1-yl)-4-methylthiophene-3-carboxylic acid (50 mg) as an off-white solid. $^1$H NMR (400 MHz, CDCl$_3$) δ 1.14-2.30 (m, 20H), 2.30-2.70 (m, 8H), 3.05-3.07 (m, 1H), 4.03-4.17 (m, 1H), 8.03 (s, 1H). MS(ES) [M+H]$^+$409.2.

f) tert-Butyl 1-(4-(((4,6-dimethyl-2-oxo-1,2-dihydropyridin-3-yl)methyl)carbamoyl)-3-methylthiophen-2-yl)-[2,4'-bipiperidine]-1'-carboxylate

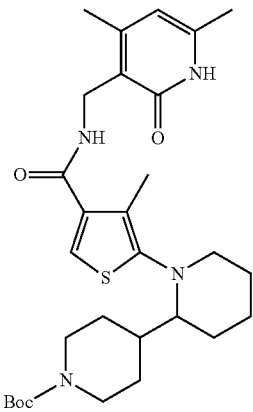 [SMILES: Cc1cc(C)c(CNC(=O)c2csc(N3CCCCC3C3CCN(C(=O)OC(C)(C)C)CC3)c2C)c(=O)[nH]1]

To a solution of 5-(1'-(tert-butoxycarbonyl)-[2,4'-bipiperidin]-1-yl)-4-methylthiophene-3-carboxylic acid (50 mg, 0.122 mmol) in DMSO (2 mL) were added 3-(aminomethyl)-4,6-dimethylpyridin-2(1H)-one hydrochloride (30.0 mg, 0.159 mmol), NMM (0.067 mL, 0.612 mmol), EDC (46.9 mg, 0.245 mmol) and HOAt (33.3 mg, 0.245 mmol). The mixture was stirred at RT for 18 h. The reaction was quenched with water. The precipitate was collected by filtration, washed with water and dried under vacuum to give tert-butyl 1-(4-(((4,6-dimethyl-2-oxo-1,2-dihydropyridin-3-yl)methyl)carbamoyl)-3-methylthiophen-2-yl)-[2,4'-bipiperidine]-1'-carboxylate (53 mg) as an off-white solid. $^1$H NMR (400 MHz, DMSO-d$_6$) δ 0.93-1.18 (m, 2H), 1.36 (s, 15H), 1.48-1.73 (m, 5H), 2.08-2.24 (m, 10H), 2.93 (d, J=11.37 Hz, 1H), 3.91 (d, J=11.37 Hz, 2H), 4.17-4.29 (m, 2H), 5.86 (s, 1H), 7.62 (s, 1H), 7.95 (t, J=5.05 Hz, 1H). MS(ES) [M+H]$^+$ 543.6.

g) 5-([2,4'-Bipiperidin]-1-yl)-N-((4,6-dimethyl-2-oxo-1,2-dihydropyridin-3-yl)methyl)-4-methylthiophene-3-carboxamide hydrochloride

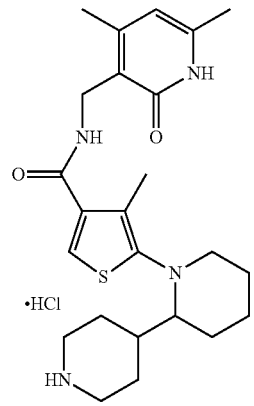 [SMILES: Cc1cc(C)c(CNC(=O)c2csc(N3CCCCC3C3CCNCC3)c2C)c(=O)[nH]1 ; Cl]

To a solution of tert-butyl 1-(4-(((4,6-dimethyl-2-oxo-1,2-dihydropyridin-3-yl)methyl)carbamoyl)-3-methylthiophen-2-yl)-[2,4'-bipiperidine]-1'-carboxylate (51 mg, 0.094 mmol) in DCM (2 mL) was added TFA (0.5 mL, 6.49 mmol). The mixture was stirred at RT for 5 h. The mixture was concentrated and the residue was purified using reverse-phase HPLC. The fractions containing the product were treated with 1 N HCl and concentrated to give 5-([2,4'-bipiperidin]-1-yl)-N-((4,6-dimethyl-2-oxo-1,2-dihydropyridin-3-yl)methyl)-4-methylthiophene-3-carboxamide (29 mg) as its hydrochloride salt (off-white solid). $^1$H NMR (400 MHz, DMSO-d$_6$) δ 1.31-1.83 (m, 10H), 2.09-2.25 (m, 8H), 2.62-2.77 (m, 1H), 2.94 (d, J=11.87 Hz, 1H), 3.20 (d, J=11.37 Hz, 2H), 4.17-4.33 (m, 2H), 5.93 (s, 1H), 7.68 (s, 1H), 8.07 (br. s., 1H). MS(ES) [M+H]$^+$ 443.2.

Example 70

N-((4,6-Dimethyl-2-oxo-1,2-dihydropyridin-3-yl)methyl)-4-methyl-5-(1,2,3,4-tetrahydroisoquinolin-5-yl)thiophene-3-carboxamide hydrochloride

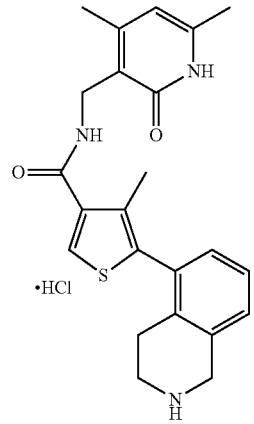 [SMILES: Cc1cc(C)c(CNC(=O)c2csc(-c3cccc4c3CCNC4)c2C)c(=O)[nH]1 ; Cl]

a) 5-Bromo-4-methylthiophene-3-carboxylic acid

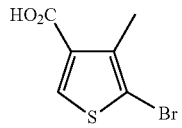

To a solution of methyl 5-bromo-4-methylthiophene-3-carboxylate (350 mg, 1.489 mmol) in MeOH (8 mL) was added 4 N NaOH (1.861 mL, 7.44 mmol). The mixture was stirred at RT for 4 h. The mixture was concentrated. The residue was treated with water, acidified using 1 N HCl and extracted with EtOAc (3×). The extract was dried over Na$_2$SO$_4$ and concentrated. The residue was dried under vacuum to give 5-bromo-4-methylthiophene-3-carboxylic acid (320 mg) as a white solid. $^1$H NMR (400 MHz, DMSO-d$_6$) δ 2.48 (s, 3H), 8.24 (s, 1H). MS(ES) [M+H]$^+$ 220.8, 222.8.

b) 5-Bromo-N-((4,6-dimethyl-2-oxo-1,2-dihydropyridin-3-yl)methyl)-4-methylthiophene-3-carboxamide

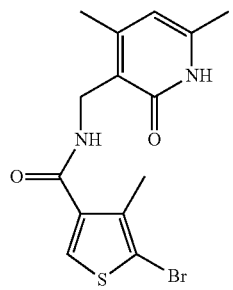 [SMILES: Cc1cc(C)c(CNC(=O)c2csc(Br)c2C)c(=O)[nH]1]

To a solution of 5-bromo-4-methylthiophene-3-carboxylic acid (320 mg, 1.447 mmol) in DMSO (8 mL) were added 3-(aminomethyl)-4,6-dimethylpyridin-2(1H)-one hydrochloride (355 mg, 1.882 mmol), NMM (0.955 mL, 8.68 mmol), EDC (555 mg, 2.89 mmol) and HOAt (394 mg, 2.89 mmol). The mixture was stirred at RT for 18 h. The reaction mixture was quenched with water and the precipitate was collected by filtration and dried under vacuum to give 5-bromo-N-((4,6-dimethyl-2-oxo-1,2-dihydropyridin-3-yl)methyl)-4-methylthiophene-3-carboxamide (460 mg) as a white solid. $^1$H NMR (400 MHz, DMSO-d$_6$) δ 2.11 (s, 3H), 2.17 (s, 3H), 2.23 (s, 3H), 4.23 (d, J=5.05 Hz, 2H), 5.86 (s, 1H), 7.93 (s, 1H), 8.18 (t, J=4.93 Hz, 1H), 11.49 (br. s., 1H). MS(ES) [M+H]$^+$ 355.0, 357.0.

c) tert-Butyl 5-(4-(((4,6-dimethyl-2-oxo-1,2-dihydropyridin-3-yl)methyl)carbamoyl)-3-methylthiophen-2-yl)-3,4-dihydroisoquinoline-2(1H)-carboxylate

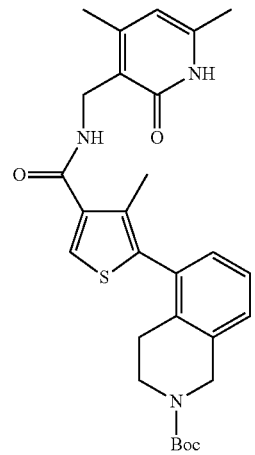 [SMILES: Cc1cc(C)c(CNC(=O)c2csc(-c3cccc4c3CCN(C(=O)OC(C)(C)C)C4)c2C)c(=O)[nH]1]

To a 10 mL microwave tube were added 5-bromo-N-((4,6-dimethyl-2-oxo-1,2-dihydropyridin-3-yl)methyl)-4-methylthiophene-3-carboxamide (60 mg, 0.169 mmol), tert-butyl 5-(4,4,5,5-tetramethyl-1,3,2-dioxaborolan-2-yl)-3,4-dihydroisoquinoline-2(1H)-carboxylate (79 mg, 0.220 mmol), DMF (2 mL), and 2 M Na$_2$CO$_3$ (0.338 mL, 0.676 mmol). The mixture was degassed for 5 min by bubbling nitrogen. Pd(PPh$_3$)$_4$ (19.52 mg, 0.017 mmol) was added and the tube was sealed. The mixture was heated at 80° C. in a microwave reactor for 9 h. The mixture was allowed to cool, diluted with water, and extracted with EtOAc (3×). The extract was dried over Na$_2$SO$_4$ and concentrated. The residue was purified using column chromatography (silica gel, 0 to 100% EtOAc/hexanes) to give tert-butyl 5-(4-(((4,6-dimethyl-2-oxo-1,2-dihydropyridin-3-yl)methyl)carbamoyl)-3-methylthiophen-2-yl)-3,4-dihydroisoquinoline-2(1H)-carboxylate (31 mg) as a pale yellow solid. $^1$H NMR (400 MHz, CDCl$_3$) δ 1.50 (s, 9H), 1.68 (br. s., 3H), 2.16 (s, 3H), 2.29 (s, 3H), 2.42 (s, 3H), 2.60 (m, 2H), 3.56 (br. s., 2H), 4.46-4.72 (m, 4H), 5.99 (s, 1H), 7.06-7.27 (m, 3H), 7.44 (br.s. 1H), 7.64 (s, 1H). MS(ES) [M+H]$^+$ 508.2.

d) N-((4,6-Dimethyl-2-oxo-1,2-dihydropyridin-3-yl)methyl)-4-methyl-5-(1,2,3,4-tetrahydroisoquinolin-5-yl)thiophene-3-carboxamide hydrochloride

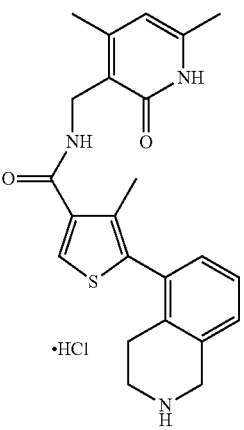 [SMILES: Cc1cc(C)c(CNC(=O)c2csc(-c3cccc4c3CCNC4)c2C)c(=O)[nH]1 ; Cl]

To a solution of tert-butyl 5-(4-(((4,6-dimethyl-2-oxo-1,2-dihydropyridin-3-yl)methyl)carbamoyl)-3-methylthiophen-2-yl)-3,4-dihydroisoquinoline-2(1H)-carboxylate (31 mg, 0.061 mmol) in DCM (3 mL) was added TFA (400 μL, 5.19 mmol). The mixture was stirred at RT for 2 h. The mixture was concentrated and the residue was re-dissolved in THF (2 mL), treated with 1 N HCl and concentrated. The residue was dried under vacuum to give N-((4,6-Dimethyl-2-oxo-1,2-dihydropyridin-3-yl)methyl)-4-methyl-5-(1,2,3,4-tetrahydroisoquinolin-5-yl)thiophene-3-carboxamide (27 mg) as its hydrochloride salt (pale brown solid). ¹H NMR (400 MHz, DMSO-d₆) δ 2.05 (s, 3H), 2.13 (s, 3H), 2.21 (s, 3H), 2.67 (t, J=6.06 Hz, 2H), 3.32 (br. s., 2H), 4.21-4.41 (m, 4H), 5.91 (s, 1H), 7.21 (dd, J=6.95, 1.64 Hz, 1H), 7.28-7.43 (m, 2H), 8.18 (t, J=4.93 Hz, 1H). MS(ES) [M+H]⁺ 443.2.

Example 71

(Z)-N-((4,6-Dimethyl-2-oxo-1,2-dihydropyridin-3-yl)methyl)-4-methyl-5-(5-morpholinopent-2-en-3-yl)thiophene-3-carboxamide

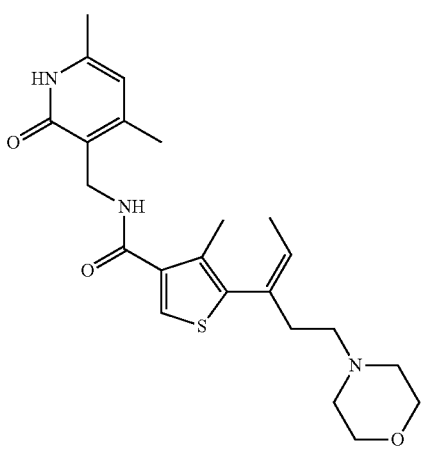 [SMILES: C/C=C(/CCN1CCOCC1)c1scc(C(=O)NCc2c(C)cc(C)[nH]c2=O)c1C]

a) Methyl 5-(3-chloropropanoyl)-4-methylthiophene-3-carboxylate

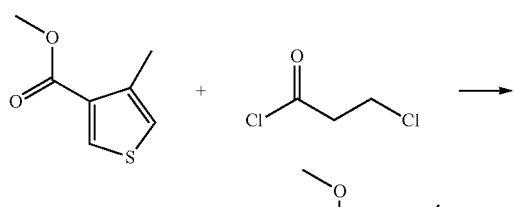

To a cooled (0° C.) mixture of aluminum chloride (186 mg, 1.398 mmol) in DCM (30 mL) was added dropwise a solution of 3-chloropropanoyl chloride (0.123 mL, 1.282 mmol) in DCM (5 mL), followed by dropwise a solution of methyl 4-methylthiophene-3-carboxylate (182 mg, 1.165 mmol) in DCM (5 mL). The reaction was stirred for 16 h.

LCMS showed 10% conversion. To the reaction was added additional aluminum chloride (186 mg, 1.398 mmol) and 3-chloropropanoyl chloride (0.123 mL, 1.282 mmol). The reaction was stirred for 16 h, at which time it was washed with water, dried over MgSO₄, filtered and concentrated under reduced pressure to give methyl 5-(3-chloropropanoyl)-4-methylthiophene-3-carboxylate (265 mg, 1.07 mmol, 92% yield). ¹H NMR (400 MHz, CDCl3) δ 2.85 (s, 3H) 3.36 (t, J=6.69 Hz, 2H) 3.86-4.01 (m, 5H) 8.27 (s, 1H). MS(ES) [M+H]⁺ 246.9.

b) Methyl 4-methyl-5-(3-morpholinopropanoyl)thiophene-3-carboxylate

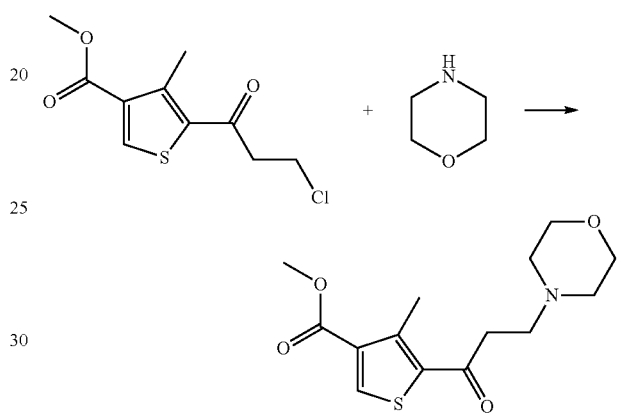

A mixture of methyl 5-(3-chloropropanoyl)-4-methylthiophene-3-carboxylate (248 mg, 1.005 mmol) and morpholine (4 mL, 45.9 mmol) was heated in a microwave reactor at 150° C. for 5 min. The mixture was concentrated under reduced pressure and diluted with water. The mixture was extracted with DCM, washed with brine, dried over MgSO₄, filtered and concentrated under reduced pressure. The residue was purified via Biotage®(0% to 100% EtOAc:Hex; 10 g-HP-silica gel column) to give methyl 4-methyl-5-(3-morpholinopropanoyl)thiophene-3-carboxylate (187 mg, 0.69 mmol, 62.6% yield) as a solid. ¹H NMR (400 MHz, CDCl3) δ 2.53 (br. s., 4H) 2.78-2.95 (m, 5H) 3.08 (t, J=6.82 Hz, 2H) 3.73 (t, J=4.29 Hz, 4H) 3.89 (s, 3H) 8.24 (s, 1H). MS(ES) [M+H]⁺ 298.0.

c) (Z)-Methyl 4-methyl-5-(5-morpholinopent-2-en-3-yl)thiophene-3-carboxylate

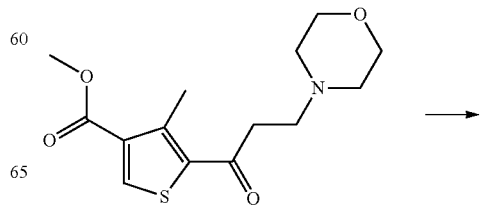

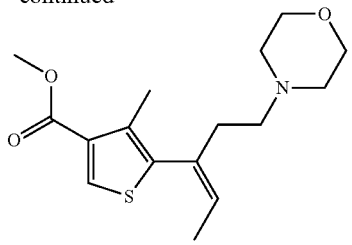

To a cooled (0° C.) solution of ethyltriphenylphosphonium bromide (278 mg, 0.748 mmol) was added dropwise 1 N t-BuOK (740 µL, 0.740 mmol). The reaction was stirred at RT for 1 h. The reaction mixture was cooled in a dry ice/acetone bath and methyl 4-methyl-5-(3-morpholinopropanoyl)thiophene-3-carboxylate (187 mg, 0.629 mmol) was added dropwise. The reaction was stirred at RT for 16 h, at which time it was concentrated under reduced pressure. The residue was purified via Biotage® (0% to 100% EtOAc: Hex; 25 g-HP-silica gel column) to give (Z)-methyl 4-methyl-5-(5-morpholinopent-2-en-3-yl)thiophene-3-carboxylate (172 mg, 0.566 mmol, 88% yield) as an oil. $^1$H NMR (400 MHz, CDCl3) δ 1.51 (d, J=6.82 Hz, 3H) 2.27 (s, 3H) 2.31-2.66 (m, 8H) 3.71 (br. s., 4H) 3.82-4.02 (m, 3H) 5.76-6.02 (m, 1H) 8.07 (s, 1H). MS(ES) [M+H]$^+$ 310.1.

d) (Z)-4-Methyl-5-(5-morpholinopent-2-en-3-yl)thiophene-3-carboxylic acid

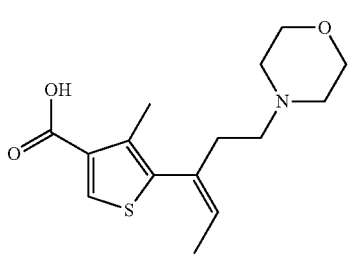

A solution of (Z)-methyl 4-methyl-5-(5-morpholinopent-2-en-3-yl)thiophene-3-carboxylate (45 mg, 0.145 mmol) and 1 N NaOH (0.218 mL, 0.218 mmol) in EtOH (10 mL) and water (10 mL) was heated at reflux for 5 h, at which time it was concentrated under reduced pressure. The residue was purified by RP-HPLC (Gilson®, Gemini NX 5u C18 110A, AXI, 100×30 mm, 5 micron, 7 min gradient: 5% CH$_3$CN/H$_2$O/0.1% formic acid to 50% CH$_3$CN/H$_2$O/0.1% formic acid) to give (Z)-4-methyl-5-(5-morpholinopent-2-en-3-yl)thiophene-3-carboxylic acid (24 mg, 0.84 mmol, 57.7% yield). $^1$H NMR (400 MHz, CDCl3) δ 11.13-12.21 (m, 1H), 8.49 (s, 1H), 8.02 (s, 1H), 5.84 (q, J=6.74 Hz, 1H), 3.85 (t, J=4.67 Hz, 4H), 2.57-3.05 (m, 8H), 2.18 (s, 3H), 1.51 (d, J=6.82 Hz, 3H). MS(ES) [M+H]$^+$ 296.0.

e) (Z)-N-((4,6-Dimethyl-2-oxo-1,2-dihydropyridin-3-yl)methyl)-4-methyl-5-(5-morpholinopent-2-en-3-yl)thiophene-3-carboxamide

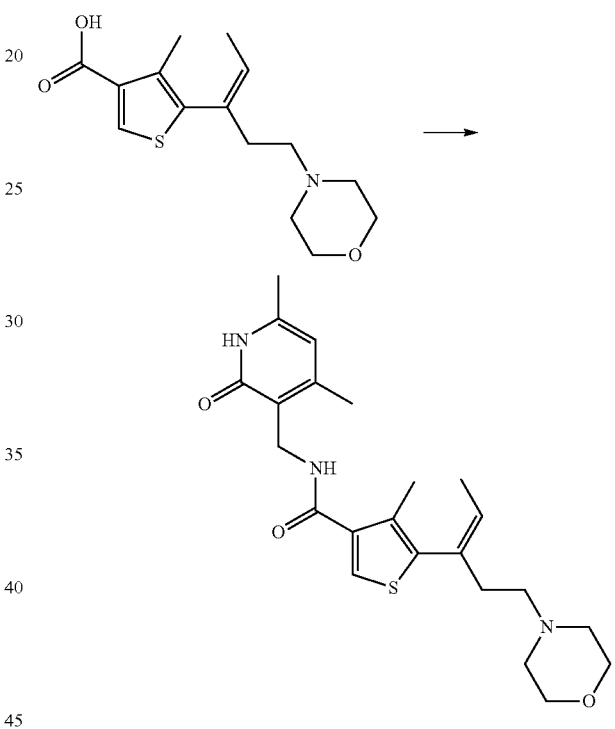

To a solution of (Z)-4-methyl-5-(5-morpholinopent-2-en-3-yl)thiophene-3-carboxylic acid (24.8 mg, 0.084 mmol) in DMSO (20 mL) was added 3-(aminomethyl)-4,6-dimethylpyridin-2(1H)-one hydrochloride (20.59 mg, 0.109 mmol), NMM (0.046 mL, 0.420 mmol), HOAt (22.85 mg, 0.168 mmol) and EDC (32.2 mg, 0.168 mmol). The mixture was stirred at RT for 18 h. The mixture was quenched with water and extracted with DCM. The DCM extracts were washed with water, dried over MgSO$_4$, filtered and concentrated under vacuum to give (Z)-N-((4,6-dimethyl-2-oxo-1,2-dihydropyridin-3-yl)methyl)-4-methyl-5-(5-morpholinopent-2-en-3-yl)thiophene-3-carboxamide (28 mg, 0.065 mmol, 78% yield) as a white solid. $^1$H NMR (400 MHz, CDCl3) δ 11.60 (br. s., 1H), 7.56 (s, 1H), 7.39 (t, J=5.81 Hz, 1H), 5.97 (s, 1H), 5.80 (d, J=6.06 Hz, 1H), 4.53 (d, J=5.81 Hz, 2H), 3.71 (br. s., 4H), 2.41 (s, 11H), 2.28 (s, 3H), 2.21 (s, 3H), 1.49 (d, J=6.57 Hz, 3H). MS(ES) [M+H]$^+$ 430.1.

Example 72

(Z)-N-((4,6-Dimethyl-2-oxo-1,2-dihydropyridin-3-yl)methyl)-4-methyl-5-(6-(4-methylpiperazin-1-yl)hex-2-en-3-yl)thiophene-3-carboxamide

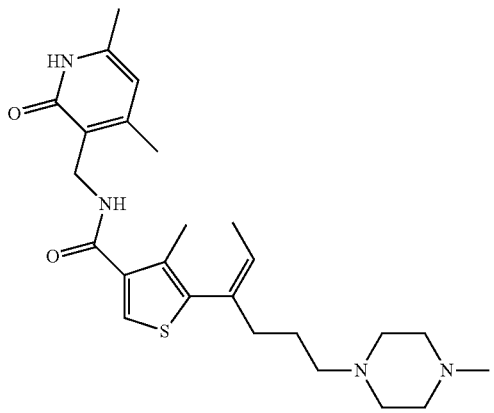

a) Methyl 4-methylthiophene-3-carboxylate

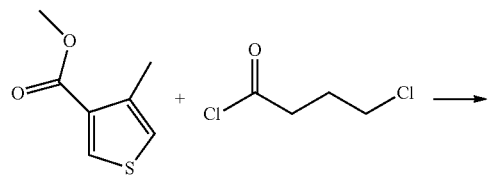

To a cooled (0° C.) mixture of aluminum chloride (4.10 g, 30.7 mmol) in DCM (30 mL) was added a solution of 4-chlorobutanoyl chloride (3.07 mL, 28.8 mmol) in DCM (5 mL), followed by dropwise addition of a solution of methyl 4-methylthiophene-3-carboxylate (3 g, 19.21 mmol) in DCM (5 mL). The reaction was stirred for 16 h, at which time LCMS showed 50% conversion. To the mixture was added aluminum chloride (4.10 g, 30.7 mmol) and 4-chlorobutanoyl chloride (3.07 mL, 28.8 mmol). The reaction was stirred for 16 h. The reaction was poured onto ice and the phases separated. The organic layer was washed with water, dried over MgSO$_4$, filtered and concentrated under reduced pressure. The residue was purified via Biotage® (0% to 100% DCM:Hex; 50 g-HP-silica gel column). The residue was triturated with heptane to give methyl 4-methylthiophene-3-carboxylate (5.3 g, 10.09 mmol, 52.5% yield) as a grey solid. $^1$H NMR (400 MHz, CDCl3) δ 8.24 (s, 1H), 3.90 (s, 3H), 3.69 (t, J=6.19 Hz, 2H), 3.09 (t, J=6.95 Hz, 2H), 2.84 (s, 3H), 2.24 (quin, J=6.57 Hz, 2H). MS(ES) [M+H]$^+$ 260.9.

b) Methyl 4-methyl-5-(4-(4-methylpiperazin-1-yl)butanoyl)thiophene-3-carboxylate

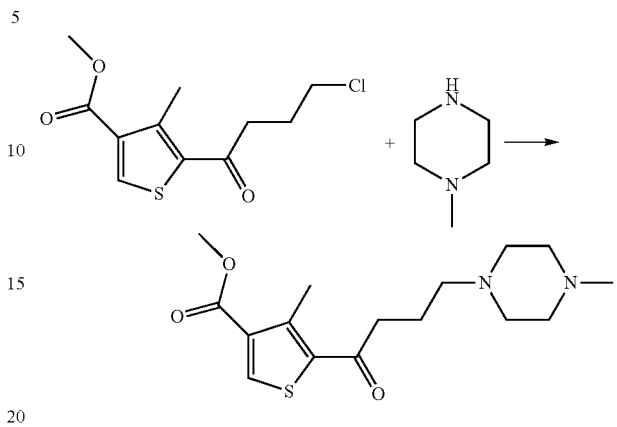

A mixture of methyl 5-(4-chlorobutanoyl)-4-methylthiophene-3-carboxylate (1.30 g, 4.99 mmol) and 1-methylpiperazine (3 mL, 4.99 mmol) was heated at 150° C. in a microwave reactor for 5 min, at which time it was concentrated under reduced pressure. The residue was diluted with DCM and washed with water, dried over MgSO$_4$, filtered and concentrated. The residue was purified via Biotage® (0% to 20% MeOH:DCM; 50 g-HP-silica gel column) to give methyl 4-methyl-5-(4-(4-methylpiperazin-1-yl)butanoyl)thiophene-3-carboxylate (645 mg, 1.988 mmol, 39.9% yield) as a off white solid. $^1$H NMR (400 MHz, CDCl3) δ 8.21 (s, 1H), 3.89 (s, 3H), 2.89 (t, J=6.95 Hz, 2H), 2.83 (s, 3H), 2.43 (t, J=7.07 Hz, 2H), 2.29 (s, 3H), 1.96 (quin, J=7.01 Hz, 2H). MS(ES) [M+H]$^+$ 325.1.

c) (Z)-Methyl 4-methyl-5-(6-(4-methylpiperazin-1-yl)hex-2-en-3-yl)thiophene-3-carboxylate

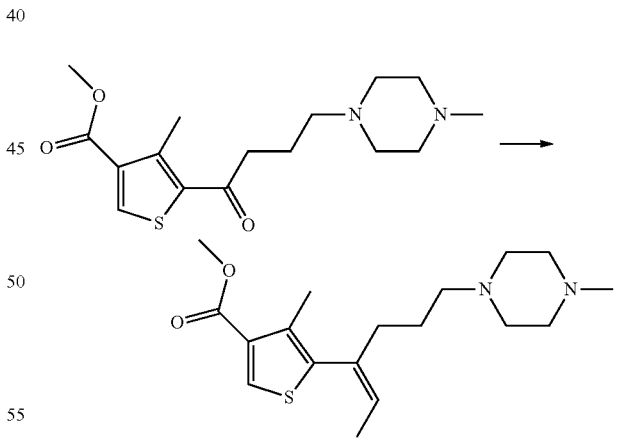

To a cooled (0° C.) solution of ethyltriphenylphosphonium bromide (1613 mg, 4.35 mmol) was added dropwise 1 N t-BuOK (4.35 mL, 4.35 mmol). The reaction was stirred at RT for 1 h. The reaction mixture was cooled in a dry ice/acetone bath and methyl 4-methyl-5-(4-(4-methylpiperazin-1-yl)butanoyl)thiophene-3-carboxylate (470 mg, 1.449 mmol) was added dropwise. The reaction was stirred at 0° C. for 3 h, at which time it was concentrated under reduced pressure. The residue was diluted with DCM, washed with water, dried over MgSO$_4$, filtered and concentrated under vacuum. The residue was purified via Biotage® (0% to 100% EtOAc:Hex then 0 to 15% MeOH; DCM; 25 g-HP-silica gel column) to give (Z)-methyl 4-methyl-5-(6-(4-methylpiperazin-1-yl)hex-2-en-3-yl)thiophene-3-carboxylate (471 mg, 1.399 mmol, 96% yield) as a oil. MS(ES) [M+H]+ 337.1 77% pure.

d) (Z)-4-Methyl-5-(6-(4-methylpiperazin-1-yl)hex-2-en-3-yl)thiophene-3-carboxylic acid hydrochloride

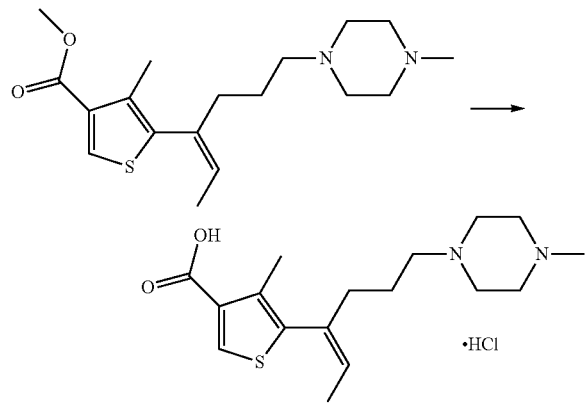

A solution of (Z)-methyl 4-methyl-5-(6-(4-methylpiperazin-1-yl)hex-2-en-3-yl)thiophene-3-carboxylate (270 mg, 0.743 mmol) and 1 N NaOH (0.218 mL, 0.218 mmol) in EtOH (10 mL) and water (10 mL) was heated at reflux for 2 h, at which time it was concentrated under reduced pressure. To the residue was added 1 N HCl until the mixture was acidic. The mixture was concentrated to give (Z)-4-methyl-5-(6-(4-methylpiperazin-1-yl)hex-2-en-3-yl)thiophene-3-carboxylic acid hydrochloride (250 mg, 0.775 mmol, 96% yield) as a solid. $^1$H NMR (400 MHz, D$_2$O) δ 8.12-8.22 (m, 1H), 5.82 (q, J=6.65 Hz, 1H), 3.26-4.06 (m, 8H), 3.05-3.25 (m, 2H), 2.93 (d, J=2.78 Hz, 3H), 2.33 (t, J=7.20 Hz, 2H), 2.11 (s, 3H), 1.60-1.80 (m, 2H), 1.38 (d, J=6.82 Hz, 3H). MS(ES) [M+H]+ 323.1.

e) (Z)-N-((4,6-Dimethyl-2-oxo-1,2-dihydropyridin-3-yl)methyl)-4-methyl-5-(6-(4-methylpiperazin-1-yl)hex-2-en-3-yl)thiophene-3-carboxamide

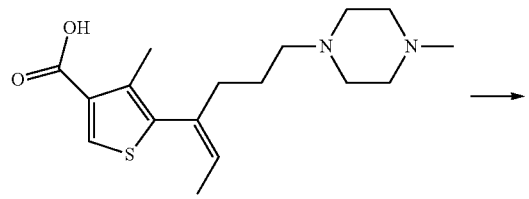

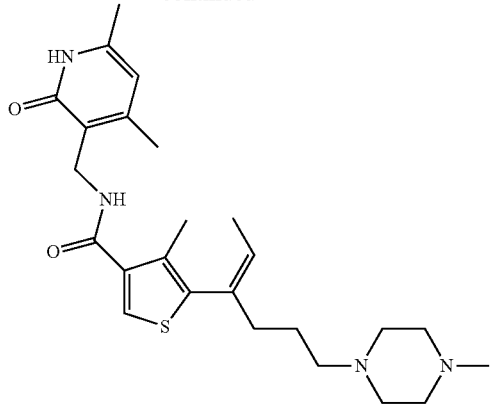 [SMILES: C/C=C(/CCCN1CCN(C)CC1)c1scc(C(=O)NCc2c(C)cc(C)[nH]c2=O)c1C]

To a solution of (Z)-4-methyl-5-(6-(4-methylpiperazin-1-yl)hex-2-en-3-yl)thiophene-3-carboxylic acid hydrochloride (250 mg, 0.697 mmol) in DMSO (20 mL) was added 3-(aminomethyl)-4,6-dimethylpyridin-2(1H)-one hydrochloride (171 mg, 0.905 mmol), NMM (0.613 mL, 5.57 mmol), HOAt (190 mg, 1.393 mmol) and EDC (267 mg, 1.393 mmol). The mixture was stirred at RT for 3 h. The residue was purified by RP-HPLC (Gilson®, Gemini NX 5u C18 110A, AXIA, 100×30 mm, 5 micron, 7 minute gradient: 5% CH$_3$CN/H$_2$O/0.1% formic acid to 40% CH$_3$CN/H$_2$O/0.1% formic acid) to give (Z)-N-((4,6-dimethyl-2-oxo-1,2-dihydropyridin-3-yl)methyl)-4-methyl-5-(6-(4-methylpiperazin-1-yl)hex-2-en-3-yl)thiophene-3-carboxamide (173 mg, 0.379 mmol, 54.4% yield) as a solid. $^1$H NMR (400 MHz, CDCl3) δ 8.40 (s, 1H), 7.56 (s, 1H), 7.32-7.47 (m, 1H), 6.00 (s, 1H), 5.74 (q, J=6.65 Hz, 1H), 4.52 (d, J=5.81 Hz, 2H), 2.65-3.06 (m, 8H), 2.54 (s, 3H), 2.38-2.50 (m, 5H), 2.26-2.36 (m, 5H), 2.18 (s, 3H), 1.45-1.62 (m, 5H). MS(ES) [M+H]+ 457.2.

Example 73

N-((4,6-Dimethyl-2-oxo-1,2-dihydropyridin-3-yl)methyl)-4-methyl-5-(6-(4-methylpiperazin-1-yl)hexan-3-yl)thiophene-3-carboxamide

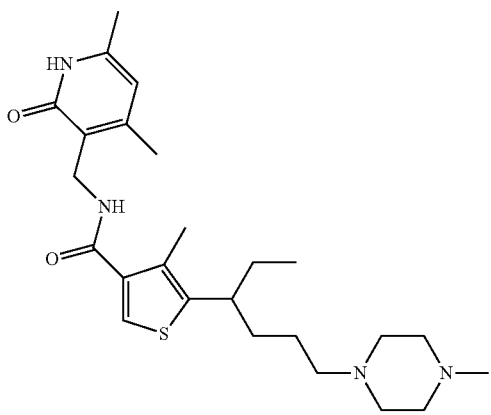 [SMILES: CCC(CCCN1CCN(C)CC1)c1scc(C(=O)NCc2c(C)cc(C)[nH]c2=O)c1C]

a) Methyl 4-methyl-5-(6-(4-methylpiperazin-1-yl)hexan-3-yl)thiophene-3-carboxylate

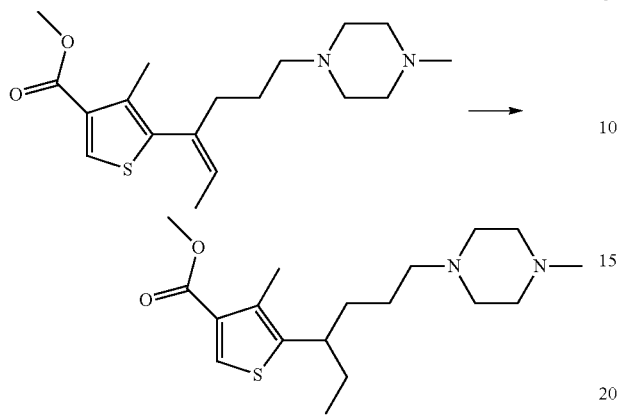

A mixture of (Z)-methyl 4-methyl-5-(6-(4-methylpiperazin-1-yl)hex-2-en-3-yl)thiophene-3-carboxylate (157 mg) in MeOH was hydrogenated on an H-Cube® (Pd/C, 100 bar, 50° C.) for 7 hours per day over 4 days to give methyl 4-methyl-5-(6-(4-methylpiperazin-1-yl)hexan-3-yl)thiophene-3-carboxylate (157 mg, 0.464 mmol, 67.6% yield) as an oil. $^1$H NMR (400 MHz, CDCl3) δ 7.95 (s, 1H), 3.78-3.93 (m, 3H), 2.50-2.93 (m, 10H), 2.32-2.45 (m, 9H), 1.64-1.81 (m, 2H), 1.32-1.61 (m, 5H), 0.80 (t, J=7.45 Hz, 3H). MS(ES) [M+H]$^+$ 339.2.

b) N-((4,6-Dimethyl-2-oxo-1,2-dihydropyridin-3-yl)methyl)-4-methyl-5-(6-(4-methylpiperazin-1-yl)hexan-3-yl)thiophene-3-carboxamide

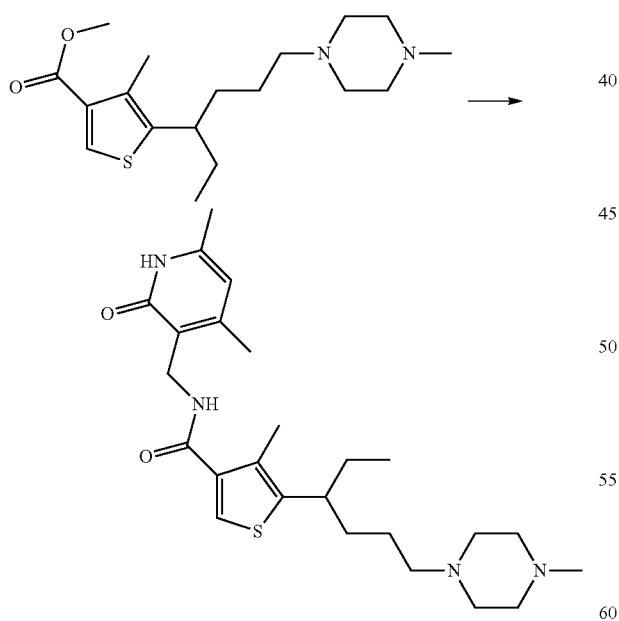

Following the general procedure of Example 72d and 72e, N-((4,6-dimethyl-2-oxo-1,2-dihydropyridin-3-yl)methyl)-4-methyl-5-(6-(4-methylpiperazin-1-yl)hexan-3-yl)thiophene-3-carboxamide (151 mg, 0.329 mmol, 71.0% yield) was prepared as a solid. $^1$H NMR (400 MHz, methanol-d$_4$) δ 8.38 (br. s., 1H), 7.60 (s, 1H), 6.13 (s, 1H), 4.32-4.64 (m, 2H), 3.37 (s, 2H), 2.91-3.10 (m, 5H), 2.82 (br. s., 3H), 2.55-2.66 (m, 5H), 2.37 (s, 3H), 2.26 (d, J=1.01 Hz, 6H), 1.70-1.95 (m, 2H), 1.34-1.64 (m, 4H), 0.84 (t, J=7.45 Hz, 3H). MS(ES) [M+H]$^+$ 459.3.

Example 74

(Z)-N-((4,6-Dimethyl-2-oxo-1,2-dihydropyridin-3-yl)methyl)-5-(6-(4-(dimethylamino)piperidin-1-yl)hex-2-en-3-yl)-4-methylthiophene-3-carboxamide formate

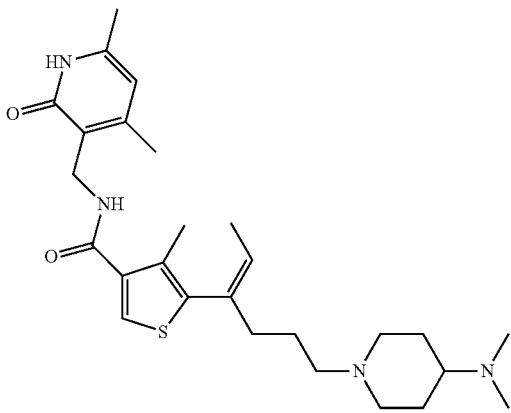 [SMILES: C/C=C(/CCCN1CCC(N(C)C)CC1)c1scc(C(=O)NCc2c(C)cc(C)[nH]c2=O)c1C]

Following the general procedure of Example 72, (Z)-N-((4,6-dimethyl-2-oxo-1,2-dihydropyridin-3-yl)methyl)-5-(6-(4-(dimethylamino)piperidin-1-yl)hex-2-en-3-yl)-4-methylthiophene-3-carboxamide (145 mg, 0.273 mmol, 69.8% yield) was prepared as its formic acid salt. $^1$H NMR (400 MHz, methanol-d$_4$) δ 8.41 (s, 1H), 7.74 (s, 1H), 6.13 (s, 1H), 5.85 (q, J=6.82 Hz, 1H), 4.46 (s, 2H), 3.37 (s, 3H), 2.70-2.75 (m, 7H), 2.61-2.69 (m, 2H), 2.32-2.52 (m, 8H), 2.26 (s, 4H), 2.17 (s, 3H), 2.11 (d, J=12.88 Hz, 2H), 1.58-1.90 (m, 5H), 1.51 (d, J=6.82 Hz, 3H). MS(ES) [M+H]$^+$ 485.3.

Following the general procedures described within, the following compounds were prepared:

Example 75

N-((4,6-dimethyl-2-oxo-1,2-dihydropyridin-3-yl)methyl)-5-(ethyl(tetrahydro-2H-pyran-4-yl)amino)-2-(furan-3-yl)-4-methylthiophene-3-carboxamide

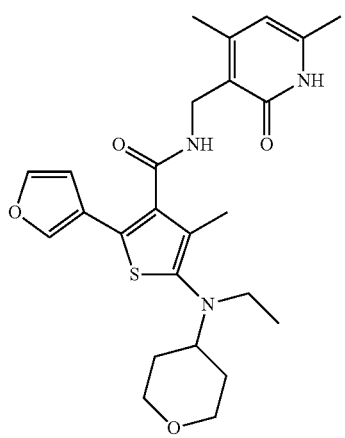 [SMILES: CCN(c1sc(-c2ccoc2)c(C(=O)NCc2c(C)cc(C)[nH]c2=O)c1C)C1CCOCC1]

207

$^1$H NMR (400 MHz, DMSO-d$_6$) δ 0.92 (t, J=6.95 Hz, 3H) 1.44 (m, J=12.00, 12.00, 12.00, 4.50 Hz, 2H) 1.72 (n, J=12.40, 1.80 Hz, 2H) 1.94 (s, 3H) 2.11 (s, 3H) 2.16 (s, 3H) 2.87-2.99 (m, 3H) 3.21-3.30 (m, 2H) 3.84 (m, J=11.40, 3.00 Hz, 2H) 4.24 (d, J=4.80 Hz, 2H) 5.85 (s, 1H) 6.56 (m, J=1.90, 0.90 Hz, 1H) 7.62 (t, J=1.64 Hz, 1H) 7.81 (m, J=1.50, 0.80 Hz, 1H) 8.22 (t, J=4.93 Hz, 1H) 11.47 (br. s., 1H). MS(ES) [M+H]$^+$ 470.4.

Example 76

N-((4,6-dimethyl-2-oxo-1,2-dihydropyridin-3-yl)methyl)-5-(ethyl(tetrahydro-2H-pyran-4-yl)amino)-2-(furan-2-yl)-4-methylthiophene-3-carboxamide

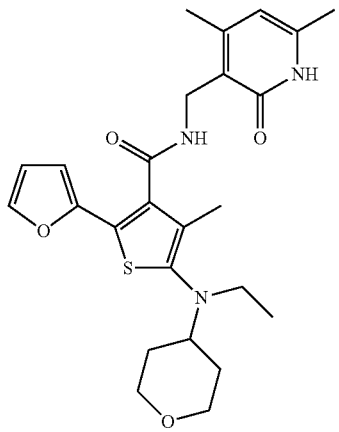 [SMILES: CCN(c1sc(-c2ccco2)c(C(=O)NCc2c(C)cc(C)[nH]c2=O)c1C)C1CCOCC1]

$^1$H NMR (400 MHz, DMSO-d$_6$) δ 0.92 (t, J=6.95 Hz, 3H) 1.38-1.50 (m, 2H) 1.69-1.76 (m, 2H) 1.94 (s, 3H) 2.11 (s, 3H) 2.19 (s, 3H) 2.89-3.00 (m, 3H) 3.22-3.31 (m, 2H) 3.84 (dd, J=11.49, 2.91 Hz, 2H) 4.27 (d, J=4.80 Hz, 2H) 5.86 (s, 1H) 6.44-6.49 (m, 2H) 7.59 (t, J=1.26 Hz, 1H) 8.27 (t, J=4.93 Hz, 1H) 11.46 (br. s., 1H). MS(ES) [M+H]$^+$ 470.2.

Example 77

N-((4,6-dimethyl-2-oxo-1,2-dihydropyridin-3-yl)methyl)-5-(((trans)-4-(dimethylamino)cyclohexyl)(ethyl)amino)-2-(furan-3-yl)-4-methylthiophene-3-carboxamide

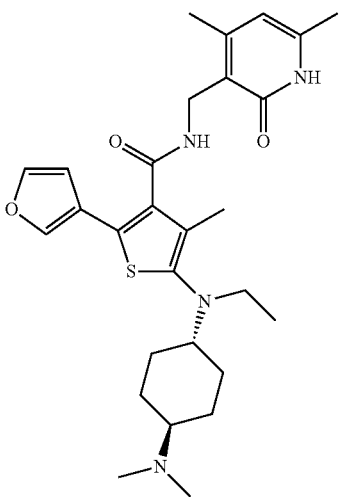 [SMILES: CCN(c1sc(-c2ccoc2)c(C(=O)NCc2c(C)cc(C)[nH]c2=O)c1C)[C@H]1CC[C@H](N(C)C)CC1]

208

$^1$H NMR (400 MHz, DMSO-d$_6$) δ 0.91 (t, J=6.95 Hz, 3H) 1.16-1.29 (m, 4H) 1.82 (d, J=9.09 Hz, 2H) 1.88-1.95 (m, 5H) 2.11 (s, 3H) 2.16 (s, 3H) 2.23 (s, 6H) 2.69 (m, J=9.60 Hz, 2H) 2.91 (q, J=6.91 Hz, 2H) 4.24 (d, J=5.05 Hz, 2H) 5.85 (s, 1H) 6.55 (dd, J=1.89, 0.88 Hz, 1H) 7.61 (t, J=1.64 Hz, 1H) 7.79 (s, 1H) 8.19 (t, J=4.93 Hz, 1H) 11.47 (br. s., 1H). MS(ES) [M+H]$^+$ 511.4.

Example 78

N-((4,6-dimethyl-2-oxo-1,2-dihydropyridin-3-yl)methyl)-5-(ethyl(tetrahydro-2H-pyran-4-yl)amino)-4-methyl-2-(1-methyl-1H-pyrazol-4-yl)thiophene-3-carboxamide

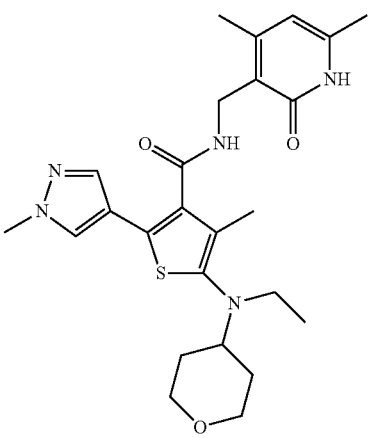

$^1$H NMR (400 MHz, DMSO-d$_6$) δ 0.92 (t, J=7.07 Hz, 3H) 1.44 (m, J=12.00, 12.00, 12.00, 4.30 Hz, 2H) 1.72 (m, J=10.60 Hz, 2H) 1.92 (s, 3H) 2.11 (s, 3H) 2.16 (s, 3H) 2.86-2.97 (m, 3H) 3.21-3.30 (m, 2H) 3.80 (s, 3H) 3.84 (m, J=11.50, 2.40 Hz, 2H) 4.24 (d, J=5.05 Hz, 2H) 5.86 (s, 1H) 7.45 (s, 1H) 7.78 (s, 1H) 8.17 (t, J=4.93 Hz, 1H) 11.47 (s, 1H). MS(ES) [M+H]$^+$ 484.3.

Assay Protocol 1

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 nL of compound from the dilution plate into reaction plates (Grenier Bio-One, 384-well, Cat#784075).

Part B. Reagent Preparation
Prepare the following solutions:
1. 50 mM Tris-HCl, pH 8: Per 1 L of base buffer, combine 1 M Tris-HCl, pH 8 (50 mL) and distilled water (950 mL).
2. 1× Assay Buffer: Per 10 mL of 1× Assay Buffer, combine 50 mM Tris-HCl, pH 8 (9958 uL), 1 M $MgCl_2$ (20 uL), 2 M DTT (20 uL), and 10% Tween-20 (2 uL) to provide a final concentration of 50 mM Tris-HCl, pH 8, 2 mM $MgCl_2$, 4 mM DTT, 0.002% Tween-20.
3. 2× Enzyme Solution: Per 10 mL of 2× Enzyme Solution, combine 1× Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and $H_2O$ (1 mL) to provide a final concentration of 40 mg/mL.
5. 2× Substrate Solution: Per 10 mL of 2× Substrate Solution, combine 1× Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine dd$H_2O$ (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-well Grenier Bio-One Plates
Compound Addition
1. Dispense 100 nL/well of 100× Compound to test wells (as noted above).
2. Dispense 100 nL/well of 100% DMSO to columns 6 & 18 for high and low controls, respectively.

Assay
1. Dispense 5 uL/well of 1× Assay Buffer to column 18 (low control reactions).
2. Dispense 5 uL/well of 2× Enzyme Solution to columns 1-17, 19-24.
3. Spin assay plates for ~1 min at 500 rpm.
4. Stack the assay plates, covering the top plate.
5. Incubate the compound/DMSO with the enzyme for 30 min at room temperature.
6. Dispense 5 uL/well of 2× Substrate Solution to columns 1-24.
7. Spin assay plates for ~1 min at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for ~1 min at 500 rpm.
4. Equilibrate the plates for >20 min.

Read plates
1. Read the assay plates on the Viewlux Plate Reader utilizing the 613 nm emission filter with a 300 s read time.

Reagent addition can be done manually or with automated liquid handler.

The final DMSO concentration in this assay is 1%.

The positive control is in column 6; negative control is in column 18.

Final starting concentration of compounds is 100 μM.

Results
Percent inhibition was calculated relative to the DMSO control for each compound concentration and the resulting values were fit using standard $IC_{50}$ fitting parameters within the ABASE data fitting software package.

The compounds of Examples 1-32 were generally tested according to the above or an analogous assay and were found to be inhibitors of EZH2. Specific biological activities tested according to such assays are listed in the following table. The $IC_{50}$ values of ≤10 nM indicate that the activity of compound was approaching the limit of detection in the assay. Repeating the assay run(s) may result in somewhat different $IC_{50}$ values.

| Example | EZH2 $IC_{50}$ (nM) |
|---|---|
| 1 | 3162 |
| 2 | 63 |
| 3 | 100 |
| 4 | 16 |
| 5 | 32 |
| 6 | 16 |
| 7 | ≤10 |
| 8 | ≤10 |
| 9 | 19,952 |
| 10 | 15,848 |
| 11 | 16 |
| 12 | ≤10 |
| 13 | 316 |
| 14 | 630 |
| 15 | 79 |
| 16 | ≤10 |
| 17 | 316 |
| 18 | ≤10 |
| 19 | ≤10 |
| 20 | 158 |
| 21 | 100 |
| 22 | 398 |
| 23 | 501 |
| 24 | 251 |
| 25 | 100 |
| 26 | 630 |
| 27 | 31 |
| 28 | 19 |
| 29 | 398 |
| 30 | 39,810 |
| 31 | 100 |
| 32 | ≤10 |

Assay Protocol 2

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on a biotinylated, unmethylated peptide substrate derived from histone H3. The peptides were captured on streptavidin-coated SPA beads and the resulting signal was read on a ViewLux plate reader.

Part A. Compound Preparation
4. Prepare 10 mM stock of compounds from solid in 100% DMSO.
5. Set up an 11-point serial dilution (1:4 dilution, top concentration 10 mM) in 100% DMSO for each test compound in a 384 well plate leaving columns 6 and 18 for DMSO controls.
6. Dispense 10 nL of compound from the dilution plate into reaction plates (Corning, 384-well polystyrene NBS, Cat#3673).

Part B. Reagent Preparation
Prepare the following solutions:
7. 1× Base Buffer, 50 mM Tris-HCl, pH 8, 2 mM $MgCl_2$: Per 1 L of base buffer, combine 1 M Tris-HCl, pH 8 (50 mL), 1 M $MgCl_2$ (2 mL), and distilled water (948 mL).
8. 1× Assay Buffer: Per 10 mL of 1× Assay Buffer, combine 1× Base Buffer (9.96 mL), 1 M DTT (40 uL), and 10% Tween-20 (1 uL) to provide a final concentration of 50 mM Tris-HCl, pH 8, 2 mM $MgCl_2$, 4 mM DTT, 0.001% Tween-20.
9. 2× Enzyme Solution: Per 10 mL of 2× Enzyme Solution, combine 1× Assay Buffer (9.99 mL) and 3.24 uM EZH2 5 member complex (6.17 uL) to provide a final enzyme concentration of 1 nM.
10. SPA Bead Solution: Per 1 mL of SPA Bead Solution, combine Streptavidin coated SPA beads (PerkinElmer, Cat# RPNQ0261, 40 mg) and 1× Assay Buffer (1 mL) to provide a working concentration of 40 mg/mL.
11. 2× Substrate Solution: Per 10 mL of 2× Substrate Solution, combine 40 mg/mL SPA Bead Solution (375 uL), 1 mM biotinylated histone H3K27 peptide (200 uL), 12.5 uM 3H-SAM (240 uL; 1 mCi/mL), 1 mM cold SAM (57 uL), and 1× Assay Buffer (9.13 mL) to provide a final concentration of 0.75 mg/mL SPA Bead Solution, 10 uM biotinylated histone H3K27 peptide, 0.15 uM 3H-SAM (~12 uCi/mL 3H-SAM), and 2.85 uM cold SAM.
12. 2.67× Quench Solution: Per 10 mL of 2.67× Quench Solution, combine 1× Assay Buffer (9.73 mL) and 10 mM cold SAM (267 uL) to provide a final concentration of 100 uM cold SAM.

Part C. Assay Reaction in 384-Well Grenier Bio-One Plates
Compound Addition
3. Stamp 10 nL/well of 1000× Compound to test wells (as noted above).
4. Stamp 10 nL/well of 100% DMSO to columns 6 & 18 (high and low controls, respectively).

Assay
10. Dispense 5 uL/well of 1× Assay Buffer to column 18 (low control reactions).
11. Dispense 5 uL/well of 2× Substrate Solution to columns 1-24 (note: substrate solution should be mixed to ensure homogeneous bead suspension before dispensing into matrix reservoir).
12. Dispense 5 uL/well of 2× Enzyme Solution to columns 1-17, 19-24.
13. Incubate the reaction for 60 min at room temperature.

Quench
5. Dispense 6 uL/well of the 2.67× Quench Solution to columns 1-24.
6. Seal assay plates and spin for ~1 min at 500 rpm.
7. Dark adapt plates in the ViewLux instrument for 15-60 min.

Read plates
2. Read the assay plates on the Viewlux Plate Reader utilizing the 613 nm emission filter or clear filter (300 s exposure).

Reagent addition can be done manually or with automated liquid handler.

Results
Percent inhibition was calculated relative to the DMSO control for each compound concentration and the resulting values were fit using standard $IC_{50}$ fitting parameters within the ABASE data fitting software package.

All of the exemplified compounds were generally tested according to the above or an analogous assay and were found to be inhibitors of EZH2. Specific biological activities tested according to such assays are listed in the following table. The $IC_{50}$ values of ≤10 nM indicate that the activity of compound was approaching the limit of detection in the assay. Repeating the assay run(s) may result in somewhat different $IC_{50}$ values.

| Example | EZH2 $IC_{50}$ (nM) |
| --- | --- |
| 1 | 25,119 |
| 2 | 200 |
| 3 | 200 |
| 4 | 25 |
| 5 | 50 |
| 6 | 16 |
| 7 | 20 |
| 8 | 13 |
| 9 | 63,096 |
| 10 | ≥100,000 |
| 11 | 20 |
| 12 | 20 |
| 13 | 1,995 |
| 14 | 1,995 |
| 15 | 630 |
| 16 | 25 |
| 17 | 630 |
| 18 | 13 |
| 19 | 20 |
| 20 | 1,585 |
| 21 | 316 |
| 22 | 6,310 |
| 23 | 3,981 |
| 24 | 3,981 |
| 25 | 630 |
| 26 | 5,012 |
| 27 | 63 |
| 28 | 63 |
| 29 | 3,162 |
| 30 | ≥100,000 |
| 31 | 794 |
| 32 | 50 |
| 33 | ≤10 |
| 34 | 100 |
| 35 | 13 |
| 36 | ≤10 |
| 37 | 501 |
| 38 | 158 |
| 39 | 50 |
| 40 | 20 |
| 41 | 20 |
| 42 | 316 |
| 43 | 16 |
| 44 | 20 |
| 45 | ≤10 |
| 46 | 316 |
| 47 | 13 |
| 48 | ≤10 |
| 49 | 126 |
| 50 | 20 |
| 51 | 25 |
| 52 | 316 |
| 53 | 16 |
| 54 | 32 |
| 55 | 79 |
| 56 | 501 |
| 57 | 200 |
| 58 | 794 |
| 59 | 316 |
| 60 | 631 |
| 61 | 501 |
| 62 | 501 |
| 63 | 501 |
| 64 | 16 |
| 65 | 200 |
| 66 | 63 |
| 67 | 20 |
| 68 | 79 |
| 69 | 501 |
| 70 | 100 |
| 71 | 1,000 |
| 72 | 251 |

-continued

| Example | EZH2 IC$_{50}$ (nM) |
|---|---|
| 73 | 126 |
| 74 | 200 |
| 75 | 25 |
| 76 | 32 |
| 77 | 32 |
| 78 | 100 |

The invention claimed is:

1. A compound according to Formula (III)(a):

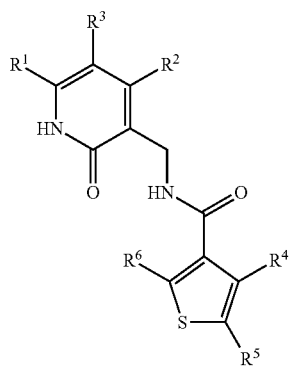

(III)(a)

wherein:
R$^1$ and R$^2$ are each independently (C$_1$-C$_4$)alkoxy, (C$_1$-C$_4$)alkyl, or halo(C$_1$-C$_4$)alkyl;
R$^3$ is hydrogen;
R$^4$ is (C$_1$-C$_3$)alkyl or halogen;
R$^5$ is (C$_3$-C$_8$)cycloalkyl(C$_1$-C$_2$)alkyl- or heterocycloalkyl(C$_1$-C$_2$)alkyl-, each of which is optionally substituted 1, 2, or 3 times, independently, by halogen, —OR$^a$, —NR$^a$R$^b$, —NHCO$_2$R$^a$, nitro, (C$_1$-C$_3$)alkyl, R$^a$R$^b$N(C$_1$-C$_3$)alkyl-, R$^a$O(C$_1$-C$_3$)alkyl-, (C$_3$-C$_8$)cycloalkyl, cyano, —CO$_2$R$^a$, —C(O)NR$^a$R$^b$, —SO$_2$NR$^a$R$^b$, heterocycloalkyl, aryl, or heteroaryl, wherein said (C$_3$-C$_8$)cycloalkyl, heterocycloalkyl, aryl, or heteroaryl is optionally substituted 1 or 2 times, independently, by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-;
R$^6$ is selected from the group consisting of hydrogen, —SO$_2$(C$_1$-C$_4$)alkyl, halogen, (C$_1$-C$_6$)alkyl, (C$_1$-C$_4$)alkoxy, phenyl, heteroaryl, and cyano, wherein said phenyl or heteroaryl group is optionally substituted 1 or 2 times, independently, by (C$_1$-C$_4$)alkoxy, —NR$^a$R$^b$, R$^a$R$^b$N(C$_1$-C$_4$)alkyl-, (C$_1$-C$_4$)alkylheterocycloalkyl-, halogen, (C$_1$-C$_4$)alkyl, (C$_3$-C$_8$)cycloalkyl, or heterocycloalkyl; and
R$^a$ and R$^b$ are each independently hydrogen, (C$_1$-C$_4$)alkyl, (C$_1$-C$_4$)alkoxy(C$_1$-C$_4$)alkyl-, (C$_3$-C$_{10}$)cycloalkyl, heterocycloalkyl, aryl, aryl(C$_1$-C$_4$)alkyl-, heteroaryl(C$_1$-C$_4$)alkyl-, or heteroaryl, wherein any said cycloalkyl, heterocycloalkyl, aryl, or heteroaryl group is optionally substituted 1, 2, or 3 times, independently, by halogen, hydroxyl, (C$_1$-C$_4$)alkoxy, amino, —NH(C$_1$-C$_4$)alkyl, —N((C$_1$-C$_4$)alkyl)$_2$, (C$_1$-C$_4$)alkyl, halo(C$_1$-C$_4$)alkyl, —CO$_2$H, —CO$_2$(C$_1$-C$_4$)alkyl, —CONH$_2$, —CONH(C$_1$-C$_4$)alkyl, —CON((C$_1$-C$_4$)alkyl)$_2$, —SO$_2$(C$_1$-C$_4$)alkyl, —SO$_2$NH$_2$, —SO$_2$NH(C$_1$-C$_4$)alkyl, or —SO$_2$N((C$_1$-C$_4$)alkyl)$_2$;
or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted 1, 2, or 3 times, independently, by (C$_1$-C$_4$)alkyl, halo(C$_1$-C$_4$)alkyl, amino, —NH(C$_1$-C$_4$)alkyl, —N((C$_1$-C$_4$)alkyl)$_2$, hydroxyl, oxo, (C$_1$-C$_4$)alkoxy, or (C$_1$-C$_4$)alkoxy(C$_1$-C$_4$)alkyl-, wherein said ring is optionally fused to a (C$_3$-C$_8$)cycloalkyl, heterocycloalkyl, aryl, or heteroaryl ring;
or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring;
or a pharmaceutically acceptable salt thereof.

2. The compound according to claim 1, wherein R$^1$ and R$^2$ are each independently (C$_1$-C$_4$)alkyl, or a pharmaceutically acceptable salt thereof.

3. The compound according to claim 1, wherein R$^1$ and R$^2$ are each methyl, or a pharmaceutically acceptable salt thereof.

4. The compound according to claim 1, wherein R$^4$ is methyl, or a pharmaceutically acceptable salt thereof.

5. The compound according to claim 3, wherein R$^4$ is methyl, or a pharmaceutically acceptable salt thereof.

6. The compound according to claim 1, wherein R$^5$ is (C$_3$-C$_8$)cycloalkyl(C$_1$-C$_2$)alkyl- which is optionally substituted by halogen, —OR$^a$, —NR$^a$R$^b$, —NHCO$_2$R$^a$, nitro, (C$_1$-C$_3$)alkyl, R$^a$R$^b$N(C$_1$-C$_3$)alkyl-, R$^a$O(C$_1$-C$_3$)alkyl-, (C$_3$-C$_8$)cycloalkyl, cyano, —CO$_2$R$^a$, —C(O)NR$^a$R$^b$, —SO$_2$NR$^a$R$^b$, heterocycloalkyl, aryl, or heteroaryl, wherein said (C$_3$-C$_8$)cycloalkyl, heterocycloalkyl, aryl, or heteroaryl is optionally substituted 1 or 2 times, independently, by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-, or a pharmaceutically acceptable salt thereof.

7. The compound according to claim 5, wherein R$^5$ is (C$_3$-C$_8$)cycloalkyl(C$_1$-C$_2$)alkyl- which is optionally substituted by halogen, —OR$^a$, —NR$^a$R$^b$, —NHCO$_2$R$^a$, nitro, (C$_1$-C$_3$)alkyl, R$^a$R$^b$N(C$_1$-C$_3$)alkyl-, R$^a$O(C$_1$-C$_3$)alkyl-, (C$_3$-C$_8$)cycloalkyl, cyano, —CO$_2$R$^a$, —C(O)NR$^a$R$^b$, —SO$_2$NR$^a$R$^b$, heterocycloalkyl, aryl, or heteroaryl, wherein said (C$_3$-C$_8$)cycloalkyl, heterocycloalkyl, aryl, or heteroaryl is optionally substituted 1 or 2 times, independently, by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-, or a pharmaceutically acceptable salt thereof.

8. The compound according to claim 1, wherein R$^5$ is (C$_3$-C$_8$)cycloalkyl(C$_1$-C$_2$)alkyl- which is substituted by heterocycloalkyl, wherein said heterocycloalkyl is optionally substituted by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-, or a pharmaceutically acceptable salt thereof.

9. The compound according to claim 5, wherein R$^5$ is (C$_3$-C$_8$)cycloalkyl(C$_1$-C$_2$)alkyl- which is substituted by heterocycloalkyl, wherein said heterocycloalkyl is optionally substituted by halogen, (C$_1$-C$_4$)alkyl, halo(C$_1$-C$_4$)alkyl, —CO(C$_1$-C$_4$)alkyl, —CO$_2$(C$_1$-C$_4$)alkyl, —NR$^a$R$^b$, —NHCO$_2$R$^a$, hydroxyl, oxo, (C$_1$-C$_4$)alkoxy, or (C$_1$-C$_4$)alkoxy(C$_1$-C$_4$)alkyl-, or a pharmaceutically acceptable salt thereof.

10. The compound according to claim 1, wherein R$^5$ is (C$_3$-C$_8$)cycloalkyl(C$_1$-C$_2$)alkyl- which is substituted by heterocycloalkyl, wherein said heterocycloalkyl is substituted by (C$_1$-C$_4$)alkoxy, or a pharmaceutically acceptable salt thereof.

11. The compound according to claim 5, wherein R$^5$ is (C$_3$-C$_8$)cycloalkyl(C$_1$-C$_2$)alkyl- which is substituted by heterocycloalkyl, wherein said heterocycloalkyl is substituted by (C$_1$-C$_4$)alkoxy, or a pharmaceutically acceptable salt thereof.

12. The compound according to claim 1, wherein R$^6$ is hydrogen, halogen, (C$_1$-C$_4$)alkyl, or (C$_1$-C$_4$)alkoxy, or a pharmaceutically acceptable salt thereof.

13. The compound according to claim 5, wherein R$^6$ is hydrogen, halogen, (C$_1$-C$_4$)alkyl, or (C$_1$-C$_4$)alkoxy, or a pharmaceutically acceptable salt thereof.

14. The compound according to claim 11, wherein R$^6$ is hydrogen, halogen, (C$_1$-C$_4$)alkyl, or (C$_1$-C$_4$)alkoxy, or a pharmaceutically acceptable salt thereof.

15. The compound according to claim 1, wherein R$^6$ is hydrogen, or a pharmaceutically acceptable salt thereof.

16. The compound according to claim 5, wherein R$^6$ is hydrogen, or a pharmaceutically acceptable salt thereof.

17. The compound according to claim 11, wherein R$^6$ is hydrogen, or a pharmaceutically acceptable salt thereof.

18. A pharmaceutical composition comprising the compound or pharmaceutically acceptable salt thereof according to claim 1 and a pharmaceutically acceptable excipient.

19. A pharmaceutical composition comprising the compound or pharmaceutically acceptable salt thereof according to claim 16 and a pharmaceutically acceptable excipient.

20. A pharmaceutical composition comprising the compound or pharmaceutically acceptable salt thereof according to claim 17 and a pharmaceutically acceptable excipient.

* * * * *